(12) United States Patent
Hilpert et al.

(10) Patent No.: US 8,785,436 B2
(45) Date of Patent: Jul. 22, 2014

(54) 1,3-OXAZINES AS BACE 1 AND/OR BACE2 INHIBITORS

(75) Inventors: Hans Hilpert, Muenchenstein (CH); Robert Narquizian, Zaessingue (FR); Emmanuel Pinard, Linsdorf (FR); Alessandra Polara, Basel (CH); Mark Rogers-Evans, Bottmingen (CH); Thomas Woltering, Freiburg (DE); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 189 days.

(21) Appl. No.: 13/467,085

(22) Filed: May 9, 2012

(65) Prior Publication Data

US 2012/0295900 A1 Nov. 22, 2012

(30) Foreign Application Priority Data

May 16, 2011 (EP) .................................. 11166208

(51) Int. Cl.
| | |
|---|---|
| C07D 413/04 | (2006.01) |
| C07D 413/10 | (2006.01) |
| C07D 413/12 | (2006.01) |
| A61K 31/5355 | (2006.01) |

(52) U.S. Cl.
USPC ............................ 514/228.8; 544/88; 544/96

(58) Field of Classification Search
CPC .. C07D 413/04; C07D 413/10; C07D 413/12; A61K 31/5355
USPC .................... 544/88, 96; 514/228.8
See application file for complete search history.

(56) References Cited

FOREIGN PATENT DOCUMENTS

| | | |
|---|---|---|
| WF | 2011/071135 | 6/2011 |
| WO | 2007/049532 | 3/2007 |
| WO | 2011/020806 | 2/2011 |
| WO | 2011/058763 | 5/2011 |
| WO | 2011/069934 | 6/2011 |
| WO | 2011/070029 | 6/2011 |

OTHER PUBLICATIONS

Zhu et al. Organic Letters (2006), 8(12), 2599-2602.*
Basset et al., Scand. J. Immunol. 51:307-311 ( 2000).
Prentki et al., J. Clin. Investig. 116(7):1802-1812 ( 2006).
Kiljanski et al., "Thyroid" 15(7):645-652 ( 2005).
Luo et al., "Nature Neuroscience" 3:231-232 ( 2001).
Gatchel et al., Proc. Natl. Acad. Sci. USA 105:1291-1296 ( 2008).
McConlogue et al., "J. Biol. Chem." 282(36):26326-26334 ( 2007).
Kondoh et al., "Breast Cancer & Research Treatment" 78(1):37-44 ( 2003).
Kihara et al., Proc. Natl. Acad. Sci. USA 106:21807-21812 ( 2009).
Hussain et al., Mol. Cell Neurosci. 16:609-619 ( 2000).
Talentov et al., "Clin. Cancer Res." 11:7234-7242 ( 2005).
Hoffmeister et al., "Journal of the Pancreas" 10(5):501-506 ( 2009).
Kim et al., "Neurobiology of Disease" 22(2):346-356 ( 2006).
Wild et al., "Diabetes Care" 27(5):1047-1053 ( 2004).
Finzi et al., "Ultrastruct. Pathol." 32(6):246-251 ( 2008).
Koistinen et al., "Muscle & Nerve" 34(4):444-450 ( 2006).
Barbiero et al., Exp. Neurol. 182:335-345 ( 2003).
Baggio et al., Annu. Rev. Med. 57:265-281 ( 2006).
Merten et al., "Zeitschrift fur Kardiologie" ((English language Summary is attached to the reference)), 93(11):855-863 ( 2004).
Hardy et al., Science 297:353-356 ( 2002).
Grewal et al., Mol. Cell Biol. 26:4970-4981 ( 2006).
Vattemi et al., "Lancer" ((9297)), 358:1962-1964 ( 2001).
Lichtenthaler et al., "J. Biol. Chem." 278(49):48713-48719 ( 2003).
Maugeri et al., "Srpski Arhivza Celokupno Lekarstuo" ((Suppl 1)), 138:50-52 ( 2010).
Lagos et al., "Blood" 109(4):1550-1558 ( 2007).
Woodard-Grice et al., "J. Biol. Chem." 283(39):26364-26373 ( 2008).
Kuhn et al., "J. Biol. Chem." 282(16):11982-11995 ( 2007).
Akpinar et al., Cell Metab. 2:385-397 ( 2005).
Fukui et al., "Cell Metab." 2:373-384 ( 2005).
Zimmet et al., "Nature" 414:782-282 ( 2001).
Toegel et al., "Osteoarthritis & Cartilage" 18(2):240-248 ( 2010).
Hodges et al., Hum. Mol. Genet. 15:965-977 ( 2006).
Li et al., "Aging Cell" 5(2):153-165 ( 2006).
Vassar et al., BACE, Science 286:735 ( 1999).
Greenberg et al., Ann. Neurol. 57:664-678 ( 2005).
Sugimoto et al., "J. Biol. Chem." 282(48):34896-34903 ( 2007).
Roberds et al., Hum. Mol. Genet. 10(12):1317-1324 ( 2001).
Hedlund et al., Cancer Research 68(2):388-394 ( 2008).
Desnues et al., Clin. Vaccine Immunol. 13:170-178 ( 2006).
Selkoe et al., "Annual Review Cell Biology" 10:373-403 ( 1994).
(International Search Report PCT/EP2012/058707 May 11, 2012).

* cited by examiner

Primary Examiner — Kahsay Habte

(57) ABSTRACT

The present invention provides compounds of formula I

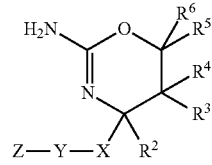

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

27 Claims, No Drawings

1,3-OXAZINES AS BACE 1 AND/OR BACE2 INHIBITORS

PRIORITY TO RELATED APPLICATION(S)

This application claims the benefit of European Patent Application No. 11166208.6, filed May 16, 2011, which is hereby incorporated by reference in its entirety.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science.* 2002 Jul. 19; 297 (5580):353-6, Selkoe, Cell biology of the amyloid beta-protein precursor and the mechanism of Alzheimer's disease, *Annu Rev Cell Biol.* 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science.* 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat. Neurosci.* 2001 March; 4(3):231-2, Roberds et al., BACE knockout mice are healthy despite lacking the primary beta-secretase activity in brain: implications for Alzheimer's disease therapeutics, *Hum Mol. Genet.* 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol. Chem.* 2007 Sep. 7; 282(36):26326). It is thus presumed that inhibitors of BACE1 activity can be useful agents for therapeutic intervention in Alzheimer's disease (AD).

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, K G M M Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Inhibitors of BACE1 and/or BACE2 can in addition be used to treat the following diseases:

IBM (inclusion body myositis) (Vattemi G. et al., Lancet. 2001 Dec. 8; 358(9297):1962-4), Down's Syndrome (Barbiero L. et al, Exp Neurol. 2003 August; 182(2):335-45), Wilson's Disease (Sugimoto I. et al., J Biol. Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., Proc Natl Acad Sci USA 2008 Jan. 29; 105(4):1291-6), Dermatomyositis (Greenberg S. A. et al., Ann Neurol. 2005 May; 57(5):664-78 and Greenberg S. A. et al., Neurol 2005 May; 57(5):664-78), Kaposi Sarcoma (Lagos D. et al, Blood, 2007 Feb. 15; 109(4):1550-8), Glioblastoma multiforme (E-MEXP-2576, http://www.ebi.ac.uk/microarray-as/aer/result?queryFor=PhysicalArrayDesign&aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2):346-56. Epub 2006 Jan. 19 and Hodges A. et al., Hum Mol. Genet. 2006 Mar. 15; 15(6):965-77. Epub 2006 Feb. 8), Multiple Mieloma (Kihara Y. et al, Proc Natl Acad Sci USA. 2009 Dec. 22; 106(51):21807-12), Malignant melanoma (Talantov D. et al, Clin Cancer Res. 2005 Oct. 15; 11(20):7234-42), Sjogren syndrome (Basset C. et al., Scand J Immunol 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol. Chem. 2008 Sep. 26; 283(39): 26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol. Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

FIELD OF THE INVENTION

The present invention provides 5,6-dihydro-4H-[1,3]oxazin-2-ylamines having BACE1 and/or BACE2 inhibitory properties, their manufacture, pharmaceutical compositions containing them and their use as therapeutically active substances.

SUMMARY OF THE INVENTION

The present invention provides novel compounds of formula I, their manufacture, pharmaceutical compositions based on a compound in accordance with the invention and their production as well as methods for the control or prevention of illnesses such as Alzheimer's disease and type 2 diabetes by administering compounds of the invention. Furthermore the use of compounds of formula I in the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease. The novel compounds of formula I have improved pharmacological properties.

The present invention provides a compound of formula I,

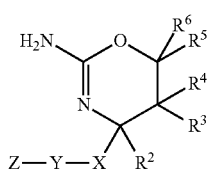

I wherein the substituents and variables are as described below and in the claims, or a pharmaceutically acceptable salt thereof.

The present compounds have Asp2 (β-secretase, BACE1 or Memapsin-2) inhibitory activity and/or BACE2 inhibitory activity. The present compounds having Asp2 (β-secretase, BACE1 or Memapsin-2) inhibitory activity can be used in the therapeutic and/or prophylactic treatment of diseases and disorders characterized by elevated β-amyloid levels and/or β-amyloid oligomers and/or β-amyloid plaques and further deposits, particularly Alzheimer's disease. The present compounds having BACE2 inhibitory activity can be used in the therapeutic and/or prophylactic treatment of diseases and disorders such as type 2 diabetes and other metabolic disorders.

DETAILED DESCRIPTION OF THE INVENTION

The present invention provides a compound of formula I and pharmaceutically acceptable salts thereof, the preparation of the above mentioned compounds, pharmaceutical compositions containing them and their manufacture as well as methods for the therapeutic and/or prophylactic treatment of diseases and disorders which are associated with inhibition of BACE1 and/or BACE2 activity, such as Alzheimer's disease and type 2 diabetes by administering compounds of the invention. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which can be linear or branched, with single or multiple branching, wherein the alkyl group containing 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. The term "$C_{1-3}$-alkyl", alone or in combination with other groups, stands for a hydrocarbon radical which can be linear or branched, wherein the alkyl group contains 1 to 3 carbon atoms. Particular "$C_{1-6}$-alkyl" groups are "$C_{1-3}$-alkyl". Specific groups are methyl and ethyl—most specifically methyl.

The term "halogen-$C_{1-6}$-alkyl", alone or in combination with other groups, refers to $C_{1-6}$-alkyl as defined herein, which is substituted by one or multiple halogen atoms, in particular 1-5 halogen atoms, more particularly 1-3 halogen atoms, most particularly 1 halogen or 3 halogen atoms. The term "halogen-$C_{1-3}$-alkyl", alone or in combination with other groups, refers to $C_{1-3}$-alkyl as defined herein, which is substituted by one or multiple halogen, in particular 1-5 halogen atoms, more particularly 1-3 halogen atoms, most particularly 1 halogen or 3 halogen atoms. A specific halogen is fluoro. A specific "halogen-$C_{1-6}$-alkyl" is fluoro-$C_{1-6}$-alkyl and a specific "halogen-$C_{1-3}$-alkyl" is fluoro-$C_{1-3}$-alkyl. Examples are difluoromethyl, trifluoromethyl, chloromethyl, fluoromethyl and the like. A specific example is trifluoromethyl.

The term "cyano", alone or in combination with other groups, refers to N≡C—.

The term "halogen", alone or in combination with other groups, denotes chloro (Cl), iodo (I), fluoro (F) and bromo (Br). Examples of "halogen" are Cl and F. A specific example is F.

The term "heteroaryl", alone or in combination with other groups, refers to an aromatic group having a single 4 to 8 membered ring or multiple condensed rings containing 6 to 14, in particular 6 to 10, ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" groups are 1H-indolyl, 1H-pyrazolyl, 3,4-dihydro-2H-benzo[1,4]oxazinyl, 3H-benzoimidazolyl, 3H-indolyl, 6,7-dihydro-5H-[1]pyrindinyl, benzooxazolyl, isoxazolyl, oxazolyl, pyrazolyl, pyridinyl, pyrimidinyl, quinolinyl, thieno[3,2-b]pyridinyl, thiophenyl and the like. Specific "heteroaryl" groups are 1H-indol-6-yl, 1H-pyrazol-3-yl, 1H-pyrazol-4-yl, 2H-pyrazol-3-yl, 3,4-dihydro-2H-benzo[1,4]oxazin-6-yl, 3H-benzoimidazol-5-yl, 3H-indol-6-yl, 6,7-dihydro-5H-[1]pyrindin-5-yl, benzooxazol-2-yl, isoxazol-3-yl, oxazol-4-yl, pyrazol-1-yl, pyridin-2-yl, pyridin-3-yl, pyrimidin-5-yl, quinolin-8-yl, thieno[3,2-b]pyridin-3-yl, thiophen-2-yl and thiophen-3-yl.

The term "heterocyclyl", alone or in combination with other groups, denotes a monovalent saturated or partly unsaturated mono- or bicyclic ring system of 4 to 9 ring atoms, containing 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for monocyclic saturated heterocyclyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, and oxazepanyl. Examples for bicyclic saturated heterocyclyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Examples for partly unsaturated heterocyclyl are dihydrofuryl, imidazolinyl, dihydro-oxazolyl, tetrahydro-pyridinyl, and dihydropyranyl. Specific "heterocyclyl" groups are oxetanyl, tetrahydrofuranyl, 5,6,7,8-tetrahydro-quinolin-5-yl, 5,6,7,8-tetrahydro-quinolin-5-yl and the like. Specific are oxetan-3-yl and tetrahydro-furan-3-yl.

The term "$C_{1-6}$-alkoxy", alone or in combination with other groups, stands for an —O—$C_{1-6}$-alkyl radical which can be linear or branched, with single or multiple branching, wherein the alkyl group contains 1 to 6 carbon atoms, for example, methoxy (OMe), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" groups have 1 to 4 carbon atoms. A specific example is methoxy.

The term "halogen-$C_{1-6}$-alkoxy", alone or in combination with other groups, refers to $C_{1-6}$-alkoxy as defined herein, which is substituted by one or multiple halogens, in particular fluoro. A particular "halogen-$C_{1-6}$-alkoxy" group is fluoro-$C_{1-6}$-alkoxy. Specific examples are difluoromethoxy and trifluoromethoxy.

The term "$C_{3-6}$-cycloalkyl", alone or in combination with other groups, denotes a monovalent saturated monocyclic or bicyclic hydrocarbon group of 3 to 6 ring carbon atoms, particularly a monovalent saturated monocyclic hydrocarbon group of 3 to 5 ring carbon atoms. Bicyclic means consisting of two saturated carbocycles having two carbon atoms in common, i.e. the bridge separating the two rings is either a single bond or a chain of one or two carbon atoms. Particular $C_{3-6}$-cycloalkyl groups are monocyclic. Examples are cyclopropyl, cyclobutanyl, cyclopentyl, cyclohexyl and cycloheptyl. Examples of bicyclic cycloalkyl are bicyclo[2.2.1]heptanyl, bicyclo[2.2.2]octanyl and adamantanyl. Particular "$C_{3-6}$-cycloalkyl" groups are cyclopropyl and cyclopentyl.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and containing one, two or three triple bonds. Examples of $C_{2-6}$-alkynyl include ethynyl, propynyl. A specific example is propynyl.

The term "aryl" denotes a monovalent aromatic carbocyclic mono- or bicyclic ring system comprising 6 to 10 carbon ring atoms. Examples of aryl moieties include phenyl and naphthyl. A specific example is phenyl.

The term "halogen-aryl", alone or in combination with other groups, refers to "aryl" as defined herein, which is substituted by one or multiple halogens, in particular fluoro. Particular "halogen-aryl" groups are halogen-phenyl, fluoro-aryl and fluoro-phenyl. A specific example is 2-fluoro-phenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Preferred are formic acid, trifluoroacetic acid and hydrochloric acid. Particular are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to a particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log$ Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" (here also $P^1$) denotes groups intended to protect an amino group and includes benzyl, benzyloxycarbonyl (carbobenzyloxy, CBZ), 9-Fluorenylmethyloxycarbonyl (FMOC), p-methoxybenzyl-oxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- and arylenesulfonyloxy, such as methanesulfonyloxy, ethanesulfonyloxy, thiomethyl, benzenesulfonyloxy, tosyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments can be combined.

One embodiment of the invention provides a compound of formula I,

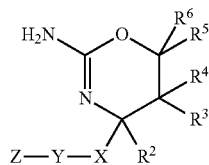

I wherein
X is selected from the group consisting of
  aryl,
  aryl substituted by 1-2 substituents individually selected from $R^1$,
  heteroaryl,
  heteroaryl substituted by 1-2 substituents individually selected from $R^1$ and halogen-aryl,
  $C_{3-6}$-cycloalkyl, and
  $C_{3-6}$-cycloalkyl substituted by 1-2 substituents individually selected from $R^1$;
Y is selected from the group consisting of
  —C=O—NH—,
  —$CH_2$—,
  —NH—
  —NH—$CHR^7$—,
  —O—$CH_2$—, and
  absent;
Z is selected from the group consisting of
  aryl,
  aryl substituted by 1-2 substituents individually selected from $R^8$,
  heteroaryl,
  heteroaryl substituted by 1-2 substituents individually selected from $R^8$,
  $C_{3-6}$-cycloalkyl,
  $C_{3-6}$-cycloalkyl substituted by 1-2 substituents individually selected from $R^8$,
  heterocyclyl,
  heterocyclyl substituted by 1-2 substituents individually selected from $R^8$,
  $C_{2-6}$-alkynyl,
  $C_{1-6}$-alkyl, and
  $C_{1-6}$-alkyl substituted by 1-3 substituents individually selected from $R^9$;
$R^1$ is selected from the group consisting of
  hydrogen,
  halogen, and
  $C_{1-6}$-alkyl;
$R^2$ is selected from the group consisting of
  hydrogen,
  $C_{1-6}$-alkyl, and
  halogen-$C_{1-3}$-alkyl;
$R^3$ is selected from the group consisting of
  hydrogen,
  halogen, and
  $C_{1-6}$-alkyl;
$R^4$ is selected from the group consisting of
  Hydrogen,
  halogen, and
  $C_{1-6}$-alkyl;
$R^5$ is selected from the group consisting of
  hydrogen and
  $C_{1-6}$-alkyl;
$R^6$ is selected from the group consisting of
  hydrogen and
  $C_{1-6}$-alkyl;
$R^7$ is selected from the group consisting of
  hydrogen and
  $C_{1-6}$-alkyl;
$R^8$ is selected from the group consisting of
  halogen,
  cyano,
  $C_{1-6}$-alkyl,
  halogen-$C_{1-6}$-alkyl,
  $C_{1-6}$-alkoxy,
  halogen-$C_{1-6}$-alkoxy,
  aryl,
  halogen-aryl, and
  $C_{3-6}$-cycloalkyl; and
$R^9$ is selected from the group consisting of
  halogen,
  cyano,
  $C_{1-6}$-alkoxy, and
  halogen-$C_{1-6}$-alkoxy,
or pharmaceutically acceptable salts thereof.

A certain embodiment of the invention provides a compound of formula I,

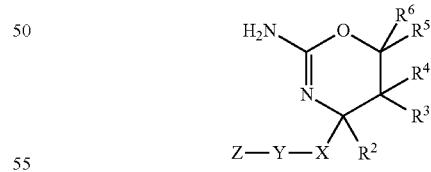

I wherein
X is selected from the group consisting of
  aryl,
  aryl substituted by 1-2 substituents individually selected from $R^1$,
  heteroaryl, and
  heteroaryl substituted by 1-2 substituents individually selected from $R^1$;
Y is selected from the group consisting of
  —(C=O)—NH—,
  —$CH_2$—, —NH—,
—NH—CHR$^7$—,
—O—CH$_2$—, and
absent;
Z is selected from the group consisting of
  aryl,
  aryl substituted by 1-2 substituents individually selected from R$^8$,
  heteroaryl,
  heteroaryl substituted by 1-2 substituents individually selected from R$^8$,
  C$_{3-6}$-cycloalkyl,
  C$_{3-6}$-cycloalkyl substituted by 1-2 substituents individually selected from R$^8$,
  heterocyclyl,
  heterocyclyl substituted by 1-2 substituents individually selected from R$^8$, and
  C$_{2-6}$-alkynyl;
R$^1$ is selected from the group consisting of
  hydrogen,
  halogen, and
  C$_{1-6}$-alkyl;
R$^2$ is selected from the group consisting of
  hydrogen,
  C$_{1-6}$-alkyl, and
  halogen-C$_{1-3}$-alkyl;
R$^3$ is selected from the group consisting of
  hydrogen,
  halogen, and
  C$_{1-6}$-alkyl;
R$^4$ is selected from the group consisting of
  hydrogen
  halogen, and
  C$_{1-6}$-alkyl;
R$^5$ is selected from the group consisting of
  hydrogen and
  C$_{1-6}$-alkyl;
R$^6$ is selected from the group consisting of
  hydrogen and
  C$_{1-6}$-alkyl;
R$^7$ is selected from the group consisting of
  hydrogen and
  C$_{1-6}$-alkyl; and
R$^8$ is selected from the group consisting of
  halogen,
  cyano,
  C$_{1-6}$-alkyl,
  halogen-C$_{1-6}$-alkyl,
  C$_{1-6}$-alkoxy,
  halogen-C$_{1-6}$-alkoxy,
  aryl,
  halogen-aryl, and
  C$_{3-6}$-cycloalkyl;
or pharmaceutically acceptable salts thereof.

A certain embodiment of the invention provides a compound of formula I as described herein, wherein R$^2$ is C$_{1-6}$-alkyl.

A certain embodiment of the invention provides a compound of formula I as described herein, wherein R$^2$ is methyl.

A certain embodiment of the invention provides a compound of formula I as described herein, wherein R$^2$ is halogen-C$_{1-3}$-alkyl.

A certain embodiment of the invention provides a compound of formula I as described herein, wherein R$^2$ is —CHF$_2$.

A certain embodiment of the invention provides a compound of formula I as described herein, wherein R$^2$ is hydrogen.

A certain embodiment of the invention provides a compound of formula I as described herein, wherein R$^3$ is halogen.

A certain embodiment of the invention provides a compound of formula I as described herein, wherein R$^3$ is F.

A certain embodiment of the invention provides a compound of formula I as described herein, wherein R$^3$ is C$_{1-6}$-alkyl.

A certain embodiment of the invention provides a compound of formula I as described herein, wherein R$^4$ is H.

A certain embodiment of the invention provides a compound of formula I as described herein, wherein R$^4$ is C$_{1-6}$-alkyl.

A certain embodiment of the invention provides a compound of formula I as described herein, wherein R$^4$ is methyl.

A certain embodiment of the invention provides a compound of formula I as described herein, wherein R$^4$ is halogen.

A certain embodiment of the invention provides a compound of formula I as described herein, wherein R$^4$ is F.

A certain embodiment of the invention provides a compound of formula I as described herein, wherein R$^4$ is H, methyl or F.

A certain embodiment of the invention provides a compound of formula I as described herein, wherein R$^5$ is H.

A certain embodiment of the invention provides a compound of formula I as described herein, wherein R$^5$ is C$_{1-6}$-alkyl.

A certain embodiment of the invention provides a compound of formula I as described herein, wherein R$^6$ is H.

A certain embodiment of the invention provides a compound of formula I as described herein, wherein R$^6$ is C$_{1-6}$-alkyl.

A certain embodiment of the invention provides a compound of formula I as described herein, wherein X is aryl substituted by halogen.

A certain embodiment of the invention provides a compound of formula I as described herein, wherein X is phenyl substituted by F.

A certain embodiment of the invention provides a compound of formula I as described herein, wherein X is aryl.

A certain embodiment of the invention provides a compound of formula I as described herein, wherein X is aryl substituted by 1-2 substituents individually selected from R$^1$.

A certain embodiment of the invention provides a compound of formula I as described herein, wherein X is heteroaryl.

A certain embodiment of the invention provides a compound of formula I as described herein, wherein X is benzoimidazolyl.

A certain embodiment of the invention provides a compound of formula I as described herein, wherein X is pyrazolyl.

A certain embodiment of the invention provides a compound of formula I as described herein, wherein X is heteroaryl substituted by 1-2 substituents individually selected from R$^1$.

A certain embodiment of the invention provides a compound of formula I as described herein, wherein X is 3,4-dihydro-2H-benzo[1,4]oxazin-6-yl substituted by F.

A certain embodiment of the invention provides a compound of formula I as described herein, wherein X is 1H-indolyl substituted by F.

A certain embodiment of the invention provides a compound of formula I as described herein, wherein X is $C_{3-6}$-cycloalkyl.

A certain embodiment of the invention provides a compound of formula I as described herein, wherein X is cyclopropyl.

A certain embodiment of the invention provides a compound of formula I as described herein, wherein X is heteroaryl substituted by halogen-aryl.

A certain embodiment of the invention provides a compound of formula I as described herein, wherein X is 1-(3-Bromo-phenyl)-1H-pyrazol-4-yl.

A certain embodiment of the invention provides a compound of formula I as described herein, wherein Y is —NHCH$_2$—, —NH— or absent.

A certain embodiment of the invention provides a compound of formula I as described herein, wherein Y is —(C=O)—NH—.

A certain embodiment of the invention provides a compound of formula I as described herein, wherein Y is —CH$_2$—.

A certain embodiment of the invention provides a compound of formula I as described herein, wherein Y is —NH—.

A certain embodiment of the invention provides a compound of formula I as described herein, wherein Y is —NH—CHR$^7$—, and R$^7$ is H.

A certain embodiment of the invention provides a compound of formula I as described herein, wherein Y is —NH—CHR$^7$—, and R$^7$ is $C_{1-6}$-alkyl.

A certain embodiment of the invention provides a compound of formula I as described herein, wherein Y is —NH—CHR$^7$—, and R$^7$ is Me.

A certain embodiment of the invention provides a compound of formula I as described herein, wherein Y is —O—CH$_2$—.

A certain embodiment of the invention provides a compound of formula I as described herein, wherein Y is absent.

A certain embodiment of the invention provides a compound of formula I as described herein, wherein Z is heteroaryl substituted by 1-2 substituents individually selected from R$^8$ or $C_{3-6}$-cycloalkyl.

A certain embodiment of the invention provides a compound of formula I as described herein, wherein Z is heteroaryl substituted by 1-2 substituents individually selected from R$^8$.

A certain embodiment of the invention provides a compound of formula I as described herein, wherein Z is heteroaryl.

A certain embodiment of the invention provides a compound of formula I as described herein, wherein Z is thiophenyl.

A certain embodiment of the invention provides a compound of formula I as described herein, wherein Z is pyrimidinyl.

A certain embodiment of the invention provides a compound of formula I as described herein, wherein Z is pyrazolyl substituted by chloro and difluoromethyl.

A certain embodiment of the invention provides a compound of formula I as described herein, wherein Z is pyrazolyl substituted by 4-fluoro-phenyl.

A certain embodiment of the invention provides a compound of formula I as described herein, wherein Z is pyrazolyl substituted by methyl.

A certain embodiment of the invention provides a compound of formula I as described herein, wherein Z is pyrazolyl substituted by chloro and methyl.

A certain embodiment of the invention provides a compound of formula I as described herein, wherein Z is pyrazolyl substituted by chloro and 2,2-difluoro-ethyl.

A certain embodiment of the invention provides a compound of formula I as described herein, wherein Z is 6,7-dihydro-5H-[1]pyrindinyl substituted by chloro.

A certain embodiment of the invention provides a compound of formula I as described herein, wherein Z is 6,7-dihydro-5H-[1]pyrindinyl substituted by cyano.

A certain embodiment of the invention provides a compound of formula I as described herein, wherein Z is benzooxazolyl substituted by chloro.

A certain embodiment of the invention provides a compound of formula I as described herein, wherein Z is isoxazolyl substituted by cyclopropyl.

A certain embodiment of the invention provides a compound of formula I as described herein, wherein Z is oxazolyl substituted by methyl and trifluoromethyl.

A certain embodiment of the invention provides a compound of formula I as described herein, wherein Z is pyridinyl substituted by cyano.

A certain embodiment of the invention provides a compound of formula I as described herein, wherein Z is pyridinyl substituted by chloro.

A certain embodiment of the invention provides a compound of formula I as described herein, wherein Z is pyridinyl substituted by trifluoromethyl.

A certain embodiment of the invention provides a compound of formula I as described herein, wherein Z is quinolinyl substituted by chloro.

A certain embodiment of the invention provides a compound of formula I as described herein, wherein Z is thieno[3,2-b]pyridin-3-yl substituted by cyano.

A certain embodiment of the invention provides a compound of formula I as described herein, wherein Z is $C_{3-6}$-cycloalkyl.

A certain embodiment of the invention provides a compound of formula I as described herein, wherein Z is cyclopentyl.

A certain embodiment of the invention provides a compound of formula I as described herein, wherein Z is cyclopropyl.

A certain embodiment of the invention provides a compound of formula I as described herein, wherein Z is $C_{3-6}$-cycloalkyl substituted by 1-2 substituents individually selected from R$^8$.

A certain embodiment of the invention provides a compound of formula I as described herein, wherein Z is $C_{3-6}$-cycloalkyl substituted by aryl.

A certain embodiment of the invention provides a compound of formula I as described herein, wherein Z is cyclopentyl substituted by phenyl.

A certain embodiment of the invention provides a compound of formula I as described herein, wherein Z is aryl.

A certain embodiment of the invention provides a compound of formula I as described herein, wherein Z is aryl substituted by 1-2 substituents individually selected from R$^8$.

A certain embodiment of the invention provides a compound of formula I as described herein, wherein Z is phenyl substituted by methoxy.

A certain embodiment of the invention provides a compound of formula I as described herein, wherein Z is phenyl substituted by difluoromethoxy.

A certain embodiment of the invention provides a compound of formula I as described herein, wherein Z is phenyl substituted by fluoro.

A certain embodiment of the invention provides a compound of formula I as described herein, wherein Z is phenyl substituted by cyano A certain embodiment of the invention provides a compound of formula I as described herein, wherein Z is phenyl substituted by chloro.

A certain embodiment of the invention provides a compound of formula I as described herein, wherein Z is phenyl substituted by trifluoromethyl.

A certain embodiment of the invention provides a compound of formula I as described herein, wherein Z is phenyl substituted by methyl.

A certain embodiment of the invention provides a compound of formula I as described herein, wherein Z is phenyl substituted twice by chloro.

A certain embodiment of the invention provides a compound of formula I as described herein, wherein Z is phenyl substituted by chloro and cyano.

A certain embodiment of the invention provides a compound of formula I as described herein, wherein Z is phenyl substituted by ethyl.

A certain embodiment of the invention provides a compound of formula I as described herein, wherein Z is phenyl substituted twice by fluoro.

A certain embodiment of the invention provides a compound of formula I as described herein, wherein Z is heterocyclyl.

A certain embodiment of the invention provides a compound of formula I as described herein, wherein Z is tetrahydrofuranyl.

A certain embodiment of the invention provides a compound of formula I as described herein, wherein Z is 1,1-dioxo-2,3-dihydro-1H-1$\lambda^6$-benzo[b]thiophen-3-yl.

A certain embodiment of the invention provides a compound of formula I as described herein, wherein Z is oxetanyl.

A certain embodiment of the invention provides a compound of formula I as described herein, wherein Z is heterocyclyl substituted by 1-2 substituents individually selected from $R^8$.

A certain embodiment of the invention provides a compound of formula I as described herein, wherein Z is 5,6,7,8-tetrahydro-quinolinyl substituted by methyl.

A certain embodiment of the invention provides a compound of formula I as described herein, wherein Z is oxetanyl substituted by methyl.

A certain embodiment of the invention provides a compound of formula I as described herein, wherein Z is $C_{2-6}$-alkynyl.

A certain embodiment of the invention provides a compound of formula I as described herein, wherein Z is prop-2-ynyl.

A certain embodiment of the invention provides a compound of formula I as described herein, wherein Z is $C_{1-6}$-alkyl.

A certain embodiment of the invention provides a compound of formula I as described herein, wherein Z is ethyl.

A certain embodiment of the invention provides a compound of formula I as described herein, wherein X—Y—Z is X—(C=O)—NH—Z.

A certain embodiment of the invention provides a compound of formula I as described herein, wherein X—Y—Z is X—NH—CHR$^7$—Z.

A certain embodiment of the invention provides a compound of formula I as described herein, wherein X—Y—Z is X—O—CH$_2$—Z.

A certain embodiment of the invention provides a compound of formula I as described herein, wherein $R^8$ is selected from the group consisting of halogen, cyano, $C_{1-6}$-alkyl, and halogen-$C_{1-6}$-alkyl.

A certain embodiment of the invention provides a compound of formula I as described herein, wherein $R^8$ is selected from the group consisting of chloro, difluoromethyl, methyl and cyano.

A certain embodiment of the invention provides a compound of formula I as described herein, wherein $R^8$ is halogen.

A certain embodiment of the invention provides a compound of formula I as described herein, wherein $R^8$ is chloro.

A certain embodiment of the invention provides a compound of formula I as described herein, wherein $R^8$ is cyano.

A certain embodiment of the invention provides a compound of formula I as described herein, wherein $R^8$ is $C_{1-6}$-alkyl.

A certain embodiment of the invention provides a compound of formula I as described herein, wherein $R^8$ is methyl.

A certain embodiment of the invention provides a compound of formula I as described herein, wherein $R^8$ is halogen-$C_{1-6}$-alkyl.

A certain embodiment of the invention provides a compound of formula I as described herein, wherein $R^8$ is difluoromethyl.

A certain embodiment of the invention provides a compound of formula I as described herein, wherein $R^8$ is $C_{1-6}$-alkoxy.

A certain embodiment of the invention provides a compound of formula I as described herein, wherein $R^8$ is halogen-$C_{1-6}$-alkoxy.

A certain embodiment of the invention provides a compound of formula I as described herein, wherein $R^8$ is aryl.

A certain embodiment of the invention provides a compound of formula I as described herein, wherein $R^8$ is phenyl.

A certain embodiment of the invention provides a compound of formula I as described herein, wherein $R^8$ is halogen-aryl.

A certain embodiment of the invention provides a compound of formula I as described herein, wherein $R^8$ is halogen-phenyl.

A certain embodiment of the invention provides a compound of formula I as described herein, wherein $R^8$ is $C_{3-6}$-cycloalkyl.

A certain embodiment of the invention provides a compound of formula I as described herein, selected from the group consisting of (S)-4-{5-[(4-Chloro-1-difluoromethyl-1H-pyrazol-3-ylmethyl)-amino]-2-fluoro-phenyl}-4-methyl-5,6-dihydro-4H-[1,3]oxazin-2-ylamine, (4R,5R)-5-Fluoro-4-[2-fluoro-5-(2-methoxy-phenylamino)-phenyl]-4-methyl-5,6-dihydro-4H-[1,3]oxazin-2-ylamine, (4R,5R)-4-[5-(2-Difluoromethoxy-phenylamino)-2-fluoro-phenyl]-5-fluoro-4-methyl-5,6-dihydro-4H-[1,3]oxazin-2-ylamine, (4R,5R)-5-Fluoro-4-{2-fluoro-5-[(thiophen-2-ylmethyl)-amino]-phenyl}-4-methyl-5,6-dihydro-4H-[1,3]oxazin-2-ylamine, (4R,5R)-5-Fluoro-4-{2-fluoro-5-[(thiophen-3-ylmethyl)-amino]-phenyl}-4-methyl-5,6-dihydro-4H-[1,3]oxazin-2-ylamine, (4R,5R)-5-Fluoro-4-[2-fluoro-5-(2-fluoro-benzylamino)-phenyl]-4-methyl-5,6-dihydro-4H-[1,3]oxazin-2-ylamine, (4R,5R)-4-[5-(Cyclopropylmethyl-amino)-2-fluoro-phenyl]-5-fluoro-4-methyl-5,6-dihydro-4H-[1,3]oxazin-2-ylamine, (4R,5R)-5-Fluoro-4-{2-fluoro-5-[1-(4-fluoro-phenyl)-1H-pyrazol-4-yl]-phenyl}-4-methyl-5,6-dihydro-4H-[1,3]oxazin-2-ylamine, (4R,5R)-5-Fluoro-4-[2-fluoro-5-(4-methyl-pyrazol-1-yl)-phenyl]-4-methyl-5,6-dihydro-4H-[1,3]oxazin-2-ylamine, (4R,5R)-4-{5-[(4-Chloro-1-difluoromethyl-1H-pyrazol-3-ylmethyl)-amino]-2-fluoro-phenyl}-5-fluoro-4,5-dimethyl-5,6-dihydro-4H-[1,3]oxazin-2-ylamine, (4R,5R)-4-{5-[(4-Chloro-1-methyl-1H-pyrazol-3-ylmethyl)-amino]-2-fluoro-phenyl}-5-fluoro-4,5-dimethyl-5,6-dihydro-4H-[1,3]oxazin-2-ylamine, (4R,5R)-5-Fluoro-4-{2-fluoro-5-[1-(2-methyl-5-trifluoromethyl-oxazol-4-yl)-ethylamino]-phenyl}-4,5-dimethyl-5,6-dihydro-4H-[1,3]oxazin-2-ylamine, (R)-4-{5-[(4-Chloro-1-difluoromethyl-1H-pyrazol-3-ylmethyl)-amino]-2-fluoro-phenyl}-5,5-difluoro-4-methyl-5,6-dihydro-4H-[1,3]oxazin-2-ylamine, (R)-4-{5-[1-(4-Chloro-1-methyl-1H-pyrazol-3-yl)-ethylamino]-2-fluoro-phenyl}-5,5-difluoro-4-methyl-5,6-dihydro-4H-[1,3]oxazin-2-ylamine, (R)-4-{5-[1-(5-Cyclopropyl-isoxazol-3-yl)-ethylamino]-2-fluoro-phenyl}-5,5-difluoro-4-methyl-5,6-dihydro-4H-[1,3]oxazin-2-ylamine, 4-[5-(5-Chloro-pyridin-3-yl)-2-fluoro-phenyl]-4-difluoromethyl-5,6-dihydro-4H-[1,3]oxazin-2-ylamine, (R)-4-[5-(5-Chloro-pyridin-3-yl)-2-fluoro-phenyl]-4-difluoromethyl-5,6-dihydro-4H-[1,3]oxazin-2-ylamine, (S)-4-[5-(5-Chloro-pyridin-3-yl)-2-fluoro-phenyl]-4-difluoromethyl-5,6-dihydro-4H-[1,3]oxazin-2-ylamine, (R)-5,5-Difluoro-4-methyl-4-[3-(3,3,3-trifluoro-propoxy)-phenyl]-5,6-dihydro-4H-[1,3]oxazin-2-ylamine, 2-[3-((R)-2-Amino-5,5-difluoro-4,6,6-trimethyl-5,6-dihydro-4H-[1,3]oxazin-4-yl)-4-fluoro-phenylamino]-benzonitrile, (R)-5,5-Difluoro-4-(2-fluoro-5-o-tolylamino-phenyl)-4,6,6-trimethyl-5,6-dihydro-4H-[1,3]oxazin-2-ylamine, (R)-4-(5-Cyclopentylamino-2-fluoro-phenyl)-5,5-difluoro-4,6,6-trimethyl-5,6-dihydro-4H-[1,3]oxazin-2-ylamine, (R)-4-(3',5'-Dichloro-4-fluoro-biphenyl-3-yl)-5,5-difluoro-4,6,6-trimethyl-5,6-dihydro-4H-[1,3]oxazin-2-ylamine, 3'-((R)-2-Amino-5,5-difluoro-4,6,6-trimethyl-5,6-dihydro-4H-[1,3]oxazin-4-yl)-6-chloro-4'-fluoro-biphenyl-3-carbonitrile, (R)-4-[5-(1,1-Dioxo-2,3-dihydro-1H-1λ⁶-benzo[b]thiophen-3-ylamino)-2-fluoro-phenyl]-5,5-difluoro-4-methyl-5,6-dihydro-4H-[1,3]oxazin-2-ylamine, 5-[3-((4R,5R)-2-Amino-5-fluoro-4-methyl-5,6-dihydro-4H-[1,3]oxazin-4-yl)-4-fluoro-phenyl]-nicotinonitrile, 7-[3-((R)-2-Amino-5,5-difluoro-4-methyl-5,6-dihydro-4H-[1,3]oxazin-4-yl)-4-fluoro-phenylamino]-6,7-dihydro-5H-[1]pyrindine-3-carbonitrile,

[3-((R)-2-Amino-5,5-difluoro-4-methyl-5,6-dihydro-4H-[1,3]oxazin-4-yl)-4-fluoro-phenyl]-(3-chloro-6,7-dihydro-5H-[1]pyrindin-7-yl)-amine, 8-[3-((R)-2-Amino-5,5-difluoro-4-methyl-5,6-dihydro-4H-[1,3]oxazin-4-yl)-4-fluoro-phenylamino]-5,6,7,8-tetrahydro-quinoline-3-carbonitrile, 4-[3-((R)-2-Amino-5,5-difluoro-4-methyl-5,6-dihydro-4H-[1,3]oxazin-4-yl)-phenoxymethyl]-benzonitrile, 3-((R)-2-Amino-5,5-difluoro-4-methyl-5,6-dihydro-4H-[1,3]oxazin-4-yl)-4-fluoro-N-prop-2-ynyl-benzamide, 3-[4-((R)-2-Amino-5,5-difluoro-4-methyl-5,6-dihydro-4H-[1,3]oxazin-4-yl)-pyrazol-1-yl]-benzonitrile, (1R,2R)-((R)-2-Amino-5,5-difluoro-4-methyl-5,6-dihydro-4H-[1,3]oxazin-4-yl)-cyclopropanecarboxylic acid(3-chloro-quinolin-8-yl)-amide, (1S,2S)-((R)-2-Amino-5,5-difluoro-4-methyl-5,6-dihydro-4H-[1,3]oxazin-4-yl)-cyclopropanecarboxylic acid(3-chloro-quinolin-8-yl)-amide, (1R,2R)-2-((R)-2-Amino-5,5-difluoro-4-methyl-5,6-dihydro-4H-[1,3]oxazin-4-yl)-cyclopropanecarboxylic acid(6-cyano-thieno[3,2-b]pyridin-3-yl)-amide, (R)-4-(5-{1-[4-Chloro-1-(2,2-difluoro-ethyl)-1H-pyrazol-3-yl]-ethylamino}-2-fluoro-phenyl)-5,5-difluoro-4-methyl-5,6-dihydro-4H-[1,3]oxazin-2-ylamine, (4R,5R)-4-[5-(3,5-Difluoro-benzylamino)-2-fluoro-phenyl]-5-fluoro-4-methyl-5,6-dihydro-4H-[1,3]oxazin-2-ylamine, (R)-4-[3-(5-Chloro-pyridin-2-yl)-7-fluoro-3,4-dihydro-2H-benzo[1,4]oxazin-6-yl]-5,5-difluoro-4-methyl-5,6-dihydro-4H-[1,3]oxazin-2-ylamine, (R)-4-[5-(6-Chloro-benzooxazol-2-yl)-2,4-difluoro-phenyl]-5,5-difluoro-4-methyl-5,6-dihydro-4H-[1,3]oxazin-2-ylamine, (R)-5,5-Difluoro-4-{2-fluoro-5-[1-(5-methyl-2H-pyrazol-3-yl)-ethylamino]-phenyl}-4-methyl-5,6-dihydro-4H-[1,3]oxazin-2-ylamine, (R)-5,5-Difluoro-4-{2-fluoro-5-[1-(2-methyl-5-trifluoromethyl-oxazol-4-yl)-ethylamino]-phenyl}-4-methyl-5,6-dihydro-4H-[1,3]oxazin-2-ylamine, (R)-5,5-Difluoro-4-{2-fluoro-5-[(3-methyl-oxetan-3-ylmethyl)-amino]-phenyl}-4-methyl-5,6-dihydro-4H-[1,3]oxazin-2-ylamine, (R)-4-[5-(Cyclopropylmethyl-amino)-2-fluoro-phenyl]-5,5-difluoro-4-methyl-5,6-dihydro-4H-[1,3]oxazin-2-ylamine, (R)-5,5-Difluoro-4-[2-fluoro-5-(tetrahydro-furan-3-ylamino)-phenyl]-4-methyl-5,6-dihydro-4H-[1,3]oxazin-2-ylamine, (R)-5,5-Difluoro-4-[2-fluoro-5-(oxetan-3-ylamino)-phenyl]-4-methyl-5,6-dihydro-4H-[1,3]oxazin-2-ylamine, (R)-5,5-Difluoro-4-{2-fluoro-5-[(tetrahydro-furan-3-ylmethyl)-amino]-phenyl}-4-methyl-5,6-dihydro-4H-[1,3]oxazin-2-ylamine, (R)-5,5-Difluoro-4-{2-fluoro-5-[1-(4-fluoro-phenyl)-1H-pyrazol-4-yl]-phenyl}-4-methyl-5,6-dihydro-4H-[1,3]oxazin-2-ylamine, (R)-4-[5-(5-Chloro-pyridin-3-yl)-2,4-difluoro-phenyl]-5,5-difluoro-4-methyl-5,6-dihydro-4H-[1,3]oxazin-2-ylamine, (R)-5,5-Difluoro-4-methyl-4-[3-(4-trifluoromethyl-benzyloxy)-phenyl]-5,6-dihydro-4H-[1,3]oxazin-2-ylamine, (R)-5,5-Difluoro-4-methyl-4-[2-(4-methyl-benzyl)-3H-benzoimidazol-5-yl]-5,6-dihydro-4H-[1,3]oxazin-2-ylamine, (R)-5,5-Difluoro-4-[5-fluoro-2-(4-methoxy-benzyl)-1H-indol-6-yl]-4-methyl-5,6-dihydro-4H-[1,3]oxazin-2-ylamine, (R)-5,5-Difluoro-4-[5-fluoro-2-(4-methyl-benzyl)-3H-indol-6-yl]-4-methyl-5,6-dihydro-4H-[1,3]oxazin-2-ylamine, (R)-5,5-Difluoro-4-[2-fluoro-5-(2-methoxy-phenylamino)-phenyl]-4,6,6-trimethyl-5,6-dihydro-4H-[1,3]oxazin-2-ylamine, (R)-5,5-Difluoro-4-[2-fluoro-5-(2-trifluoromethyl-phenylamino)-phenyl]-4,6,6-trimethyl-5,6-dihydro-4H-[1,3]oxazin-2-ylamine, (R)-5,5-Difluoro-4-[2-fluoro-5-(6-trifluoromethyl-pyridin-2-ylamino)-phenyl]-4,6,6-trimethyl-5,6-dihydro-4H-[1,3]oxazin-2-ylamine, (R)-5,5-Difluoro-4-[2-fluoro-5-(3-phenyl-cyclopentylamino)-phenyl]-4,6,6-trimethyl-5,6-dihydro-4H-[1,3]oxazin-2-ylamine,
(R)-4-[5-(5-Chloro-pyridin-3-yl)-2-fluoro-phenyl]-5,5-difluoro-4,6,6-trimethyl-5,6-dihydro-4H-[1,3]oxazin-2-ylamine,
(R)-4-[2-(4-Ethyl-benzyl)-3H-benzoimidazol-5-yl]-5,5-difluoro-4-methyl-5,6-dihydro-4H-[1,3]oxazin-2-ylamine,
(R)-4-[5-((RS)-2,2-Difluoro-cyclopropylmethoxy)-phenyl]-5,5-difluoro-4-methyl-5,6-dihydro-4H-[1,3]oxazin-2-ylamine,
(R)-4-[1-(3-Ethynyl-phenyl)-1H-pyrazol-4-yl]-5,5-difluoro-4-methyl-5,6-dihydro-4H-[1,3]oxazin-2-ylamine,
(R)-4-(2,4-Difluoro-5-pyrimidin-5-yl-phenyl)-5,5-difluoro-4-methyl-5,6-dihydro-4H-[1,3]oxazin-2-ylamine,
(R)-4-[5-(2-Chloro-phenylamino)-2-fluoro-phenyl]-5,5-difluoro-4,6,6-trimethyl-5,6-dihydro-4H-[1,3]oxazin-2-ylamine,
(S)-4-(5-Cyclopentylamino-2-fluoro-phenyl)-4-methyl-5,6-dihydro-4H-[1,3]oxazin-2-ylamine,
(R)-4-[3-(4-Chloro-benzyloxy)-phenyl]-5,5-difluoro-4-methyl-5,6-dihydro-4H-[1,3]oxazin-2-ylamine,
(R)-4-(3-Cyclopropylmethoxy-phenyl)-5,5-difluoro-4-methyl-5,6-dihydro-4H-[1,3]oxazin-2-ylamine, and
(1S,2S)-rel-2-((R)-2-Amino-5,5-difluoro-4-methyl-5,6-dihydro-4H-[1,3]oxazin-4-yl)-cyclopropanecarboxylic acid (3-chloro-quinolin-8-yl)-amide;
or a pharmaceutical acceptable salt thereof.

A certain embodiment of the invention provides a compound of formula I as described herein, selected from the group consisting of
(S)-4-{5-[(4-Chloro-1-difluoromethyl-1H-pyrazol-3-ylmethyl)-amino]-2-fluoro-phenyl}-4-methyl-5,6-dihydro-4H-[1,3]oxazin-2-ylamine,
(4R,5R)-4-[5-(2-Difluoromethoxy-phenylamino)-2-fluoro-phenyl]-5-fluoro-4-methyl-5,6-dihydro-4H-[1,3]oxazin-2-ylamine,
(4R,5R)-4-[5-(Cyclopropylmethyl-amino)-2-fluoro-phenyl]-5-fluoro-4-methyl-5,6-dihydro-4H-[1,3]oxazin-2-ylamine,
(4R,5R)-4-{5-[(4-Chloro-1-difluoromethyl-1H-pyrazol-3-ylmethyl)-amino]-2-fluoro-phenyl}-5-fluoro-4,5-dimethyl-5,6-dihydro-4H-[1,3]oxazin-2-ylamine,
(4R,5R)-4-{5-[(4-Chloro-1-methyl-1H-pyrazol-3-ylmethyl)-amino]-2-fluoro-phenyl}-5-fluoro-4,5-dimethyl-5,6-dihydro-4H-[1,3]oxazin-2-ylamine,
(4R,5R)-5-Fluoro-4-[2-fluoro-5-(2-fluoro-benzylamino)-phenyl]-4-methyl-5,6-dihydro-4H-[1,3]oxazin-2-ylamine,
(4R,5R)-5-Fluoro-4-[2-fluoro-5-(2-methoxy-phenylamino)-phenyl]-4-methyl-5,6-dihydro-4H-[1,3]oxazin-2-ylamine,
(4R,5R)-5-Fluoro-4-[2-fluoro-5-(4-methyl-pyrazol-1-yl)-phenyl]-4-methyl-5,6-dihydro-4H-[1,3]oxazin-2-ylamine,
(4R,5R)-5-Fluoro-4-{2-fluoro-5-[(thiophen-2-ylmethyl)-amino]-phenyl}-4-methyl-5,6-dihydro-4H-[1,3]oxazin-2-ylamine,
(4R,5R)-5-Fluoro-4-{2-fluoro-5-[(thiophen-3-ylmethyl)-amino]-phenyl}-4-methyl-5,6-dihydro-4H-[1,3]oxazin-2-ylamine,
(4R,5R)-5-Fluoro-4-{2-fluoro-5-[1-(2-methyl-5-trifluoromethyl-oxazol-4-yl)-ethylamino]-phenyl}-4,5-dimethyl-5,6-dihydro-4H-[1,3]oxazin-2-ylamine,
(4R,5R)-5-Fluoro-4-{2-fluoro-5-[1-(4-fluoro-phenyl)-1H-pyrazol-4-yl]-phenyl}-4-methyl-5,6-dihydro-4H-[1,3]oxazin-2-ylamine,
(R)-4-(2,4-Difluoro-5-pyrimidin-5-yl-phenyl)-5,5-difluoro-4-methyl-5,6-dihydro-4H-[1,3]oxazin-2-ylamine,
(R)-4-(3',5'-Dichloro-4-fluoro-biphenyl-3-yl)-5,5-difluoro-4,6,6-trimethyl-5,6-dihydro-4H-[1,3]oxazin-2-ylamine,
(R)-4-(5-{1-[4-Chloro-1-(2,2-difluoro-ethyl)-1H-pyrazol-3-yl]-ethylamino}-2-fluoro-phenyl)-5,5-difluoro-4-methyl-5,6-dihydro-4H-[1,3]oxazin-2-ylamine,
(R)-4-(5-Cyclopentylamino-2-fluoro-phenyl)-5,5-difluoro-4,6,6-trimethyl-5,6-dihydro-4H-[1,3]oxazin-2-ylamine,
(R)-4-[3-(4-Chloro-benzyloxy)-phenyl]-5,5-difluoro-4-methyl-5,6-dihydro-4H-[1,3]oxazin-2-ylamine,
(R)-4-[3-(5-Chloro-pyridin-2-yl)-7-fluoro-3,4-dihydro-2H-benzo[1,4]oxazin-6-yl]-5,5-difluoro-4-methyl-5,6-dihydro-4H-[1,3]oxazin-2-ylamine,
(R)-4-[5-(1,1-Dioxo-2,3-dihydro-1H-1λ6-benzo[b]thiophen-3-ylamino)-2-fluoro-phenyl]-5,5-difluoro-4-methyl-5,6-dihydro-4H-[1,3]oxazin-2-ylamine,
(R)-4-[5-(2-Chloro-phenylamino)-2-fluoro-phenyl]-5,5-difluoro-4,6,6-trimethyl-5,6-dihydro-4H-[1,3]oxazin-2-ylamine,
(R)-4-[5-(5-Chloro-pyridin-3-yl)-2,4-difluoro-phenyl]-5,5-difluoro-4-methyl-5,6-dihydro-4H-[1,3]oxazin-2-ylamine,
(R)-4-[5-(5-Chloro-pyridin-3-yl)-2-fluoro-phenyl]-5,5-difluoro-4,6,6-trimethyl-5,6-dihydro-4H-[1,3]oxazin-2-ylamine,
(R)-4-[5-(6-Chloro-benzooxazol-2-yl)-2,4-difluoro-phenyl]-5,5-difluoro-4-methyl-5,6-dihydro-4H-[1,3]oxazin-2-ylamine,
(R)-4-[5-(Cyclopropylmethyl-amino)-2-fluoro-phenyl]-5,5-difluoro-4-methyl-5,6-dihydro-4H-[1,3]oxazin-2-ylamine,
(R)-4-{5-[(4-Chloro-1-difluoromethyl-1H-pyrazol-3-ylmethyl)-amino]-2-fluoro-phenyl}-5,5-difluoro-4-methyl-5,6-dihydro-4H-[1,3]oxazin-2-ylamine,
(R)-4-{5-[1-(4-Chloro-1-methyl-1H-pyrazol-3-yl)-ethylamino]-2-fluoro-phenyl}-5,5-difluoro-4-methyl-5,6-dihydro-4H-[1,3]oxazin-2-ylamine,
(R)-4-{5-[1-(5-Cyclopropyl-isoxazol-3-yl)-ethylamino]-2-fluoro-phenyl}-5,5-difluoro-4-methyl-5,6-dihydro-4H-[1,3]oxazin-2-ylamine,
(R)-5,5-Difluoro-4-(2-fluoro-5-o-tolylamino-phenyl)-4,6,6-trimethyl-5,6-dihydro-4H-[1,3]oxazin-2-ylamine,
(R)-5,5-Difluoro-4-[2-fluoro-5-(2-methoxy-phenylamino)-phenyl]-4,6,6-trimethyl-5,6-dihydro-4H-[1,3]oxazin-2-ylamine,
(R)-5,5-Difluoro-4-[2-fluoro-5-(2-trifluoromethyl-phenylamino)-phenyl]-4,6,6-trimethyl-5,6-dihydro-4H-[1,3]oxazin-2-ylamine,
(R)-5,5-Difluoro-4-[2-fluoro-5-(3-phenyl-cyclopentylamino)-phenyl]-4,6,6-trimethyl-5,6-dihydro-4H-[1,3]oxazin-2-ylamine,
(R)-5,5-Difluoro-4-[2-fluoro-5-(6-trifluoromethyl-pyridin-2-ylamino)-phenyl]-4,6,6-trimethyl-5,6-dihydro-4H-[1,3]oxazin-2-ylamine,
(R)-5,5-Difluoro-4-[2-fluoro-5-(oxetan-3-ylamino)-phenyl]-4-methyl-5,6-dihydro-4H-[1,3]oxazin-2-ylamine,
(R)-5,5-Difluoro-4-[2-fluoro-5-(tetrahydro-furan-3-ylamino)-phenyl]-4-methyl-5,6-dihydro-4H-[1,3]oxazin-2-ylamine,
(R)-5,5-Difluoro-4-[5-fluoro-2-(4-methoxy-benzyl)-1H-indol-6-yl]-4-methyl-5,6-dihydro-4H-[1,3]oxazin-2-ylamine,
(R)-5,5-Difluoro-4-[5-fluoro-2-(4-methyl-benzyl)-3H-indol-6-yl]-4-methyl-5,6-dihydro-4H-[1,3]oxazin-2-ylamine, (R)-5,5-Difluoro-4-{2-fluoro-5-[3-methyl-oxetan-3-ylmethyl)-amino]-phenyl}-4-methyl-5,6-dihydro-4H-[1,3]oxazin-2-ylamine,
(R)-5,5-Difluoro-4-{2-fluoro-5-[(tetrahydro-furan-3-ylmethyl)-amino]-phenyl}-4-methyl-5,6-dihydro-4H-[1,3]oxazin-2-ylamine,
(R)-5,5-Difluoro-4-{2-fluoro-5-[1-(2-methyl-5-trifluoromethyl-oxazol-4-yl)-ethylamino]-phenyl}-4-methyl-5,6-dihydro-4H-[1,3]oxazin-2-ylamine,
(R)-5,5-Difluoro-4-{2-fluoro-5-[1-(4-fluoro-phenyl)-1H-pyrazol-4-yl]-phenyl}-4-methyl-5,6-dihydro-4H-[1,3]oxazin-2-ylamine,
(R)-5,5-Difluoro-4-{2-fluoro-5-[1-(5-methyl-2H-pyrazol-3-yl)-ethylamino]-phenyl}-4-methyl-5,6-dihydro-4H-[1,3]oxazin-2-ylamine,
(R)-5,5-Difluoro-4-methyl-4-[2-(4-methyl-benzyl)-3H-benzoimidazol-5-yl]-5,6-dihydro-4H-[1,3]oxazin-2-ylamine,
(R)-5,5-Difluoro-4-methyl-4-[3-(4-trifluoromethyl-benzyloxy)-phenyl]-5,6-dihydro-4H-[1,3]oxazin-2-ylamine,
(S)-4-(5-Cyclopentylamino-2-fluoro-phenyl)-4-methyl-5,6-dihydro-4H-[1,3]oxazin-2-ylamine,
[3-((R)-2-Amino-5,5-difluoro-4-methyl-5,6-dihydro-4H-[1,3]oxazin-4-yl)-4-fluoro-phenyl]-(3-chloro-6,7-dihydro-5H-[1]pyrindin-7-yl)-amine,
2-[3-((R)-2-Amino-5,5-difluoro-4,6,6-trimethyl-5,6-dihydro-4H-[1,3]oxazin-4-yl)-4-fluoro-phenylamino]-benzonitrile,
3'-((R)-2-Amino-5,5-difluoro-4,6,6-trimethyl-5,6-dihydro-4H-[1,3]oxazin-4-yl)-6-chloro-4'-fluoro-biphenyl-3-carbonitrile,
3-((R)-2-Amino-5,5-difluoro-4-methyl-5,6-dihydro-4H-[1,3]oxazin-4-yl)-4-fluoro-N-prop-2-ynyl-benzamide,
4-[3-((R)-2-Amino-5,5-difluoro-4-methyl-5,6-dihydro-4H-[1,3]oxazin-4-yl)-phenoxymethyl]-benzonitrile,
5-[3-((4R,5R)-2-Amino-5-fluoro-4-methyl-5,6-dihydro-4H-[1,3]oxazin-4-yl)-4-fluoro-phenyl]-nicotinonitrile,
7-[3-((R)-2-Amino-5,5-difluoro-4-methyl-5,6-dihydro-4H-[1,3]oxazin-4-yl)-4-fluoro-phenylamino]-6,7-dihydro-5H-[1]pyrindine-3-carbonitrile, and
8-[3-((R)-2-Amino-5,5-difluoro-4-methyl-5,6-dihydro-4H-[1,3]oxazin-4-yl)-4-fluoro-phenylamino]-5,6,7,8-tetrahydro-quinoline-3-carbonitrile,
or a pharmaceutical acceptable salt thereof.

A certain embodiment of the invention provides a compound of formula I as described herein, selected from the group consisting of
(4R,5R)-4-[5-(Cyclopropylmethyl-amino)-2-fluoro-phenyl]-5-fluoro-4-methyl-5,6-dihydro-4H-[1,3]oxazin-2-ylamine,
(4R,5R)-4-{5-[(4-Chloro-1-difluoromethyl-1H-pyrazol-3-ylmethyl)-amino]-2-fluoro-phenyl}-5-fluoro-4,5-dimethyl-5,6-dihydro-4H-[1,3]oxazin-2-ylamine,
(4R,5R)-4-{5-[(4-Chloro-1-methyl-1H-pyrazol-3-ylmethyl)-amino]-2-fluoro-phenyl}-5-fluoro-4,5-dimethyl-5,6-dihydro-4H-[1,3]oxazin-2-ylamine,
[3-((R)-2-Amino-5,5-difluoro-4-methyl-5,6-dihydro-4H-[1,3]oxazin-4-yl)-4-fluoro-phenyl]-(3-chloro-6,7-dihydro-5H-[1]pyrindin-7-yl)-amine,
5-[3-((4R,5R)-2-Amino-5-fluoro-4-methyl-5,6-dihydro-4H-[1,3]oxazin-4-yl)-4-fluoro-phenyl]-nicotinonitrile, and
7-[3-((R)-2-Amino-5,5-difluoro-4-methyl-5,6-dihydro-4H-[1,3]oxazin-4-yl)-4-fluoro-phenylamino]-6,7-dihydro-5H-[1]pyrindine-3-carbonitrile.

A certain embodiment of this invention provides a process for preparing a compound as described herein, which process comprises reacting a compound of formula I' to a compound of formula I

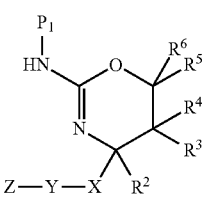

wherein X, Y, Z, $R^1$, $R^2$, $R^3$, $R^4$, $R^5$ and $R^6$ are as defined herein and $P_1$ is an amino-protecting group as defined herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of diabetes.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of Alzheimer's disease, diabetes or type 2 diabetes.

A certain embodiment of the invention provides a compound of formula I as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides the use of a compound of formula I as described herein for the manufacture of a medicament for the therapeutic and/or prophylactic treatment of Alzheimer's disease, diabetes or type 2 diabetes.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of type 2 diabetes.

A certain embodiment of the invention provides the use of a compound of formula I as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of diabetes.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of Alzheimer's disease, diabetes or type 2 diabetes.

A certain embodiment of the invention provides a compound of formula I as described herein for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

A certain embodiment of the invention provides a method for the use in the therapeutic and/or prophylactic treatment of Alzheimer's disease, diabetes or type 2 diabetes, which method comprises administering a compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

A certain embodiment of the invention provides a method for the use in the therapeutic and/or prophylactic treatment of diabetes, which method comprises administering a compound of formula I as described herein to a human being or animal.

A certain embodiment of the invention provides a method for the use in the therapeutic and/or prophylactic treatment of type 2 diabetes, which method comprises administering a compound of formula I as described herein to a human being or animal.

A certain embodiment of the invention provides a method for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric form

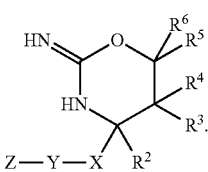

Id

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric center of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Stereoisomers of compounds of formula I are compounds of formula Ia or compounds of formula Ib, preferably compounds of formula Ia, wherein the residues have the meaning as described in any of the embodiments.

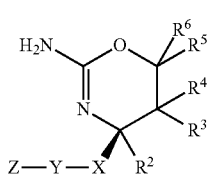

Ia

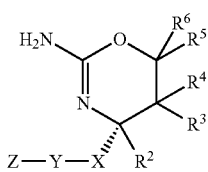

Ib

In the embodiments, where optically pure enantiomers are provided, optically pure enantiomer means that the compound contains >90% of the desired isomer by weight, preferably >95% of the desired isomer by weight, or more preferably >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

Sulfinyl imines of general formula A2 can be prepared in analogy to T. P. Tang & J. A. Ellman, J. Org. Chem. 1999, 64, 12, by condensation of an aryl ketone A1 and a sulfinamide, e.g. an alkyl sulfinamide, most preferably (R)-(+)-tert-butyl-sulfinamide, in the presence of a Lewis acid such as e.g. a titanium(IV)alkoxide, more preferably titanium(IV)ethoxide in a solvent such as an ether, e.g. diethyl ether or more preferably tetrahydrofuran.

The conversion of the sulfinyl imine A2 to the sulfinamide ester A3 proceeds stereoselectively by the chiral directing group as described by Tang & Ellman.

The sulfinyl imine A2 can be reacted with a titanium enolate generated from e.g. an alkyl acetate or alkyl 2-halogen-propanoate, preferably ethyl acetate or 2-fluoro-propanoate, lithium diisopropylamide and chlorotriisopropoxytitanium at low temperature, preferably at −78° C. in a solvent such as an ether, e.g. diethyl ether or more preferably tetrahydrofuran. Alternatively sulfinamide ester A3 can be produced from sulfinyl imine A2 by Reformatsky reaction of a bromoacetic ester derivative, preferably ethyl 2-bromo-2-fluoroacetate or 2-bromo-2,2-difluoroacetate, and zinc dust, optionally in the presence of copper(I) chloride, in a solvent such as an ether, e.g. diethyl ether or more preferably THF, at temperatures from 0 to 70° C., preferably at 23° C.

The alcohol of formula A4 can be prepared by the reduction of an ethylester of formula A3 with an alkali hydride, preferably lithium borohydride or lithium aluminium hydride, in a solvent such as an ether, e.g. diethyl ether or more preferably tetrahydrofuran.

Hydrolysis of the chiral directing group in the sulfinamide alcohol of formula A4 to give the aminoalcohol of formula A5 can be accomplished with a mineral acid, e.g. sulfuric acid or preferably hydrochloric acid, in a solvent such as an ether, e.g. diethyl ether, tetrahydrofuran or more preferably 1,4-dioxane.

The aminooxazine of formula A6 can be prepared by reaction of an aminoalcohol of formula A5 with cyanogen bromide in a solvent such as an alcohol, preferably ethanol.

Scheme A: Synthesis of compounds of formula I.1.

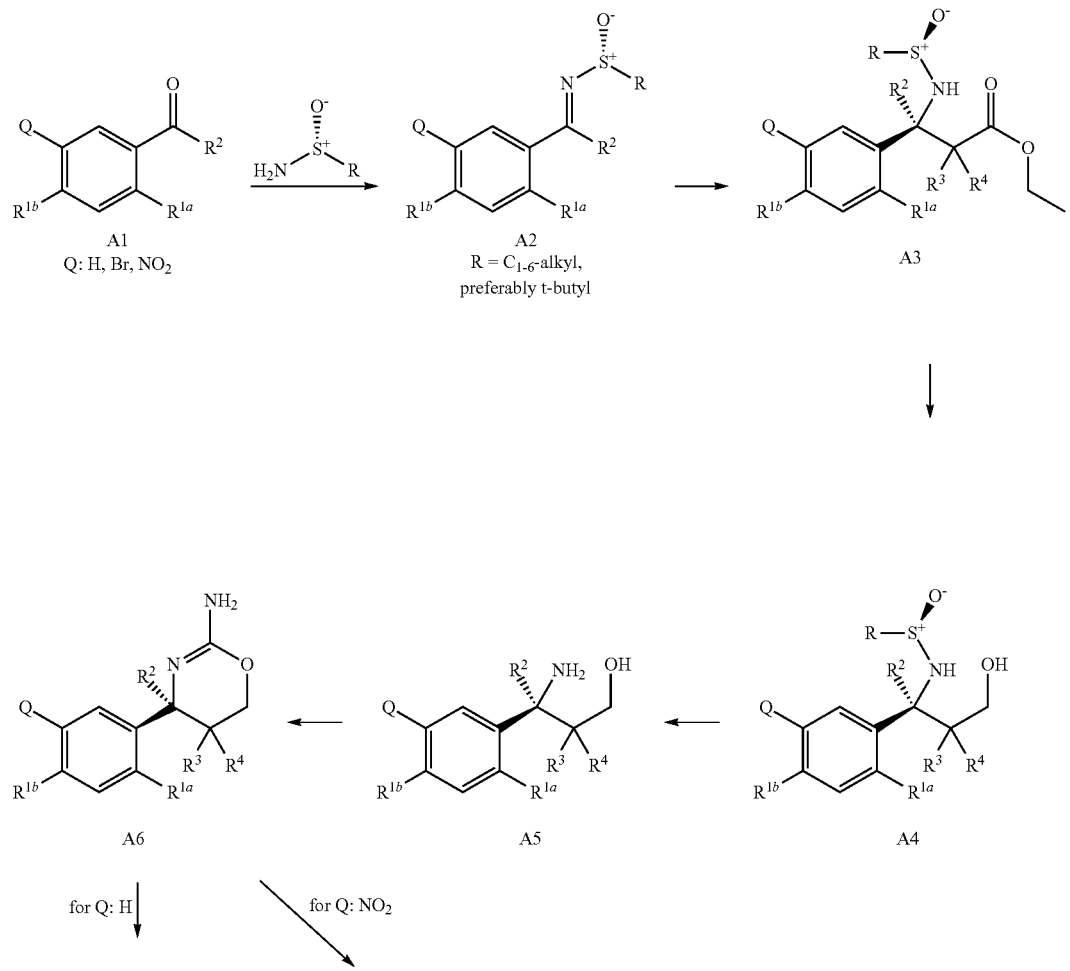

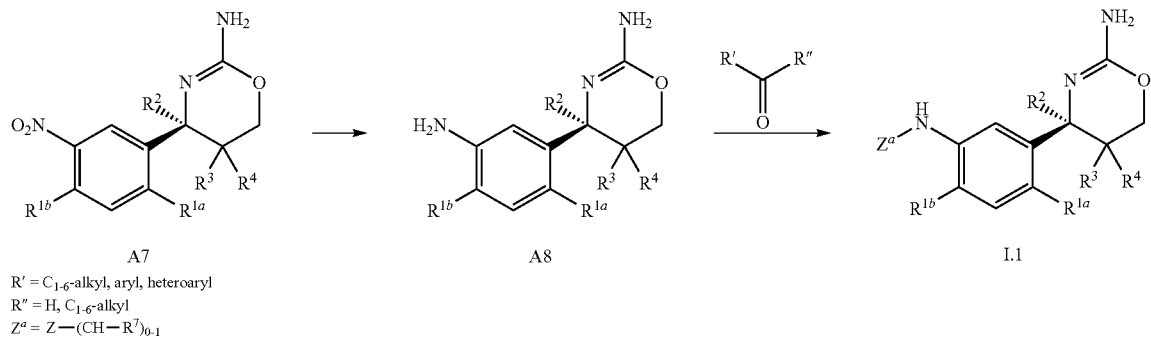

A7
R' = C_{1-6}-alkyl, aryl, heteroaryl
R'' = H, C_{1-6}-alkyl
$Z^a$ = Z—(CH—$R^7$)$_{0-1}$ The nitro derivative of formula A7 can be prepared by nitration of the oxazine A6, wherein Q is hydrogen, following a standard procedure involving neat sulfuric acid and fuming nitric acid without using a solvent.

The reduction of the nitro group in compounds of formula A7 to give anilines of formula A8 can be accomplished by hydrogenation using a catalyst, such as palladium on carbon, in protic solvents, such as alcohols, in particular ethanol or methanol.

Alternatively, the reduction of derivatives of formula A6, wherein Q is a nitro group, to give anilines of formula A8 can be accomplished by hydrogenation using a catalyst, such as palladium on carbon, in protic solvents, such as alcohols, in particular ethanol or methanol.

Target amines of formula I.1 can be prepared via reductive amination of anilines of formula A8 performed with a borohydride reducing agent, e.g. sodium borohydride, preferably sodium triacetoxyborohydride and a weak acid, e.g. acetic acid, in a solvent such as tetrahydrofuran or dichloromethane.

Scheme B: Synthesis of intermediate of formula B5 and of the compounds of formula I.2.

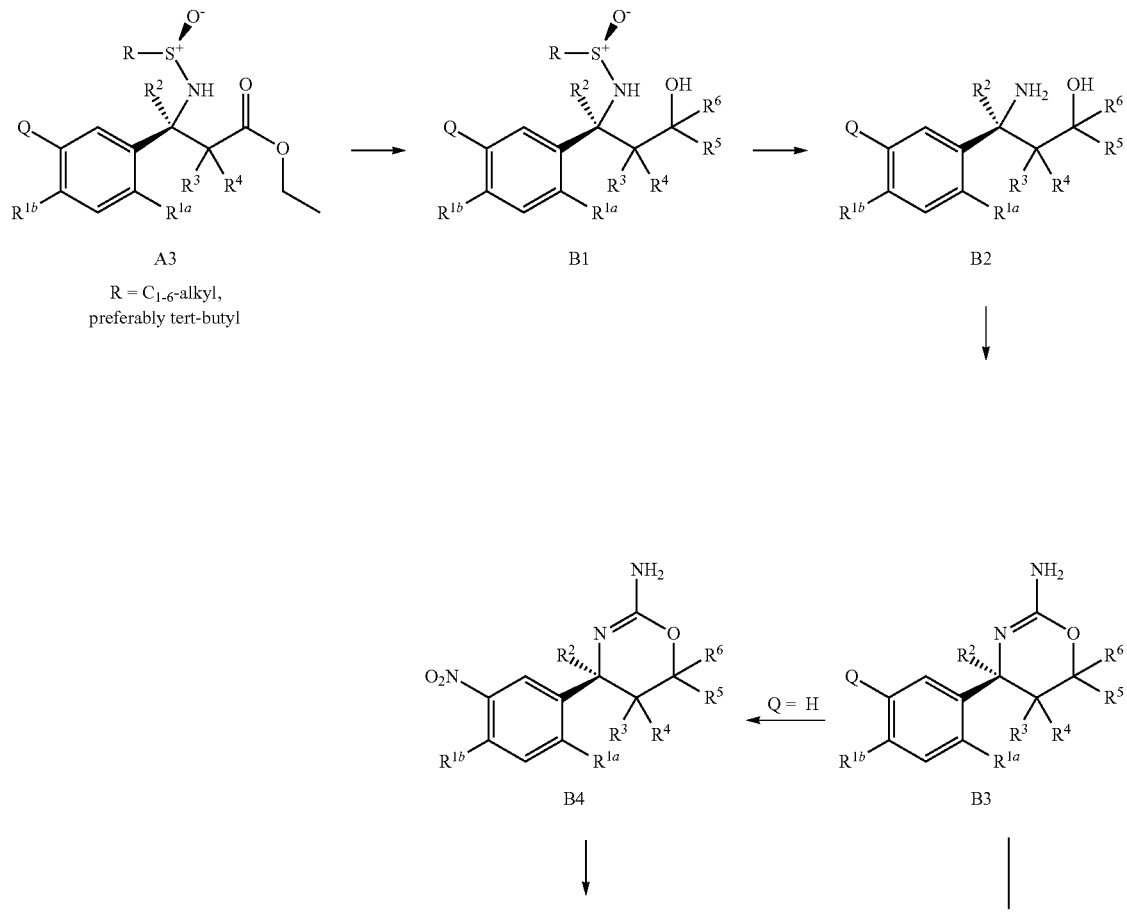

R = C_{1-6}-alkyl,
preferably tert-butyl

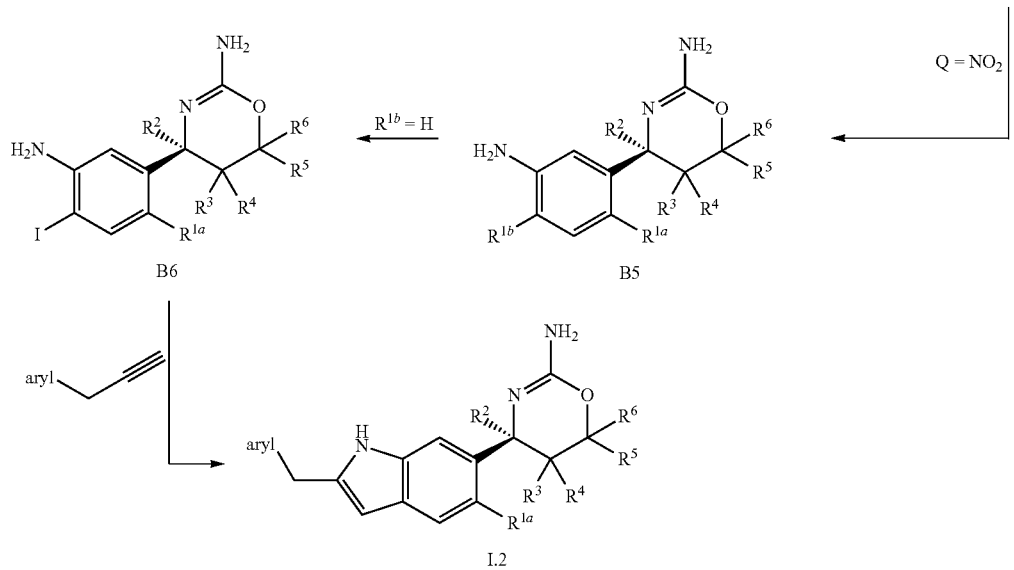

Sulfinamide esters of formula A3 can be transformed into alcohols of formula B1 by the reaction of the ethylester with an excess of a Grignard or an organolithium reagent, e.g. methyl- or ethylmagnesium halide, methyllithium etc., in a solvent such as an ether, e.g. diethyl ether or more preferably tetrahydrofuran, at temperatures between −78 and 70° C., preferably at 0 to 23° C.

Hydrolysis of the chiral directing group in the alcohols of formula B1 to give the amino alcohols of formula B2 can be accomplished with a mineral acid, e.g. sulfuric acid or preferably hydrochloric acid in a solvent such as an ether, e.g. diethyl ether or tetrahydrofuran, more preferably 1,4-dioxane, at temperatures from 0 to 23° C.

The aminooxazines of formula B3 can be prepared by reaction of the amino alcohols of formula B2 with cyanogen bromide in a solvent such as an alcohol, preferably ethanol.

The nitro derivative of formula B4 can be prepared by nitration of the oxazine B3, wherein Q is hydrogen, following a standard procedure involving neat sulfuric acid and fuming nitric acid without using a solvent.

The reduction of the nitro group in compounds of formula B4 to give anilines of formula B5 can be accomplished by hydrogenation using a catalyst, such as palladium on carbon, in protic solvents, such as alcohols, in particular ethanol or methanol.

Alternatively, the reduction of derivatives of formula B3, wherein Q is a nitro group, to give anilines of formula B5 can be accomplished by hydrogenation using a catalyst, such as palladium on carbon, in protic solvents, such as alcohols, in particular ethanol or methanol.

Anilines of formula B5, wherein $R^{1b}$ is hydrogen can be transformed to iodo derivatives of formula B6 by iodonium donating systems using iodides as an iodide source, like e.g. ammonium iodide, together with a strong oxidizing agent, like e.g. hydrogen peroxide, in a polar solvent, like e.g. acetic acid, and as described by N. Narender et al. in Tetrahedron Letters 48 (2007) 6124-6128.

Indol derivatives of formula I.2 can be prepared in a one-pot palladium-catalyzed heteroannulation of ortho-iodoanilines of formula B6 with alkyne derivatives in presence of a base as described e.g. by R. C. Larock et al. in J. Org. Chem. 2006, 71(1), 62-69.

Scheme C: Synthesis of N-protected intermediates.

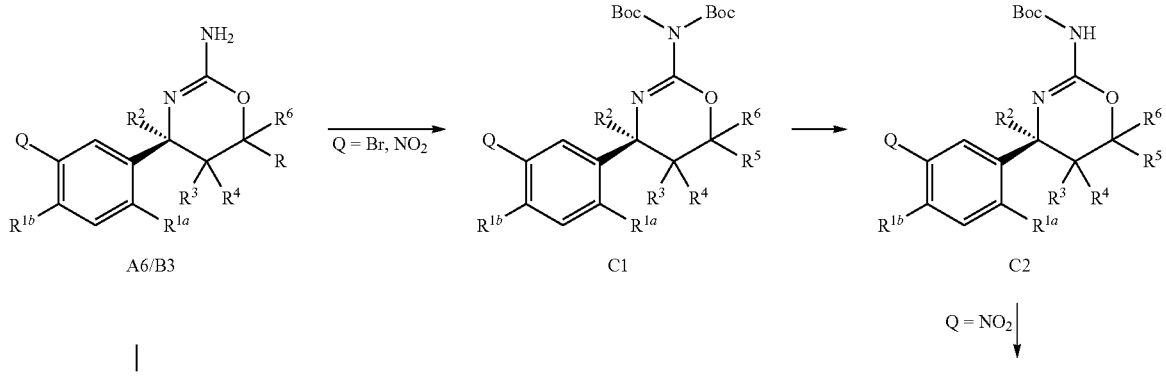

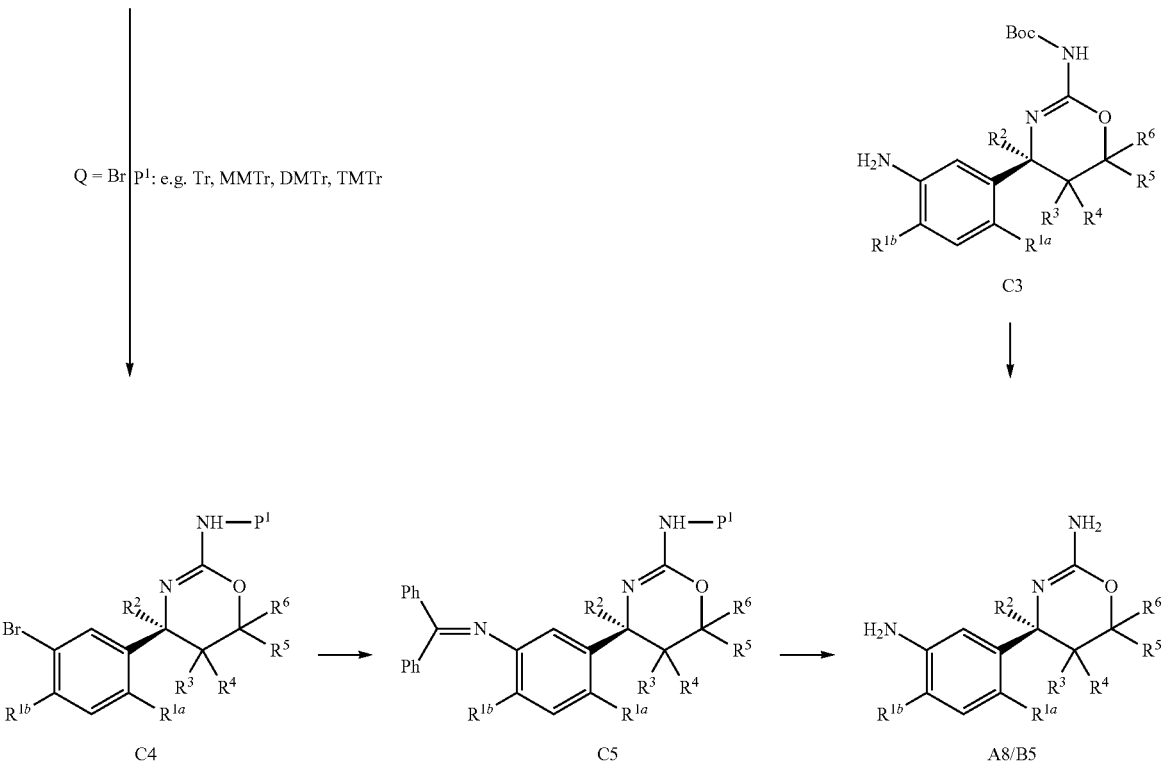

Another typical procedure for the preparation of compounds of formula A8 and of formula B5 via N-protected intermediates is illustrated in Scheme C.

Protection of the amino group in compounds of formula A6 or of formula B3, wherein Q is bromine, to produce aryl bromides of formula C4 can be performed with triarylmethyl chlorides, such as triphenylmethyl chloride (Tr-Cl), p-methoxyphenyldiphenylmethyl chloride (MMTr-Cl), di(p-methoxyphenyl)phenylmethyl chloride (DMTr-Cl) or tri(p-methoxyphenyl)methyl chloride (TMTr-Cl), preferably DMTr-Cl, under basic conditions, e.g. in the presence of an amine, such as triethylamine or diisopropylethylamine, in a chlorinated solvent, such as dichloromethane or chloroform, at temperatures between 0° C. and ambient temperature.

Aryl bromides of formula C4 can be reacted with ammonia equivalents, such as benzophenone imine, in the presence of a suitable transition metal catalyst, such as bis(dibenzylideneacetone)palladium (0) ((dba)$_2$Pd) or tris(dibenzylideneacetone) dipalladium (0) [(dba)$_3$Pd$_2$], and a suitable ligand, such as rac-2,2'-bis(diphenylphosphino)-1,1'-binaphthyl (rac-BINAP), 2-dicyclohexylphosphino-2',4',6'-triisopropylbiphenyl (X-PHOS) or 2-di-tert-butylphosphino-2',4',6'-triisopropylbiphenyl (t-Bu X-PHOS), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C., to produce compounds of formula C5.

Deprotection of both amino groups in compounds of formula C5 can be achieved by a one-pot procedure by first reacting it with a strong organic acid, such as trifluoroacetic acid, in chlorinated solvents, such as dichloromethane or chloroform, under anhydrous conditions at temperatures between 0° C. and ambient temperature to cleave the P$^1$-group. Then the addition of water to cleave the benzophenone imine and reaction at ambient temperature produces diamines of formula A8 and of formula B5.

An alternative procedure for the preparation of compounds of formula A8 and of formula B5 is also illustrated in Scheme C.

The protection of the amino group in compounds of formula A6 or of formula B3, wherein Q is bromine or a nitro group, to produce compounds of general formula C1, can be performed by reaction with di-tert-butyl dicarbonate under basic conditions, e.g. in the presence of an amine, such as triethylamine or diisopropylethylamine, in a solvent, such as tetrahydrofuran, at temperatures between 0° C. and ambient temperature and in presence of 4-dimethylamino-pyridine as a catalyst.

Selective cleavage of one of the tert-butoxy carbonyl groups in compounds of formula C1 can be performed by acid, such as trifluoroacetic acid, to produce compounds of formula C2 together with small amounts of compounds of formula A6 or of formula B3.

The reduction of the nitro group in the protected aminooxazines of formula C2, wherein Q is a nitro group, to the protected anilines of formula C3 can be accomplished by hydrogenation using a catalysts such as palladium on carbon in protic solvents, such as alcohols, preferably ethanol or methanol.

Optionally, the protecting tert-butoxy carbonyl group in compounds of formula C3 can be cleaved to produce diamines of formula A8 and of formula B5. The cleavage can be performed by acid, such as trifluoroacetic acid, in inert solvents, such as dichloromethane, at temperatures between 0° C. and ambient temperature.

Scheme D: Synthesis of compounds of formula I.3.

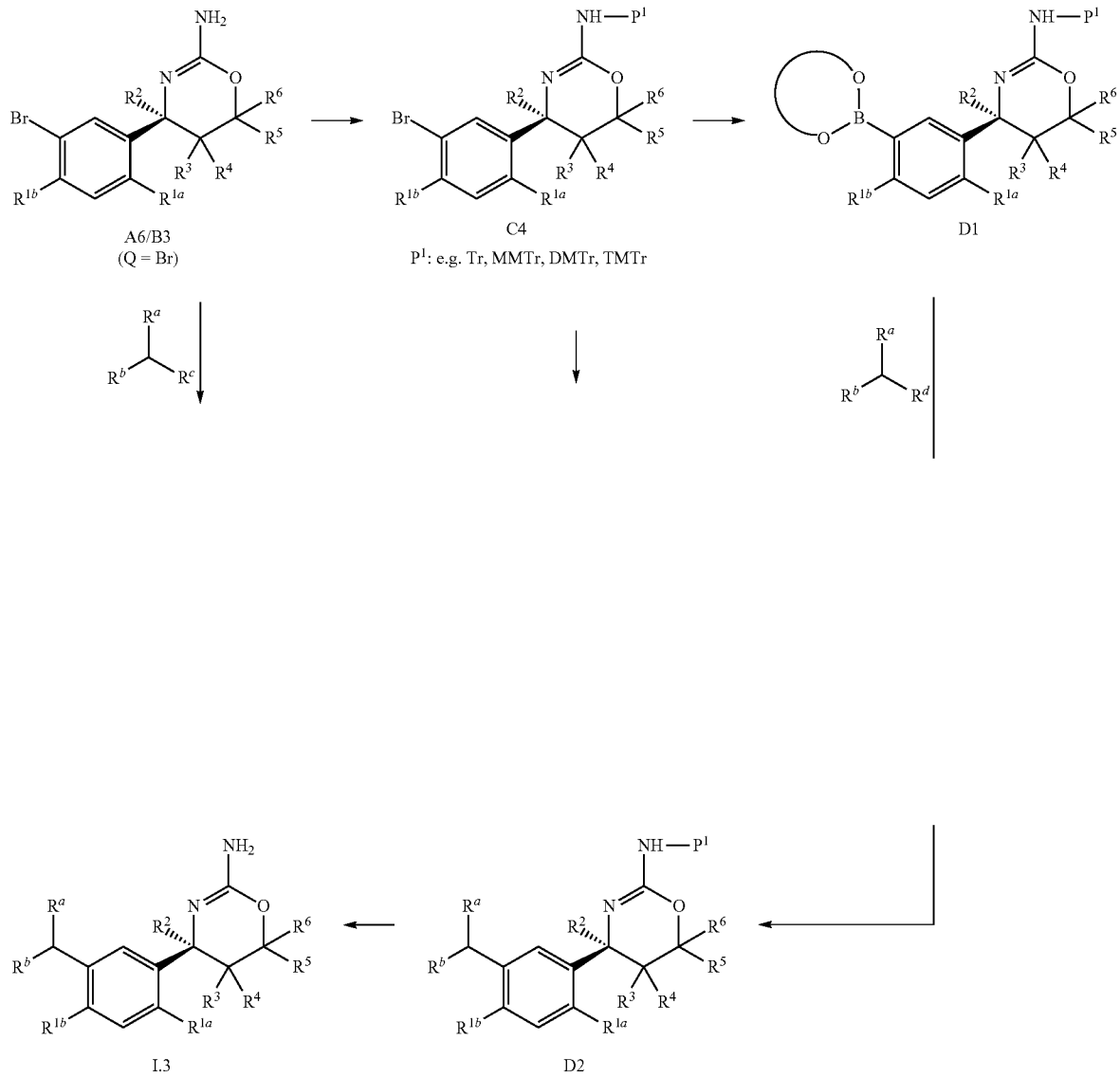

Palladium-catalyzed cross coupling between compounds of formula A6 or of formula B3 and derivatives of formula $(R^aR^b)C$—$R^c$, wherein $R^c$ has the meaning of a boronic acid or ester, under conditions (Suzuki-Miyaura-coupling) known to those skilled in the art yields the target compounds of formula I.3.

Alternatively, compounds of formula A6 or of formula B3 can be used in their protected form. Compounds of formula A6 or of formula B3 can be reacted with a triphenylmethyl protecting group, preferably 4,4'-dimethoxytrityl and a base, e.g an alkyl amine, preferably triethyl amine, in an inert solvent such as dichloromethane, to yield derivatives of formula C4.

Palladium-catalyzed cross coupling between organoboronic acids or esters thereof and derivatives of formula C4 under conditions (Suzuki-Miyaura-coupling) known to those skilled in the art yields compounds of formula D2.

Deprotection of the protected amine D2 to the target amine of formula I.3 can be accomplished involving a strong carbonic acid, e.g. in case of the dimethoxytrityl protecting group trifluoroacetic acid, in a halogenated solvent, e.g dichloromethane, at temperatures between 0° C. and 23° C.

The conversion of compounds of formula C4 to the N-protected derivatives of formula D2 can be accomplished via the boronic acid derivatives of formula D1. Boronic acid derivatives D1 can be obtained by reaction of an aryl halogenide of formula C4 with alkyl borates or tetraalkoxydiboranes, preferably with bis(pinacolato)diborane or 5,5,5',5'-tetramethyl-[2,2']bi[[1,3,2]dioxaborinanyl], in presence of a metal catalyst like e.g. bis(triphenylphosphino)palladium(II)dichloride or [1,1'-bis(diphenylphosphino) ferrocen]-palladium(II) dichloride, and a base like e.g. potassium acetate in an inert solvent like dioxane at temperatures between room temperature and 130° C.

Further palladium-catalyzed cross coupling between organoboronic esters of formula D1 and derivatives of formula $(R^aR^b)C$—$R^d$, wherein $R^d$ has the meaning of a leaving group, under conditions (Suzuki-Miyaura-coupling) known to those skilled in the art yields compounds of formula D2.

Scheme E: Synthesis of compounds of formula I.4.

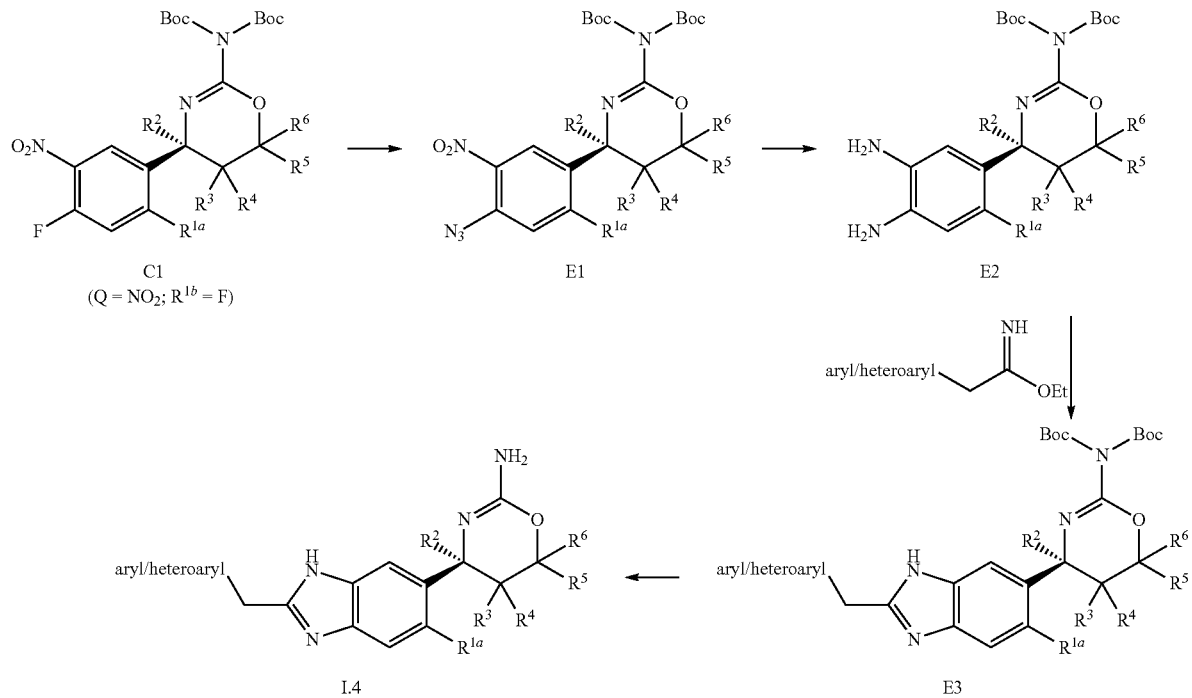

The synthesis of compounds of formula E1 can be accomplished by a nucleophilic substitution reaction in compounds of formula C1, wherein Q is a nitro group and $R^{1b}$ is fluorine, with azides, like e.g. sodium azide, in polar solvents like e.g. dimethylsulfoxide.

Bis-aniline derivatives of formula E2 can be prepared by hydrogenation of compounds of formula E1 in polar solvents, like e.g. methanol, and with palladium on carbon as the catalyst.

The synthesis of benzimidazole derivatives of formula E3 can be accomplished by cyclization of bis-aniline derivatives of formula E2 with aryl- or heteroaryl-substituted acetimidates in solvents like e.g. ethanol and at temperatures between room temperature and 130° C., preferably at 80° C.

The cleavage of the protecting tert-butoxy carbonyl groups in compounds of formula E3 to produce compounds of general formula I.4 can be effected by acid, such as trifluoroacetic acid, in inert solvents, such as dichloromethane, at temperatures between 0° C. and ambient temperature.

Scheme F: Synthesis of compounds of formula I.5.

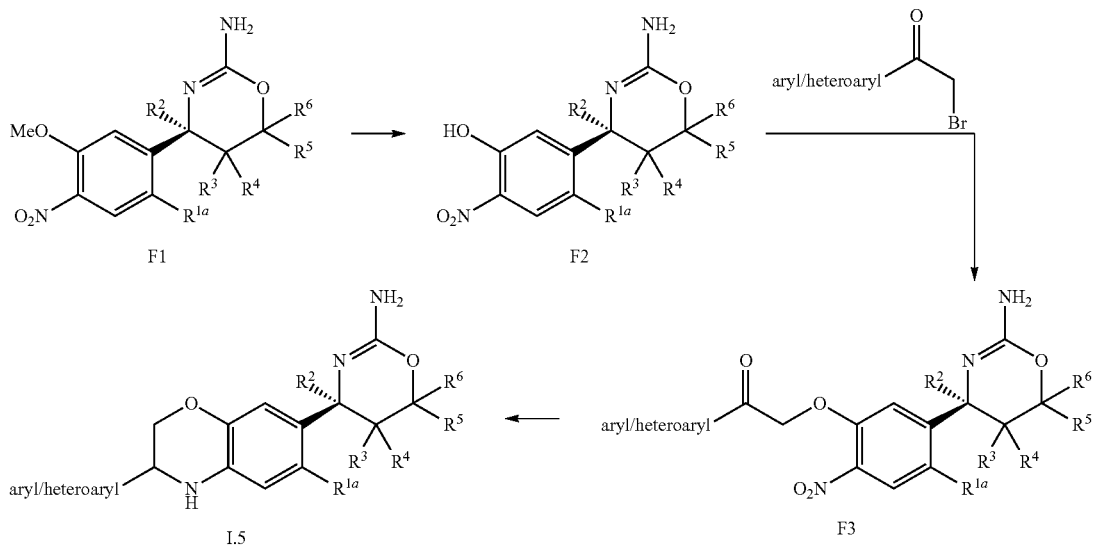

Phenols of formula F2 can be prepared by cleavage of methyl ethers of formula F1 with boron halogenides, preferably boron tribromide, in inert solvents such as dichloromethane at temperatures between −10° C. and room temperature.

Alkylation of phenols of formula F2 with aryl- or heteroaryl-substituted bromo- or chloro-ethanones in presence of a base such as cesium carbonate in inert solvents, like e.g. acetone, and at temperatures between 0° C. and 50° C., preferably room temperature, yields derivatives of formula F3.

The cyclization to prepare compounds of formula I.5 can be accomplished starting from nitro derivatives of formula F3 by reduction of the nitro group and intramolecular reductive amination in a one-pot procedure using hydrogen as the reducing agent and Raney nickel as the catalyst.

can be performed by reaction with di-tert-butyl dicarbonate under basic conditions, e.g. in the presence of an amine, such as triethylamine or diisopropylethylamine, in a solvent, such as tetrahydrofuran, at temperatures between 0° C. and ambient temperature and in presence of 4-dimethylamino-pyridine as a catalyst.

Hydrogenolysis of the benzyloxy derivatives G2 in solvents such as ethanol and with palladium on carbon as the catalyst yields the intermediate phenol of formula G3.

Alkylation of compounds of formula G3 with compounds of formula aryl-$CH_2$—$R^d$, wherein $R^d$ represents a leaving group, in presence of a base such as potassium carbonate in polar inert solvents such as N,N-dimethylformamide at temperatures between room temperature and 80° C. yields derivatives of formula G4.

Scheme G: Synthesis of compounds of formula I.6.

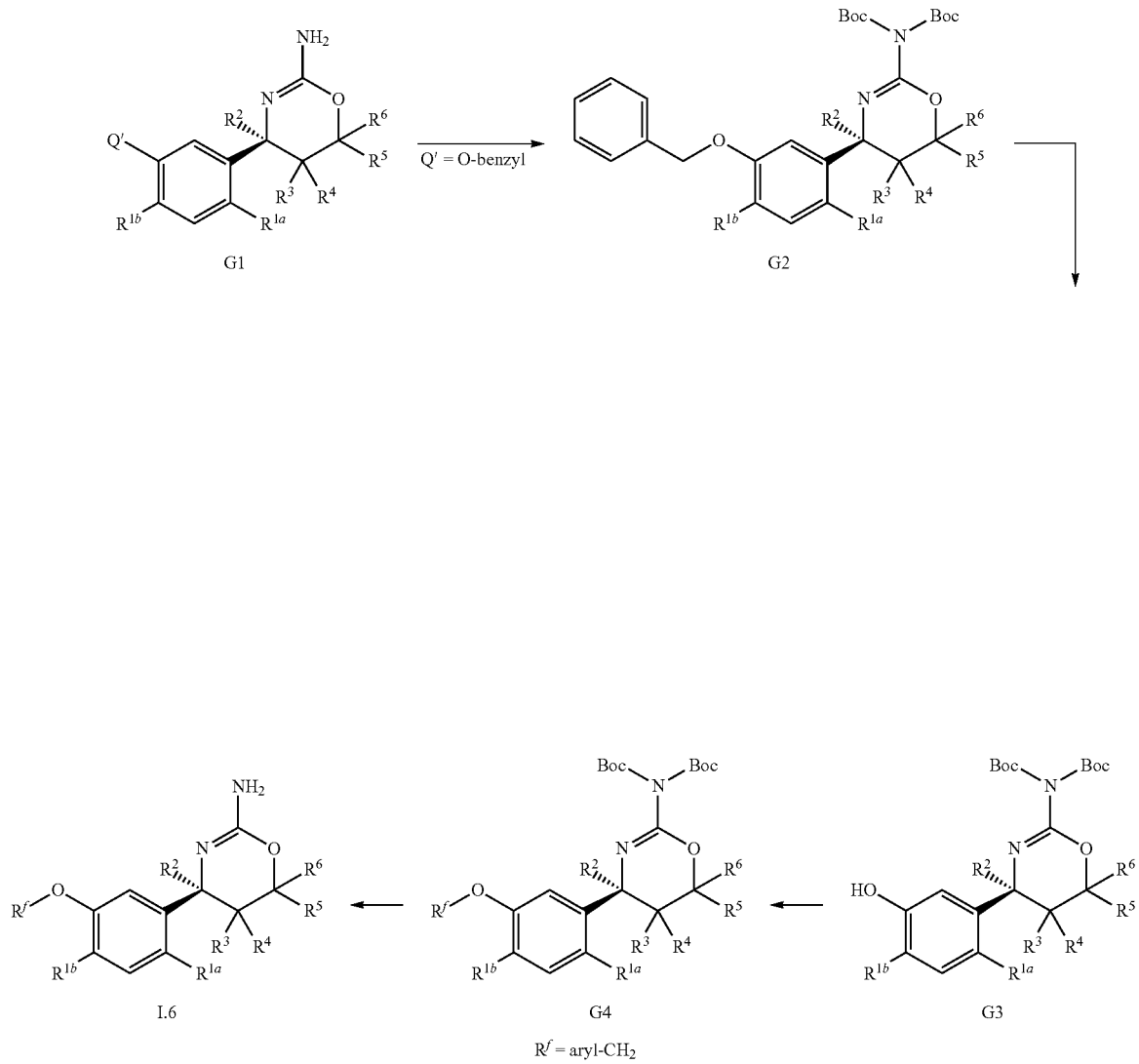

Compounds of formula G1 can be prepared in analogy to the procedures described in Scheme A and B starting from the corresponding benzyloxy-phenyl ketones. The protection of the amino group in compounds of formula G1, wherein Q is a benzyloxy group, to produce compounds of formula G2, The cleavage of the protecting tert-butoxy carbonyl groups in compounds of formula G4 to produce compounds of general formula I.6 can be effected by acid, such as trifluoroacetic acid, in inert solvents, such as dichloromethane, at temperatures between 0° C. and ambient temperature.

Scheme H: Synthesis of compounds of formula I.7.

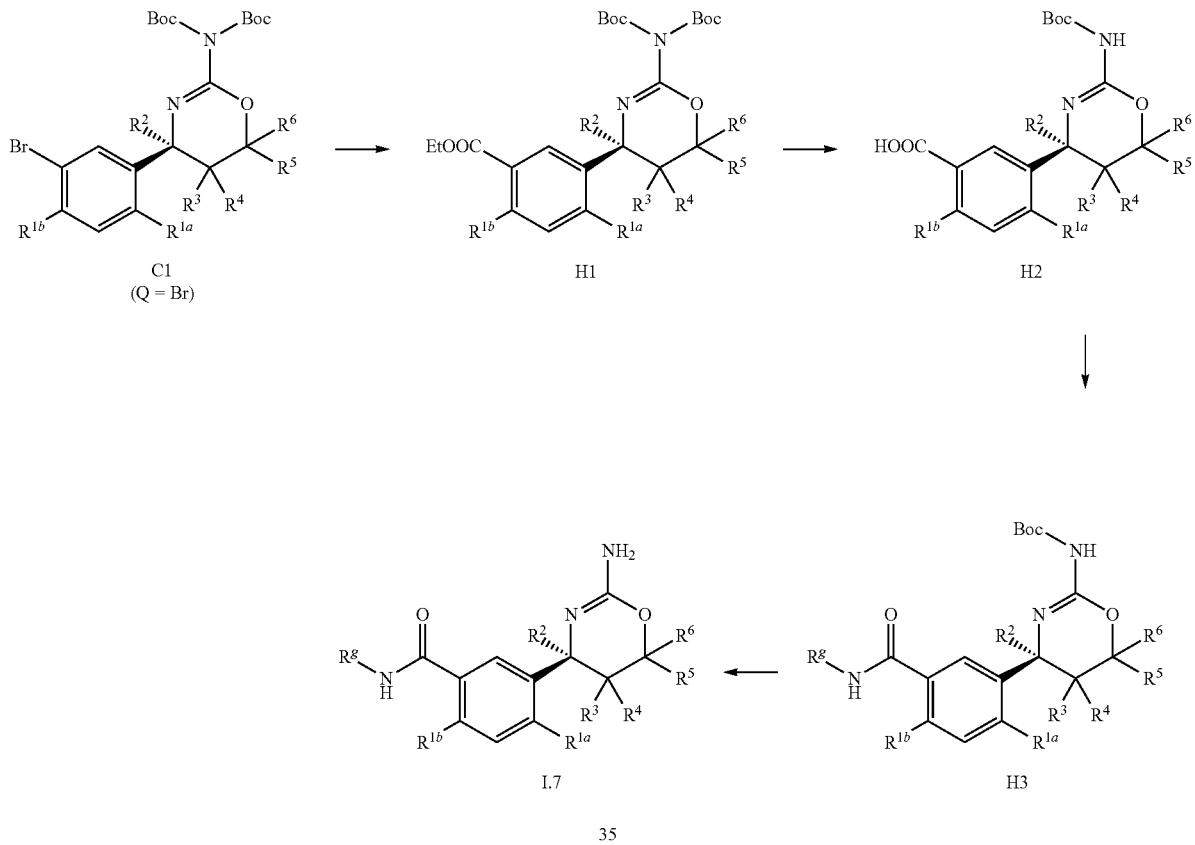

Acids of formula H2 can be obtained by palladium-catalyzed carbonylation of compounds of formula C1 with, e.g. 1,1'-bis(diphenylphosphino)ferrocene-palladium(II) dichloride or palladium(II)acetate and 1,3-bis(diphenylphosphino) propane as the catalyst, in presence of a base such as triethylamine. Preferably the reaction is performed in alcohols, e.g. methanol or ethanol, to yield the corresponding esters of formula H1 which are saponified under standard conditions to acids of formula H2.

Coupling of amines of formula $R^g$—$NH_2$ and carboxylic acids of formula H2 to give amides of formula H3 can be effected in a solvent such as methanol with 4-(4,6-dimethoxy[1.3.5]triazin-2-yl)-4-methylmorpholinium chloride hydrate (DMTMM) or other condensating agents, such as O-(benzotriazol-1-yl)-N,N,N',N'-tetramethyluronium-hexafluorophosphate (HBTU) or O-(7-azabenzotriazol-1-yl)-N,N,N',N'-tetramethyluronium-hexafluorophosphate (HATU), in the presence of an amine, such as triethylamine or diisopropylethylamine, in a solvent, such as acetonitrile or N,N-dimthylformamide, at temperatures between 0° C. and ambient temperature.

The cleavage of the protecting tert-butoxy carbonyl group in compounds of formula H3 to produce compounds of formula I.7 can be effected by acid, such as trifluoroacetic acid, in inert solvents, such as dichloromethane, at temperatures between 0° C. and ambient temperature.

Sulfinyl imines of general formula J2 can be prepared in analogy to T. P. Tang & J. A. Ellman, J. Org. Chem. 1999, 64, 12, by condensation of an aryl ketone J1 and a sulfinamide, e.g. an alkyl sulfinamide, most preferably (R)-(+)-tert-butylsulfinamide, in the presence of a Lewis acid such as e.g. a titanium(IV)alkoxide, more preferably titanium(IV)ethoxide in a solvent such as an ether, e.g. diethyl ether or more preferably tetrahydrofuran.

The conversion of the sulfinyl imine J2 to the sulfinamide ester J3 proceeds stereoselectively by the chiral directing group as described by Tang & Ellman.

The sulfinyl imine J2 can be reacted with a titanium enolate generated from e.g. an alkyl acetate or alkyl 2-halogen-propanoate, preferably ethyl acetate or 2-fluoro-propanoate, lithium diisopropylamide and chlorotriisopropoxytitanium at low temperature, preferably at −78° C. in a solvent such as an ether, e.g. diethyl ether or more preferably tetrahydrofuran. Alternatively sulfinamide ester J3 can be produced from sulfinyl imine J2 by Reformatsky reaction of a bromoacetic ester derivative, preferably ethyl 2-bromo-2-fluoroacetate or 2-bromo-2,2-difluoroacetate, and zinc dust, optionally in the presence of copper(I) chloride, in a solvent such as an ether, e.g. diethyl ether or more preferably tetrahydrofuran, at temperatures from 0 to 70° C., preferably at 23° C.

The alcohol of formula J4, wherein $R^5$, $R^6$ is hydrogen, can be prepared by the reduction of an ethylester of formula J3 with an alkali hydride, preferably lithium borohydride or lithium aluminium hydride, in a solvent such as an ether, e.g. diethyl ether or more preferably tetrahydrofuran.

Alcohols of formula J4, wherein $R^5$, $R^6$ is different from hydrogen, can be prepared by the reaction of esters of formula J3 with an excess of a Grignard or an organolithium reagent, e.g. methyl- or ethylmagnesium halide, methyllithium etc., in a solvent such as an ether, e.g. diethylether or more preferably tetrahydrofuran, at temperatures between −78 and 70° C., preferably at 0 to 23° C.

Scheme J: Synthesis of compounds of formula I.8.

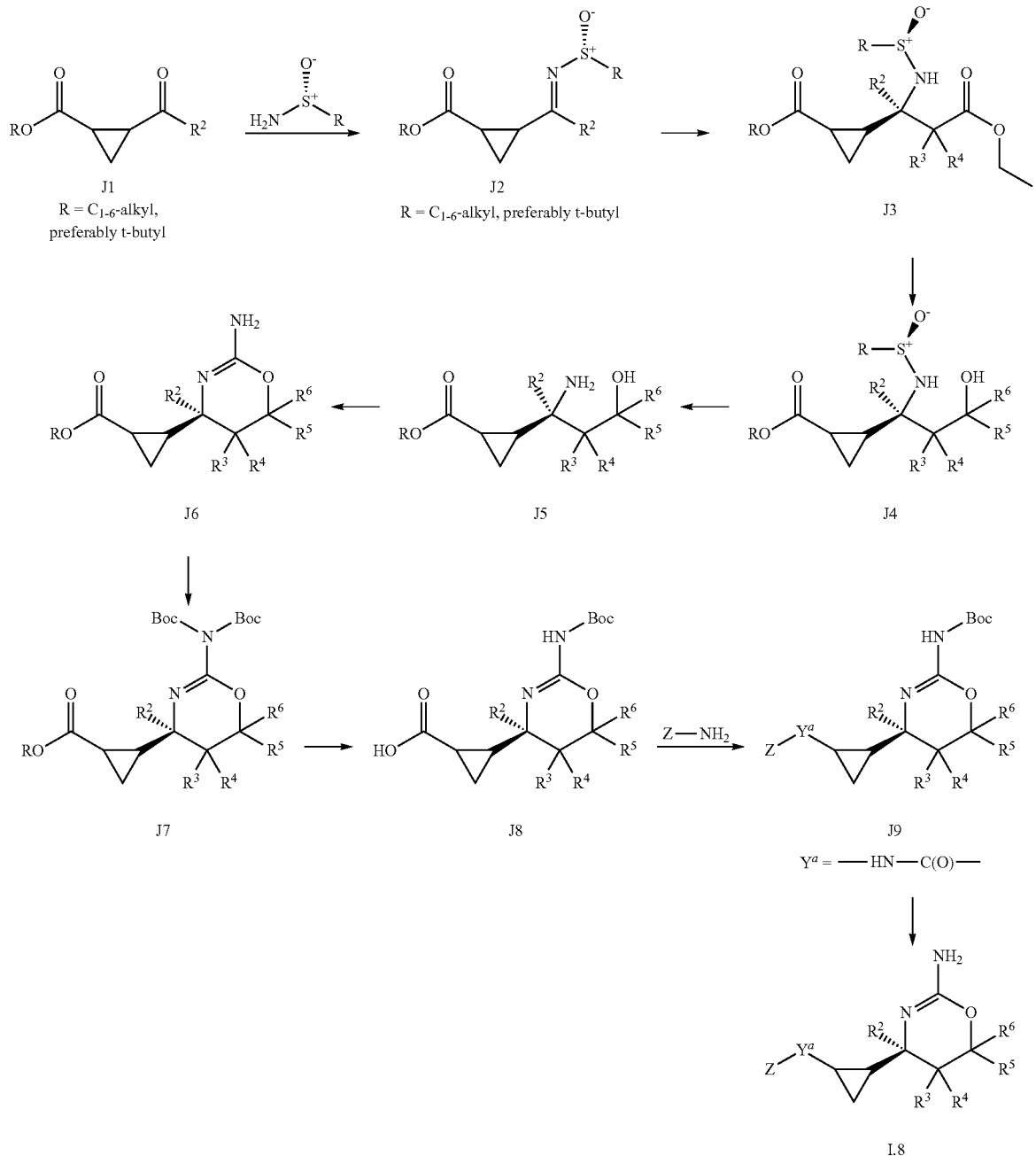

Hydrolysis of the chiral directing group and concomitant transesterification in the sulfinamide alcohol of formula J4 to give the aminoalcohol of formula J5 can be accomplished under acidic conditions by treatment with thionyl chloride in a solvent such as an alcohol, e.g. methanol or ethanol, at a temperature between room temperature and 100° C., preferably at reflux temperature.

The aminooxazine of formula J6 can be prepared by reaction of an aminoalcohol of formula J5 with cyanogen bromide in a solvent such as an alcohol, preferably ethanol.

The protection of the amino group in compounds of formula J6 to produce compounds of general formula J7 can be performed by reaction with di-tert-butyl dicarbonate under basic conditions, e.g. in the presence of an amine, such as triethylamine or diisopropylethylamine, in a solvent, such as tetrahydrofuran, at temperatures between 0° C. and ambient temperature and in presence of 4-dimethylamino-pyridine as a catalyst.

Hydrolysis of the ester group and concomitant cleavage of one of the amino protecting groups in compounds of formula J7 can be performed by treatment with aqueous solutions of alkali hydroxides, like e.g. sodium hydroxide or lithium hydroxide, in solvents like alcohols, e.g. methanol or ethanol to yield carboxylic acids of formula J8.

Coupling of amines of formula Z—NH$_2$ and carboxylic acids of formula J8 to give amides of formula J9 can be effected in a solvent such as methanol with 4-(4,6-dimethoxy[1.3.5]triazin-2-yl)-4-methylmorpholinium chloride hydrate (DMTMM) or other condensating agents, such as O-(benzotriazol-1-yl)-N,N,N',N'-tetramethyluronium-hexafluorophosphate (HBTU) or O-(7-azabenzotriazol-1-yl)-N,N,N',N'-tetramethyluronium-hexafluorophosphate (HATU), in the presence of an amine, such as triethylamine or diisopropylethylamine, in a solvent, such as acetonitrile or N,N-dimthylformamide, at temperatures between 0° C. and ambient temperature.

The cleavage of the protecting tert-butoxy carbonyl group in compounds of formula J9 to produce compounds of formula I.8 can be effected by acid, such as trifluoroacetic acid or hydrochloric acid, in inert solvents, such as dichloromethane, at temperatures between 0° C. and ambient temperature.

Sulfinyl imines of general formula K2 can be prepared in analogy to T. P. Tang & J. A. Ellman, J. Org. Chem. 1999, 64, 12, by condensation of an aryl ketone K1 and a sulfinamide, e.g. an alkyl sulfinamide, most preferably (R)-(+)-tert-butylsulfinamide, in the presence of a Lewis acid such as e.g. a titanium(IV)alkoxide, more preferably titanium(IV)ethoxide in a solvent such as an ether, e.g. diethyl ether or more preferably tetrahydrofuran.

The conversion of the sulfinyl imine K2 to the sulfinamide ester K3 proceeds stereoselectively by the chiral directing group as described by Tang & Ellman.

The sulfinyl imine K2 can be reacted with a titanium enolate generated from e.g. an alkyl acetate or alkyl 2-halogenpropanoate, preferably ethyl acetate or 2-fluoro-propanoate, lithium diisopropylamide and chlorotriisopropoxytitanium at low temperature, preferably at −78° C. in a solvent such as an ether, e.g. diethyl ether or more preferably tetrahydrofuran. Alternatively sulfinamide ester K3 can be produced from sulfinyl imine K2 by Reformatsky reaction of a bromoacetic ester derivative, preferably ethyl 2-bromo-2-fluoroacetate or 2-bromo-2,2-difluoroacetate, and zinc dust, optionally in the presence of copper(I) chloride, in a solvent such as an ether, e.g. diethyl ether or more preferably tetrahydrofuran, at temperatures from 0 to 70° C., preferably at 23° C.

The alcohol of formula K4, wherein $R^5$, $R^6$ is hydrogen, can be prepared by the reduction of an ester of formula K3 with an alkali hydride, preferably lithium borohydride or lithium aluminium hydride, in a solvent such as an ether, e.g. diethyl ether or more preferably tetrahydrofuran.

Alcohols of formula K4, wherein $R^5$, $R^6$ is different from hydrogen, can be prepared by the reaction of esters of formula K3 with an excess of a Grignard or an organolithium reagent, e.g. methyl- or ethylmagnesium halide, methyllithium etc., in a solvent such as an ether, e.g. diethylether or more preferably tetrahydrofuran, at temperatures between −78 and 70° C., preferably at 0 to 23° C.

Hydrolysis of the chiral directing group in the sulfinamide alcohol of formula K4 to give the aminoalcohol of formula K5 can be accomplished under acidic conditions by treatment with mineral acid, e.g. sulfuric acid or preferably hydrochloric acid, in a solvent such as an ether, e.g. diethyl ether, tetrahydrofuran or more preferably 1,4-dioxane, at a temperature 0° C. and 50° C., preferably at room temperature.

The aminooxazine of formula K7 can be prepared directly by reaction of an aminoalcohol of formula K5 with cyanogen bromide in a solvent such as an alcohol, preferably ethanol.

Alternatively aminooxazines of formula K7 can be obtained via the isolated intermediate cyanato derivative of formula K6. Aminoalcohols of formula K5 can be reacted with cyanogen bromide in presence of an alkali acetate in a solvent such as an alcohol, preferably ethanol, at a temperature between room temperature and 60° C., preferably 40° C. to yield cyanato derivatives of formula K6.

The formation of aminooxazines of formula K7 can be accomplished by reaction of cyanato derivatives of formula K6 with ammonium hydroxide in a solvent such as an alcohol, preferably methanol, at a temperature between room temperature and 100° C., preferably at 60° C.

Scheme K: Synthesis of building blockK7.

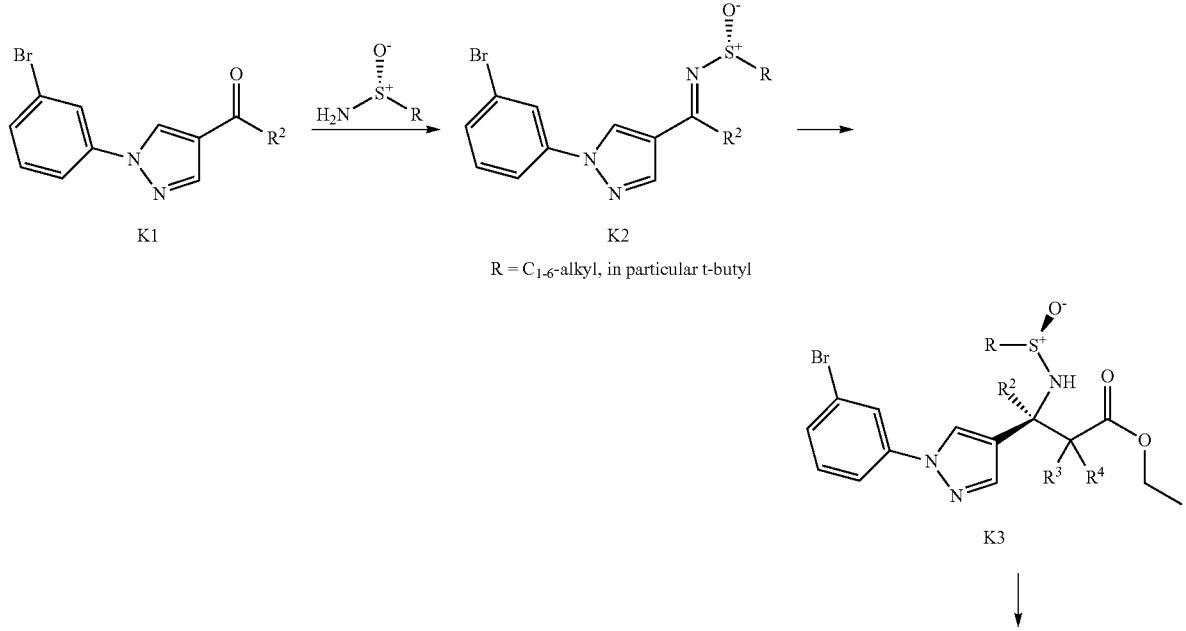

R = $C_{1-6}$-alkyl, in particular t-butyl

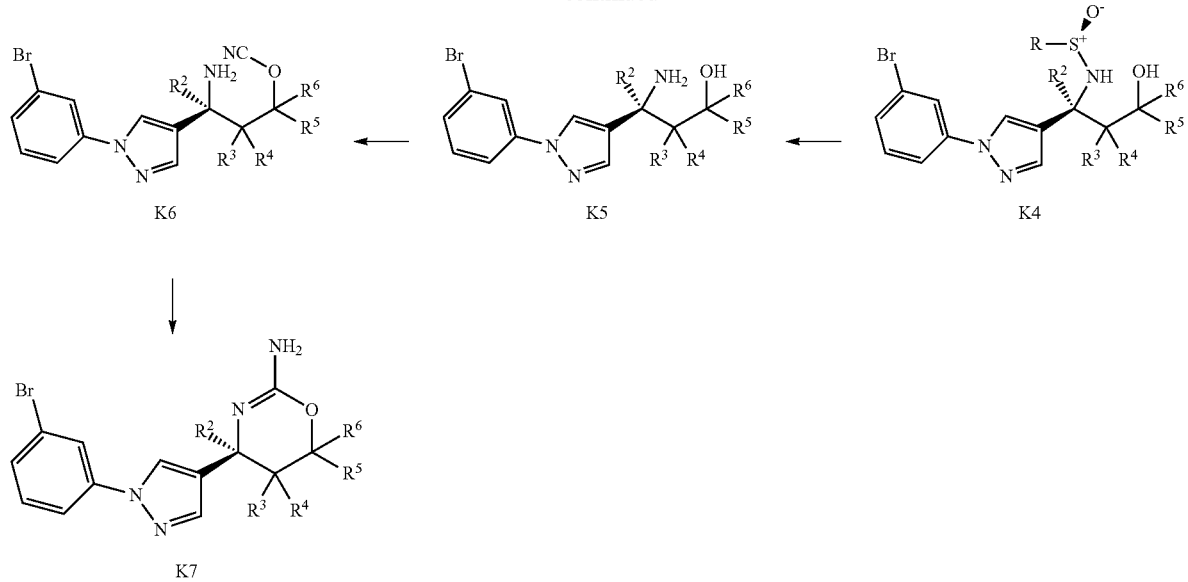

The protection of the amino group in compounds of formula J6 to produce compounds of general formula J7 can be performed by reaction with di-tert-butyl dicarbonate under basic conditions, e.g. in the presence of an amine, such as triethylamine or diisopropylethylamine, in a solvent, such as tetrahydrofuran, at temperatures between 0° C. and ambient temperature and in presence of 4-dimethylamino-pyridine as a catalyst.

Hydrolysis of the ester group and concomitant cleavage of one of the amino protecting groups in compounds of formula J7 can be performed by treatment with aqueous solutions of alkali hydroxides, like e.g. sodium hydroxide or lithium hydroxide, in solvents like alcohols, e.g. methanol or ethanol to yield carboxylic acids of formula J8.

Coupling of amines of formula Z—$NH_2$ and carboxylic acids of formula J8 to give amides of formula J9 can be effected in a solvent such as methanol with 4-(4,6-dimethoxy[1.3.5]triazin-2-yl)-4-methylmorpholinium chloride hydrate (DMTMM) or other condensating agents, such as O-(benzotriazol-1-yl)-N,N,N',N'-tetramethyluronium-hexafluoro-phosphate (HBTU) or O-(7-azabenzotriazol-1-yl)-N,N,N',N'-tetramethyluronium-hexafluorophosphate (HATU), in the presence of an amine, such as triethylamine or diisopropylethylamine, in a solvent, such as acetonitrile or N,N-dimthylformamide, at temperatures between 0° C. and ambient temperature.

The cleavage of the protecting tert-butoxy carbonyl group in compounds of formula J9 to produce compounds of formula I.8 can be effected by acid, such as trifluoroacetic acid or hydrochloric acid, in inert solvents, such as dichloromethane, at temperatures between 0° C. and ambient temperature.

The corresponding pharmaceutically acceptable salts with acids can be obtained by standard methods known to the person skilled in the art, e.g. by dissolving the compound of formula I in a suitable solvent such as e.g. dioxan or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate. Specific is hydrochloride.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention can be derivatised at functional groups to provide derivatives which are capable of conversion back to the parent compound in vivo.

Pharmacological Tests

The compounds of formula I and their pharmaceutically acceptable salts possess valuable pharmacological properties. The compounds of the present invention are associated with inhibition of BACE1 and/or BACE2 activity. The compounds were investigated in accordance with the test given hereinafter.

Cellular Aβ-Lowering Assay:

a) Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9, 1481-1486;

1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/$H_2O_2$ in citric acid buffer. After stopping the reaction with one volume 1 $NH_2SO_4$ the reaction was measured in an ELISA reader at 450 nm wavelength. The concentrations of Aβ in the culture supernatants were calculated from a standard curve obtained with known amounts of pure Aβ peptide.

b) Alternatively, the Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in 1/3 volume of culture medium (final DMSO concentration was kept at 1% v/v). After 18-20 hrs incubation at 37° C. and 5% $CO_2$ in a humidified incubator, the culture supernatants were harvested for the determination of Aβ 40 concentrations using Perkin-Elmer Human Amyloid beta 1-40 (high specificity) Kit (Cat# AL275C).

In a Perkin-Elmer White Optiplate-384 (Cat#6007290), 2 ul culture supernatants were combined with 2 μl of a 10× AlphaLISA Anti-hAβ Acceptor beads+Biotinylated Antibody Anti-Aβ 1-40 Mix (50 μg/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The IC50 values were calculated using the Excel XLfit software.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

TABLE 1

| Exam. | Structure | BACE1 cell act. Aβ40 $IC_{50}$ [μM] | BACE2 cell act. $IC_{50}$ [μM] |
|---|---|---|---|
| 1 | 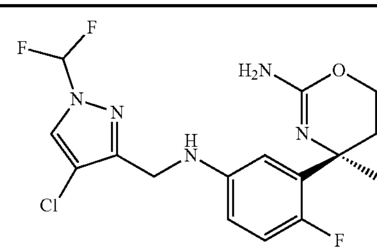 | 0.013 [a] | 0.180 |
| 2 | 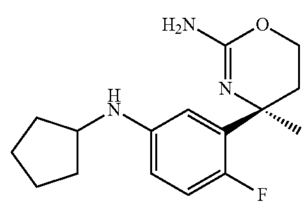 [SMILES: C[C@@]1(c2cc(NC3CCCC3)ccc2F)CCOC(N)=N1] | 0.340 [a] | — |
| 3 | 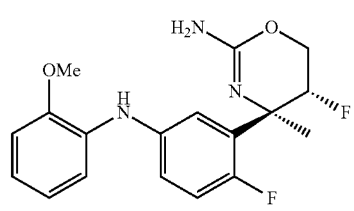 [SMILES: COc1ccccc1Nc1ccc(F)c([C@@]2(C)N=C(N)OC[C@@H]2F)c1] | 0.310 [a] | 0.970 |

TABLE 1-continued
| Exam. | Structure | BACE1 cell act. Aβ40 IC$_{50}$ [μM] | BACE2 cell act. IC$_{50}$ [μM] |
|---|---|---|---|
| 4 | 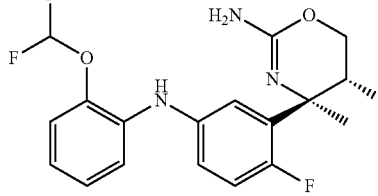 | 0.370 [a] | 1.810 |
| 5 | 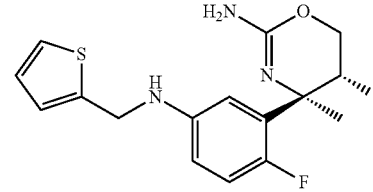 | 0.540 [a] | 1.129 |
| 6 | 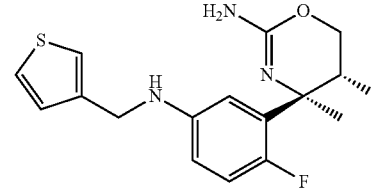 | 0.660 [a] | — |
| 7 | 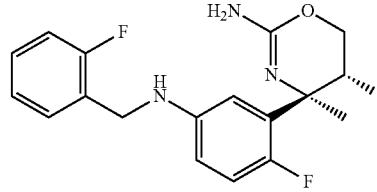 | 0.780 [a] | 0.240 |
| 8 | 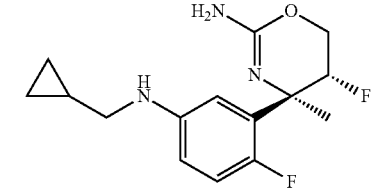 [SMILES: C[C@]1(c2cc(NCC3CC3)ccc2F)N=C(N)OC[C@@H]1F] | 0.022 [a] | 0.164 |
| 9 | 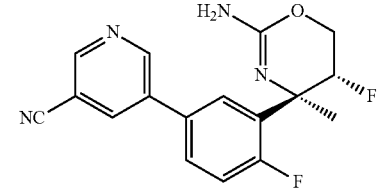 [SMILES: C[C@]1(c2cc(-c3cncc(C#N)c3)ccc2F)N=C(N)OC[C@@H]1F] | 0.190 [a] | — |
| 10 | 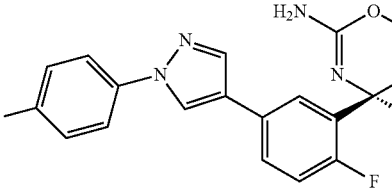 | 0.360 [a] | — |

TABLE 1-continued

| Exam. | Structure | BACE1 cell act. Aβ40 IC$_{50}$ [μM] | BACE2 cell act. IC$_{50}$ [μM] |
|---|---|---|---|
| 11 | 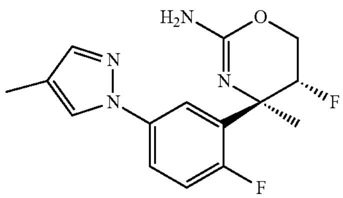 [SMILES: Cc1cnn(-c2ccc(F)c([C@@]3(C)N=C(N)OC[C@@H]3F)c2)c1] | 1.300 [a] | — |
| 12 | 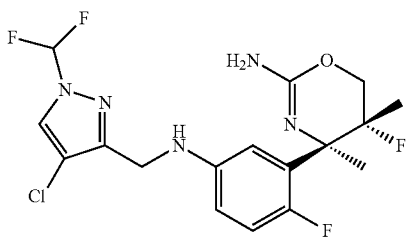 [SMILES: C[C@]1(F)COC(N)=N[C@]1(C)c1cc(NCc2nn(C(F)F)cc2Cl)ccc1F] | 0.039 [a] | 0.588 |
| 13 | 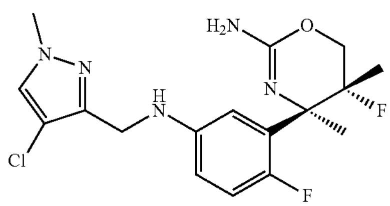 [SMILES: Cn1cc(Cl)c(CNc2ccc(F)c([C@@]3(C)N=C(N)OC[C@]3(C)F)c2)n1] | 0.048 [a] | 0.079 |
| 14 | 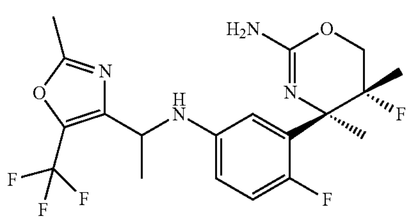 [SMILES: Cc1nc(C(C)Nc2ccc(F)c([C@@]3(C)N=C(N)OC[C@]3(C)F)c2)c(C(F)(F)F)o1] | — | 0.068 |
| 15 | 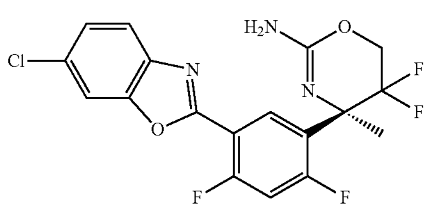 [SMILES: C[C@]1(c2cc(-c3nc4ccc(Cl)cc4o3)c(F)cc2F)N=C(N)OCC1(F)F] | 1.280 [b] | — |
| 16 | 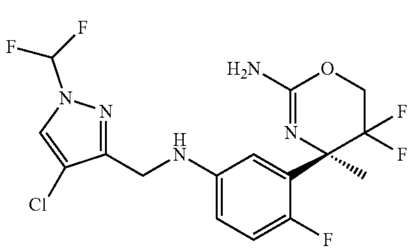 [SMILES: C[C@]1(c2cc(NCc3nn(C(F)F)cc3Cl)ccc2F)N=C(N)OCC1(F)F] | 0.113 [a] | 2.524 |
| 17 | 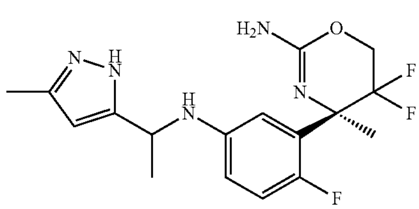 [SMILES: Cc1cc(C(C)Nc2ccc(F)c([C@@]3(C)N=C(N)OCC3(F)F)c2)[nH]n1] | 0.430 [a] | — |

TABLE 1-continued

| Exam. | Structure | BACE1 cell act. Aβ40 IC$_{50}$ [μM] | BACE2 cell act. IC$_{50}$ [μM] |
|---|---|---|---|
| 18 | 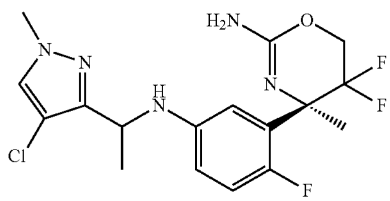 [SMILES: CC(Nc1ccc(F)c([C@@]2(C)N=C(N)OCC2(F)F)c1)c1nn(C)cc1Cl] | 1.230 [a] | — |
| 19 | 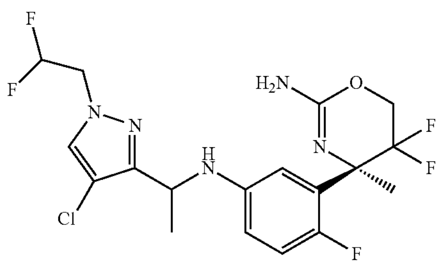 [SMILES: CC(Nc1ccc(F)c([C@@]2(C)N=C(N)OCC2(F)F)c1)c1nn(CC(F)F)cc1Cl] | 1.795 [a] | — |
| 20 | 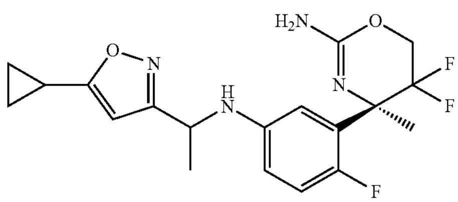 [SMILES: CC(Nc1ccc(F)c([C@@]2(C)N=C(N)OCC2(F)F)c1)c1cc(C2CC2)on1] | 2.000 [a] | — |
| 21 | 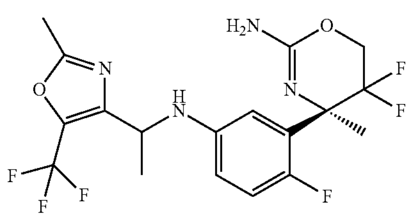 [SMILES: Cc1nc(C(C)Nc2ccc(F)c([C@@]3(C)N=C(N)OCC3(F)F)c2)c(C(F)(F)F)o1] | — | — |
| 22 | 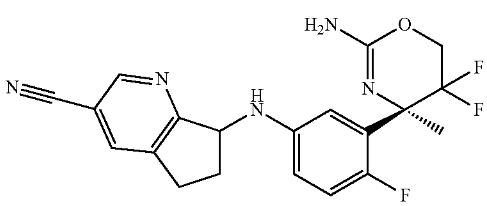 [SMILES: C[C@]1(c2cc(NC3CCc4cc(C#N)cnc43)ccc2F)N=C(N)OCC1(F)F] | 0.011 [a] | 0.753 |
| 23 | 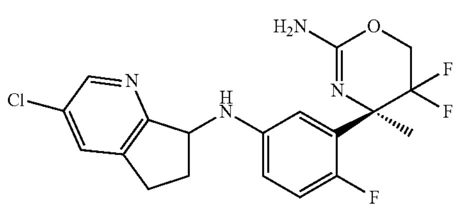 [SMILES: C[C@]1(c2cc(NC3CCc4cc(Cl)cnc43)ccc2F)N=C(N)OCC1(F)F] | 0.073 [a] | 1.704 |
| 24 | 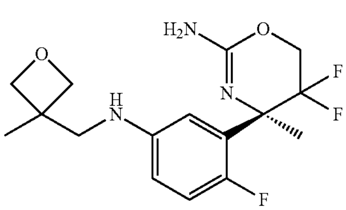 [SMILES: CC1(CNc2ccc(F)c([C@@]3(C)N=C(N)OCC3(F)F)c2)COC1] | 0.300 [a] | — |

TABLE 1-continued

| Exam. | Structure | BACE1 cell act. Aβ40 IC$_{50}$ [μM] | BACE2 cell act. IC$_{50}$ [μM] |
|---|---|---|---|
| 25 | 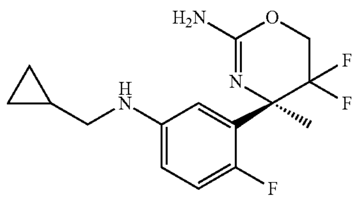 [SMILES: C[C@]1(c2cc(NCC3CC3)ccc2F)N=C(N)OCC1(F)F] | 0.310 [a] | 1.654 |
| 26 | 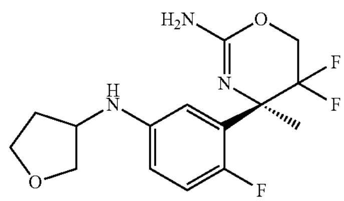 [SMILES: C[C@]1(c2cc(NC3CCOC3)ccc2F)N=C(N)OCC1(F)F] | 0.400 [a] | — |
| 27 | 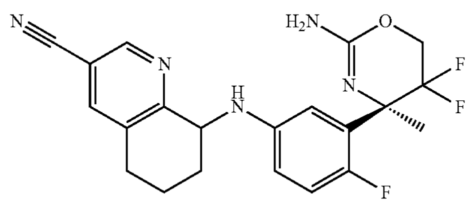 [SMILES: C[C@]1(c2cc(NC3CCCc4cc(C#N)cnc43)ccc2F)N=C(N)OCC1(F)F] | 0.460 [a] | — |
| 28 | 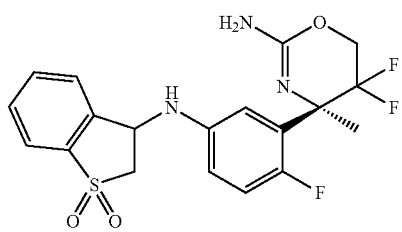 [SMILES: C[C@]1(c2cc(NC3CS(=O)(=O)c4ccccc43)ccc2F)N=C(N)OCC1(F)F] | 1.630 [a] | — |
| 29 | 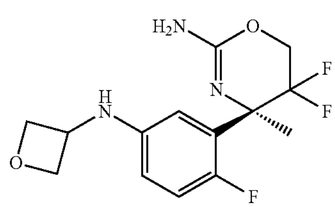 [SMILES: C[C@]1(c2cc(NC3COC3)ccc2F)N=C(N)OCC1(F)F] | 1.960 [a] | — |
| 30 | 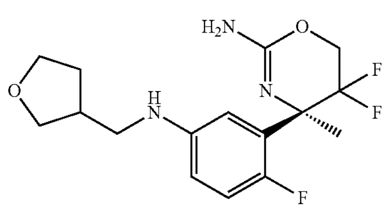 [SMILES: C[C@]1(c2cc(NCC3CCOC3)ccc2F)N=C(N)OCC1(F)F] | 2.160 [a] | — |
| 31 | 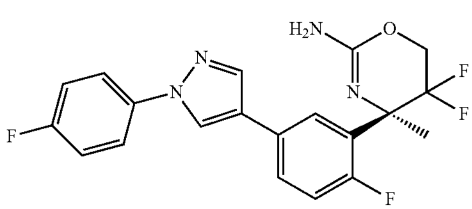 [SMILES: C[C@]1(c2cc(-c3cnn(-c4ccc(F)cc4)c3)ccc2F)N=C(N)OCC1(F)F] | 8.440 [a] | — |

TABLE 1-continued

| Exam. | Structure | BACE1 cell act. Aβ40 IC$_{50}$ [μM] | BACE2 cell act. IC$_{50}$ [μM] |
|---|---|---|---|
| 32 | 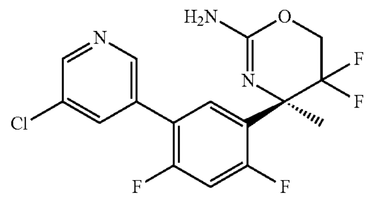 [SMILES: C[C@]1(c2cc(-c3cncc(Cl)c3)c(F)cc2F)N=C(N)OCC1(F)F] | 0.880 [b] | — |
| 33 | 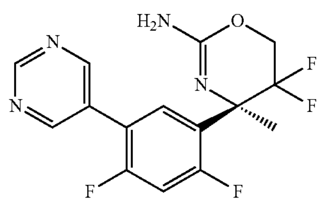 [SMILES: C[C@]1(c2cc(-c3cncnc3)c(F)cc2F)N=C(N)OCC1(F)F] | 0.380 [b] | — |
| 34 | 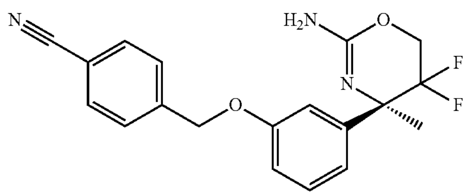 [SMILES: C[C@]1(c2cccc(OCc3ccc(C#N)cc3)c2)N=C(N)OCC1(F)F] | 1.400 [a] | — |
| 35 | 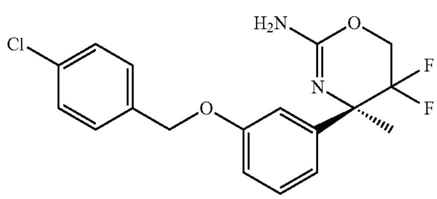 [SMILES: C[C@]1(c2cccc(OCc3ccc(Cl)cc3)c2)N=C(N)OCC1(F)F] | 4.000 [a] | — |
| 36 | 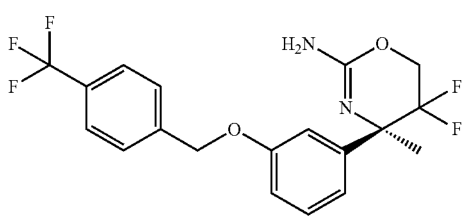 [SMILES: C[C@]1(c2cccc(OCc3ccc(C(F)(F)F)cc3)c2)N=C(N)OCC1(F)F] | 7.740 [a] | — |
| 37 | 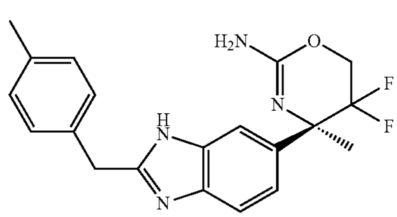 [SMILES: Cc1ccc(Cc2nc3ccc([C@@]4(C)N=C(N)OCC4(F)F)cc3[nH]2)cc1] | 0.300 [a] | — |
| 38 | 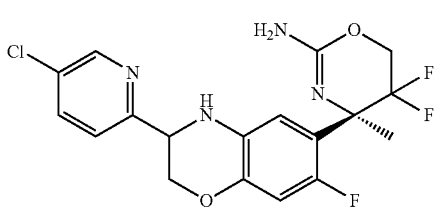 [SMILES: C[C@]1(c2cc3c(cc2F)OCC(c2ccc(Cl)cn2)N3)N=C(N)OCC1(F)F] | 5.460 [a] | — |

TABLE 1-continued

| Exam. | Structure | BACE1 cell act. Aβ40 IC$_{50}$ [μM] | BACE2 cell act. IC$_{50}$ [μM] |
|---|---|---|---|
| 39 | 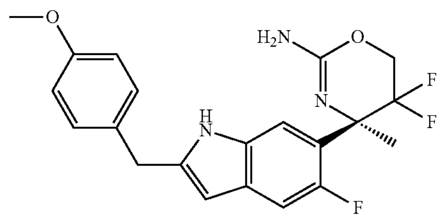 [SMILES: COc1ccc(Cc2cc3cc(F)c([C@@]4(C)N=C(N)OCC4(F)F)cc3[nH]2)cc1] | 5.670 [a] | — |
| 40 | 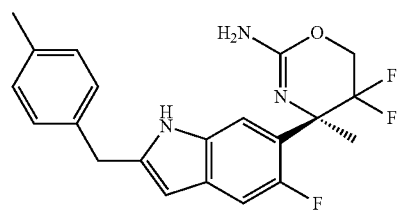 [SMILES: Cc1ccc(Cc2cc3cc(F)c([C@@]4(C)N=C(N)OCC4(F)F)cc3[nH]2)cc1] | 6.020 [a] | 10.861 |
| 41 | 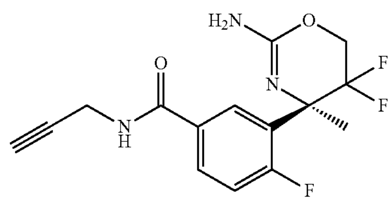 [SMILES: C#CCNC(=O)c1ccc(F)c([C@@]2(C)N=C(N)OCC2(F)F)c1] | 6.620 [a] | — |
| 42 | 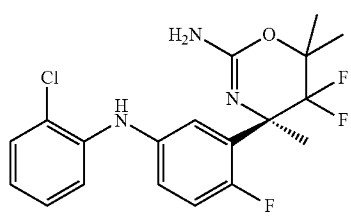 [SMILES: CC1(C)OC(N)=N[C@](C)(c2cc(Nc3ccccc3Cl)ccc2F)C1(F)F] | 1.470 [a] | — |
| 43 | 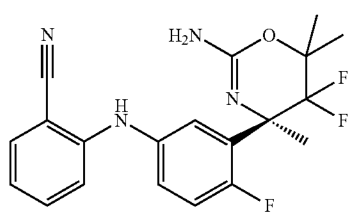 [SMILES: CC1(C)OC(N)=N[C@](C)(c2cc(Nc3ccccc3C#N)ccc2F)C1(F)F] | 1.650 [a] | 4.136 |
| 44 | 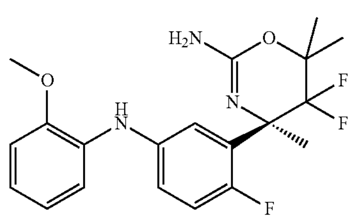 [SMILES: COc1ccccc1Nc1ccc(F)c([C@@]2(C)N=C(N)OC(C)(C)C2(F)F)c1] | 2.090 [a] | 2.980 |
| 45 | 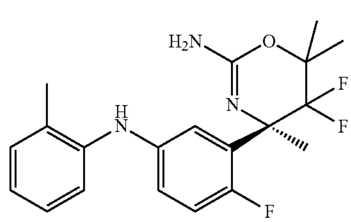 | 2.920 [a] | — |

TABLE 1-continued

| Exam. | Structure | BACE1 cell act. Aβ40 IC$_{50}$ [μM] | BACE2 cell act. IC$_{50}$ [μM] |
|---|---|---|---|
| 46 | 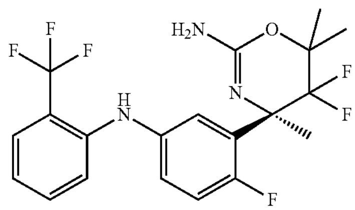 [SMILES: CC1(C)OC(N)=N[C@](C)(c2cc(Nc3ccccc3C(F)(F)F)ccc2F)C1(F)F] | 6.920 [a] | — |
| 47 | 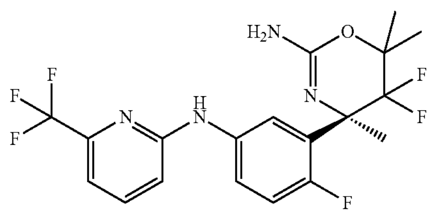 [SMILES: CC1(C)OC(N)=N[C@](C)(c2cc(Nc3cccc(C(F)(F)F)n3)ccc2F)C1(F)F] | 4.170 [b] | 2.752 |
| 48 | 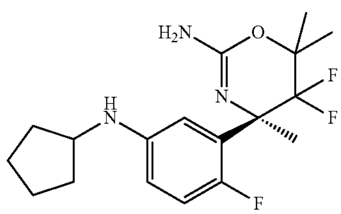 [SMILES: CC1(C)OC(N)=N[C@](C)(c2cc(NC3CCCC3)ccc2F)C1(F)F] | 0.290 [a] | 1.425 |
| 49 | 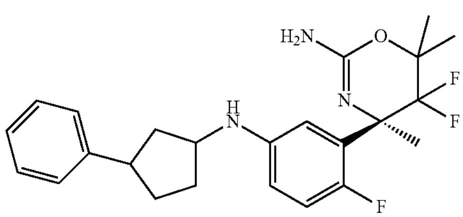 [SMILES: CC1(C)OC(N)=N[C@](C)(c2cc(NC3CCC(c4ccccc4)C3)ccc2F)C1(F)F] | 1.210 [b] | — |
| 50 | 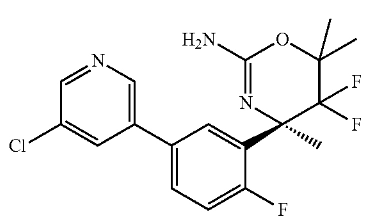 [SMILES: CC1(C)OC(N)=N[C@](C)(c2cc(-c3cncc(Cl)c3)ccc2F)C1(F)F] | 9.080 [a] | — |
| 51 | 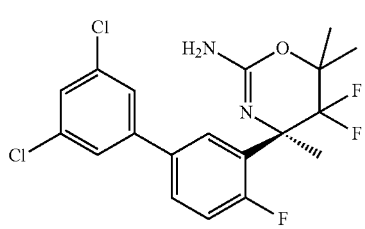 [SMILES: CC1(C)OC(N)=N[C@](C)(c2cc(-c3cc(Cl)cc(Cl)c3)ccc2F)C1(F)F] | 14.460 [a] | 3.351 |

TABLE 1-continued

| Exam. | Structure | BACE1 cell act. Aβ40 IC$_{50}$ [μM] | BACE2 cell act. IC$_{50}$ [μM] |
|---|---|---|---|
| 52 | 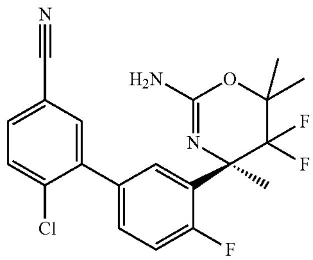 [SMILES: CC1(C)OC(N)=N[C@](C)(c2cc(-c3cc(C#N)ccc3Cl)ccc2F)C1(F)F] | 2.880 [b] | — |
| 53 | 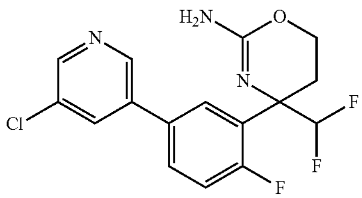 [SMILES: NC1=NC(c2cc(-c3cncc(Cl)c3)ccc2F)(C(F)F)CCO1] | 0.502 [b] | — |
| 54B | 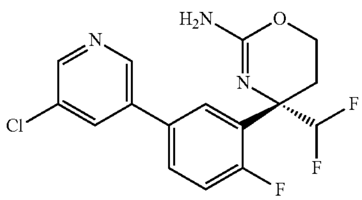 [SMILES: NC1=N[C@@](c2cc(-c3cncc(Cl)c3)ccc2F)(C(F)F)CCO1] | 0.220 [b] | — |
| 55 | 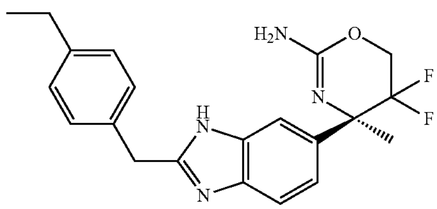 [SMILES: CCc1ccc(Cc2nc3ccc([C@@]4(C)N=C(N)OCC4(F)F)cc3[nH]2)cc1] | 1.446 [b] | — |
| 56 | 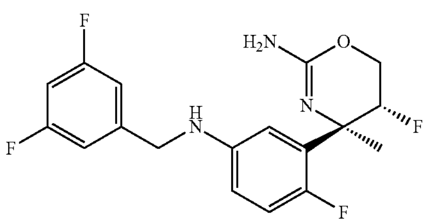 [SMILES: C[C@]1(c2cc(NCc3cc(F)cc(F)c3)ccc2F)N=C(N)OC[C@@H]1F] | 0.800 [b] | — |
| 57 | 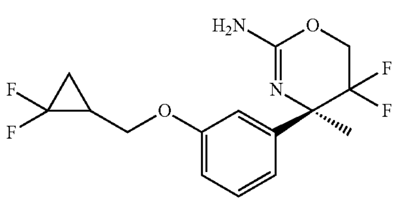 [SMILES: C[C@]1(c2cccc(OCC3CC3(F)F)c2)N=C(N)OCC1(F)F] | 3.700 [b] | — |
| 58 | 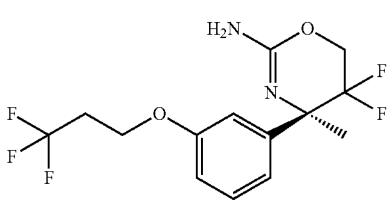 [SMILES: C[C@]1(c2cccc(OCCC(F)(F)F)c2)N=C(N)OCC1(F)F] | 2.010 [b] | — |

TABLE 1-continued

| Exam. | Structure | BACE1 cell act. Aβ40 IC$_{50}$ [μM] | BACE2 cell act. IC$_{50}$ [μM] |
|---|---|---|---|
| 59 | 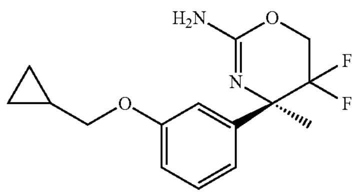 [SMILES: C[C@]1(c2cccc(OCC3CC3)c2)N=C(N)OCC1(F)F] | 3.119 [b] | — |
| 60 | 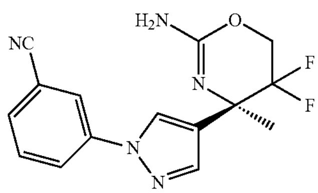 [SMILES: C[C@]1(c2cnn(-c3cccc(C#N)c3)c2)N=C(N)OCC1(F)F] | 4.620 [b] | — |
| 61 | 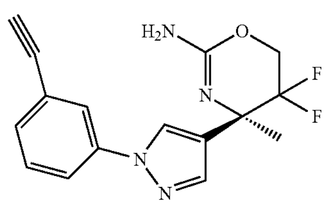 [SMILES: C#Cc1cccc(-n2cc([C@@]3(C)N=C(N)OCC3(F)F)cn2)c1] | 0.720 [b] | — |
| 62 | 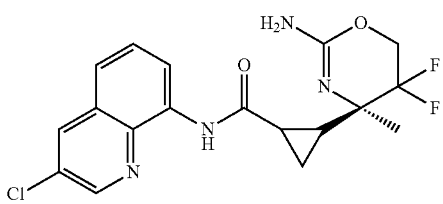 [SMILES: C[C@]1(C2CC2C(=O)Nc2cccc3cc(Cl)cnc23)N=C(N)OCC1(F)F] | 0.420 [b] | — |
| 63 | 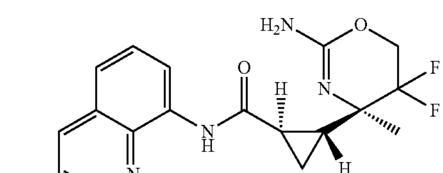 | 0.360 [b] | 1.350 |
| 65 | 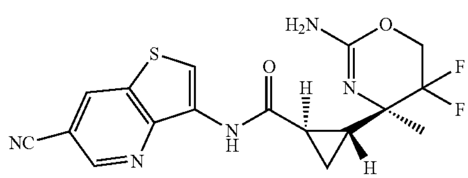 [SMILES: C[C@]1([C@@H]2C[C@H]2C(=O)Nc2csc3cc(C#N)cnc23)N=C(N)OCC1(F)F] | 0.180 [b] | — |
| K7.1 | 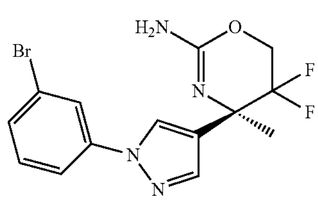 | 1.440 [b] | — |

IC$_{50}$ values of selected examples, [a] and indicate the respective cellular assay used Pharmaceutical Compositions The compounds of formula I and the pharmaceutically acceptable salts can be used as therapeutically active substances, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, preferably 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |

TABLE 4-continued possible soft gelatin capsule ingredient composition

| ingredient | mg/capsule |
|---|---|
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following examples are provided for illustration of the invention. They should not be considered as limiting the scope of the invention, but merely as being representative thereof.

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

Synthesis of the Intermediate Sulfinyl Imines A2

General Procedure

A solution of the (R)-(+)-tert-butylsulfinamide (66 mmol) in tetrahydrofuran (350 ml) was treated subsequently with the ketone A1 (72.6 mmol) and titanium(IV)ethoxide (132 mmol), and the solution was stirred at reflux temperature for 5 hours. For the workup, the mixture was cooled to 22° C. and treated with brine (400 ml). The suspension was stirred for 10 minutes, then filtered over Dicalite®. The layers were separated, the aqueous layer was extracted with ethyl acetate, the combined organic layers were washed with water, dried and concentrated in vacuo. The residue was purified by chromatography on silica using cylohexane/ethyl acetate as the eluent to give the pure sulfinyl imine A2.

Intermediate A2.1

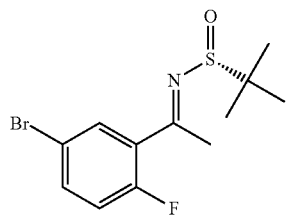 [SMILES: C/C(=N\[S@](=O)C(C)(C)C)c1cc(Br)ccc1F]

Starting from commercially available 1-(2-fluoro-5-bromo-phenyl)-ethanone {CAS [477-89-3]}, the product (R)-2-methyl-propane-2-sulfinic acid [1-(2-fluoro-5-bromo-phenyl)-(E)-ethylidene]-amide was obtained as a pale red oil. MS (ISP): m/z=320.3 [M+H]$^+$.
Intermediate A2.2 (Q=Br, $R^{1a}$ and $R^{1b}$=F, $R^2$=Me)

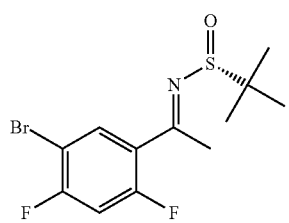 [SMILES: C/C(=N\[S@](=O)C(C)(C)C)c1cc(Br)c(F)cc1F]

Starting from commercially available 1-(5-bromo-2,4-difluorophenyl)-ethanone {CAS [864773-64-8]} the product (R)-2-methyl-propane-2-sulfinic acid [1-(5-bromo-2,4-difluoro-phenyl)-eth-(E)-ylidene]-amide was obtained as a pale red oil. MS (ISP): m/z=338.1 [M+H]$^+$ and 340.1 [M+2+H]$^+$.
Intermediate A2.3

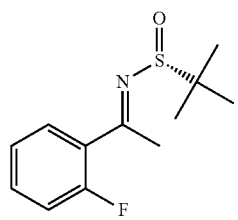 [SMILES: C/C(=N\[S@](=O)C(C)(C)C)c1ccccc1F]

Starting from commercially available 1-(2-fluorophenyl) ethanone the product (R)-2-methyl-propane-2-sulfinic acid [1-(2-fluoro-phenyl)-eth-(E)-ylidene]-amide was obtained as a brown oil. MS (ISP): m/z=242.3 [M+H]$^+$.
Intermediate A2.4

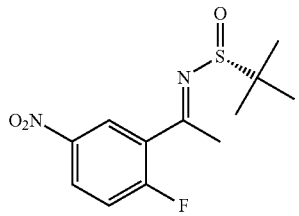 [SMILES: C/C(=N\[S@](=O)C(C)(C)C)c1cc([N+](=O)[O-])ccc1F]

Starting from 1-(2-fluoro-5-nitro-phenyl)-ethanone, the product (R)-2-methyl-propane-2-sulfinic acid [1-(2-fluoro-5-nitro-phenyl)-(E)-ethylidene]-amide was obtained as a pale yellow solid. MS (ISP): m/z=287.0 [M+H]$^+$.

Intermediate A2.5

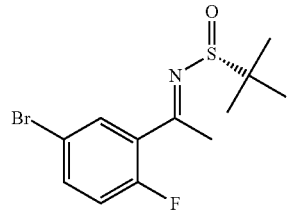 [SMILES: C/C(=N\[S@](=O)C(C)(C)C)c1cc(Br)ccc1F]

Starting from commercially available 1-(2-fluoro-5-bromo-phenyl)-ethanone {CAS [477-89-3]}, the product (R)-2-methyl-propane-2-sulfinic acid [1-(2-fluoro-5-bromo-phenyl)-(E)-ethylidene]-amide was obtained as a pale red oil. MS (ISP): m/z=320.3 [M+H]$^+$.
Intermediate A2.6

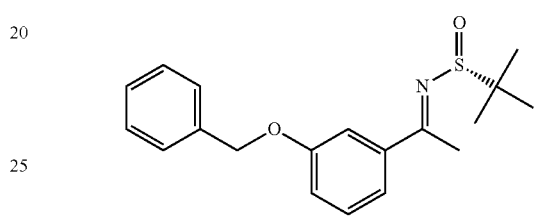

Starting from commercially available 1-(3-benzyloxy-phenyl)-ethanone, the product (R)-2-methyl-propane-2-sulfinic acid [1-(3-benzyloxy-phenyl)-eth-(E)-ylidene]-amide was obtained as a yellow oil. MS (ISP): m/z=330.2 [M+H]$^+$.
Intermediate A2.7

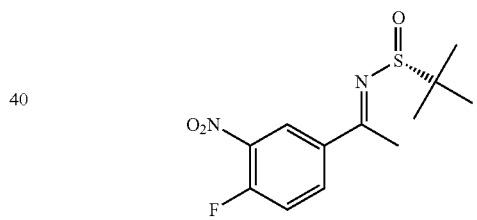

Starting from the commercially available 1-(4-fluoro-3-nitro-phenyl)-ethanone, the product (R)-2-methyl-propane-2-sulfinic acid [1-(4-fluoro-3-nitro-phenyl)-eth-(E)-ylidene]-amide was obtained as a pale yellow solid. MS (ISP): m/z=287.0 [M+H]$^+$.
Intermediate A2.8

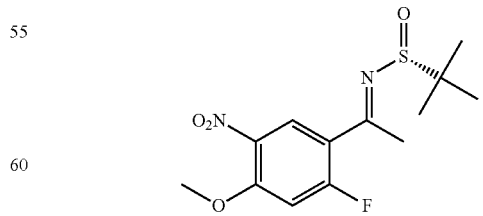

Starting from 1-(2-fluoro-4-methoxy-5-nitro-phenyl)-ethanone, the (R)-2-methyl-propane-2-sulfinic acid [1-(2-fluoro-4-methoxy-5-nitro-phenyl)-eth-(E)-ylidene]-amide was obtained as a red oil. MS (ISP): m/z=317.1 [M+H]$^+$.

The 1-(2-fluoro-4-methoxy-5-nitro-phenyl)-ethanone was obtained as follows:

Sulfuric acid (157 g, 85.2 ml, 1.6 mol) was cooled to −20° C. and 1-(2-fluoro-4-methoxyphenyl)ethanone (25 g, 149 mmol) was added portionwise in a manner that the temperature was kept below −15° C. Thereafter, a solution of sulfuric acid (64.4 g, 35 ml, 657 mmol) and fumic nitric acid (18.7 g, 12.4 ml, 297 mmol) was added dropwise within 20 minutes keeping the temperature below −15° C. After completion of the addition the viscous reaction mixture was stirred for additional 20 minutes at −15° C. For the workup, the reaction mixture was poured into a mixture of ice and water (400 ml) and stirring was continued for 10 minutes. The off-white suspension was filtrated and washed several times with water. The light yellow solid was dried at 45° C. before it was crystallized from a mixture of ethyl acetate and heptane (200 ml-600 ml, addition of charcoal). The 1-(2-fluoro-4-methoxy-5-nitro-phenyl)-ethanone (26.1 g, 82% yield) was obtained as pale yellow crystals. MS (ISP): m/z=214.2 [M+H]$^+$. In addition, the regioisomer 1-(2-fluoro-4-methoxy-3-nitro-phenyl)-ethanone (0.6 g, 2% yield) was obtained as a white solid.

Intermediate A2.9

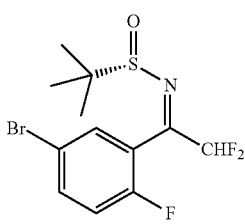 [SMILES: CC(C)(C)[S@](=O)/N=C(\c1cc(Br)ccc1F)C(F)F]

Starting from 1-(5-bromo-2-fluorophenyl)-2,2-difluoroethanone and (S)-(−)-2-methyl-2-propanesulfinamide, the (S,E)-N-(1-(5-bromo-2-fluorophenyl)-2,2-difluoroethylidene)-2-methylpropane-2-sulfinamide (14.49 g, 78.0% yield) was obtained as a yellow oil. MS (ISP): m/z=355.9 [M+H]$^+$ and 357.9 [M+2+H]$^+$.

The 1-(5-bromo-2-fluorophenyl)-2,2-difluoroethanone was obtained as follows:

A solution of diisopropylamine (12.7 g, 17.9 ml, 126 mmol) in tetrahydrofuran (375 ml) was cooled to −78° C. and n-butyllithium (1.6 M in hexane) (78.6 ml, 126 mmol) was added dropwise. After stirring for 10 minutes commercially available 1-bromo-4-fluorobenzene {CAS[460-00-4]} (20 g, 12.4 ml, 114 mmol) was added dropwise at max. −60° C. Stirring was continued at −70° C. for 2.5 hours. Then ethyl difluoroacetate (17.0 g, 13.7 ml, 137 mmol) was added dropwise. The mixture was warmed to −10° C. and then quenched by pouring the mixture onto 1 M hydrochloric acid. The mixture was extracted twice with ethyl acetate, dried over sodium sulphate, filtered and evaporated to give a yellow liquid (34 g; 118%). The residue was purified by chromatography on 200 g silica gel with a 3:1-mixture of cyclohexane and ethyl acetate as the eluent to give 1-(5-bromo-2-fluorophenyl)-2,2-difluoroethanone (26.5 g, 91.6% yield) as a yellow liquid. MS (EI): m/z=252.0 [M]$^+$ and 254.0 [M+2]$^+$.

Synthesis of the Intermediate Sulfinamide Esters A3

General Procedure (Via Reformatsky Reaction)

In a dry apparatus a suspension of freshly activated zinc powder (1.63 g, 24.9 mmol) in dry tetrahydrofuran (70 ml) was heated under an inert atmosphere to reflux. A solution of the sulfinyl imine A2 (24.9 mmol) and the bromo-acetate (24.9 mmol) in dry tetrahydrofuran (15 ml) was added dropwise over a period of 15 min and the suspension was heated to reflux for 5 hours. The cooled mixture was partitioned between aqueous saturated ammonium chloride and ethyl acetate, the organic layer was dried and evaporated. The crude material was purified by flash chromatography using heptane/ethyl acetate as the eluent to give the sulfinamide ester A3.

Intermediate A3.1

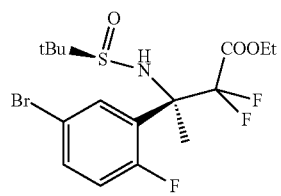 [SMILES: CCOC(=O)C(F)(F)[C@](C)(N[S@](=O)C(C)(C)C)c1cc(Br)ccc1F]

Starting from (R)-2-methyl-propane-2-sulfinic acid [1-(2-fluoro-5-bromo-phenyl)-(E)-ethylidene]-amide (intermediate A2.1) and ethyl 2-bromo-2,2-difluoroacetate, the product (3R)-ethyl 3-((R)-1,1-dimethylethylsulfinamido)-2,2-difluoro-3-(2-fluoro-5-bromo-phenyl)butanoate was obtained as an orange oil. MS (ISP): m/z=446.1 [M+H]$^+$.

Intermediate A3.2

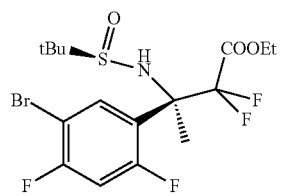 [SMILES: CCOC(=O)C(F)(F)[C@](C)(N[S@](=O)C(C)(C)C)c1cc(Br)c(F)cc1F]

Starting from (R)-2-methyl-propane-2-sulfinic acid [1-(5-bromo-2,4-difluoro-phenyl)-eth-(E)-ylidene]-amide (intermediate A2.2) and ethyl 2-bromo-2,2-difluoroacetate, the product (R)-3-(5-bromo-2,4-difluoro-phenyl)-2,2-difluoro-3-((R)-2-methyl-propane-2-sulfinylamino)-butyric acid ethyl ester was obtained as an orange oil. MS (ISP): m/z=462.1 [M+H]$^+$ and 464.1 [M+2+H]$^+$.

Intermediates A3.3 and A3.4

A3.3

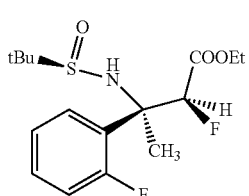

A3.4

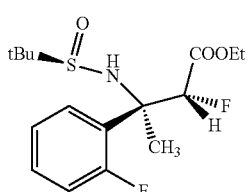

Starting from (R)-2-methyl-propane-2-sulfinic acid [1-(2-fluorophenyl)-(E)-ethylidene]-amide (intermediate A2.1)

and ethyl 2-bromo-2-fluoroacetate, the faster eluting minor isomer (2S,3R)-2-fluoro-3-(2-fluoro-phenyl)-3-((R)-2-methyl-propane-2-sulfinylamino)-butyric acid ethyl ester (intermediate A3.3) was obtained as a dark brown oil. MS (ISP): m/z=348.2 [M+H]$^+$.

The second fraction contained the slower eluting major isomer (2R,3R)-2-fluoro-3-(2-fluoro-phenyl)-β-(R)-2-methyl-propane-2-sulfinylamino)-butyric acid ethyl ester (intermediate A3.4) as a brown oil. MS (ISP): m/z=348.2 [M+H]$^+$.

Syntheses of the Intermediate Sulfinamide Esters A3.5 and A3.6

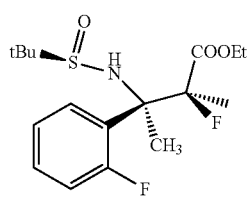

A3.5

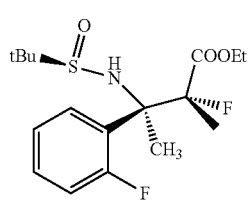

A3.6

In a dry apparatus under an inert atmosphere a solution of diisopropylamine (3.35 g, 101 mmol) in tetrahydrofuran (25 ml) was treated with n-butyl lithium (1.6M in hexane, 20.7 ml). The solution was stirred at −7° C. for 40 minutes. Thereafter, the solution was cooled to −75° C. and a solution of ethyl 2-fluoropropanoate (3.98 g, 33.2 mmol) in tetrahydrofuran (5 ml) was added dropwise. After 40 minutes a solution of chlorotitanium triisopropoxide (8.64 g, 33.2 mmol) in tetrahydrofuran (15 ml) was slowly added dropwise. After 40 minutes at −72° C. to the orange coloured solution was added dropwise a solution of (R)-2-methyl-propane-2-sulfinic acid [1-(2-fluorophenyl)-(E)-ethylidene]-amide (intermediate A2.3) (4.0 g, 16.6 mmol) in tetrahydrofuran (5 ml). Stirring was continued at −72° C. for 4 hours, then the reaction mixture was kept at −20° C. for 17 hours. For the workup, the reaction mixture was quenched with an aqueous solution of ammonium chloride (13%, 100 ml). The precipitate formed was diluted with water and the resulting mixture extracted three times with ethyl acetate. The organic layers were washed with brine, then combined, dried and evaporated at reduced pressure. Purification of the crude product by chromatography on silica gel using a 5:2-mixture auf heptane and ethyl acetate as the eluent yielded a 1:2-mixture of the (2S,3R)-2-fluoro-3-(2-fluoro-phenyl)-2-methyl-3-((R)-2-methyl-propane-2-sulfinylamino)-butyric acid ethyl ester (A3.5) and (2R,3R)-2-fluoro-3-(2-fluoro-phenyl)-2-methyl-3-((R)-2-methyl-propane-2-sulfinylamino)-butyric acid ethyl ester (A3.6) (4.43 g, 74%) as a light yellow oil. MS (ISP): m/z=362.2 [M+H]$^+$.

Intermediate A3.7 (Preparation in Analogy to A3.5)

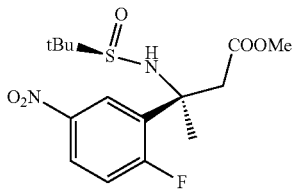 [SMILES: COC(=O)C[C@](C)(N[S@](=O)C(C)(C)C)c1cc([N+](=O)[O-])ccc1F]

Starting from (R)-2-methyl-propane-2-sulfinic acid [1-(2-fluoro-5-nitro-phenyl)-(E)-ethylidene]-amide (intermediate A2.4), the product (S)-3-(2-fluoro-5-nitro-phenyl)-3-((R)-2-methyl-propane-2-sulfinylamino)-butyric acid methyl ester was obtained as a yellow solid. MS (ISP): m/z=361.2 [M+H]$^+$.

Intermediate A3.8 (General Procedure Via Reformatsky Reaction)

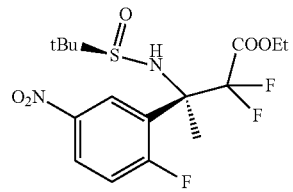 [SMILES: CCOC(=O)C(F)(F)[C@](C)(N[S@](=O)C(C)(C)C)c1cc([N+](=O)[O-])ccc1F]

Starting from (R)-2-methyl-propane-2-sulfinic acid [1-(2-fluoro-5-nitro-phenyl)-(E)-ethylidene]-amide (intermediate A2.4), the product (R)-2,2-difluoro-3-(2-fluoro-5-nitro-phenyl)-3-(R)-2-methyl-propane-2-sulfinylamino)-butyric acid ethyl ester was obtained as an orange oil. MS (ISP): m/z=411.2 [M+H]$^+$.

Intermediates A3.9 and A3.10 (General Procedure Via Reformatsky Reaction)

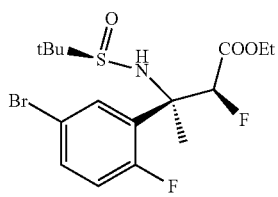

A3.9

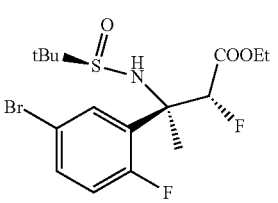

A3.10

Starting from (R)-2-methyl-propane-2-sulfinic acid [1-(2-fluoro-5-bromo-phenyl)-(E)-ethylidene]-amide (intermediate A2.5), the two epimeric products were obtained after chromatography: (2S,3R)-3-(5-bromo-2-fluoro-phenyl)-2-fluoro-3-((R)-2-methyl-propane-2-sulfinylamino)-butyric acid ethyl ester (4% yield) (A3.9) as the first eluting epimer, MS (ISP): m/z=426.0 [M+H]$^+$ and 428.1 [M+2+H]$^+$; (2R,3R)-3-(5-bromo-2-fluoro-phenyl)-2-fluoro-3-((R)-2-methyl-propane-2-sulfinylamino)-butyric acid ethyl ester (27% yield) (A3.10) as the second eluting epimer; and a mixture of the two epimers (21% yield), all fractions as pale yellow oils.

Synthesis of the Intermediate Sulfinamide Esters A3.11 and A3.12

Intermediate A3.11

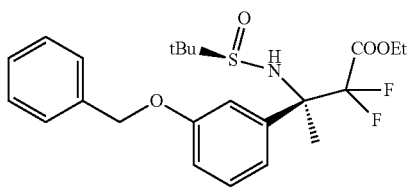 [SMILES: CCOC(=O)C(F)(F)[C@](C)(N[S@](=O)C(C)(C)C)c1cccc(OCc2ccccc2)c1]

Zinc (5.07 g, 77.5 mmol) and cuprous chloride (2.64 g, 25.8 mmol) were stirred in a dried apparatus and heated for 1 minute with a heat gun under a flow of argon. After cooling to room temperature, tetrahydrofuran (85.1 ml) was added. The reaction mixture was stirred in a 70° C. oil bath for 30 minutes, then cooled to room temperature. A solution of ethyl bromodifluoroacetate (13.5 g, 8.54 ml, 64.6 mmol) in tetrahydrofuran (25.5 ml) was added dropwise while maintaining the temperature between 26 and 29° C. After stirring for 10 minutes at 23° C., a solution of (R,E)-N-(1-(3-(benzyloxy)phenyl)ethylidene)-2-methylpropane-2-sulfinamide (intermediate A2.6) (8.51 g, 25.8 mmol) in tetrahydrofuran (25.5 ml) was added dropwise and stirring continued for 24 hours at room temperature. For the workup, the reaction mixture was cooled to 0° C. and ethanol (3 ml) was added dropwise. The mixture was filtered through a pad of Dicalite® and washed with ethyl acetate. The filtrate was concentrated at reduced pressure. The residue was taken in ethyl acetate (40 ml) and water was added. The emulsion was filtered again through a pad of Dicalite®. The layers were separated and the aqueous layer was extracted with ethyl acetate. The combined organic layers were dried over sodium sulphate and evaporated at reduced pressure. The crude product (13.7 g, yellow oil) was purified by chromatography on silica gel using a gradient of heptane/ethyl acetate=100:0 to 50:50 as the eluent. The (R)-3-(3-benzyloxy-phenyl)-2,2-difluoro-3-((R)-2-methyl-propane-2-sulfinylamino)-butyric acid ethyl ester (7.72 g, 66% yield) was obtained as a yellow oil. MS (ISP): m/z=454.2 [M+H]$^+$.

Intermediate A3.12

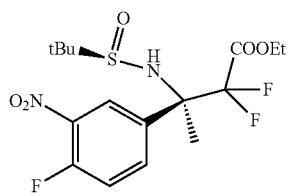 [SMILES: CCOC(=O)C(F)(F)[C@](C)(N[S@](=O)C(C)(C)C)c1ccc(F)c([N+](=O)[O-])c1]

Starting from (R)-2-methyl-propane-2-sulfinic acid [1-(4-fluoro-3-nitro-phenyl)-eth-(E)-ylidene]-amide (intermediate A2.7), the product (R)-2,2-difluoro-3-(4-fluoro-3-nitro-phenyl)-3-((R)-2-methyl-propane-2-sulfinylamino)-butyric acid ethyl ester was obtained as a pale yellow solid. MS (ISP): m/z=411.2 [M+H]$^+$.

Intermediate A3.13

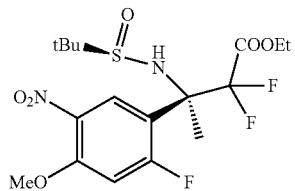 [SMILES: CCOC(=O)C(F)(F)[C@](C)(N[S@](=O)C(C)(C)C)c1cc([N+](=O)[O-])c(OC)cc1F]

Starting from (R)-2-methyl-propane-2-sulfinic acid [1-(2-fluoro-4-methoxy-5-nitro-phenyl)-eth-(E)-ylidene]-amide (intermediate A2.8), the product (R)-2,2-difluoro-3-(2-fluoro-4-methoxy-5-nitro-phenyl)-3-((R)-2-methyl-propane-2-sulfinylamino)-butyric acid ethyl ester was obtained as a red oil. MS (ISP): m/z=441.2 [M+H]$^+$.

Syntheses of the Intermediate Sulfinamide Esters A3.14

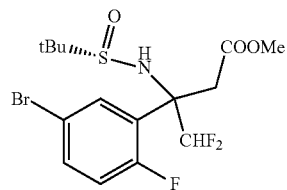

A solution of diisopropylamine (6.52 g, 9.19 ml, 64.5 mmol) in tetrahydrofuran (115 ml) was treated dropwise at −70° C. with n-butylithium (1.6 M in hexane) (40.3 ml, 64.5 mmol) and stirring was continued for 15 minutes at −70° C. The solution was treated with methyl acetate (4.77 g, 5.13 ml, 64.5 mmol) and after 30 minutes chlorotitanium triisopropoxide (0.85 M in tetrahydrofuran) (85.7 ml, 72.85 mmol) was added dropwise After stirring at −70° C. for 30 min., the mixture was treated with a solution of (S,E)-N-(1-(5-bromo-2-fluorophenyl)-2,2-difluoroethylidene)-2-methylpropane-2-sulfinamide (intermediate A2.9) (8.2 g, 23.0 mmol) in tetrahydrofuran (76.4 ml) and stirring was continued at −70° C. for 2 hours. For the workup, the mixture was quenched with a saturated aqueous solution of ammonium chloride (100 ml), diluted with ethyl acetate (200 ml). After filtration over Dicalite®, the organic layer was separated and washed with water and brine. The aqueous layers were re-extracted with ethyl acetate. The combined organic layers were dried over sodium sulphate, filtered and evaporated to give a yellow oil (11.5 g; 116%). The residue was purified by chromatography on 50 g silica gel using a gradient of ethyl acetate/heptane=0:100 to 50:50 as the eluent to give a 1:1 diastereomeric mixture of methyl 3-(5-bromo-2-fluorophenyl)-3-((S)-1,1-dimethylethylsulfinamido)-4,4-difluorobutanoate (7 g, 16.3 mmol, 70.7% yield) as a colorless oil. MS (ISP): m/z=430.2 [M+H]$^+$ and 432.1 [M+2+H]$^+$.

Syntheses of the Intermediate Sulfinamide Esters A3.15 and A3.16

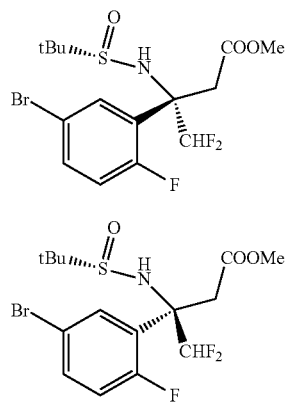

Chiral separation of methyl 3-(5-bromo-2-fluorophenyl)-3-((S)-1,1-dimethylethylsulfinamido)-4,4-difluorobutanoate (3.8 g, 8.83 mmol) (intermediate A3.14) by preparative chiral HPLC on Reprosil Chiral NR column with a mixture of 5% ethanol/n-heptane as the eluent yielded the (S)-methyl 3-(5-bromo-2-fluorophenyl)-3-((S)-1,1-dimethylethylsulfinamido)-4,4-difluorobutanoate (1.55 g, 40.8% yield) (intermediate A3.15) as a colorless oil and the (R)-methyl 3-(5-bromo-2-fluorophenyl)-3-((S)-1,1-dimethylethylsulfinamido)-4,4-difluorobutanoate (1.65 g, 43.4% yield)) (intermediate A3.15) as a colorless oil.

Synthesis of the Intermediate Sulfinamide Alcohols A4

General Procedure

A solution of the sulfinamide ester A3 (12.7 mmol) in dry tetrahydrofuran (50 ml) was treated at 0° C. with lithium borohydride (25.3 mmol) and stirring was continued at 0° C. for 4 h. The reaction mixture was quenched by addition of acetic acid (2 ml) and water (50 ml), extracted with ethyl acetate and the organic layer was dried and evaporated. The residue was purified by chromatography on silica using a mixture of n-heptane and ethyl acetate as the eluent to give the pure intermediate sulfinamide alcohol A4.

Intermediate A4.1

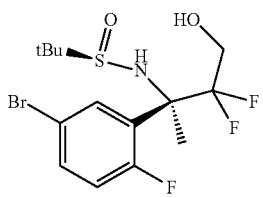 [SMILES: CC(C)(C)[S@@](=O)N[C@](C)(c1cc(Br)ccc1F)C(F)(F)CO]

Starting from (3R)-ethyl 3-((R)-1,1-dimethylethylsulfinamido)-2,2-difluoro-3-(2-fluoro-5-bromo-phenyl)butanoate (intermediate A3.1), the product (R)-2-methyl-propane-2-sulfinic acid [(R)-1-(5-bromo-2-fluoro-phenyl)-2,2-difluoro-3-hydroxy-1-methyl-propyl]-amide was obtained as a colorless solid. MS (ISP): m/z=402.2 [M+H]+.

Intermediate A4.2

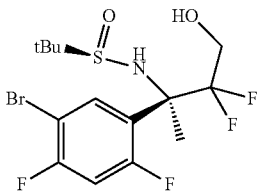 [SMILES: CC(C)(C)[S@@](=O)N[C@](C)(c1cc(Br)c(F)cc1F)C(F)(F)CO]

Starting from (R)-3-(5-bromo-2,4-difluoro-phenyl)-2,2-difluoro-3-((R)-2-methyl-propane-2-sulfinylamino)-butyric acid ethyl ester (intermediate A3.2), the product (R)-2-methyl-propane-2-sulfinic acid [(R)-1-(5-bromo-2,4-difluoro-phenyl)-2,2-difluoro-3-hydroxy-1-methyl-propyl]-amide. MS (ISP): m/z=420.0 [M+H]+ and 422.0 [M+2+H]+.

Intermediate A4.3

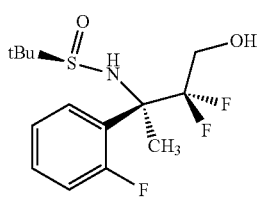

Starting from (2S,3R)-2-fluoro-3-(2-fluoro-phenyl)-3-((R)-2-methyl-propane-2-sulfinylamino)-butyric acid ethyl ester (intermediate A3.3), the (R)-2-methyl-propane-2-sulfinic acid [(1R,2S)-2-fluoro-1-(2-fluoro-phenyl)-3-hydroxy-1-methyl-propyl]-amide was obtained as a colorless viscous oil. MS (ISP): m/z=306.1 [M+H]+.

Intermediate A4.4

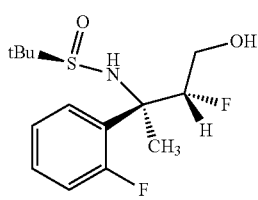

Starting from (2R,3R)-2-fluoro-3-(2-fluoro-phenyl)-β-(R)-2-methyl-propane-2-sulfinylamino)-butyric acid ethyl ester (intermediate A3.4), the (R)-2-methyl-propane-2-sulfinic acid [(1R,2R)-2-fluoro-1-(2-fluoro-phenyl)-3-hydroxy-1-methyl-propyl]-amide was obtained as pale red crystals. MS (ISP): m/z=306.1 [M+H]+.

Alternatively, the two epimers A4.3 and A4.4 can be obtained by reduction of their mixture as described above followed by separation on chiral HPLC (Chirapak AD) where A4.3 is the second eluting epimer, A4.4 the first eluting epimer.

Intermediate A4.5

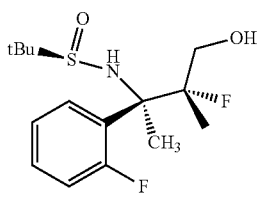 [SMILES: CC(C)(C)[S@@](=O)N[C@](C)(c1ccccc1F)[C@@](C)(F)CO]

Starting from the 1:2-mixture of the (2S,3R)-2-fluoro-3-(2-fluoro-phenyl)-2-methyl-3-((R)-2-methyl-propane-2-sulfinylamino)-butyric acid ethyl ester (intermediate A3.5) and (2R,3R)-2-fluoro-3-(2-fluoro-phenyl)-2-methyl-3-((R)-2-methyl-propane-2-sulfinylamino)-butyric acid ethyl ester (intermediate A3.6), the (R)-2-methyl-propane-2-sulfinic acid [(1R,2R)-2-fluoro-1-(2-fluoro-phenyl)-3-hydroxy-1,2-dimethyl-propyl]-amide (intermediate A4.5) was obtained as a white solid. MS (ISP): m/z=320.1 [M+H]$^+$. The minor isomer was not isolated.

Intermediate A4.6

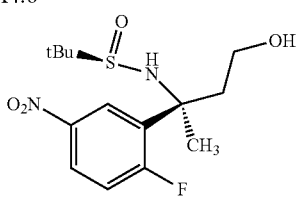

Starting from (S)-3-(2-fluoro-5-nitro-phenyl)-3-((R)-2-methyl-propane-2-sulfinylamino)-butyric acid methyl ester (intermediate A3.7), the product (R)-2-methyl-propane-2-sulfinic acid [(S)-1-(2-fluoro-5-nitro-phenyl)-3-hydroxy-1-methyl-propyl]-amide was obtained as a light yellow solid. MS (ISP): m/z=333.3 [M+H]$^+$.

Intermediate A4.7

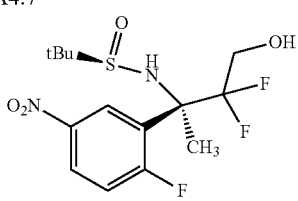

Starting from (R)-2,2-difluoro-3-(2-fluoro-5-nitro-phenyl)-3-((R)-2-methyl-propane-2-sulfinylamino)-butyric acid ethyl ester (intermediate A3.8), the product (R)-2-methyl-propane-2-sulfinic acid [(R)-2,2-difluoro-1-(2-fluoro-5-nitro-phenyl)-3-hydroxy-1-methyl-propyl]-amide was obtained as a light yellow solid. MS (ISP): m/z=369.0 [M+H]$^+$.

Intermediate A4.8

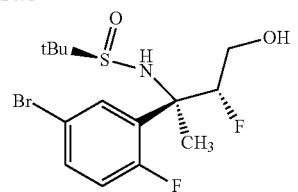 [SMILES: CC(C)(C)[S@@](=O)N[C@](C)(c1cc(Br)ccc1F)[C@@H](F)CO]

Starting from (2R,3R)-3-(5-bromo-2-fluoro-phenyl)-2-fluoro-3-((R)-2-methyl-propane-2-sulfinylamino)-butyric acid ethyl ester (intermediate A3.10), the product (R)-2-methyl-propane-2-sulfinic acid [(1R,2R)-1-(5-bromo-2-fluoro-phenyl)-2-fluoro-3-hydroxy-1-methyl-propyl]-amide was obtained as a white foam. MS (ISP): m/z=384.1 [M+H]$^+$ and 386.3 [M+2+H]$^+$.

Intermediate A4.9

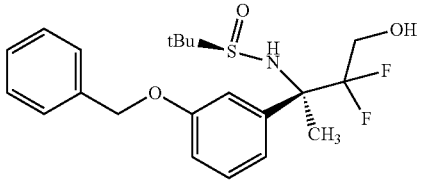 [SMILES: CC(C)(C)[S@@](=O)N[C@](C)(c1cccc(OCc2ccccc2)c1)C(F)(F)CO]

Starting from (R)-3-(3-benzyloxy-phenyl)-2,2-difluoro-3-((R)-2-methyl-propane-2-sulfinylamino)-butyric acid ethyl ester (intermediate A3.11), the product (R)-2-methyl-propane-2-sulfinic acid [(R)-1-(3-benzyloxy-phenyl)-2,2-difluoro-3-hydroxy-1-methyl-propyl]-amide was obtained as a white solid. MS (ISP): m/z=412.3 [M+H]$^+$.

Intermediate A4.10

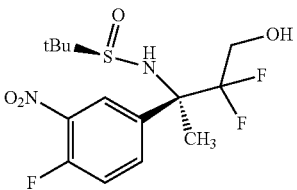 [SMILES: CC(C)(C)[S@@](=O)N[C@](C)(c1ccc(F)c([N+](=O)[O-])c1)C(F)(F)CO]

Starting from (R)-2,2-difluoro-3-(4-fluoro-3-nitro-phenyl)-3-((R)-2-methyl-propane-2-sulfinylamino)-butyric acid ethyl ester (intermediate A3.12), the product (R)-2-methyl-propane-2-sulfinic acid [(R)-2,2-difluoro-1-(4-fluoro-3-nitro-phenyl)-3-hydroxy-1-methyl-propyl]-amide was obtained as an off-white solid. MS (ISP): m/z=369.1 [M+H]$^+$.

Intermediate A4.11

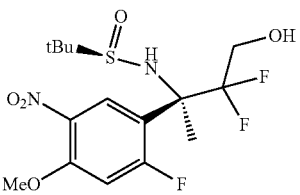 [SMILES: COc1cc(F)c([C@@](C)(N[S@](=O)C(C)(C)C)C(F)(F)CO)cc1[N+](=O)[O-]]

Starting from (R)-2,2-difluoro-3-(2-fluoro-4-methoxy-5-nitro-phenyl)-3-(R)-2-methyl-propane-2-sulfinylamino)-butyric acid ethyl ester (intermediate A3.13), the product (R)-2-methyl-propane-2-sulfinic acid [(R)-2,2-difluoro-1-(2-fluoro-4-methoxy-5-nitro-phenyl)-3-hydroxy-1-methyl-propyl]-amide was obtained as a yellow solid. MS (ISP): m/z=399.1 [M+H]$^+$.

Intermediate A4.12

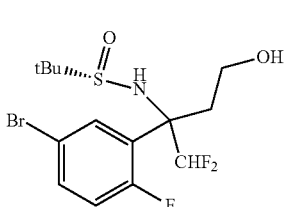

A4.12

Starting from methyl 3-(5-bromo-2-fluorophenyl)-3-((S)-1,1-dimethylethylsulfinamido)-4,4-difluorobutanoate (intermediate A3.14), the product (S)-N-(2-(5-bromo-2-fluorophenyl)-1,1-difluoro-4-hydroxybutan-2-yl)-2-methylpropane-2-sulfinamide was obtained as a colorless oil. MS (ISP): m/z=402.0 [M+H]$^+$ and 404.0 [M+2+H]$^+$.

Synthesis of the Intermediate Sulfinamide Alcohols B1

Intermediate B1.1

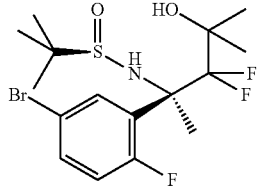 [SMILES: CC(C)(C)[S@@](=O)N[C@](C)(c1cc(Br)ccc1F)C(F)(F)C(C)(C)O]

A solution of (R)-ethyl 3-(5-bromo-2-fluorophenyl)-3-((R)-1,1-dimethylethylsulfinamido)-2,2-difluorobutanoate (intermediate A3.1) (10.5 g, 23.6 mmol) in anhydrous tetrahydrofuran (150 ml) was cooled to −78° C. and was treated dropwise with a solution of methylmagnesium bromide (3.2 M in 2-methyl-tetrahydrofuran; 59.1 ml, 189 mmol). The cooling bath was removed, and the mixture was stirred at 23° C. for 18 hours. For the workup, the reaction mixture was poured cautiously into a saturated solution of ammonium chloride and extracted with ethyl acetate. The organic layer was washed with brine and dried over sodium sulphate. Removal of the solvent in vacuum left the (R)-N-((R)-2-(5-bromo-2-fluorophenyl)-3,3-difluoro-4-hydroxy-4-methyl-pentan-2-yl)-2-methylpropane-2-sulfinamide (10.565 g, 23.6 mmol, 99.7% yield) as a yellow gum, which was used in the next step without further purification. MS (ISP): m/z=430.1 [(M+H)$^+$] and 432.1 [(M+2H)$^+$].

Synthesis of the Intermediate Amino Alcohols A5 or B2

General Procedure:

A solution of the sulfinamide alcohols A4 or B1 (10.3 mmol) in methanol or tetrahydrofuran (30 to 60 ml) was treated with a solution of hydrochloric acid in 1,4-dioxane (4 M, 10-13 ml) and stirring was continued at 23° C. for 2 to 18 h. The mixture was partitioned between ethyl acetate and an aqueous solution of sodium carbonate (2 M), the organic layer was dried over sodium sulphate, filtered and evaporated to give a residue which was purified by chromatography on silica using a mixture of n-heptane and ethyl acetate as the eluent to give the pure aminoalcohols A5 or B2.

Intermediate Amino Alcohol A5.1

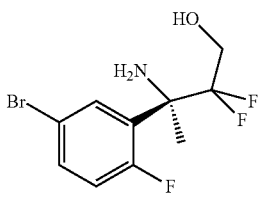 [SMILES: C[C@@](N)(c1cc(Br)ccc1F)C(F)(F)CO]

Starting from (R)-2-methyl-propane-2-sulfinic acid [(R)-1-(5-bromo-2-fluoro-phenyl)-2,2-difluoro-3-hydroxy-1-methyl-propyl]-amide (intermediate A4.1) the product (R)-3-amino-3-(5-bromo-2-fluoro-phenyl)-2,2-difluoro-butan-1-ol was obtained as a light brown oil. MS (ISP): m/z=298.2 [M+H]$^+$ and 300.2 [M+2H]$^+$.

Intermediate Amino Alcohol A5.2

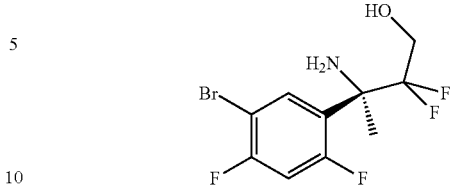

Starting from (R)-2-methyl-propane-2-sulfinic acid [(R)-1-(5-bromo-2,4-difluoro-phenyl)-2,2-difluoro-3-hydroxy-1-methyl-propyl]-amide (intermediate A4.2) the product (R)-3-amino-3-(5-bromo-2,4-difluoro-phenyl)-2,2-difluoro-butan-1-ol was obtained as a colorless waxy solid. MS (ISP): m/z=315.9 [M+H]$^+$ and 317.9 [M+2H]$^+$.

Intermediate Amino Alcohol A5.3

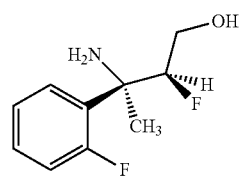

Starting from (R)-2-methyl-propane-2-sulfinic acid [(1R, 2S)-2-fluoro-1-(2-fluoro-phenyl)-3-hydroxy-1-methyl-propyl]-amide (intermediate A4.3), the (2S,3R)-3-amino-2-fluoro-3-(2-fluoro-phenyl)-butan-1-ol (98% yield) was obtained as a colorless oil. MS (ISP): m/z=202.3 [M+H]$^+$.

Intermediate Amino Alcohol A5.4

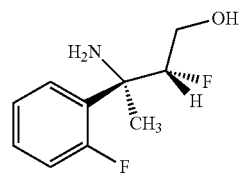

Starting from (R)-2-methyl-propane-2-sulfinic acid [(1R, 2R)-2-fluoro-1-(2-fluoro-phenyl)-3-hydroxy-1-methyl-propyl]-amide (intermediate A4.4), the (2R,3R)-3-amino-2-fluoro-3-(2-fluoro-phenyl)-butan-1-ol (95% yield) was obtained as a light brown oil. MS (ISP): m/z=202.2 [M+H]$^+$.

Intermediate Amino Alcohol A5.5

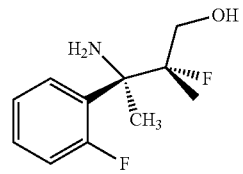

Starting from (R)-2-methyl-propane-2-sulfinic acid [(1R, 2R)-2-fluoro-1-(2-fluoro-phenyl)-3-hydroxy-1,2-dimethyl-propyl]-amide (intermediate A4.5), the (2R,3R)-3-amino-2-fluoro-3-(2-fluoro-phenyl)-2-methyl-butan-1-ol was obtained as a colorless oil. MS (ISP): m/z=216.3 [M+H]$^+$.

Intermediate Amino Alcohol A5.6

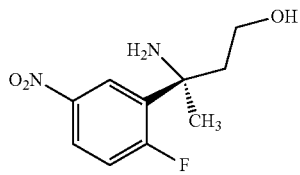 [SMILES: C[C@](N)(CCO)c1cc([N+](=O)[O-])ccc1F]

Starting from (R)-2-methyl-propane-2-sulfinic acid [(S)-1-(2-fluoro-5-nitro-phenyl)-3-hydroxy-1-methyl-propyl]-amide (intermediate A4.6), the product (S)-3-amino-3-(2-fluoro-5-nitro-phenyl)-butan-1-ol was obtained as a yellow solid. MS (ISP): m/z=229.2 [M+H]$^+$.

Intermediate Amino Alcohol A5.7

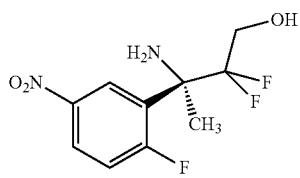 [SMILES: C[C@@](N)(c1cc([N+](=O)[O-])ccc1F)C(F)(F)CO]

Starting from (R)-2-methyl-propane-2-sulfinic acid [(R)-2,2-difluoro-1-(2-fluoro-5-nitro-phenyl)-3-hydroxy-1-methyl-propyl]-amide (intermediate A4.7), the product (R)-3-amino-2,2-difluoro-3-(2-fluoro-5-nitro-phenyl)-butan-1-ol (2.5 g) was obtained as a light yellow solid. MS (ISP): m/z=265.1 [M+H]$^+$.

Intermediate Amino Alcohol A5.8

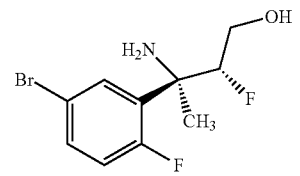

Starting from (R)-2-methyl-propane-2-sulfinic acid [(1R,2R)-1-(5-bromo-2-fluoro-phenyl)-2-fluoro-3-hydroxy-1-methyl-propyl]-amide (intermediate A4.8), the product (2R,3R)-3-amino-3-(5-bromo-2-fluoro-phenyl)-2-fluoro-butan-1-ol was obtained as a colorless oil. MS (ISP): m/z=280.0 [M+H]$^+$ and 282.0 [M+2+H]$^+$.

Intermediate Amino Alcohol A5.9

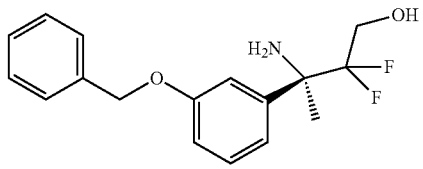 [SMILES: C[C@@](N)(c1cccc(OCc2ccccc2)c1)C(F)(F)CO]

Starting from (R)-2-methyl-propane-2-sulfinic acid [(R)-1-(3-benzyloxy-phenyl)-2,2-difluoro-3-hydroxy-1-methyl-propyl]amide (intermediate A4.9), the product (R)-3-amino-3-(3-benzyloxy-phenyl)-2,2-difluoro-butan-1-ol was obtained as a pale yellow oil. MS (ISP): m/z=308.2 [M+H]$^+$.

Intermediate Amino Alcohol A5.10

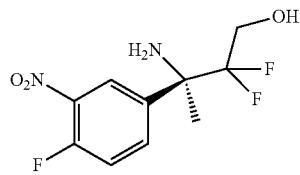 [SMILES: C[C@@](N)(c1ccc(F)c([N+](=O)[O-])c1)C(F)(F)CO]

Starting from (R)-2-methyl-propane-2-sulfinic acid [(R)-2,2-difluoro-1-(4-fluoro-3-nitro-phenyl)-3-hydroxy-1-methyl-propyl]-amide (intermediate A4.10), the product (R)-3-amino-2,2-difluoro-3-(4-fluoro-3-nitro-phenyl)-butan-1-ol was obtained as a colorless oil. MS (ISP): m/z=265.1 [M+H]$^+$.

Intermediate Amino Alcohol A5.11

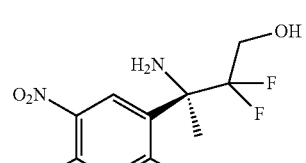

Starting from (R)-2-methyl-propane-2-sulfinic acid [(R)-2,2-difluoro-1-(2-fluoro-4-methoxy-5-nitro-phenyl)-3-hydroxy-1-methyl-propyl]-amide (intermediate A4.11), the product (R)-3-amino-2,2-difluoro-3-(2-fluoro-4-methoxy-5-nitro-phenyl)-butan-1-ol was obtained as a yellow solid. MS (ISP): m/z=259.2 [M+H]$^+$.

Intermediate A5.12

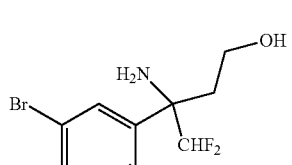

Starting from (S)-N-(2-(5-bromo-2-fluorophenyl)-1,1-difluoro-4-hydroxybutan-2-yl)-2-methylpropane-2-sulfinamide (intermediate A4.12) the product 3-amino-3-(5-bromo-2-fluorophenyl)-4,4-difluorobutan-1-ol was obtained as a colorless oil. MS (ISP): m/z=298.1 [M+H]$^+$ and 300.1 [M+2+H]$^+$.

Intermediate Amino Alcohol B2.1

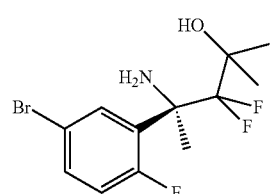

Starting from (R)-2-methyl-propane-2-sulfinic acid [(R)-1-(5-bromo-2-fluoro-phenyl)-2,2-difluoro-3-hydroxy-1,3-dimethyl-butyl]-amide (intermediate B1.1), the product (R)-4-amino-4-(5-bromo-2-fluoro-phenyl)-3,3-difluoro-2- methyl-pentan-2-ol was obtained as a white solid. MS (ISP): m/z=326.2 [M+H]⁺ and 328.2 [M+2+H]⁺.

Syntheses of the Intermediate Amino Oxazines A6 and B3

General Procedure

A dried tube was charged with a mixture of the amino alcohol A5 or B2 (18.8 mmol), cyanogen bromide (33.9 mmol) and ethanol (61 ml). The tube was sealed and heated at 90° C. for 16 hours. For the workup, the reaction mixture was cooled and evaporated at reduced pressure. The residue was partitioned between ethyl acetate (150 ml) and a saturated aqueous solution of sodium carbonate (50 ml). The aqueous layer was separated and re-extracted with ethyl acetate (2×50 ml). The organic layers were washed with brine (50 ml), then combined, dried over sodium sulphate and evaporated at reduced pressure. The product was used in the next step without further purification.

Intermediate Amino Oxazine A6.1

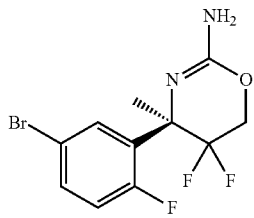 [SMILES: C[C@]1(c2cc(Br)ccc2F)N=C(N)OCC1(F)F]

Starting from (R)-3-amino-3-(5-bromo-2-fluoro-phenyl)-2,2-difluoro-butan-1-ol (intermediate A5.1) the product (R)-4-(5-bromo-2-fluoro-phenyl)-5,5-difluoro-4-methyl-5,6-dihydro-4H-[1,3]oxazin-2-ylamine was obtained as a light yellow oil. MS (ISP): m/z=323.1 [M+H]⁺ and 325.1 [M+2+H]⁺.

Intermediate Amino Oxazine A6.2

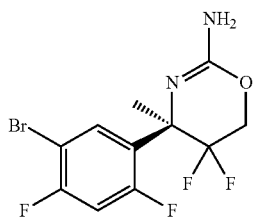 [SMILES: C[C@]1(c2cc(Br)c(F)cc2F)N=C(N)OCC1(F)F]

Starting from (R)-3-amino-3-(5-bromo-2,4-difluoro-phenyl)-2,2-difluoro-butan-1-ol (intermediate A5.2) the product (R)-4-(5-bromo-2,4-difluoro-phenyl)-5,5-difluoro-4-methyl-5,6-dihydro-4H-[1,3]oxazin-2-ylamine was obtained as a light yellow foam. MS (ISP): m/z=341.0 [M+H]⁺ and 342.9 [M+2+H]⁺.

Intermediate Amino Oxazine A6.3

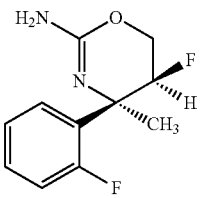 [SMILES: C[C@]1(c2ccccc2F)N=C(N)OC[C@H]1F]

Starting from (2S,3R)-3-amino-2-fluoro-3-(2-fluoro-phenyl)-butan-1-ol (intermediate A5.3), the (4R,5S)-5-fluoro-4-(2-fluoro-phenyl)-4-methyl-5,6-dihydro-4H-[1,3]oxazin-2-ylamine was obtained as a colorless viscous oil. MS (ISP): m/z=227.2 [M+H]⁺.

Intermediate Amino Oxazine A6.4

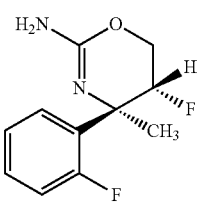 [SMILES: C[C@]1(c2ccccc2F)N=C(N)OC[C@@H]1F]

Starting from (2R,3R)-3-amino-2-fluoro-3-(2-fluoro-phenyl)-butan-1-ol (intermediate A5.4), the (4R,5R)-5-fluoro-4-(2-fluoro-phenyl)-4-methyl-5,6-dihydro-4H-[1,3]oxazin-2-ylamine was obtained as a light yellow solid. MS (ISP): m/z=227.2 [M+H]⁺.

Intermediate Amino Oxazine A6.5

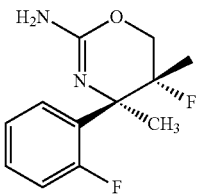 [SMILES: C[C@]1(F)COC(N)=N[C@]1(C)c1ccccc1F]

Starting from (2R,3R)-3-amino-2-fluoro-3-(2-fluoro-phenyl)-2-methyl-butan-1-ol (intermediate A5.5), the (4R,5R)-5-fluoro-4-(2-fluoro-phenyl)-4,5-dimethyl-5,6-dihydro-4H-[1,3]oxazin-2-ylamine was obtained as a white solid. MS (ISP): m/z=241.2 [M+H]⁺.

Intermediate Amino Oxazine A6.6

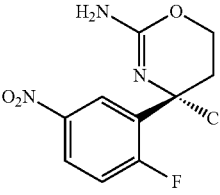

Starting from (S)-3-amino-3-(2-fluoro-5-nitro-phenyl)-butan-1-ol (intermediate A5.6), the product (S)-4-(2-fluoro-5-nitro-phenyl)-4-methyl-5,6-dihydro-4H-[1,3]oxazin-2-ylamine was obtained as a yellow solid. MS (ISP): m/z=254.2 [M+H]⁺.

Intermediate Amino Oxazine A6.7

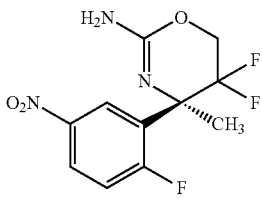 [SMILES: C[C@]1(c2cc([N+](=O)[O-])ccc2F)N=C(N)OCC1(F)F]

Starting from (R)-3-amino-2,2-difluoro-3-(2-fluoro-5-nitro-phenyl)-butan-1-ol (intermediate A5.7), the product (R)-5,5-difluoro-4-(2-fluoro-5-nitro-phenyl)-4-methyl-5,6-dihydro-4H-[1,3]oxazin-2-ylamine was obtained as a light yellow solid. MS (ISP): m/z=290.2 [M+H]$^+$.

Intermediate Amino Oxazine A6.8

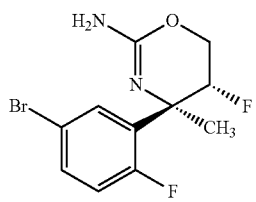

Starting from (2R,3R)-3-amino-3-(5-bromo-2-fluoro-phenyl)-2-fluoro-butan-1-ol (intermediate A5.8), the product (4R,5R)-4-(5-bromo-2-fluoro-phenyl)-5-fluoro-4-methyl-5,6-dihydro-4H-[1,3]oxazin-2-ylamine was obtained as a pale yellow solid. MS (ISP): m/z=305.0 [M+H]$^+$ and 307.0 [M+2+H]$^+$.

Intermediate Amino Oxazine A6.9

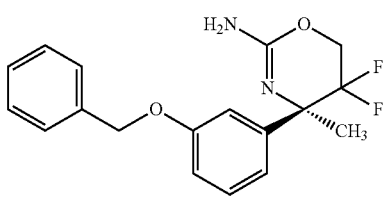 [SMILES: C[C@]1(c2cccc(OCc3ccccc3)c2)N=C(N)OCC1(F)F]

Starting from (R)-3-amino-3-(3-benzyloxy-phenyl)-2,2-difluoro-butan-1-ol (intermediate A5.9), the product (R)-4-(3-benzyloxy-phenyl)-5,5-difluoro-4-methyl-5,6-dihydro-4H-[1,3]oxazin-2-ylamine was obtained as a yellow oil. MS (ISP): m/z=333.3 [M+H]$^+$.

Intermediate Amino Oxazine A6.10

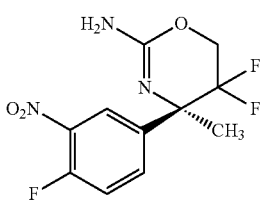 [SMILES: C[C@]1(c2ccc(F)c([N+](=O)[O-])c2)N=C(N)OCC1(F)F]

Starting from (R)-3-amino-2,2-difluoro-3-(4-fluoro-3-nitro-phenyl)-butan-1-ol (intermediate A5.10); the product (R)-5,5-difluoro-4-(4-fluoro-3-nitro-phenyl)-4-methyl-5,6-dihydro-4H-[1,3]oxazin-2-ylamine was obtained as a pale yellow solid. MS (ISP): m/z=290.1 [M+H]$^+$.

Intermediate Amino Oxazine A6.11

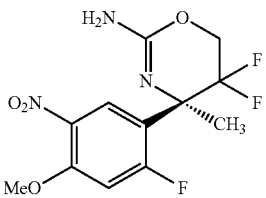 [SMILES: COc1cc(F)c([C@@]2(C)N=C(N)OCC2(F)F)cc1[N+](=O)[O-]]

Starting from (R)-3-amino-2,2-difluoro-3-(2-fluoro-4-methoxy-5-nitro-phenyl)-butan-1-ol (intermediate A5.11), the product (R)-5,5-difluoro-4-(2-fluoro-4-methoxy-5-nitro-phenyl)-4-methyl-5,6-dihydro-4H-[1,3]oxazin-2-ylamine was obtained as a yellow solid. MS (ISP): m/z=320.1 [M+H]$^+$.

Intermediate A6.12

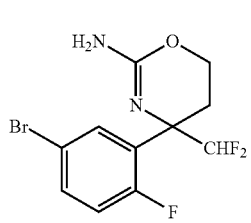

A6.12

Starting from 3-amino-3-(5-bromo-2-fluorophenyl)-4,4-difluorobutan-1-ol (intermediate A5.12) the product 4-(5-bromo-2-fluorophenyl)-4-(difluoromethyl)-5,6-dihydro-4H-1,3-oxazin-2-amine was obtained as a white solid. MS (ISP): m/z=322.9 [M+H]$^+$ and 325.0 [M+2+H]$^+$.

Intermediate Amino Oxazine B3.1

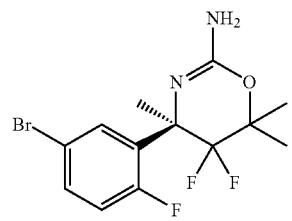 [SMILES: CC1(C)OC(N)=N[C@](C)(c2cc(Br)ccc2F)C1(F)F]

Starting from (R)-4-amino-4-(5-bromo-2-fluoro-phenyl)-3,3-difluoro-2-methyl-pentan-2-ol (intermediate B2.1), the product (R)-4-(5-bromo-2-fluoro-phenyl)-5,5-difluoro-4,6,6-trimethyl-5,6-dihydro-4H-[1,3]oxazin-2-ylamine was obtained as a colorless oil. MS (ISP): m/z=351.1 [M+H]$^+$ and 353.1 [M+2+H]$^+$.

Syntheses of the Intermediate Nitro Oxazines A7

General Procedure

A dispersion of the amino oxazine A6 (2.8 mmol) in sulfuric acid (22.1 g, 216 mmol) was cooled to 0° C. and stirring was continued until a complete solution was obtained. At 0° C. fuming nitric acid (300 mg, 214 µl, 4.29 mmol) was added dropwise in 4 portions. After complete addition, the ice bath was removed and stirring continued for 30 minutes at room temperature. For the workup, the solution was added dropwise to a mixture of crushed ice (50 g) and water (50 g). With an aqueous solution of sodium hydroxide the pH was adjusted to 7-8. The aqueous layer was extracted twice with ethyl acetate, thereafter the combined organic layers were washed with brine, then dried over sodium sulphate and evaporated at reduced pressure. The product was engaged in the step without further purification.
Intermediate Nitro Oxazine A7.1

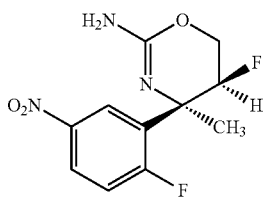 [SMILES: C[C@]1(c2cc([N+](=O)[O-])ccc2F)N=C(N)OC[C@H]1F]

Starting from (4R,5S)-5-fluoro-4-(2-fluoro-phenyl)-4-methyl-5,6-dihydro-4H-[1,3]oxazin-2-ylamine (intermediate A6.3), the product (4R,5S)-5-fluoro-4-(2-fluoro-5-nitro-phenyl)-4-methyl-5,6-dihydro-4H-[1,3]oxazin-2-ylamine was obtained as light yellow foam. MS (ISP): m/z=272.1 [M+H]$^+$.
Intermediate Nitro Oxazine A7.2

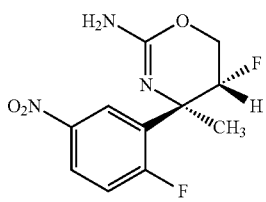 [SMILES: C[C@]1(c2cc([N+](=O)[O-])ccc2F)N=C(N)OC[C@@H]1F]

Starting from (4R,5R)-5-fluoro-4-(2-fluoro-phenyl)-4-methyl-5,6-dihydro-4H-[1,3]oxazin-2-ylamine (intermediate A6.4), the product (4R,5R)-5-fluoro-4-(2-fluoro-5-nitro-phenyl)-4-methyl-5,6-dihydro-4H-[1,3]oxazin-2-ylamine was obtained as a white foam. MS (ISP): m/z=272.3 [M+H]$^+$.
Intermediate nitro oxazine A7.3

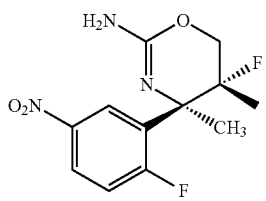 [SMILES: C[C@]1(F)COC(N)=N[C@]1(C)c1cc([N+](=O)[O-])ccc1F]

Starting from (4R,5R)-5-fluoro-4-(2-fluoro-phenyl)-4,5-dimethyl-5,6-dihydro-4H-[1,3]oxazin-2-ylamine (intermediate A6.5), the product (4R,5R)-5-fluoro-4-(2-fluoro-5-nitro-phenyl)-4,5-dimethyl-5,6-dihydro-4H-[1,3]oxazin-2-ylamine was obtained as a pale yellow oil. MS (ISP): m/z=286.1 [M+H]$^+$.

Syntheses of the Intermediate Anilines A8

General Procedure

A solution of the nitro oxazine A7 (3 mmol) in ethanol (31 ml) was hydrogenated at atmospheric pressure using palladium (10% on carbon) (159 mg, 150 µmol) as the catalyst. After 90 minutes the reaction was complete. The reaction mixture was filtrated over a layer of Dicalite®, which was washed with ethanol (3×20 ml). The combined solutions of ethanol were evaporated at reduced pressure. The product was engaged in the step without further purification.
Intermediate Aniline A8.1

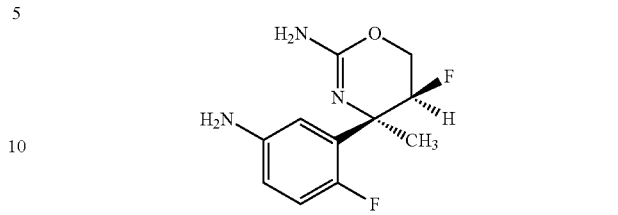

Starting from (4R,5S)-5-fluoro-4-(2-fluoro-5-nitro-phenyl)-4-methyl-5,6-dihydro-4H-[1,3]oxazin-2-ylamine (intermediate A7.1), the product (4R,5S)-4-(5-amino-2-fluoro-phenyl)-5-fluoro-4-methyl-5,6-dihydro-4H-[1,3]oxazin-2-ylamine was obtained as white foam. MS (ISP): m/z=242.2 [M+H]$^+$.
Intermediate aniline A8.2

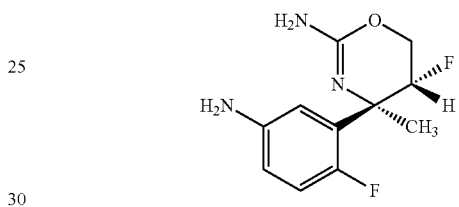

Starting from (4R,5R)-5-fluoro-4-(2-fluoro-5-nitro-phenyl)-4-methyl-5,6-dihydro-4H-[1,3]oxazin-2-ylamine (intermediate A7.2), the (4R,5R)-4-(5-amino-2-fluoro-phenyl)-5-fluoro-4-methyl-5,6-dihydro-4H-[1,3]oxazin-2-ylamine was obtained as a white foam. MS (ISP): m/z=242.3 [M+H]$^+$.
Intermediate Aniline A8.3

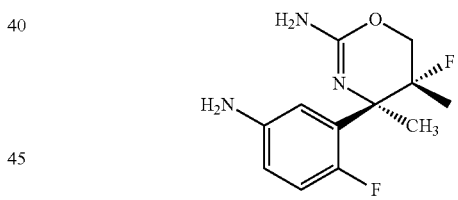

Starting from (4R,5R)-5-fluoro-4-(2-fluoro-5-nitro-phenyl)-4,5-dimethyl-5,6-dihydro-4H-[1,3]oxazin-2-ylamine (intermediate A7.3), the (4R,5R)-4-(5-amino-2-fluoro-phenyl)-5-fluoro-4,5-dimethyl-5,6-dihydro-4H-[1,3]oxazin-2-ylamine was obtained as a white solid. MS (ISP): m/z=265.2 [M+H]$^+$.
Intermediate Aniline A8.4

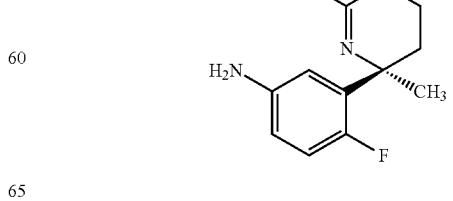

Starting from (S)-4-(2-fluoro-5-nitro-phenyl)-4-methyl-5,6-dihydro-4H-[1,3]oxazin-2-ylamine (intermediate A6.6), the product (S)-4-(5-amino-2-fluoro-phenyl)-4-methyl-5,6-dihydro-4H-[1,3]oxazin-2-ylamine was obtained as a brown sticky solid. MS (ISP): m/z=224.4 [M+H]+.

Intermediate Aniline A8.5

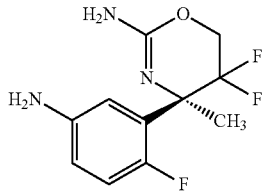

Starting from (R)-5,5-difluoro-4-(2-fluoro-5-nitro-phenyl)-4-methyl-5,6-dihydro-4H-[1,3]oxazin-2-ylamine (intermediate A6.7), the product (R)-4-(5-amino-2-fluoro-phenyl)-5,5-difluoro-4-methyl-5,6-dihydro-4H-[1,3]oxazin-2-ylamine was obtained as a colorless foam. MS (ISP): m/z=260.1 [M+H]+.

Synthesis of the Intermediate Iodo Aniline B6.1

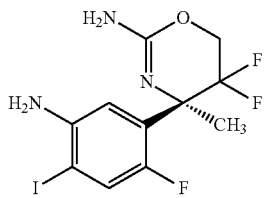

A solution of (R)-4-(5-amino-2-fluoro-phenyl)-5,5-difluoro-4-methyl-5,6-dihydro-4H-[1,3]oxazin-2-ylamine (intermediate A8.5) (500 mg, 1.9 mmol) and ammonium iodide (308 mg, 2.1 mmol) in acetic acid (9.6 ml) was treated at room temperature with an aqueous solution of hydrogen peroxide (35%, 0.19 ml, 2.1 mmol). After stirring overnight 50% of the starting material was left. Another equivalent of ammonium iodide and hydrogen peroxide was added and stirring continued at room temperature overnight. For the workup, the reaction mixture was filtered, the filtrate treated with sodium thiosulphate, then extracted with ethyl acetate (3×). The combined organic layers were washed with a saturated solution of sodium hydrogen carbonate, then dried over sodium sulphate and evaporated at reduced pressure. In order to eliminate residual acetic acid, the crude product was dissolved in dichloromethane and extracted again with a saturated solution of sodium hydrogen carbonate. The crude product was purified by chromatography on an Isolute flash $NH_2$ column using a gradient of heptane/ethyl acetate=100/0 to 0/100 as the eluent. The (R)-4-(5-amino-2-fluoro-4-iodo-phenyl)-5,5-difluoro-4-methyl-5,6-dihydro-4H-[1,3]oxazin-2-ylamine was obtained as a yellow solid (415 mg, 56% of theory). MS (ISP): m/z=386.0 [M+H]+.

Synthesis of the Intermediate N-Boc Protected Amine C3.1

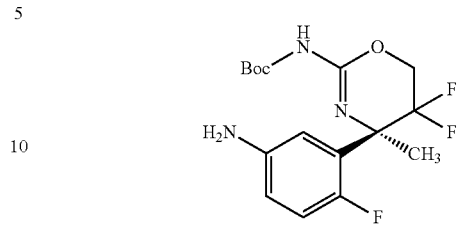

a) [(R)-5,5-Difluoro-4-(2-fluoro-5-nitro-phenyl)-4-methyl-5,6-dihydro-4H-[1,3]oxazin-2-yl]-di(carbamic acid tert-butyl ester) (intermediate C1.1)

A solution of (R)-5,5-difluoro-4-(2-fluoro-5-nitrophenyl)-4-methyl-5,6-dihydro-4H-1,3-oxazin-2-amine (intermediate A6.7) (2.52 g, 8.71 mmol) in tetrahydrofuran (87 ml) was treated with triethylamine (2.29 g, 3.16 ml, 22.7 mmol) and the mixture stirred for 5 minutes. Di-tert-butyl-dicarbonate (3.99 g, 18.3 mmol) was added followed by 4-dimethylaminopyridine (319 mg, 2.61 mmol) and the mixture stirred at room temperature for 2 hours. For the workup, the solvent was removed at reduced pressure leaving an orange gum. The crude material was purified by flash chromatography on silica gel using a gradient of heptane/ethyl acetate=100:0 to, 70:30 as the eluent. The [(R)-5,5-difluoro-4-(2-fluoro-5-nitro-phenyl)-4-methyl-5,6-dihydro-4H-[1,3]oxazin-2-yl]-di(carbamic acid tert-butyl ester) was obtained as a white crystalline solid (3.48 g, 81.6% yield).

b) [(R)-5,5-Difluoro-4-(2-fluoro-5-nitro-phenyl)-4-methyl-5,6-dihydro-4H-[1,3]oxazin-2-yl]-carbamic acid tert-butyl ester (intermediate C2.1)

A solution of [(R)-5,5-difluoro-4-(2-fluoro-5-nitro-phenyl)-4-methyl-5,6-dihydro-4H-[1,3]oxazin-2-yl]-di(carbamic acid tert-butyl ester) (489 mg, 1 mmol) in dichloromethane (2 ml), was cooled to 0° C. Trifluoroacetic acid (228 mg, 154 µl, 2.00 mmol) was added slowly and the mixture stirred at this temperature for 4 hours. The reaction was followed by TLC and when no more conversion was detected, the reaction mixture was warmed up to room temperature. After additional two hours, a considerable amount of free amine was formed and the reaction was stopped. For the workup, the mixture was poured into a saturated aqueous solution of sodium hydrogencarbonate. Extraction with ethyl acetate, drying of the combined organic layers over sodium sulphate, and evaporation at reduced pressure yielded the crude product as a yellow oil. The crude material was purified by flash chromatography on silica gel using a gradient of heptane/ethyl acetate=80:20 to 60:40 as the eluent. The [(R)-5,5-difluoro-4-(2-fluoro-5-nitro-phenyl)-4-methyl-5,6-dihydro-4H-[1,3]oxazin-2-yl]-carbamic acid tert-butyl ester (270 mg, 69% yield) was obtained as a white crystalline solid, together with starting material (65 mg) and the (R)-5,5-difluoro-4-(2-fluoro-5-nitrophenyl)-4-methyl-5,6-dihydro-4H-1,3-oxazin-2-amine (26 mg, 9% yield).

c) [(R)-4-(5-Amino-2-fluoro-phenyl)-5,5-difluoro-4-methyl-5,6-dihydro-4H-[1,3]oxazin-2-yl]-carbamic acid tert-butyl ester (intermediate C3.1)

Following the general procedure for the synthesis of the intermediate anilines A8, the hydrogenation of the [(R)-5,5-difluoro-4-(2-fluoro-5-nitro-phenyl)-4-methyl-5,6-dihydro-4H-[1,3]oxazin-2-yl]-carbamic acid tert-butyl ester (522 mg, 1.34 mmol) yielded the title compound (500 mg, 100%) as a grey foam which was engaged in the next step without further purification. MS (ISP): m/z=304.2 [M−C$_4$H$_8$+H]$^+$.

Synthesis of the Intermediate DMTr-Protected Amino Oxazines C4

General Procedure

A solution of the amino oxazine A6 or B3 (2.4 mmol) and triethylamine (0.66 ml; 4.8 mmol) in dichloromethane (25 ml) at 0° C. was treated with 4,4'-dimethoxytrityl chloride (DMTr-Cl) (0.89 g; 2.6 mmol). The green reaction mixture was stirred at 23° C. for 2 hours. For the workup, the reaction mixture was extracted with water, the organic layer separated and dried over sodium sulphate. Evaporation gave a crude product which was purified by silica gel column chromatography with n-heptane and ethyl acetate as the eluent to give the pure DMTr-protected amino oxazine C4.

Intermediate C4.1

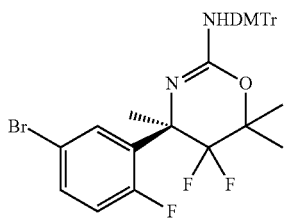

Starting from (R)-4-(5-bromo-2-fluoro-phenyl)-5,5-difluoro-4,6,6-trimethyl-5,6-dihydro-4H-[1,3]oxazin-2-ylamine (intermediate B3.1), the product [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine was obtained as a white foam. MS (ISP): m/z=653.3 [M+H]$^+$ and 655.3 [M+2+H]$^+$.

Intermediate C4.2

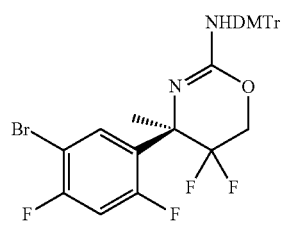

Starting from (R)-4-(5-bromo-2,4-difluoro-phenyl)-5,5-difluoro-4-methyl-5,6-dihydro-4H-[1,3]oxazin-2-ylamine (intermediate A6.2), the product [bis-(4-methoxy-phenyl)-phenyl-methyl]-[(R)-4-(5-bromo-2,4-difluoro-phenyl)-5,5-difluoro-4-methyl-5,6-dihydro-4H-[1,3]oxazin-2-yl]-amine was obtained as a white foam. MS (ISP): m/z=643.2 [M+H]$^+$ and 645.2 [M+2+H]$^+$.

Intermediate C4.3

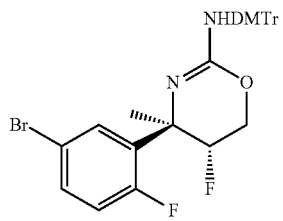

Starting from (4R,5R)-4-(5-bromo-2-fluoro-phenyl)-5-fluoro-4-methyl-5,6-dihydro-4H-[1,3]oxazin-2-ylamine (intermediate A6.8), the product [bis-(4-methoxy-phenyl)-phenyl-methyl]-[(4R,5R)-4-(5-bromo-2-fluoro-phenyl)-5-fluoro-4-methyl-5,6-dihydro-4H-[1,3]oxazin-2-yl]-amine was obtained as a white foam. MS (ISP): m/z=607.3 [M+H]$^+$ and 609.2 [M+2+H]$^+$.

Synthesis of the Intermediate Boronic Esters D1

Intermediate D1.1

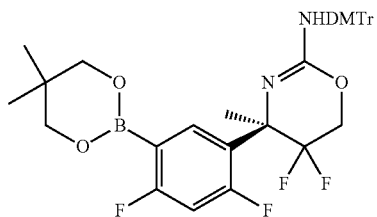

A dried pressure tube was charged with potassium acetate (165 mg; 1.68 mmol), bis(triphenylphosphin)palladium(II) chloride (16.7 mg, 23.3 mmol), 5,5,5',5'-tetramethyl-2,2'-bi (1,3,2-dioxaborinane) (126 mg; 0.56 mmol), and dioxane (5 ml). After addition of [bis-(4-methoxy-phenyl)-phenyl-methyl]-[(R)-4-(5-bromo-2,4-difluoro-phenyl)-5,5-difluoro-4-methyl-5,6-dihydro-4H-[1,3]oxazin-2-yl]-amine (intermediate C4.2) the tube was flushed with argon, sealed and heated at 110° C. for 15 hours. For the workup, the reaction mixture was cooled to room temperature and evaporated at reduced pressure. The residue was partitioned between dichloromethane (50 ml) and water (20 ml). The organic layer was washed with brine (20 ml), dried over sodium sulphate and evaporated at reduced pressure. The crude [bis-(4-methoxy-phenyl)-phenyl-methyl]-{(R)-4-[5-(5,5-dimethyl-[1,3,2]dioxaborinan-2-yl)-2,4-difluoro-phenyl]-5,5-difluoro-4-methyl-5,6-dihydro-4H-[1,3]oxazin-2-yl}-amine was directly engaged in the next step without further purification. MS (ISP): m/z=609.1 [M+H]$^+$.

Synthesis of the Intermediate N-Di-Boc Protected Amine E3.1

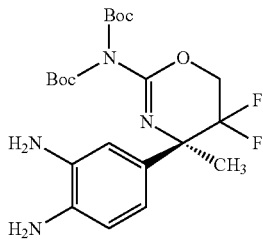

a) In a manner analogous to that described in C3.1 a), the reaction of (R)-5,5-difluoro-4-(4-fluoro-3-nitro-phenyl)-4-methyl-5,6-dihydro-4H-[1,3]oxazin-2-ylamine (intermediate A6.10) with di-tert-butyl-dicarbonate yielded the [(R)-5,5-difluoro-4-(4-fluoro-3-nitro-phenyl)-4-methyl-5,6-dihydro-4H-[1,3]oxazin-2-yl]-di(carbamic acid tert-butyl ester) (intermediate E1.1) as a pale yellow oil. MS (ISP): m/z=490.2 [M+H]$^+$.

b) A solution of [(R)-5,5-difluoro-4-(4-fluoro-3-nitro-phenyl)-4-methyl-5,6-dihydro-4H-[1,3]oxazin-2-yl]-di(carbamic acid tert-butyl ester) (intermediate E1.1) (864 mg, 1.77 mmol) in dimethylsulfoxide (9 ml) was treated under an atmosphere of nitrogen at room temperature with sodium azide (232 mg, 3.53 mmol). The reaction mixture was stirred at room temperature for 5 hours. For the workup, the mixture was diluted with ethyl acetate and washed 3 times with water. The organic layer was dried over sodium sulphate and evaporated at reduced pressure to yield the [(R)-4-(4-azido-3-nitro-phenyl)-5,5-difluoro-4-methyl-5,6-dihydro-4H-[1,3]oxazin-2-yl]-di(carbamic acid tert-butyl ester) (intermediate E2.1) (870 mg, 96% yield) as a yellow foam. MS (ISP): m/z=513.5 [M+H]$^+$.

c) A solution of [(R)-4-(4-azido-3-nitro-phenyl)-5,5-difluoro-4-methyl-5,6-dihydro-4H-[1,3]oxazin-2-yl]-di(carbamic acid tert-butyl ester) (intermediate E2.1) (860 mg, 1.68 mmol) in methanol (39 ml) was hydrogenated at room temperature for 3 hours using palladium on charcoal as the catalyst. For the workup, the reaction mixture was filtrated and the ethanol evaporated at reduced pressure. The residual light brown foam (711 mg) was purified by flash chromatography on silica gel using a gradient of heptane/ethyl acetate=100:0 to 25:75 as the eluent. The [(R)-4-(3,4-diamino-phenyl)-5,5-difluoro-4-methyl-5,6-dihydro-4H-[1,3]oxazin-2-yl]-carbamic acid tert-butyl ester (intermediate E3.1) (582 mg, 76% yield) was obtained as an off-white foam. MS (ISP): m/z=457.3 [M+H]$^+$.

Synthesis of the Intermediate Nitro Phenol F2.1

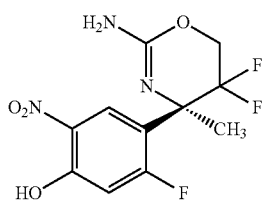 [SMILES: C[C@]1(c2cc([N+](=O)[O-])c(O)cc2F)N=C(N)OCC1(F)F]

A solution of (R)-5,5-difluoro-4-(2-fluoro-4-methoxy-5-nitro-phenyl)-4-methyl-5,6-dihydro-4H-[1,3]oxazin-2-ylamine (intermediate A6.11) (558 mg, 1.75 mmol) in dichloromethane (16 ml) was cooled to 0° C. and treated with a solution of boron tribromide in dichloromethane (1M, 2.62 ml). After stirring at room temperature for 2 hours, the reaction mixture was diluted with dichloromethane, then extracted with water (3 ml). The organic layer was separated, dried over sodium sulphate and evaporated. The crude product was purified by flash chromatography on silica gel using a gradient of hexane/ethyl acetate=100:0 to 0:100 as the eluent. The 4-((R)-2-amino-5,5-difluoro-4-methyl-5,6-dihydro-4H-[1,3]oxazin-4-yl)-5-fluoro-2-nitro-phenol (intermediate F2.1) (300 mg, 56% yield) was obtained as a brown solid. MS (ISP): m/z=457.3 [M+H]$^+$.

Synthesis of the Intermediate N-Di-Boc Protected Amine G3.1

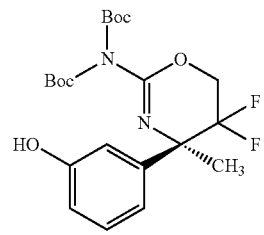 [SMILES: CC(C)(C)OC(=O)N(C(=O)OC(C)(C)C)C1=N[C@](C)(c2cccc(O)c2)C(F)(F)CO1]

a) In a manner analogous to that described in C3.1 a), the reaction of (R)-4-(3-benzyloxy-phenyl)-5,5-difluoro-4-methyl-5,6-dihydro-4H-[1,3]oxazin-2-ylamine (intermediate A6.9) with di-tert-butyl-dicarbonate yielded the [(R)-4-(3-benzyloxy-phenyl)-5,5-difluoro-4-methyl-5,6-dihydro-4H-[1,3]oxazin-2-yl]-di(carbamic acid tert-butyl ester) (intermediate G2.1) as a yellow oil. MS (ISP): m/z=533.3 [M+H]$^+$.

b) A solution of [(R)-4-(3-benzyloxy-phenyl)-5,5-difluoro-4-methyl-5,6-dihydro-4H-[1,3]oxazin-2-yl]-di(carbamic acid tert-butyl ester) (intermediate G2.1) (2.068 g, 3.88 mmol) in ethanol (40 ml) was pre-treated with activated charcoal at room temperature. After filtration and evaporation at reduced pressure, the residual colorless oil was dissolved in ethanol (40 ml) and treated with palladium (10% on charcoal) as the catalyst. The hydrogenolysis was complete after 3 hours at room temperature. After filtration, the solvent was removed at reduced pressure leaving 1.4 g of a white foam. The crude product was purified by chromatography on silica gel using a gradient of heptane/ethyl acetate=100:0 to 70:30 as the eluent. The [(R)-5,5-difluoro-4-(3-hydroxy-phenyl)-4-methyl-5,6-dihydro-4H-[1,3]oxazin-2-yl]-di(carbamic acid tert-butyl ester) (intermediate G3.1) (1.21 g, 71% yield) was obtained as a white foam. MS (ISP): m/z=443.3 [M+H]$^+$.

Synthesis of the Intermediate N-Boc Protected Amine H2.1

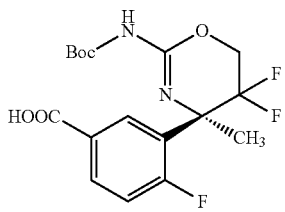 [SMILES: CC(C)(C)OC(=O)NC1=N[C@](C)(c2cc(C(=O)O)ccc2F)C(F)(F)CO1]

a) In a manner analogous to that described in C3.1 a), the reaction of (R)-4-(5-bromo-2-fluoro-phenyl)-5,5-difluoro-4- methyl-5,6-dihydro-4H-[1,3]oxazin-2-ylamine (intermediate A6.1) with di-tert-butyl-dicarbonate yielded the [(R)-4-(5-bromo-2-fluoro-phenyl)-5,5-difluoro-4-methyl-5,6-dihydro-4H-[1,3]oxazin-2-yl]-di(carbamic acid tert-butyl ester) (intermediate C1.2) as a white solid. MS (ISP): m/z=523.1 [M+H]$^+$.

b) A solution of [(R)-4-(5-bromo-2-fluoro-phenyl)-5,5-difluoro-4-methyl-5,6-dihydro-4H-[1,3]oxazin-2-yl]-di(carbamic acid tert-butyl ester) (intermediate C1.2) (1.2 g, 2.29 mmol), 1,3-bis(diphenylphosphino)propane (236 mg, 562 µmol), and triethylamine (2.32 g, 3.19 ml, 22.9 mmol) in a mixture of ethanol (12.0 ml) and dimethylsulfoxide (12.0 ml) was treated with palladium(II)acetate (48.5 mg, 216 µmol). The mixture was stirred for 8 hours under an atmosphere of carbon monoxide at 70° C. and 2 bar. For the workup, the catalyst was filtrated, washed with ethanol, and the ethanol was removed at reduced pressure. The residual solution was diluted with ethyl acetate, washed with water (2×40 ml) and once with brine. The organic layer was dried over sodium sulphate, filtered and evaporated at reduced pressure. The crude product was purified by flash chromatography on silica gel using a gradient of heptane/ethyl acetate=100:0 to 80:20 as the eluent. The 3-((R)-2-(di-tert-butoxycarbonyl)amino-5,5-difluoro-4-methyl-5,6-dihydro-4H-[1,3]oxazin-4-yl)-4-fluoro-benzoic acid ethyl ester (intermediate H1.1) (312 mg, 26% yield) was obtained as a white solid. MS (ISP): m/z=517.3 [M+H]$^+$.

c) A solution of 3-((R)-2-(di-tert-butoxycarbonyl)amino-5,5-difluoro-4-methyl-5,6-dihydro-4H-[1,3]oxazin-4-yl)-4-fluoro-benzoic acid ethyl ester (intermediate H1.1) (922 mg, 1.79 mmol) in ethanol (9.44 ml) was treated with a solution of sodium hydroxide (2N, 3.57 ml). The mixture was stirred at 70° C. for 1.5 hours. For the workup, the solvent was evaporated at reduced pressure and the residue treated with water and hydrochloric acid (1N) under cooling with ice. The resulting white precipitation was filtered, rinsed with water and dried to give a first fraction of product (374 mg). The aqueous layer was extracted three times with dichloromethane. The combined extracts were dried over sodium sulphate, filtered and evaporated at reduced pressure to yield a second fraction of product (215 mg). The 3-((R)-2-tert-butoxycarbonylamino-5,5-difluoro-4-methyl-5,6-dihydro-4H-[1,3]oxazin-4-yl)-4-fluoro-benzoic (intermediate H2.1) (589 mg, 85% yield) was obtained as a white amorphous material. MS (ISN): m/z=387.2 [M−H]$^−$.

Synthesis of the Intermediate Sulfinyl Imines J2

Intermediate J2.1

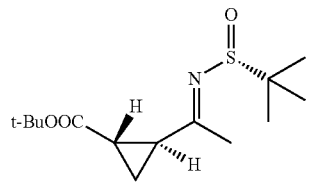

A solution of (R)-2-methylpropane-2-sulfinamide (3.20 g, 26.4 mmol) and (1R,2R)-rel-2-acetyl-cyclopropanecarboxylic acid tert-butyl ester (5.35 g, 29.0 mmol) in tetrahydrofuran (181 ml) was treated at 23° with titanium(IV)ethoxide (12.0 g, 11.0 ml, 52.8 mmol). The light yellow mixture was stirred at 70° C. for 2 hours. For the workup, the mixture was cooled to 25° C. and poured into ice-cold brine (100 mL) under vigourous stirring. After dilution with ethyl acetate (100 mL) the mixture was filtered over Dicalite®. The solvents were evaporated at reduced pressure to yield a light yellow oil (9.03 g). The crude oil was purified by chromatography on silica gel using a gradient of heptane/ethyl acetate=100:0 to 50:50 as the eluent. The (1R,2R)-rel-2-{1-[(E)-(R)-2-methyl-propane-2-sulfinylimino]-ethyl}-cyclopropane-carboxylic acid tert-butyl ester (3.68 g, 49% yield) was obtained as a colorless oil {MS (ISP): m/z=288.1 [M+H]$^+$} together with the (1R,2R)-rel-2-{1-[(E)-(R)-2-methyl-propane-2-sulfinylimino]-ethyl}-cyclopropane-carboxylic acid ethyl ester (0.32 g, 5% yield); MS (ISP): m/z=260.1 [M+H]$^+$.

The (1R,2R)-rel-2-acetyl-cyclopropanecarboxylic acid tert-butyl ester was obtained as follows:
A solution of (dimethyl-λ4-sulfanylidene)-acetic acid tert-butyl ester (6.3 g, 35.7 mmol) (CAS 195453-96-4; K. Saigo et al., J. Org. Chem. 2006, 71, 1633-1639) in dichloromethane (36 ml) was treated dropwise at 15° C. with but-3-en-2-one (2.64 g, 3.1 ml, 35.7 mmol) keeping the internal temperature below 27° C. The yellow mixture was stirred overnight at room temperature. For the workup, all volatiles were evaporated to give a yellow oil. The crude oil was purified by chromatography on silica gel using a gradient of heptane/ethyl acetate=100:0 to 80:20 as the eluent. The (1R,2R)-rel-2-acetyl-cyclopropanecarboxylic acid tert-butylester was obtained as a colorless oil (5.48 g, 83% yield). MS (ISP): m/z=185.0 [M+H]$^+$.

Synthesis of the Intermediate Sulfinamide Esters J3

Intermediate J3.1

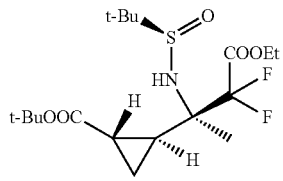

Zinc (2.47 g, 37.8 mmol) and copper(I) chloride (1.25 g, 12.6 mmol) were stirred in a dried apparatus and heated for 1 minute with a heat gun under argon flow. After cooling to room temperature, tetrahydrofuran (54.4 ml) was added. The reaction brown mixture was stirred at 70° C. for 30 minutes. Thereafter, the mixture was cooled to room temperature and a solution of ethyl bromodifluoroacetate (6.59 g, 4.16 ml, 31.5 mmol) in tetrahydrofuran (18 ml) was added dropwise maintaining the temperature between 26° C. and 29° C. After stirring for 30 minutes, a solution of (1R,2R)-rel-2-{1-[(E)-(R)-2-methyl-propane-2-sulfinylimino]-ethyl}-cyclopropane-carboxylic acid ethyl ester (3.62 g, 12.6 mmol) in tetrahydrofuran (11 ml) was added dropwise at 25° C. The mixture was stirred at room temperature overnight, then cooled to 0° C. and ethanol (1.44 ml) was added. The mixture was filtered over Dicalite® and washed with ethyl acetate. The solvent was removed at reduced pressure to give a dark green oil. The residue was taken up in ethyl acetate, washed once with water and filtered again over Dicalite®. The organic layer was washed twice with water, dried over sodium sulphate and concentrated at reduced pressure. The crude green oil (4.3 g) was purified by chromatography on silica gel using a gradient of heptane/ethyl acetate=100:0 to 50:50 as the eluent. The (1S,2S)-rel-2-[(R)-2-ethoxycarbonyl-2,2-difluoro-1-methyl-1-((R)-2-methyl-propane-2-sulfinylamino)-ethyl]-cyclopropanecarboxylic acid tert-butylester (2.33 g, 45% yield) was obtained as a yellow oil. MS (ISP): m/z=412.3 [M+H]$^+$.

Intermediate J3.2 and J3.3

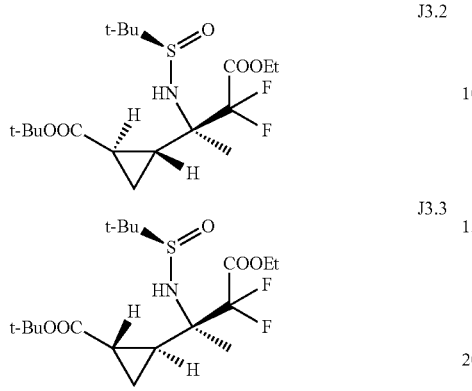

Starting from (1S,2S)-rel-2-[(R)-2-ethoxycarbonyl-2,2-difluoro-1-methyl-1-((R)-2-methyl-propane-2-sulfinylamino)-ethyl]-cyclopropanecarboxylic acid tert-butylester the chromatography on silica gel using a gradient of heptane/ethyl acetate=100:0 to 50:50 as the eluent yielded in a 1:1-ratio the (1R,2R)-2-[(R)-2-ethoxycarbonyl-2,2-difluoro-1-methyl-1-((R)-2-methyl-propane-2-sulfinylamino)-ethyl]-cyclopropanecarboxylic acid tert-butylester as the first eluting isomer {MS (ISP): m/z=412.3 [M+H]$^+$} and the (1S,2S)-2-[(R)-2-ethoxycarbonyl-2,2-difluoro-1-methyl-1-((R)-2-methyl-propane-2-sulfinylamino)-ethyl]-cyclopropanecarboxylic acid tert-butylester as the later eluting isomer {MS (ISP): m/z=412.3 [M+H]$^+$} both as yellow oils (74% total yield).

Synthesis of the Intermediate Sulfinamide Alcohols J4

Intermediate J4.1

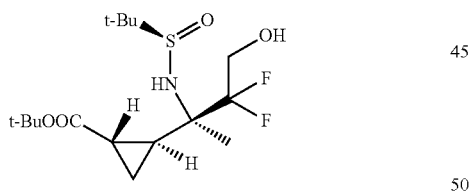

A solution of (1S,2S)-rel-2-[(R)-2-ethoxycarbonyl-2,2-difluoro-1-methyl-1-((R)-2-methyl-propane-2-sulfinylamino)-ethyl]-cyclopropanecarboxylic acid tert-butylester (2.23 g, 5.42 mmol) in tetrahydrofuran (20 ml) was treated dropwise under nitrogen at 0° C. with a solution of lithium borohydride (2M in tetrahydrofuran; 5.42 ml, 10.8 mmol), at such a rate that the temperature was kept below 6° C. The orange reaction mixture was stirred at 0° C. for 3 hours. For the workup, acetic acid (654 mg, 623 μl, 10.8 mmol) was added dropwise, keeping the temperature below 10° C., followed by water (0.8 ml). After 70 minutes of stirring, brine and ethyl acetate were added and the mixture was extracted twice with ethyl acetate. The organic layer was washed with brine, dried over sodium sulphate and evaporated. A light green oil was obtained (2.31 g) which was purified by chromatography on silica gel using a gradient of heptane/ethyl acetate=100:0 to 0:100 as the eluent. The (1S,2S)-rel-2-[(R)-2,2-difluoro-3-hydroxy-1-methyl-1-((R)-2-methyl-propane-2-sulfinylamino)-propyl]-cyclopropanecarboxylic acid tert-butyl ester (1.19 g, 59% yield) was obtained as a colorless oil. MS (ISP): m/z=370.1 [M+H]$^+$.

Intermediate J4.2

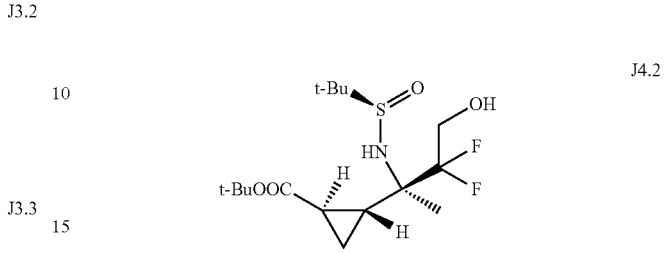

Starting from (1R,2R)-2-[(R)-2-ethoxycarbonyl-2,2-difluoro-1-methyl-1-((R)-2-methyl-propane-2-sulfinylamino)-ethyl]-cyclopropanecarboxylic acid tert-butylester (intermediate J3.2) the reduction with lithium borohydride yielded the (1R,2R)-2-[(R)-2,2-difluoro-3-hydroxy-1-methyl-1-((R)-2-methyl-propane-2-sulfinylamino)-propyl]-cyclopropanecarboxylic acid tert-butyl ester (81% yield) as a colorless oil. MS (ISP): m/z=370.1 [M+H]$^+$.

Intermediate J4.3

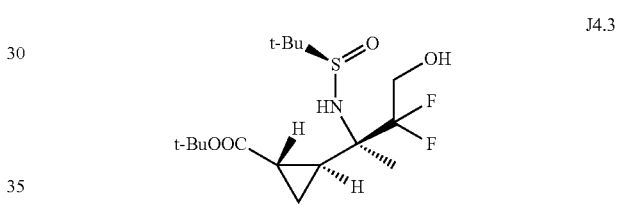

Starting from (1S,2S)-2-[(R)-2-ethoxycarbonyl-2,2-difluoro-1-methyl-1-((R)-2-methyl-propane-2-sulfinylamino)-ethyl]-cyclopropanecarboxylic acid tert-butylester (intermediate J3.3) the reduction with lithium borohydride yielded the (1S,2S)-2-[(R)-2,2-difluoro-3-hydroxy-1-methyl-1-((R)-2-methyl-propane-2-sulfinylamino)-propyl]-cyclopropanecarboxylic acid tert-butyl ester (80% yield) as a white solid. MS (ISP): m/z=370.2 [M+H]$^+$.

Synthesis of the Intermediate Alcohols J5

Intermediate J5.1

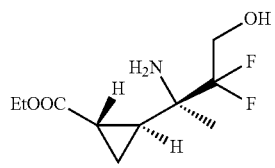 [SMILES: CCOC(=O)[C@H]1C[C@@H]1[C@@](C)(N)C(F)(F)CO]

A solution of (1S,2S)-rel-2-[(R)-2,2-difluoro-3-hydroxy-1-methyl-1-((R)-2-methyl-propane-2-sulfinylamino)-propyl]-cyclopropanecarboxylic acid tert-butyl ester (1.16 g, 3.14 mmol) in ethanol (22.5 ml) was treated dropwise at 0° C. with thionyl chloride (1.89 g, 1.15 ml, 15.7 mmol). The yellow mixture was then stirred at 85° C. for 2 hours. For the workup, the solvent was evaporated at reduced pressure, then water and diethyl ether were added. The aqueous layer was treated with carbonate, thereafter extracted three times with dichloromethane. The combined organic layers were dried over sodium sulphate and evaporated. The light yellow oil (708 mg) was purified by chromatography on silica gel using a gradient of heptane/ethyl acetate=100:0 to 0:100 as the eluent. The (1S,2S)-rel-2-((R)-1-amino-2,2-difluoro-3-hydroxy-1-methyl-propyl)-cyclopropane-carboxylic acid ethyl ester (566 mg, 76% yield) was obtained as a light yellow oil. MS (ISP): m/z=238.2 [M+H]+.

Intermediate J5.2

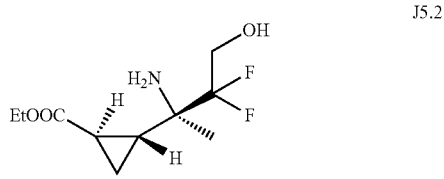 [SMILES: CCOC(=O)[C@@H]1C[C@H]1[C@@](C)(N)C(F)(F)CO]

Starting from (1R,2R)-2-[(R)-2,2-difluoro-3-hydroxy-1-methyl-1-((R)-2-methyl-propane-2-sulfinylamino)-propyl]-cyclopropanecarboxylic acid tert-butyl ester (intermediate J4.2) the cleavage of the chiral auxiliary yielded the (1R,2R)-2-((R)-1-amino-2,2-difluoro-3-hydroxy-1-methyl-propyl)-cyclopropane-carboxylic acid ethyl ester (85% yield) as a light yellow oil. MS (ISP): m/z=238.2 [M+H]+.

Intermediate J5.3

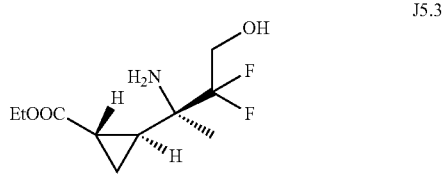 [SMILES: CCOC(=O)[C@H]1C[C@@H]1[C@@](C)(N)C(F)(F)CO]

Starting from (1S,2S)-2-[(R)-2,2-difluoro-3-hydroxy-1-methyl-1-((R)-2-methyl-propane-2-sulfinylamino)-propyl]-cyclopropanecarboxylic acid tert-butyl ester (intermediate J4.3) the cleavage of the chiral auxiliary yielded the (1S,2S)-2-((R)-1-amino-2,2-difluoro-3-hydroxy-1-methyl-propyl)-cyclopropane-carboxylic acid ethyl ester (92% yield) as a light yellow oil. MS (ISP): m/z=238.2 [M+H]+.

Synthesis of the Intermediate Oxazines J6

Intermediate J6.1

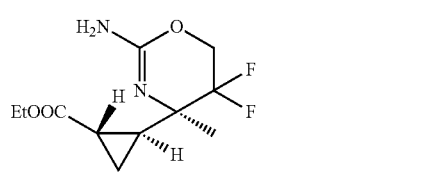 [SMILES: CCOC(=O)[C@H]1C[C@@H]1[C@@]1(C)N=C(N)OCC1(F)F]

A mixture of (1S,2S)-rel-2-((R)-1-amino-2,2-difluoro-3-hydroxy-1-methyl-propyl)-cyclopropane-carboxylic acid ethyl ester (542 mg, 2.28 mmol) and cyanogen bromide in acetonitrile (5M; 685 μl, 3.43 mmol) in ethanol (14 ml) was heated at 75° C. for 7 hours. In order to complete the reaction another volume of cyanogen bromide in acetonitrile (5M; 228 μl, 1.14 mmol, Eq: 0.50) was added and heating continued at 75° C. for 6 hours, and again cyanogen bromide in acetonitrile (228 μl, 1.14 mmol, Eq: 0.50) was added and heating continued at 75° C. for 24 hours. For the workup, the solution was evaporated, the residual oil was washed once with a solution of sodium carbonate (2M) and twice with ethyl acetate, then dried over sodium sulphate, filtered and concentrated at reduced pressure. The light yellow oil (731 mg) was purified by chromatography on silica gel using a gradient of heptane/ethyl acetate=100:0 to 50:50 as the eluent. The (1S,2S)-rel-2-((R)-2-amino-5,5-difluoro-4-methyl-5,6-dihydro-4H-[1,3]oxazin-4-yl)-cyclopropanecarboxylic acid ethyl ester (404 mg, 67% yield) was obtained as a colorless oil. MS (ISP): m/z=263.2 [M+H]+.

Intermediate J6.2

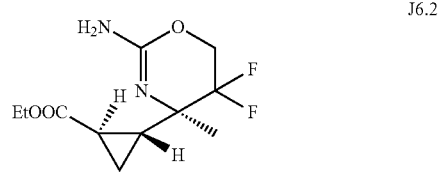 [SMILES: CCOC(=O)[C@@H]1C[C@H]1[C@@]1(C)N=C(N)OCC1(F)F]

Starting from (1R,2R)-2-((R)-1-amino-2,2-difluoro-3-hydroxy-1-methyl-propyl)-cyclopropane-carboxylic acid ethyl ester (intermediate J5.2) the cyclization with cyanogen bromide yielded the (1R,2R)-2-((R)-2-amino-5,5-difluoro-4-methyl-5,6-dihydro-4H-[1,3]oxazin-4-yl)-cyclopropanecarboxylic acid ethyl ester (88% yield) as a white solid. MS (ISP): m/z=263.2 [M+H]+.

Intermediate J6.3

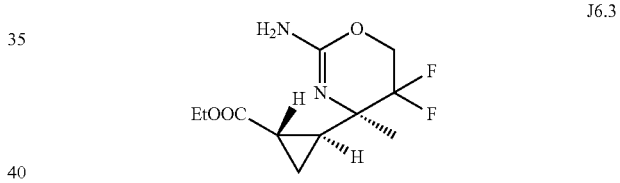

Starting from (1S,2S)-2-((R)-1-amino-2,2-difluoro-3-hydroxy-1-methyl-propyl)-cyclopropane-carboxylic acid ethyl ester (intermediate J5.3) the cyclization with cyanogen bromide yielded the (1S,2S)-2-((R)-2-amino-5,5-difluoro-4-methyl-5,6-dihydro-4H-[1,3]oxazin-4-yl)-cyclopropanecarboxylic acid ethyl ester (61% yield) as a white solid. MS (ISP): m/z=263.2 [M+H]+.

Synthesis of the Intermediate N-Di-Boc Protected Oxazine J7

Intermediate J7.1

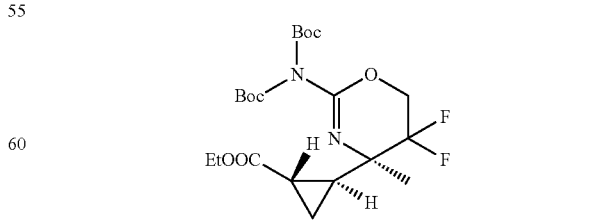

A solution of (1S,2S)-rel-2-((R)-2-amino-5,5-difluoro-4-methyl-5,6-dihydro-4H-[1,3]oxazin-4-yl)-cyclopropanecarboxylic acid ethyl ester (391 mg, 1.49 mmol), triethylamine (394 mg, 542 μl, 3.88 mmol) and 4-dimethylaminopyridine (74.3 mg, 596 μmol) in tetrahydrofuran (17 ml) was treated dropwise with a solution of di-tert-butyl dicarbonate (789 mg, 3.58 mmol) in tetrahydrofuran (0.5 ml) at room temperature. The mixture was then heated in at 60° C. overnight. In order to complete the reaction to the di-Boc-derivative, a solution of 4-dimethylaminopyridine (37.2 mg, 298 μmol) and di-tert-butyl dicarbonate (65.7 mg, 298 μmol,) in tetrahydrofuran (0.5 ml) was added and the completion of the reaction followed by TLC. For the workup, the solvent was removed at reduced pressure, and the residue was dissolved in ethyl acetate. The solution was washed twice with water, once with brine, then it was dried over sodium sulphate and concentrated at reduced pressure. The crude orange crude oil (829 mg) was purified by chromatography on silica gel using a gradient of heptane/ethyl acetate=100:0 to 90:10 as the eluent. The (1S,2S)-rel-ethyl 2-((R)-2-(bis(tert-butoxycarbonyl)amino)-5,5-difluoro-4-methyl-5,6-dihydro-4H-1,3-oxazin-4-yl)cyclopropanecarboxylate (532 mg, 77% yield) was obtained as a colorless oil. MS (ISP): m/z=463.3 [M+H]$^+$.

Intermediate J7.2

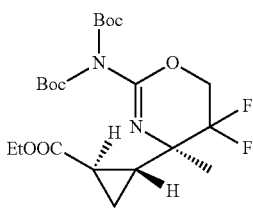

J7.2

Starting from (1R,2R)-2-((R)-2-amino-5,5-difluoro-4-methyl-5,6-dihydro-4H-[1,3]oxazin-4-yl)-cyclopropanecarboxylic acid ethyl ester (intermediate J6.2) the product (1R,2R)-ethyl 2-((R)-2-(bis(tert-butoxycarbonyl)amino)-5,5-difluoro-4-methyl-5,6-dihydro-4H-1,3-oxazin-4-yl)cyclopropanecarboxylate (57% yield) was obtained as a colorless oil. MS (ISP): m/z=463.3 [M+H]$^+$.

Intermediate J7.3

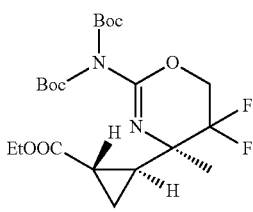 [SMILES: CCOC(=O)[C@H]1C[C@@H]1[C@@]1(C)N=C(N(C(=O)OC(C)(C)C)C(=O)OC(C)(C)C)OCC1(F)F]

J7.3

Starting from (1S,2S)-2-((R)-2-amino-5,5-difluoro-4-methyl-5,6-dihydro-4H-[1,3]oxazin-4-yl)-cyclopropanecarboxylic acid ethyl ester (intermediate J6.3) the product (1S,2S)-ethyl 2-((R)-2-(bis(tert-butoxycarbonyl)amino)-5,5-difluoro-4-methyl-5,6-dihydro-4H-1,3-oxazin-4-yl) cyclopropanecarboxylate (81% yield) was obtained as a colorless oil. MS (ISP): m/z=463.3 [M+H]$^+$.

Synthesis of the Intermediate N-Di-Boc Protected Oxazine J8

Intermediate J8.1

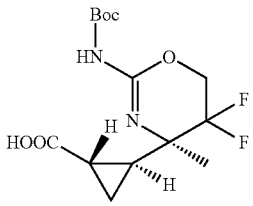 [SMILES: CC(C)(C)OC(=O)NC1=N[C@](C)([C@H]2C[C@@H]2C(=O)O)C(F)(F)CO1]

A solution of (1S,2S)-rel-ethyl 2-((R)-2-(bis(tert-butoxycarbonyl)amino)-5,5-difluoro-4-methyl-5,6-dihydro-4H-1,3-oxazin-4-yl)cyclopropanecarboxylate (519 mg, 1.12 mmol) in ethanol (10 ml) and sodium hydroxide (2M; 2.24 ml, 4.49 mmol) was heated at 40° C. for 90 minutes. Thereafter hydrochloric acid (1N) was added dropwise under cooling with ice until a neutral pH was reached. For the workup, the solvent was removed at reduced pressure, the residue taken up in water and dichloromethane, and the mixture acidified by dropwise addition of hydrochloric acid (1N) under cooling with ice. The aqueous layer which was extracted 3 times with dichloromethane, then sodium chloride was added to the aqueous layer which was extracted again 3 times with dichloromethane. The combined organic layers were dried over sodium sulphate and concentrated at reduced pressure to give the crude (1S,2S)-rel-2-((R)-2-tert-butoxycarbonylamino-5,5-difluoro-4-methyl-5,6-dihydro-4H-[1,3]oxazin-4-yl)-cyclopropane-carboxylic acid (240 mg, 64% yield) which was used in the next step without further purification. MS (ISP): m/z=335.1 [M+H]$^+$.

Intermediate J8.2

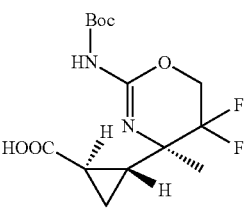

J8.2

Starting from (1R,2R)-ethyl 2-((R)-2-(bis(tert-butoxycarbonyl)amino)-5,5-difluoro-4-methyl-5,6-dihydro-4H-1,3-oxazin-4-yl)cyclopropanecarboxylate (intermediate J7.2) the product (1R,2R)-2-((R)-2-tert-butoxycarbonylamino-5,5-difluoro-4-methyl-5,6-dihydro-4H-[1,3]oxazin-4-yl)-cyclopropane-carboxylic acid (48% yield) was obtained as a white solid. MS (ISP): m/z=335.1 [M+H]$^+$.

Intermediate J8.3

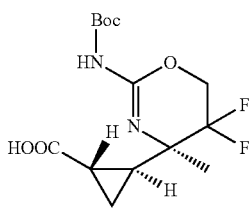

J8.3

Starting from (1S,2S)-ethyl 2-((R)-2-(bis(tert-butoxycarbonyl)amino)-5,5-difluoro-4-methyl-5,6-dihydro-4H-1,3-oxazin-4-yl)cyclopropanecarboxylate (intermediate J7.3) the product (1S,2S)-2-((R)-2-tert-butoxycarbonylamino-5,5-difluoro-4-methyl-5,6-dihydro-4H-[1,3]oxazin-4-yl)-cyclopropane-carboxylic acid (15% yield) was obtained as a white solid. MS (ISP): m/z=335.2 [M+H]$^+$.

Synthesis of the Intermediate Ketone K1

Intermediate K1.1

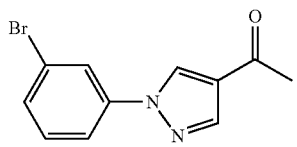

A solution of N,N-dimethylethylenediamine (1.8 ml, 16.76 mmol) in toluene (30 ml) was treated dropwise at 0° C. under an argon atmosphere with trimethylaluminum (2M in toluene, 22.86 ml, 45.7 mmol). The reaction mixture was stirred at 25° C. for 1 hour before adding 1-(3-bromo-phenyl)-1H-pyrazole-4-carboxylic acid ethyl ester (3.8 g, 12.8 mmol) (CAS 784142-89-8; WO2004092140). The resulting mixture was heated to reflux for 12 hours. For the workup, the mixture was cooled to 25° C., quenched with hydrochloric acid (1N) and extracted with ethyl acetate (3×100 ml). The combined organic layers were washed with brine (50 ml), dried over sodium sulphate and evaporated at reduced pressure. The crude material thus obtained was purified by column chromatography on silica gel using a 9:1-mixture of hexane and ethyl acetate as the eluent to give the 1-[1-(3-bromo-phenyl)-1H-pyrazol-4-yl]ethanone (2.4 g, 83.5%) as an off-white solid. MS (ISP): m/z=310 [M+CH$_3$CN]$^+$.

Synthesis of the Intermediate Sulfinyl Imine K2

Intermediate K2.1

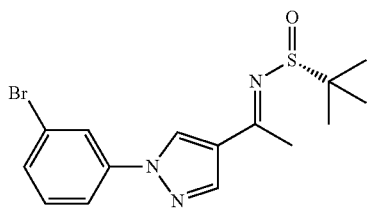 [SMILES: C/C(=N\[S@](=O)C(C)(C)C)c1cnn(-c2cccc(Br)c2)c1]

A solution of 1-[1-(3-bromo-phenyl)-1H-pyrazol-4-yl]-ethanone (1.0 g, 4.53 mmol), (R)-2-methylpropane-2-sulfinic acid amide (0.66 g, 5.43 mmol) and titanium (IV) ethoxide (2.1 ml, 9.96 mmol) in tetrahydrofuran (20 ml) was refluxed for 12 hours. The reaction mixture was cooled to 25° C., quenched with brine (20 ml), and extracted with ethyl acetate (5×20 ml). The combined organic layers were washed with brine (50 ml), dried over sodium sulphate, and evaporated at reduced pressure. The crude material thus obtained was purified by column chromatography on silica gel using a gradient of hexane/ethyl acetate=85:15 to 80:20 as the eluent to give the (R)-2-methyl-propane-2-sulfinic acid [1-[1-(3-bromo-phenyl)-1H-pyrazol-4-yl]-eth-(E)-ylidene]-amide (1.0 g, 60% yield) as a yellow solid. MS (ISP): m/z=368.0 [M+H]$^+$.

Synthesis of the Intermediate Sulfinamide Ester K3

Intermediate K3.1

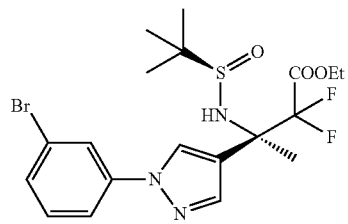 [SMILES: CCOC(=O)C(F)(F)[C@](C)(N[S@](=O)C(C)(C)C)c1cnn(-c2cccc(Br)c2)c1]

A suspension of activated zinc (1.7 g, 26.6 mmol) and CuCl (269 mg, 2.72 mmol) in dry tetrahydrofuran (15 ml) was refluxed for 30 minutes under vigorous stirring. A solution of bromo-difluoroacetic acid methylester (0.87 ml, 6.79 mmol) in tetrahydrofuran (5 ml) was added dropwise at 25° C. and the mixture was stirred for 30 minutes. Thereafter, a solution of (R)-2-methyl-propane-2-sulfinic acid [1-[1-(3-bromo-phenyl)-1H pyrazol-4-yl]-eth-(E)-ylidene]-amide (1.0 g, 2.72 mmol) in tetrahydrofuran (5 ml) was added dropwise at 25° C., and stirring continued for 30 minutes. For the workup, ethanol (0.3 ml, 4.89 mmol) was added to the reaction mixture at 25° C., and the resultant mixture was filtered over a layer of Celite®. The filtrate was diluted with water (20 ml), and extracted with ethyl acetate (5×30 ml). The combined organic layers were washed with brine (50 ml), dried over sodium sulphate, and evaporated at reduced pressure. The crude material thus obtained was purified by column chromatography on silica gel using a gradient of hexane/ethyl acetate=60:40 to 50:50 as the eluent to give the (R)-3-[1-(3-bromo-phenyl)-1H-pyrazol-4-yl]-2,2-difluoro-3-((R)-2-methyl-propane-2-sulfinylamino)-butyric acid ethyl ester (600 mg, 45% yield) as a yellow solid. MS (ISP): m/z=490.0 [M+H]$^+$.

Synthesis of the Intermediate Sulfinamide Alcohol K4

Intermediate K4.1

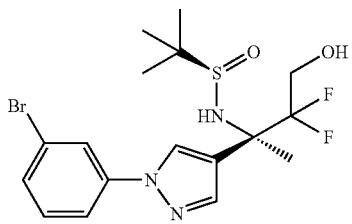 [SMILES: CC(C)(C)[S@@](=O)N[C@](C)(c1cnn(-c2cccc(Br)c2)c1)C(F)(F)CO]

A solution of (R)-3-[1-(3-bromo-phenyl)-1H-pyrazol-4-yl]-2,2-difluoro-3-((R)-2-methyl-propane-2-sulfinylamino)- butyric acid ethyl ester (700 mg, 2.42 mmol) in tetrahydrofuran (5 ml) was treated slowly with lithium borohydride (2M solution in tetrahydrofuran, 0.78 ml, 2.66 mmol) at 0° C., and the mixture was stirred at 25° C. for 2 hours. For the workup, acetic acid (0.26 ml, 4.5 mmol) was added slowly over a period of 15 minutes followed by water (2 ml), and the mixture was stirred for 30 minutes at 25° C. before it was quenched with a solution of sodium hydrogencarbonate (20 ml) and extracted with ethyl acetate (3×100 ml). The combined organic layers were washed with brine (75 ml), dried over sodium sulphate, and evaporated at reduced pressure. The crude material thus obtained was purified by column chromatography on silica gel using a gradient of hexane/ethyl acetate=85:15 to 80:20 as the eluent to give the (R)-2-methyl-propane-2-sulfinic {(R)-1-[1-(3-bromo-phenyl)-1H-pyrazol-4-yl]-2,2-difluoro-3-hydroxy-1-methyl-propyl}-amide (460 mg, 67% yield) as a deep brown solid. MS (ISP): m/z=450.2 [M+H]$^+$.

Synthesis of the Intermediate Amino Alcohol K5

Intermediate K5.1

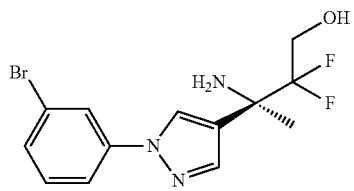 [SMILES: C[C@@](N)(c1cnn(-c2cccc(Br)c2)c1)C(F)(F)CO]

A solution of (R)-2-methyl-propane-2-sulfinic acid {(R)-1-[1-(3-bromo-phenyl)-1H-pyrazol-4-yl]-2,2-difluoro-3-hydroxy-1-methyl-propyl}-amide (590 mg, 1.2 mmol) in methanol (5 ml) was treated at 0° C. with hydrochloric acid (4N in dioxane, 2.6 ml, 10.2 mmol), and the reaction mixture was stirred at 25° C. for 2 hours. For the workup, the solution was concentrated at reduced pressure, and the resultant residue was diluted with water (10 ml). The aqueous layer was treated with a saturated solution of sodium hydrogencarbonate to a pH of about 8, then extracted with ethyl acetate (4×10 ml). The combined organic layers were washed with brine (15 ml), dried over sodium sulphate, and evaporated at reduced pressure. The crude material thus obtained was purified by column chromatography on silica gel using a gradient of hexane/ethyl acetate=85:15 to 80:20 as the eluent to give the (R)-3-amino-3-[1-(3-bromo-phenyl)-1H-pyrazol-4-yl]-2,2-difluoro-butan-1-ol (400 mg, 96% yield) as a light yellow solid which was used in the next step without further purification. MS (ISP): m/z=346.5 [M+H]$^+$.

Synthesis of the Intermediate Cyanato Alcohol K6

Intermediate K6.1

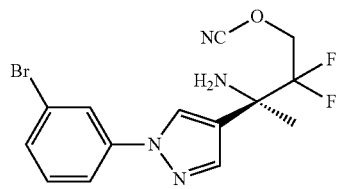 [SMILES: C[C@@](N)(c1cnn(-c2cccc(Br)c2)c1)C(F)(F)COC#N]

A solution of (R)-3-amino-3-[1-(3-bromo-phenyl)-1H-pyrazol-4-yl]-2,2-difluoro-butan-1-ol (5.1 g, 14.73 mmol) and sodium acetate (3.62 g, 44.2 mmol) in ethanol (90 ml) was warmed to 40° C. Cyanogen bromide (1.71 g, 16.21 mmol) was added and the mixture allowed to stir at 40° C. for 16 hours. Removal of the solvent at reduced pressure followed by purification of the resultant crude material by column chromatography on silica gel using a 3:2-mixture of hexane and ethyl acetate as the eluent yielded the (R)-1-[1-(3-bromo-phenyl)-1H-pyrazol-4-yl]-3-cyanato-2,2-difluoro-1-methyl-propylamine (3.2 g, 58% yield) as a colorless sticky solid. MS (ISP): m/z=369.2 [M+H]$^+$.

Synthesis of the Intermediate Amino Oxazine K7

Intermediate K7.1

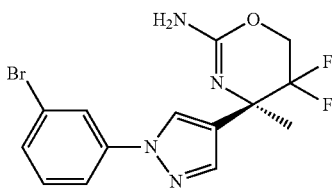 [SMILES: C[C@]1(c2cnn(-c3cccc(Br)c3)c2)N=C(N)OCC1(F)F]

In a sealed tube a solution of (R)-1-[1-(3-bromo-phenyl)-1H-pyrazol-4-yl]-3-cyanato-2,2-difluoro-1-methylpropylamine (3.0 g, 8.08 mmol) and ammonium hydroxide (25% in water, 7 ml) in methanol (10 ml) was heated to 60° C. for 16 hours. For the workup, the solution was evaporated at reduced pressure. The crude material thus obtained was purified by column chromatography on silica gel using a 95:5-mixture of dichloromethane and methanol as the eluent to give the (R)-4-[1-(3-bromo-phenyl)-1H-pyrazol-4-yl]-5,5-difluoro-4-methyl-5,6-dihydro-4H-[1,3]oxazin-2-ylamine (2.0 g, 54% yield) as a white solid. MS (ISP): m/z=371.2 [M+H]$^+$.

The following examples have a basic group. Depending on the reaction and purification conditions they were isolated in either the free base form, or as a salt, or in both free base and salt forms.

Example 1

(S)-4-{5-[(4-Chloro-1-difluoromethyl-1H-pyrazol-3-ylmethyl)-amino]-2-fluoro-phenyl}-4-methyl-5,6-dihydro-4H-[1,3]oxazin-2-ylamine In a 5 ml-reaction tube a solution of (S)-4-(5-amino-2-fluoro-phenyl)-4-methyl-5,6-dihydro-4H-[1,3]oxazin-2-ylamine (intermediate A8.4) (22 mg, 0.1 mmol) in methanol (0.3 ml) was treated at room temperature at under an inert atmosphere with 4-chloro-1-difluoromethyl-1H-pyrazole-3-carbaldehyde (19.9 mg, 110 μmol). The tube was closed and the reaction mixture was stirred at 25° C. for 60 minutes. Then decaborane (24.4 mg, 200 μmol) was added in one portion, the tube was closed, and the mixture was warmed to 45° C. for 15 hours. For the workup, the reaction solution was quenched with a solution of sodium carbonate (10%). Methanol was removed at reduced pressure, then the residue was extracted three times with ethyl acetate. The combined organic layers were dried over sodium sulphate and evaporated at reduce pressure. The crude product was purified by basic preparative HPLC and after evaporation triturated with a mixture of ether and heptane. The (S)-4-{5-[(4-chloro-1-difluoromethyl-1H-pyrazol-3-ylmethyl)-amino]-2-fluoro-phenyl}-4-methyl-5,6-dihydro-4H-[1,3]oxazin-2-ylamine (8 mg, 20% yield) was obtained as a colorless oil. MS (ISP): m/z=388.2 [M+H]$^+$.

The 4-chloro-1-difluoromethyl-1H-pyrazole-3-carbaldehyde was prepared as follows:

a) 1-Difluoromethyl-1H-pyrazole-3-carboxylic acid methyl ester

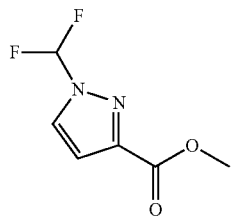

A solution of 1-difluoromethyl-1H-pyrazole-3-carboxylic acid (CAS [925179-02-8]) (500 mg, 3.1 mmol) in methanol (18 ml) was cooled to 0° C. and treated with sulfuric acid (98%, 0.2 ml, 3.1 mmol). The mixture was heated to reflux for 2 hours, cooled to 23° C. and concentrated at reduced pressure. The residue was partitioned between ethyl acetate and water, the organic layer was washed with water until the water phase showed a neutral pH, dried and evaporated to give the title compound (535 mg) as a colorless liquid which was used without further purification. MS (ISP): m/z=177.1 [M+H]$^+$.

b) 4-Chloro-1-difluoromethyl-1H-pyrazole-3-carboxylic acid methyl ester

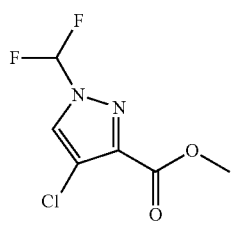

A mixture of 1-difluoromethyl-1H-pyrazole-3-carboxylic acid methyl ester (535 mg, 3 mmol) and N-chloro-succinimide (1.22 g, 9.1 mmol) in N,N-dimethylformamide (5 ml) was heated at 50° C. overnight. The reaction mixture was cooled, partitioned between ethyl acetate and water, the organic layer was washed with water, dried, evaporated and the residue was purified by chromatography on silica gel using cyclohexane/ethyl acetate (3:1) as the eluent to give the title compound (540 mg) as a white solid. MS (ISP): m/z=209.9 [M]$^+$.

c) 4-Chloro-1-difluoromethyl-1H-pyrazole-3-carboxylic acid

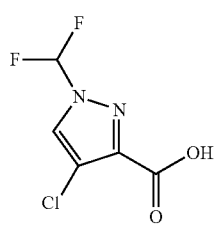 [SMILES: O=C(O)c1nn(C(F)F)cc1Cl]

A solution of 4-chloro-1-difluoromethyl-1H-pyrazole-3-carboxylic acid methyl ester (540 mg, 2.6 mmol) in tetrahydrofuran (18 ml) was treated at 23° C. with a solution of lithium hydroxide (135 mg, 5.6 mmol) in a 1:1-mixture of water and methanol (12 ml). After 1 hour the reaction was complete, and the solvents were evaporated at reduced pressure. The residue was partitioned between 2 M aqueous hydrochloric acid and ethyl acetate. The organic layer was dried, evaporated, the residue was triturated with pentane and the solid was dried to give the title compound (477 mg) as a white solid. MS (ISP): m/z=195.0 [M−H]$^-$.

d) 4-Chloro-1-difluoromethyl-1H-pyrazole-3-carboxylic acid methoxy-methyl-amide

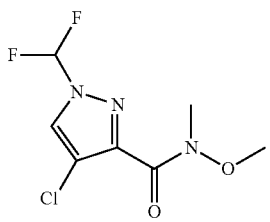

A solution of 4-chloro-1-difluoromethyl-1H-pyrazole-3-carboxylic acid (150 mg, 0.76 mmol) in dichloromethane (5 ml) was subsequently treated at 23° C. with N,O-dimethyl-hydroxylamine hydrochloride (78 mg, 0.80 mmol), N-methylmorpholine (0.09 ml, 0.8 mmol) and N-(3-dimethylaminopropyl)-N'-ethyl-carbodiimide hydrochloride (154 mg, 0.8 mmol) and stirring was continued for 16 hours. The mixture was washed with 1 M aqueous hydrochloric acid and water, the organic layer was dried, evaporated and the residue purified by chromatography on silica gel using cyclohexane/ethyl acetate (2:1) as the eluent to give the title compound (164 mg) as a colorless oil. MS (ISP): m/z=240.1 [M]$^+$.

e) 4-Chloro-1-difluoromethyl-1H-pyrazole-3-carbaldehyde

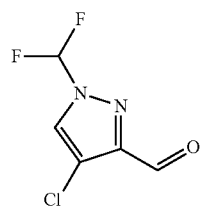

To a solution of 4-chloro-1-difluoromethyl-1H-pyrazole-3-carboxylic acid methoxy-methyl-amide (164 mg, 0.68 mmol) in tetrahydrofuran (5 ml) was added at 0° C. a solution of lithium aluminiumhydride (1M in tetrahydrofuran, 0.35 ml) and stirring was continued for 30 minutes. The mixture was quenched at −15° C. with a saturated aqueous solution of potassium hydrogensulphate and extracted with diethyl ether. The organic layer was dried, evaporated and the residue purified by chromatography on silica gel using cyclohexane/ethyl acetate (4:1) as the eluent to give the title compound (71 mg) as a pale yellow oil.

Example 2

(S)-4-(5-Cyclopentylamino-2-fluoro-phenyl)-4-methyl-5,6-dihydro-4H-[1,3]oxazin-2-ylamine A solution of cyclopentanone (26.2 µl, 296 µmol) and (S)-4-(5-amino-2-fluoro-phenyl)-4-methyl-5,6-dihydro-4H-[1,3]oxazin-2-ylamine (intermediate A8.4) (60 mg, 269 µmol) in dichloromethane (2 ml) was treated with acetic acid (30.8 µl, 538 µmol) followed by sodium triacetoxyborohydride (85.4 mg, 403 µmol). The reaction mixture was stirred at room temperature for 2.5 hours. For the workup, the reaction mixture was quenched with a saturated solution of sodium hydrogencarbonate, then extracted with ethyl acetate. The organic layer was washed twice with water, dried over sodium sulphate, and evaporated at reduced pressure. The crude product was purified by chromatography on a silica-NH$_2$ phase using a gradient of n-hexane/ethyl acetate=50:50 to 0:100 as the eluent to yield the (S)-4-(5-cyclopentylamino-2-fluoro-phenyl)-4-methyl-5,6-dihydro-4H-[1,3]oxazin-2-ylamine (5 mg, 6% yield). MS (ISP): m/z=292.1 [M+H]$^+$.

Example 3

(4R,5R)-5-Fluoro-4-[2-fluoro-5-(2-methoxy-phenylamino)-phenyl]-4-methyl-5,6-dihydro-4H-[1,3]oxazin-2-ylamine a) [Bis-(4-methoxy-phenyl)-phenyl-methyl]-{(4R,5R)-5-fluoro-4-[2-fluoro-5-(2-methoxy-phenylamino)-phenyl]-4-methyl-5,6-dihydro-4H-[1,3]oxazin-2-yl}-amine In a dry tube under an atmosphere of argon to a solution of [bis-(4-methoxy-phenyl)-phenyl-methyl]-[(4R,5R)-4-(5-bromo-2-fluoro-phenyl)-5-fluoro-4-methyl-5,6-dihydro-4H-[1,3]oxazin-2-yl]-amine (intermediate C4.3) (150 mg, 247 µmol) in dioxane (5 ml) was added consecutively sodium tert-butoxide (26.1 mg, 272 µmol), 2-di-tert-butylphosphino-2'4',6'-triisopropylbiphenyl (10.5 mg, 24.7 µmol), tris(dibenzylideneacetone)dipalladium(0)chloroform adduct (7.9 mg, 7.41 µmol), and 2-methoxyaniline (60.8 mg, 55.7 µl, 494 µmol). The tube was sealed and heated 115° C. under stirring during 15 hours. For the workup, the reaction mixture was evaporated at reduced pressure, and the residue was purified by chromatography on a silica-NH$_2$ phase using a gradient of heptane/ethyl acetate=100:0 to 60:30 as the eluent. The [bis-(4-methoxy-phenyl)-phenyl-methyl]-{(4R,5R)-5-fluoro-4-[2-fluoro-5-(2-methoxy-phenylamino)-phenyl]-4-methyl-5,6-dihydro-4H-[1,3]oxazin-2-yl}-amine (51 mg, 32% yield) was obtained as a pale yellow foam. MS (ISP): m/z=650.5 [M+H]$^+$.

b) (4R,5R)-5-Fluoro-4-[2-fluoro-5-(2-methoxy-phenylamino)-phenyl]-4-methyl-5,6-dihydro-4H-[1,3]oxazin-2-ylamine A solution of [bis-(4-methoxy-phenyl)-phenyl-methyl]-{(4R,5R)-5-fluoro-4-[2-fluoro-5-(2-methoxy-phenylamino)-phenyl]-4-methyl-5,6-dihydro-4H-[1,3]oxazin-2-yl}-amine (49.8 mg, 76.6 µmol) in dichloromethane (2 ml) was treated at room temperature with trifluoroacetic acid (89.2 mg, 59.9 µl, 766 µmol), and the mixture was stirred for 15 hours. After evaporation at reduced pressure, the dark red residue was purified by chromatography on a silica-NH$_2$ phase using a gradient of heptane/ethyl acetate=100:0 to 50:50 as the eluent. The (4R,5R)-5-fluoro-4-[2-fluoro-5-(2-methoxy-phenylamino)-phenyl]-4-methyl-5,6-dihydro-4H-[1,3]oxazin-2-ylamine (22 mg, 82% yield) was obtained as a white foam. MS (ISP): m/z=348.2 [M+H]$^+$.

Example 4

(4R,5R)-4-[5-(2-Difluoromethoxy-phenylamino)-2-fluoro-phenyl]-5-fluoro-4-methyl-5,6-dihydro-4H-[1,3]oxazin-2-ylamine a) [Bis-(4-methoxy-phenyl)-phenyl-methyl]-{(4R,5R)-4-[5-(2-difluoromethoxy-phenylamino)-2-fluoro-phenyl]-5-fluoro-4-methyl-5,6-dihydro-4H-[1,3]oxazin-2-yl}-amine In a manner analogous to that described in Example 3 a), the amination of [bis-(4-methoxy-phenyl)-phenyl-methyl]-[(4R,5R)-4-(5-bromo-2-fluoro-phenyl)-5-fluoro-4-methyl-5,6-dihydro-4H-[1,3]oxazin-2-yl]-amine (intermediate C4.3) with 2-(difluoromethoxy)aniline yielded the title compound (45% yield) as a pale yellow foam. MS (ISP): m/z=686.5 [M+H]$^+$.

b) (4R,5R)-4-[5-(2-Difluoromethoxy-phenylamino)-2-fluoro-phenyl]-5-fluoro-4-methyl-5,6-dihydro-4H-[1,3]oxazin-2-ylamine In a manner analogous to that described in Example 3b), the hydrolysis of the protecting group in the [bis-(4-methoxy-phenyl)-phenyl-methyl]-{(4R,5R)-4-[5-(2-difluoromethoxy-phenylamino)-2-fluoro-phenyl]-5-fluoro-4-methyl-5,6-dihydro-4H-[1,3]oxazin-2-yl}-amine yielded the title compound (78% yield) as a pale yellow foam. MS (ISP): m/z=384.3 [M+H]$^+$.

Example 5

(4R,5R)-5-Fluoro-4-{2-fluoro-5-[(thiophen-2-ylmethyl)-amino]-phenyl}-4-methyl-5,6-dihydro-4H-[1,3]oxazin-2-ylamine In a manner analogous to that described in Example 2, the reductive amination of (4R,5R)-4-(5-amino-2-fluoro-phenyl)-5-fluoro-4-methyl-5,6-dihydro-4H-[1,3]oxazin-2-ylamine (intermediate A8.2) with thiophene-2-carbaldehyde yielded the title compound (63% yield) as a white solid. MS (ISP): m/z=338.3 [M+H]$^+$.

Example 6

(4R,5R)-5-Fluoro-4-{2-fluoro-5-[(thiophen-3-ylmethyl)-amino]-phenyl}-4-methyl-5,6-dihydro-4H-[1,3]oxazin-2-ylamine In a manner analogous to that described in Example 2, the reductive amination of (4R,5R)-4-(5-amino-2-fluoro-phenyl)-5-fluoro-4-methyl-5,6-dihydro-4H-[1,3]oxazin-2-ylamine (intermediate A8.2) with thiophene-3-carbaldehyde yielded the title compound (56% yield) as a white solid. MS (ISP): m/z=338.4 [M+H]$^+$.

Example 7

(4R,5R)-5-Fluoro-4-[2-fluoro-5-(2-fluoro-benzylamino)-phenyl]-4-methyl-5,6-dihydro-4H-[1,3]oxazin-2-ylamine In a manner analogous to that described in Example 2, the reductive amination of (4R,5R)-4-(5-amino-2-fluoro-phenyl)-5-fluoro-4-methyl-5,6-dihydro-4H-[1,3]oxazin-2-ylamine (intermediate A8.2) with 2-fluorobenzaldehyde yielded the title compound (56% yield) as a white foam. MS (ISP): m/z=350.4 [M+H]⁺.

Example 8

(4R,5R)-4-[5-(Cyclopropylmethyl-amino)-2-fluoro-phenyl]-5-fluoro-4-methyl-5,6-dihydro-4H-[1,3]oxazin-2-ylamine In a manner analogous to that described in Example 2, the reductive amination of (4R,5R)-4-(5-amino-2-fluoro-phenyl)-5-fluoro-4-methyl-5,6-dihydro-4H-[1,3]oxazin-2-ylamine (intermediate A8.2) with cyclopropanecarbaldehyde yielded the title compound (67% yield) as a white foam. MS (ISP): m/z=296.4 [M+H]⁺.

Example 9

5-[3-((4R,5R)-2-Amino-5-fluoro-4-methyl-5,6-dihydro-4H-[1,3]oxazin-4-yl)-4-fluoro-phenyl]-nicotinonitrile a) 5-[3-((4R,5R)-2-{[Bis-(4-methoxy-phenyl)-phenyl-methyl]-amino}-5-fluoro-4-methyl-5,6-dihydro-4H-[1,3]oxazin-4-yl)-4-fluoro-phenyl]-nicotinonitrile In a dry tube under an atmosphere of argon to a solution of [bis-(4-methoxy-phenyl)-phenyl-methyl]-[(4R,5R)-4-(5-bromo-2-fluoro-phenyl)-5-fluoro-4-methyl-5,6-dihydro-4H-[1,3]oxazin-2-yl]-amine (intermediate C4.3) (250 mg, 412 μmol) and 5-(4,4,5,5-tetramethyl-1,3,2-dioxaborolan-2-yl)nicotinonitrile (142 mg, 617 μmol) in 1,2-dimethoxyethane (3 ml) were added consecutively an aqueous solution of sodium carbonate (2M, 0.6 ml), triphenylphosphine (22.3 mg, 82.3 μmol), and, after flushing the mixture with argon, palladium(II)acetate (9.24 mg, 41.2 μmol). The tube was sealed and heated under stirring at 105° C. for 15 hours. After evaporation at reduced pressure, the residue was purified by chromatography on a silica-NH₂ phase using a gradient of heptane/ethyl acetate=100:0 to 60:30 as the eluent. The 5-[3-((4R,5R)-2-{[bis-(4-methoxy-phenyl)-phenyl-methyl]-amino}-5-fluoro-4-methyl-5,6-dihydro-4H-[1,3]oxazin-4-yl)-4-fluoro-phenyl]-nicotinonitrile (260 mg, 100% yield) as a white foam. MS (ISP): m/z=631.4 [M+H]⁺.

b) 5-[3-((4R,5R)-2-Amino-5-fluoro-4-methyl-5,6-dihydro-4H-[1,3]oxazin-4-yl)-4-fluoro-phenyl]-nicotinonitrile In a manner analogous to that described in Example 3b), the hydrolysis of the protecting group in the 5-[3-((4R,5R)-2-{[bis-(4-methoxy-phenyl)-phenyl-methyl]-amino}-5-fluoro-4-methyl-5,6-dihydro-4H-[1,3]oxazin-4-yl)-4-fluoro-phenyl]-nicotinonitrile yielded the title compound (92% yield) as a white solid. MS (ISP): m/z=329.4 [M+H]⁺.

Example 10

(4R,5R)-5-Fluoro-4-{2-fluoro-5-[1-(4-fluoro-phenyl)-1H-pyrazol-4-yl]-phenyl}-4-methyl-5,6-dihydro-4H-[1,3]oxazin-2-ylamine Hydrochloride a) [Bis-(4-methoxy-phenyl)-phenyl-methyl]-((4R,5R)-5-fluoro-4-{2-fluoro-5-[1-(4-fluoro-phenyl)-1H-pyrazol-4-yl]-phenyl}-4-methyl-5,6-dihydro-4H-[1,3]oxazin-2-yl)-amine In a manner analogous to that described in Example 9 a), the cross coupling reaction of [bis-(4-methoxy-phenyl)-phenyl-methyl]-[(4R,5R)-4-(5-bromo-2-fluoro-phenyl)-5-fluoro-4-methyl-5,6-dihydro-4H-[1,3]oxazin-2-yl]-amine (intermediate C4.3) with 1-(4-fluorophenyl)-1H-pyrazol-4-ylboronic acid (CAS [1072945-89-1]) and tetrakis(triphenylphosphine)-palladium(0) as the catalyst yielded the title compound (75% yield) as a white foam. MS (ISP): m/z=689.3 [M+H]⁺.

b) (4R,5R)-5-Fluoro-4-{2-fluoro-5-[1-(4-fluoro-phenyl)-1H-pyrazol-4-yl]-phenyl}-4-methyl-5,6-dihydro-4H-[1,3]oxazin-2-ylamine hydrochloride In a manner analogous to that described in Example 3b), the hydrolysis of the protecting group in the [bis-(4-methoxy-phenyl)-phenyl-methyl]-((4R,5R)-5-fluoro-4-{2-fluoro-5-[1-(4-fluoro-phenyl)-1H-pyrazol-4-yl]-phenyl}-4-methyl-5,6-dihydro-4H-[1,3]oxazin-2-yl)-amine yielded the title compound, which was treated with hydrochloric acid (4M in dioxane). After evaporation at reduced pressure the residue was triturated with diethylether. The (4R,5R)-5-Fluoro-4-{2-fluoro-5-[1-(4-fluoro-phenyl)-1H-pyrazol-4-yl]-phenyl}-4-methyl-5,6-dihydro-4H-[1,3]oxazin-2-ylamine hydrochloride (74% yield) was obtained as a reddish solid. MS (ISP): m/z=387.2 [M+H]⁺.

Example 11

(4R,5R)-5-Fluoro-4-[2-fluoro-5-(4-methyl-pyrazol-1-yl)-phenyl]-4-methyl-5,6-dihydro-4H-[1,3]oxazin-2-ylamine a) [Bis-(4-methoxy-phenyl)-phenyl-methyl]-{(4R,5R)-5-fluoro-4-[2-fluoro-5-(4-methyl-pyrazol-1-yl)-phenyl]-4-methyl-5,6-dihydro-4H-[1,3]oxazin-2-yl}-amine In a manner analogous to that described in Example 3 a), the amination of [bis-(4-methoxy-phenyl)-phenyl-methyl]-[(4R,5R)-4-(5-bromo-2-fluoro-phenyl)-5-fluoro-4-methyl-5,6-dihydro-4H-[1,3]oxazin-2-yl]-amine (intermediate C4.3) with 4-methyl-1H-pyrazole yielded the title compound (28% yield) as a white foam. MS (ISP): m/z=609.2 [M+H]⁺.

b) (4R,5R)-5-Fluoro-4-[2-fluoro-5-(4-methyl-pyrazol-1-yl)-phenyl]-4-methyl-5,6-dihydro-4H-[1,3]oxazin-2-ylamine In a manner analogous to that described in Example 3b), the hydrolysis of the protecting group in the [bis-(4-methoxy-phenyl)-phenyl-methyl]-{(4R,5R)-5-fluoro-4-[2-fluoro-5-(4-methyl-pyrazol-1-yl)-phenyl]-4-methyl-5,6-dihydro-4H-[1,3]oxazin-2-yl}-amine yielded the title compound (73% yield) as a white solid. MS (ISP): m/z=307.2 [M+H]⁺.

Example 12

(4R,5R)-4-{5-[(4-Chloro-1-difluoromethyl-1H-pyrazol-3-ylmethyl)-amino]-2-fluoro-phenyl}-5-fluoro-4,5-dimethyl-5,6-dihydro-4H-[1,3]oxazin-2-ylamine In a manner analogous to that described in Example 1, the reductive amination of (4R,5R)-4-(5-amino-2-fluoro-phenyl)-5-fluoro-4,5-dimethyl-5,6-dihydro-4H-[1,3]oxazin-2-ylamine (intermediate A8.3) with 4-chloro-1-difluoromethyl-1H-pyrazole-3-carbaldehyde yielded the title compound (42% yield) as a colorless solid. MS (ISP): m/z=420.1 [M+H]⁺.

Example 13

(4R,5R)-4-{5-[(4-Chloro-1-methyl-1H-pyrazol-3-ylmethyl)-amino]-2-fluoro-phenyl}-5-fluoro-4,5-dimethyl-5,6-dihydro-4H-[1,3]oxazin-2-ylamine In a manner analogous to that described in Example 1, the reductive amination of (4R,5R)-4-(5-amino-2-fluoro-phenyl)-5-fluoro-4,5-dimethyl-5,6-dihydro-4H-[1,3]oxazin-2-ylamine (intermediate A8.3) with 4-chloro-1-methyl-1H-pyrazole-3-carbaldehyde (CAS [175204-81-6]) yielded the title compound (63% yield) as a white crystalline solid. MS (ISP): m/z=384.2 [M+H]$^+$.

Example 14

(4R,5R)-5-Fluoro-4-{2-fluoro-5-[(RS)-1-(2-methyl-5-trifluoromethyl-oxazol-4-yl)-ethylamino]-phenyl}-4,5-dimethyl-5,6-dihydro-4H-[1,3]oxazin-2-ylamine In a manner analogous to that described in Example 1, the reductive amination of (4R,5R)-4-(5-amino-2-fluoro-phenyl)-5-fluoro-4,5-dimethyl-5,6-dihydro-4H-[1,3]oxazin-2-ylamine (intermediate A8.3) with 1-(2-methyl-5-trifluoromethyl-oxazol-4-yl)-ethanone yielded the title compound (64% yield) as a 1:1-mixture of epimers and as a white solid. MS (ISP): m/z=433.3 [M+H]$^+$.

The 1-(2-methyl-5-trifluoromethyl-oxazol-4-yl)-ethanone was obtained as follows:

a) 2-Methyl-5-trifluoromethyl-oxazole-4-carboxylic acid methoxy-methyl-amide In a manner analogous to that described in Example 1 d), the condensation of 2-methyl-5-trifluoromethyl-oxazole-4-carboxylic acid and N,O-dimethylhydroxylamine hydrochloride by N-(3-dimethylaminopropyl)-N'-ethyl-carbodiimide hydrochloride yielded the title compound (92% yield) as a colorless oil. MS (ISP): m/z=239.0 [M+H]$^+$.

b) 1-(2-Methyl-5-trifluoromethyl-oxazol-4-yl)-ethanone

Under an atmosphere of nitrogen, a solution of methylmagnesium bromide (3M in diethylether; 0.63 ml, 1.89 mmol) was cooled to 0° C. A solution of 2-methyl-5-trifluoromethyl-oxazole-4-carboxylic acid methoxy-methyl-amide (300 mg, 1.26 mmol) in diethylether (3 ml) was added dropwise. The reaction mixture was left to warm to room temperature and stirring was continued for 15 minutes. For the workup, the reaction mixture was cooled to 0° C. and quenched with hydrochloric acid (1N, 3 ml). After 5 minutes of stirring, the mixture was extracted with diethylether. The organic layer was dried over sodium sulphate, then evaporated. The crude product was purified by chromatography on silica gel using a 4:1-mixture of cyclohexane and ethyl acetate as the eluent. The 1-(2-methyl-5-trifluoromethyl-oxazol-4-yl)-ethanone (155 mg, 64% yield) was obtained as a colorless liquid.

Example 15

(R)-4-[5-(6-Chloro-benzooxazol-2-yl)-2,4-difluoro-phenyl]-5,5-difluoro-4-methyl-5,6-dihydro-4H-[1,3]oxazin-2-ylamine Hydrochloride a) [Bis-(4-methoxy-phenyl)-phenyl-methyl]-{(R)-4-[5-(6-chloro-benzooxazol-2-yl)-2,4-difluoro-phenyl]-5,5-difluoro-4-methyl-5,6-dihydro-4H-[1,3]oxazin-2-yl}-amine In a tube a mixture of [bis-(4-methoxy-phenyl)-phenyl-methyl]-{(R)-4-[5-(5,5-dimethyl-[1,3,2]dioxaborinan-2-yl)-2,4-difluoro-phenyl]-5,5-difluoro-4-methyl-5,6-dihydro-4H-[1,3]oxazin-2-yl}-amine (intermediate D1.1) (130 mg, 144 μmol), 2,6-dichlorobenzo[d]oxazole (30.4 mg, 159 μmol), and cesium carbonate (188 mg, 576 μmol) in tetrahydrofuran (4 ml) and water (2 ml) was purged with argon for 5 minutes. Thereafter, [1,1'-bis(diphenylphosphino)ferrocene]dichloropalladium(II) complex with dichloromethane (5.88 mg, 7.21 μmol) was added, the tube was sealed and the mixture heated at 80° C. for 16 hours. After evaporation, the residue was purified by chromatography on silica gel using a gradient of heptane/ethyl acetate=100:0 to 70:30 as the eluent. The [bis-(4-methoxy-phenyl)-phenyl-methyl]-{(R)-4-[5-(6-chloro-benzooxazol-2-yl)-2,4-difluoro-phenyl]-5,5-difluoro-4-methyl-5,6-dihydro-4H-[1,3]oxazin-2-yl]-amine (52 mg, 50% yield) was obtained as a pale yellow solid. MS (ISP): m/z=716.1 [M+H]$^+$.

b) (R)-4-[5-(6-Chloro-benzooxazol-2-yl)-2,4-difluoro-phenyl]-5,5-difluoro-4-methyl-5,6-dihydro-4H-[1,3]oxazin-2-ylamine Hydrochloride In a manner analogous to that described in Example 3 b), the hydrolysis of the protecting group in the [bis-(4-methoxy-phenyl)-phenyl-methyl]-{(R)-4-[5-(6-chloro-benzooxazol-2-yl)-2-fluoro-phenyl]-5,5-difluoro-4-methyl-5,6-dihydro-4H-[1,3]oxazin-2-yl}-amine yielded the (R)-4-[5-(6-chloro-benzooxazol-2-yl)-2,4-difluoro-phenyl]-5,5-difluoro-4-methyl-5,6-dihydro-4H-[1,3]oxazin-2-ylamine. After chromatography on a silica-NH$_2$ phase using a gradient of heptane/ethyl acetate=100:0 to 40:60 as the eluent, the evaporated fractions were dissolved in dioxane (1 ml) and treated with hydrochloric acid (4M in dioxane; 0.1 ml). Evaporation and trituration of the residue in a mixture (2 ml) of diethylether and heptane yielded the title compound (73% yield) as an off-white solid. MS (ISP): m/z=414.2 [M+H]$^+$ and 416.2 [M+2+H]$^+$.

Example 16

(R)-4-{5-[(4-Chloro-1-difluoromethyl-1H-pyrazol-3-ylmethyl)-amino]-2-fluoro-phenyl}-5,5-difluoro-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with 4-chloro-1-difluoromethyl-1H-pyrazole-3-carbaldehyde yielded the title compound (71% yield) as an amorphous colorless material. MS (ISP): m/z=424.1 [M+H]$^+$.

Example 17

(R)-5,5-Difluoro-4-{2-fluoro-5-[(RS)-1-(5-methyl-2H-pyrazol-3-yl)-ethylamino]-phenyl}-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with 1-(3-methyl-1H-pyrazol-5-yl)ethanone (CAS [17357-74-3]) yielded the title compound (25% yield) as a 1:1-mixture of epimers and as a colorless solid. MS (ISP): m/z=368.2 [M+H]$^+$.

Example 18

(R)-4-{5-[(RS)-1-(4-Chloro-1-methyl-1H-pyrazol-3-yl)-ethylamino]-2-fluoro-phenyl}-5,5-difluoro-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with 1-(4-chloro-1-methyl-1H-pyrazol-3-yl)ethanone (CAS [1004194-08-4]) yielded the title compound (33% yield) as a 1:1-mixture of epimers and as a colorless solid. MS (ISP): m/z=402.4 [M+H]$^+$.

Example 19

(R)-4-(5-{(RS)-1-[4-Chloro-1-(2,2-difluoro-ethyl)-1H-pyrazol-3-yl]-ethylamino}-2-fluoro-phenyl)-5,5-difluoro-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with 1-(4-chloro-1-(2,2-difluoroethyl)-1H-pyrazol-3-yl)ethanone yielded the title compound (58% yield) as a 1:1-mixture of epimers and as a colorless solid. MS (ISP): m/z=452.2 [M+H]$^+$.

The 1-(4-chloro-1-(2,2-difluoroethyl)-1H-pyrazol-3-yl)ethanone was obtained as follows:

a) 4-Chloro-1-(2,2-difluoro-ethyl)-1H-pyrazole-3-carboxylic acid methoxy-methyl-amide In a manner analogous to that described in Example 1d), the condensation of 4-chloro-1-(2,2-difluoroethyl)-1H-pyrazole-3-carboxylic acid and N,O-dimethylhydroxylamine hydrochloride by N-(3-dimethylaminopropyl)-N'-ethyl-carbodiimide hydrochloride yielded the title compound (98% yield) as a colorless oil. MS (ISP): m/z=254.1 [M+H]$^+$.

b) 1-(4-Chloro-1-(2,2-difluoroethyl)-1H-pyrazol-3-yl)ethanone

In a manner analogous to that described in Example 14 b), the Grignard reaction of 4-chloro-1-(2,2-difluoro-ethyl)-1H-pyrazole-3-carboxylic acid methoxy-methyl-amide with methylmagnesium bromide yielded the title compound (66% yield) as a colorless oil. MS (ISP): m/z=209.0 [M+H]$^+$.

Example 20

(R)-4-{5-[(RS)-1-(5-Cyclopropyl-isoxazol-3-yl)-ethylamino]-2-fluoro-phenyl}-5,5-difluoro-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with 1-(5-cyclopropylisoxazol-3-yl)ethanone yielded the title compound (72% yield) as a 1:1-mixture of epimers and as a colorless solid. MS (ISP): m/z=395.3 [M+H]$^+$.

The 1-(5-cyclopropylisoxazol-3-yl)ethanone was obtained as follows:

a) 5-Cyclopropyl-isoxazole-3-carboxylic acid methoxy-methyl-amide

In a manner analogous to that described in Example 1 d), the condensation of 5-cyclopropyl-isoxazole-3-carboxylic acid and N,O-dimethylhydroxylamine hydrochloride by N-(3-dimethylaminopropyl)-N'-ethyl-carbodiimide hydrochloride yielded the title compound (96% yield) as a pale yellow oil. MS (ISP): m/z=197.2 [M+H]$^+$.

b) 1-(5-Cyclopropylisoxazol-3-yl)ethanone

In a manner analogous to that described in Example 14 b), the Grignard reaction of 5-cyclopropyl-isoxazole-3-carboxylic acid methoxy-methyl-amide with methylmagnesium bromide yielded the title compound (74% yield) as a colorless liquid.

Example 21

(R)-5,5-Difluoro-4-{2-fluoro-5-[(RS)-1-(2-methyl-5-trifluoromethyl-oxazol-4-yl)-ethylamino]-phenyl}-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with 1-(2-methyl-5-trifluoromethyl-oxazol-4-yl)-ethanone (Example 14) yielded the title compound (52% yield) as a 1:1-mixture of epimers and as a colorless solid. MS (ISP): m/z=437.3 [M+H]$^+$.

Example 22

(RS)-7-[3-((R)-2-Amino-5,5-difluoro-4-methyl-5,6-dihydro-4H-[1,3]oxazin-4-yl)-4-fluoro-phenylamino]-6,7-dihydro-5H-[1]pyrindine-3-carbonitrile a) {(R)-4-[5-((RS)-3-Cyano-6,7-dihydro-5H-[1]pyrindin-7-ylamino)-2-fluoro-phenyl]-5,5-difluoro-4-methyl-5,6-dihydro-4H-[1,3]oxazin-2-yl}-carbamic acid tert-butyl ester In a manner analogous to that described in Example 1, the reductive amination of [(R)-4-(5-amino-2-fluoro-phenyl)-5,5-difluoro-4-methyl-5,6-dihydro-4H-[1,3]oxazin-2-yl]-carbamic acid tert-butyl ester (intermediate C3.1) with 7-oxo-6,7-dihydro-5H-cyclopenta[b]pyridine-3-carbonitrile yielded the title compound (56% yield) as a mixture of epimers and as a yellow solid. MS (ISP): m/z=502.2 [M+H]$^+$.

b) (RS)-7-[3-((R)-2-Amino-5,5-difluoro-4-methyl-5,6-dihydro-4H-[1,3]oxazin-4-yl)-4-fluoro-phenylamino]-6,7-dihydro-5H-[1]pyrindine-3-carbonitrile A solution of {(R)-4-[5-((RS)-3-cyano-6,7-dihydro-5H-[1]pyrindin-7-ylamino)-2-fluoro-phenyl]-5,5-difluoro-4-methyl-5,6-dihydro-4H-[1,3]oxazin-2-yl}-carbamic acid tert-butyl ester (110 mg, 219 µmol) in hydrochloric acid (4M in dioxane; 1.65 ml, 6.58 mmol) was stirred at room temperature and the progress of reaction was followed on TLC. After completion, the mixture was poured into an aqueous saturated solution of sodium bicarbonate, then extracted with ethyl acetate. The combined organic layers were dried over sodium sulphate and the solvent removed leaving a yellow solid. The crude material was purified by flash chromatography on silica gel using a gradient of heptane/ethyl acetate=100:0 to 0:100 as the eluent. The (RS)-7-[3-((R)-2-amino-5,5-difluoro-4-methyl-5,6-dihydro-4H-[1,3]oxazin-4-yl)-4-fluoro-phenylamino]-6,7-dihydro-5H-[1]pyrindine-3-carbonitrile (12 mg, 14% yield) was obtained as a mixture of epimers and as a yellow solid. MS (ISP): m/z=402.4 [M+H]$^+$.

The 7-oxo-6,7-dihydro-5H-[1]pyrindine-3-carbonitrile was prepared as follows:

a) 6,7-Dihydro-5H-[1]pyrindine-3-carbonitrile

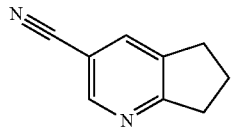 [SMILES: N#Cc1cnc2c(c1)CCC2]

A mixture of 3-chloro-6,7-dihydro-5H-[1]pyrindine (7.1 g, 46.2 mmol), sodium carbonate (980 mg, 9.25 mmol), potassium hexacyanoferrate(II)trihydrates (7.81 g, 18.5 mmol), palladium(II) acetate (104 mg, 462 μmol) and butyldi-1-adamantylphosphine (497 mg, 1.39 mmol) was dissolved in N-methyl-2-pyrrolidinone (46.2 ml), the solution flushed with argon and heated to 160° C. for 16 hours. After cooling to 23° C., the mixture was poured into water, extracted with dichloromethane, the combined extracts dried over sodium sulphate and the solvent evaporated leaving a dark blue liquid. The crude material was purified by silica gel flash chromatography with n-heptane/ethyl acetate to give the 6,7-dihydro-5H-[1]pyrindine-3-carbonitrile as a white solid (4.82 g, 72% yield). MS (ISP): m/z=145.1 [M+H]$^+$.

b) 1-Oxy-6,7-dihydro-5H-[1]pyrindine-3-carbonitrile

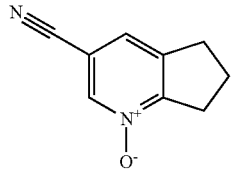 [SMILES: N#Cc1cc2c([n+]([O-])c1)CCC2]

To a solution of 6,7-dihydro-5H-[1]pyrindine-3-carbonitrile (6.23 g, 43.2 mmol) in acetic acid (54 ml) at 40° C. was portionwise added sodium perborate tetrahydrate (7.31 g, 47.5 mmol) and the mixture was stirred at 40° C. for 30 hours. Added more sodium perborate tetrahydrate (1.05 g, 6.82 mmol) after 24 h. The acetic acid was removed by evaporation, the residue taken up in a saturated solution of sodium hydrogencarbonate, extracted with dichloromethane (3×150 ml), the combined organic layers were dried over sodium sulphate. Removal of the solvent in vacuum left the 1-oxy-6,7-dihydro-5H-[1]pyrindine-3-carbonitrile (6.5 g, 90.6 yield %) as a white solid. MS (ISP): m/z=161.1 [M+H]$^+$.

c) 7-Hydroxy-6,7-dihydro-5H-[1]pyrindine-3-carbonitrile

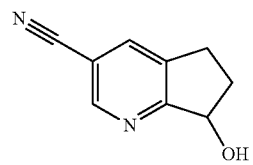 [SMILES: N#Cc1cnc2c(c1)CCC2O]

To a solution of 1-oxy-6,7-dihydro-5H-[1]pyrindine-3-carbonitrile (1.82 g, 11.4 mmol) in dichloromethane (40 ml) at 0° C. was added dropwise trifluoroacetic anhydride (14.3 g, 9.63 ml, 68.2 mmol) and the mixture was stirred at 0 to 23° C. for 18 hours. Poured into icecold solution of sodium hydroxide (1N), stirred for 30 minutes and extracted twice with dichloromethane. The combined organic layers were dried over sodium sulphate, the solvent was removed in vacuum to leave a brown residue, which was purified by silica gel column chromatography with n-heptane/ethyl acetate to give the 7-hydroxy-6,7-dihydro-5H-[1]pyrindine-3-carbonitrile (1.14 g, 63%) as a yellow solid. MS (ISP): m/z=161.1 [M+H]$^+$.

d) 7-Oxo-6,7-dihydro-5H-[1]pyrindine-3-carbonitrile

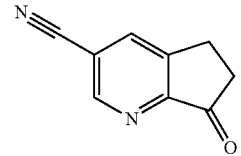

To a solution of 7-hydroxy-6,7-dihydro-5H-[1]pyrindine-3-carbonitrile (1.05 g, 6.56 mmol) in dichloromethane (50 ml) at 0° C. was added Dess-Martin periodinane (2.92 g, 6.88 mmol) and the mixture was stirred at 23° C. for 2 hours. Poured on a solution of sodium carbonate (1M) and extracted twice with dichloromethane. The organic layers were washed with a diluted solution of sodium hydrogensulfite and brine, dried over sodium sulphate, filtered and evaporated to give a grey solid. The residue was purified by silica gel flash chromatography with n-heptane/ethyl acetate to give the 7-oxo-6,7-dihydro-5H-[1]pyrindine-3-carbonitrile (855 mg, 78%) as a dark green solid. MS (ISP): m/z=159.1 [M+H]$^+$.

Example 23

[3-((R)-2-Amino-5,5-difluoro-4-methyl-5,6-dihydro-4H-[1,3]oxazin-4-yl)-4-fluoro-phenyl]-((RS)-3-chloro-6,7-dihydro-5H-[1]pyrindin-7-yl)-amine a) {(R)-4-[5-((RS)-3-Chloro-6,7-dihydro-5H-[1]pyrindin-7-ylamino)-2-fluoro-phenyl]-5,5-difluoro-4-methyl-5,6-dihydro-4H-[1,3]oxazin-2-yl}-carbamic acid tert-butyl ester In a manner analogous to that described in Example 1, the reductive amination of [(R)-4-(5-amino-2-fluoro-phenyl)-5, 5-difluoro-4-methyl-5,6-dihydro-4H-[1,3]oxazin-2-yl]-carbamic acid tert-butyl ester (intermediate C3.1) with 3-chloro-5,6-dihydro-[1]pyrindin-7-one yielded the title compound (100% yield) as a mixture of epimers and as a pale yellow solid. MS (ISP): m/z==511.3 [M+H]⁺ and 513.4 [M+2+H]⁺.

b) [3-((R)-2-Amino-5,5-difluoro-4-methyl-5,6-dihydro-4H-[1,3]oxazin-4-yl)-4-fluoro-phenyl]-((RS)-3-chloro-6,7-dihydro-5H-[1]pyrindin-7-yl)-amine In a manner analogous to that described in Example 22 b), the cleavage of the protecting group yielded the title compound (50% yield) as a mixture of epimers and as a white crystalline solid. MS (ISP): m/z=411.2 [M+H]⁺.

The 3-chloro-5,6-dihydro-[1]pyrindin-7-one was prepared as follows:

a) 3-Chloro-6,7-dihydro-5H-[1]pyrindine

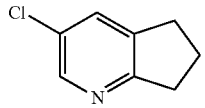

A solution of 5-chloro-2-(pent-4-ynyl)pyrimidine (H. C. van der Plas, Tetrahedron 1989, 45, 5151-5162) (4.95 g (27.4 mmol) in nitrobenzene (50 ml) was heated to 210° C. for 1.5 hours under a continuous stream of nitrogen. The reaction was followed by TLC (silica gel, heptane:ethyl acetate=2:1; UV detection 254 nm). After completion, the reaction mixture was purified by flash chromatography on silica gel using a gradient of heptane/ethyl acetate=100:0 to 80:20 as the eluent. The 3-chloro-6,7-dihydro-5H-[1]pyrindine was obtained as a light brown solid (3.21 g, 76% yield). MS (ISP): m/z=154 [M+H]⁺.

b) 3-Chloro-6,7-dihydro-5H-[1]pyrindine 1-oxide

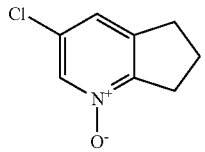 [SMILES: [O-][n+]1cc(Cl)cc2c1CCC2]

A solution of 3-chloro-6,7-dihydro-5H-[1]pyrindine (3.03 g, 19.7 mmol) in acetic acid (19.7 ml) was treated at room temperature with hydrogen peroxide (3.45 ml, 39.5 mmol). The mixture was heated to 70° C. and stirred at this temperature overnight. After completion, the reaction mixture was allowed to cool and was concentrated at reduced pressure. Water was added and the mixture was evaporated again. This procedure was repeated another 2 times. The residue was dissolved in ethyl acetate, washed with a saturated aqueous solution of sodium hydrogen carbonate and brine, then dried over sodium sulfate and evaporated at reduced pressure. The crude 3-chloro-6,7-dihydro-5H-[1]pyrindine 1-oxide was obtained as dark green crystals (2.07 g, 62% yield). MS (ISP): m/z=170 [M+H]⁺.

c) Acetic acid 3-chloro-6,7-dihydro-5H-[1]pyrindin-7-yl ester

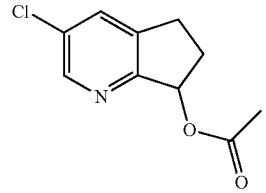

A solution of 3-chloro-6,7-dihydro-5H-[1]pyrindine 1-oxide (2.07 g, 12.2 mmol) in acetic acid anhydride (62.2 ml, 659 mmol) was stirred at 110° C. for 20 hours. For the workup, the solvent was removed at reduced pressure and the residue quenched with saturated aqueous solution of sodium hydrogen carbonate. The aqueous phase was extracted with dichloromethane, the resulting organic layers combined and dried over sodium sulphate. After evaporation of the solvent, the residue was purified by flash chromatography on silica gel using a gradient of heptane/ethyl acetate=100:0 to 70:30 as the eluent. The acetic acid 3-chloro-6,7-dihydro-5H-[1]pyrindin-7-yl ester was obtained as a red liquid (1.57 g, 61% yield). MS (ISP): m/z=212 [M+H]⁺.

d) 3-Chloro-6,7-dihydro-5H-[1]pyrindin-7-ol

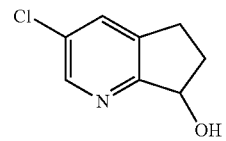 [SMILES: OC1CCc2cc(Cl)cnc21]

A solution of acetic acid 3-chloro-6,7-dihydro-5H-[1]pyrindin-7-yl ester (1.57 g, 7.42 mmol) in methanol (35.7 ml) was treated with a solution of sodium hydroxide (1M; 8.9 ml). The mixture was stirred at room temperature for 1.5 hours. The reaction was followed by TLC (silica gel, heptane:ethyl acetate=1:1; UV detection 254 nm). After completion, the reaction mixture was treated with water and extracted with dichloromethane. The combined organic layers were dried over sodium sulphate, then evaporated leaving a dark red liquid (1.15 g, 91% yield) which crystallised on standing. Following NMR the product was pure enough for the next step of the synthesis. MS (ISP): m/z=170 [M+H]⁺.

e) 3-Chloro-5,6-dihydro-[1]pyrindin-7-one

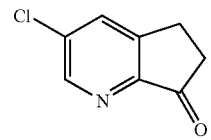 [SMILES: O=C1CCc2cc(Cl)cnc21]

A solution of 3-chloro-6,7-dihydro-5H-[1]pyrindin-7-ol (570 mg, 3.36 mmol) in dimethylsulphoxide (17.7 ml) was treated at room temperature with triethylamine (2.81 ml, 20.2 mmol) followed by sulfur trioxide-pyridine complex (1.6 g, 10.1 mmol). The solution was stirred at room temperature for 1 hour. After completion, the reaction mixture was treated with water and extracted with dichloromethane. The combined organic layers were dried over sodium sulphate, then evaporated leaving a dark red liquid. The crude material was purified by flash chromatography on silica gel using a gradient of heptane/ethyl acetate=70:30 to 30:70 as the eluent. The 3-chloro-5,6-dihydro-[1]pyrindin-7-one was obtained as a pink solid (472 mg, 84% yield). MS (ISP): m/z=168 [M+H]$^+$.

Example 24

(R)-5,5-Difluoro-4-{2-fluoro-5-[(3-methyl-oxetan-3-ylmethyl)-amino]-phenyl}-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with 3-methyl-oxetane-3-carbaldehyde (CAS [99419-31-5]) yielded the title compound (41% yield). MS (ISP): m/z=344.1 [M+H]$^+$.

Example 25

(R)-4-[5-(Cyclopropylmethyl-amino)-2-fluoro-phenyl]-5,5-difluoro-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with cyclopropanecarbaldehyde (CAS [1489-69-6]) yielded the title compound (38% yield). MS (ISP): m/z=314.3 [M+H]$^+$.

Example 26

(R)-5,5-Difluoro-4-{2-fluoro-5-[(RS)-(tetrahydro-furan-3-yl)amino]-phenyl}-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with dihydro-furan-3-one (CAS [22929-52-8]) yielded the title compound (44% yield) as a mixture of epimers and as a white crystalline solid. MS (ISP): m/z=330.1 [M+H]$^+$ Example 27

(RS)-8-[3-((R)-2-Amino-5,5-difluoro-4-methyl-5,6-dihydro-4H-[1,3]oxazin-4-yl)-4-fluoro-phenylamino]-5,6,7,8-tetrahydro-quinoline-3-carbonitrile a) {(R)-4-[5-((RS)-3-Cyano-5,6,7,8-tetrahydro-quinolin-8-ylamino)-2-fluoro-phenyl]-5,5-difluoro-4-methyl-5,6-dihydro-4H-[1,3]oxazin-2-yl}-carbamic acid tert-butyl ester
In a manner analogous to that described in Example 1, the reductive amination of [(R)-4-(5-amino-2-fluoro-phenyl)-5,5-difluoro-4-methyl-5,6-dihydro-4H-[1,3]oxazin-2-yl]-carbamic acid tert-butyl ester (intermediate C3.1) with 8-oxo-5,6,7,8-tetrahydro-quinoline-3-carbonitrile yielded the title compound (56% yield) as a mixture of epimers and as a white foam. MS (ISN): m/z=514.2 [M−H]$^-$.

b) (RS)-8-[3-((R)-2-Amino-5,5-difluoro-4-methyl-5,6-dihydro-4H-[1,3]oxazin-4-yl)-4-fluoro-phenylamino]-5,6,7,8-tetrahydro-quinoline-3-carbonitrile In a manner analogous to that described in Example 22 b), the cleavage of the protecting group yielded the title compound (78% yield) as a mixture of epimers and as a white foam. MS (ISP): m/z=416.1 [M+H]$^+$.

The 8-oxo-5,6,7,8-tetrahydroquinoline-3-carbonitrile was prepared as follows:

a) 5,6,7,8-Tetrahydroquinoline-3-carbonitrile

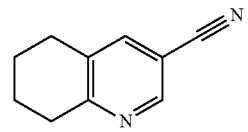 [SMILES: N#Cc1cnc2c(c1)CCCC2]

A mixture of commercially available 2-chloro-5,6,7,8-tetrahydroquinoline-3-carbonitrile [CAS no 65242-27-5] (1 g, 5.19 mmol), zinc dust (activated) (602 mg, 9.2 mmol) and sodium acetate trihydrate (694 mg, 479 μl, 5.1 mmol) in acetic acid (5.19 g, 4.95 ml, 86.4 mmol) was stirred at 60° C. for 2 hours. Water (2.5 ml) was added and the mixture stirred at 60° C. for another 5 hours. After cooling to 23° C., the mixture was basified with an aqueous solution of sodium hydroxide (1M) and filtered through Celite®. The filtrate was extracted with tetrahydrofuran, the organic layers dried over sodium sulphate and the solvent evaporated leaving a yellow liquid. The crude material was purified by silica gel flash chromatography with n-heptane/ethyl acetate to give the 5,6,7,8-tetrahydroquinoline-3-carbonitrile as a white solid (433 mg, 53% yield). MS (ISP): m/z=159.1 [M+H]$^+$.

b) 3-Cyano-5,6,7,8-tetrahydroquinoline 1-oxide

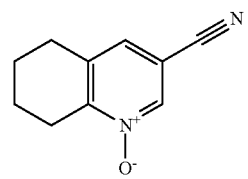 [SMILES: N#Cc1cc2c([n+]([O-])c1)CCCC2]

To a solution of 5,6,7,8-tetrahydroquinoline-3-carbonitrile (633 mg, 4.00 mmol) in acetic acid (5 ml) at 40° C. was portionwise added sodium perborate tetrahydrate (677 mg, 4.4 mmol) and the mixture was stirred at 40° C. for 16 hours. The acetic acid was removed by evaporation at reduced pressure, the residue was basified with a saturated aqueous solution of sodium hydrogencarbonate, and the mixture extracted thrice with ethyl acetate. The combined extracts were dried over sodium sulphate and the solvent removed in vacuum to give the 3-cyano-5,6,7,8-tetrahydroquinoline 1-oxide (645 mg, 93% yield) as a white solid. MS (ISP): m/z=175.1 [M+H]+.

c) 8-Hydroxy-5,6,7,8-tetrahydroquinoline-3-carbonitrile

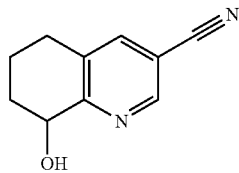 [SMILES: N#Cc1cnc2c(c1)CCCC2O]

To a solution of 3-cyano-5,6,7,8-tetrahydroquinoline 1-oxide (645 mg, 3.7 mmol) was added dropwise under ice cooling trifluoroacetic anhydride (6.22 g, 4.18 ml, 29.6 mmol). The light yellow solution was stirred at 23° C. for 18 h. The mixture was quenched with a solution of sodium hydroxide (1N) and stirred vigorously for 30 minutes, then extracted twice with dichloromethane. The combined organic layers were dried over sodium sulphate, filtered and evaporated. The residue was purified by silica gel flash chromatography with n-heptane/ethyl acetate to give the 8-hydroxy-5,6,7,8-tetrahydroquinoline-3-carbonitrile (562 mg, 87% yield) as a white solid. MS (ISP): m/z=175.1 [M+H]+.

d) 8-Oxo-5,6,7,8-tetrahydroquinoline-3-carbonitrile

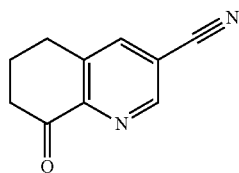 [SMILES: N#Cc1cnc2c(c1)CCCC2=O]

To a solution of 8-hydroxy-5,6,7,8-tetrahydroquinoline-3-carbonitrile (555 mg, 3.19 mmol) in dimethylsuloxide (15 ml) at 23° C. was added triethylamine (1.93 g, 2.66 ml, 19.1 mmol) and sulfur trioxide-pyridin complex (1.52 g, 9.56 mmol). The brown solution was stirred at 23° C. for 2 hours. The reaction mixture was poured on water and extracted twice with ethyl acetate. The combined organic layers were washed with brine, dried over sodium sulphate, filtered and evaporated to give of a light brown solid, which was purified by silica gel flash chromatography with dichloromethane/methanol to give the 8-oxo-5,6,7,8-tetrahydroquinoline-3-carbonitrile (286 mg, 52% yield) as a light yellow solid. MS (ISP): m/z=173.1 [M+H]+.

Example 28

(R)-4-[5-((RS)-1,1-Dioxo-2,3-dihydro-1H-1λ6-benzo[b]thiophen-3-ylamino)-2-fluoro-phenyl]-5,5-difluoro-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with 1,1-dioxo-1,2-dihydro-1λ6-benzo[b]thiophen-3-one (CAS [1127-35-1]) yielded the title compound (30% yield) as a mixture of epimers and as a colorless solid. MS (ISP): m/z=426.1 [M+H]+.

Example 29

(R)-5,5-Difluoro-4-[2-fluoro-5-(oxetan-3-ylamino)-phenyl]-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with oxetan-3-one (CAS [6704-31-0]) yielded the title compound (8% yield). MS (ISP): m/z=316.0 [M+H]+.

Example 30

(R)-5,5-Difluoro-4-{2-fluoro-5-{[(RS)-1-(tetrahydro-furan-3-yl)methyl]-amino}-phenyl}-4-methyl-5,6-dihydro-4H-[1,3]oxazin-2-ylamine In a manner analogous to that described in Example 1, the reductive amination of (R)-4-(5-amino-2-fluoro-phenyl)-5,5-difluoro-4-methyl-5,6-dihydro-4H-[1,3]oxazin-2-ylamine (intermediate A8.5) with tetrahydrofuran-3-carbaldehyde (CAS [79710-86-4]) yielded the title compound (47% yield) as a mixture of epimers. MS (ISP): m/z=344.1 [M+H]+.

Example 31

(R)-5,5-Difluoro-4-{2-fluoro-5-[1-(4-fluoro-phenyl)-1H-pyrazol-4-yl]-phenyl}-4-methyl-5,6-dihydro-4H-[1,3]oxazin-2-ylamine In a tube a mixture of (R)-4-(5-bromo-2-fluoro-phenyl)-5,5-difluoro-4-methyl-5,6-dihydro-4H-[1,3]oxazin-2-ylamine (intermediate A6.1) (60 mg, 186 μmol), 1-(4-fluorophenyl)-1H-pyrazol-4-ylboronic acid (39.0 mg, 186 μmol), and cesium carbonate (242 mg, 743 μmol) in tetrahydrofuran (4 ml) and water (2 ml) was purged with argon for minutes. Thereafter, [1,1'-bis(diphenylphosphino)ferrocene]dichloropalladium(II) complex with dichloromethane (7.58 mg, 9.28 μmol) was added, the tube was sealed and the mixture heated at 80° C. for 16 hours. After evaporation, the residue was purified by chromatography on a silica-NH2 phase using a gradient of heptane/ethyl acetate=100:0 to 40:60 as the eluent. The (R)-5,5-Difluoro-4-{2-fluoro-5-[1-(4-fluoro-phenyl)-1H-pyrazol-4-yl]-phenyl}-4-methyl-5,6-dihydro-4H-[1,3]oxazin-2-ylamine (36 mg, 48% yield) was obtained as a yellow solid. MS (ISP): m/z=405.0 [M+H]+.

Example 32

(R)-4-[5-(5-Chloro-pyridin-3-yl)-2,4-difluoro-phenyl]-5,5-difluoro-4-methyl-5,6-dihydro-4H-[1,3]oxazin-2-ylamine In a manner analogous to that described in Example 31, the cross-coupling reaction of (R)-4-(5-bromo-2,4-difluoro-phenyl)-5,5-difluoro-4-methyl-5,6-dihydro-4H-[1,3]oxazin-2-ylamine (intermediate A6.2) and 5-chloropyridin-3-ylboronic acid yielded the title compound as a pale yellow solid. MS (ISP): m/z=373.8 [M+H]+.

Example 33

(R)-4-(2,4-Difluoro-5-pyrimidin-5-yl-phenyl)-5,5-difluoro-4-methyl-5,6-dihydro-4H-[1,3]oxazin-2-ylamine In a manner analogous to that described in Example 31, the cross-coupling reaction of (R)-4-(5-bromo-2,4-difluoro-phenyl)-5,5-difluoro-4-methyl-5,6-dihydro-4H-[1,3]oxazin-2-ylamine (intermediate A6.2) and pyrimidin-5-ylboronic acid yielded the title compound as a yellow solid. MS (ISP): m/z=341.1 [M+H]$^+$.

Example 34

4-[3-((R)-2-Amino-5,5-difluoro-4-methyl-5,6-dihydro-4H-[1,3]oxazin-4-yl)-phenoxymethyl]-benzonitrile a) {(R)-4-[3-(4-Cyano-benzyloxy)-phenyl]-5,5-difluoro-4-methyl-5,6-dihydro-4H-[1,3]oxazin-2-yl}-di(carbamic acid tert-butyl ester)

A solution of [(R)-5,5-difluoro-4-(3-hydroxy-phenyl)-4-methyl-5,6-dihydro-4H-[1,3]oxazin-2-yl]-di(carbamic acid tert-butyl ester) (intermediate G3.1) (40 mg, 90.4 µmol) in N,N-dimethylformamide (1 ml) was treated with potassium carbonate (18.7 mg, 136 µmol) and 4-bromomethyl-benzonitrile (21.5 mg, 108 µmol). The mixture was stirred at room temperature for 27 hours. For the workup, the solvent was removed at reduced pressure. The residue was partitioned between ethyl acetate and water. The organic layer was washed with water, then the combined aqueous layers were back-extracted once with ethyl acetate. The combined organic layers were dried over sodium sulphate, filtered and concentrated in vacuo. The crude product was purified by chromatography on silica gel using a gradient of heptan/ethyl acetate=100:0 to 80:20 as the eluent. The {(R)-4-[3-(4-cyano-benzyloxy)-phenyl]-5,5-difluoro-4-methyl-5,6-dihydro-4H-[1,3]oxazin-2-yl}-di(carbamic acid tert-butyl ester) (46 mg, 91% yield) was obtained as a colorless oil. MS (ISP): m/z=558.2 [M+H]$^+$.

b) 4-[3-((R)-2-Amino-5,5-difluoro-4-methyl-5,6-dihydro-4H-[1,3]oxazin-4-yl)-phenoxymethyl]-benzonitrile A solution of {(R)-4-[3-(4-cyano-benzyloxy)-phenyl]-5,5-difluoro-4-methyl-5,6-dihydro-4H-[1,3]oxazin-2-yl}-di(carbamic acid tert-butyl ester) (46 mg, 82.5 µmol) in dichloromethane (526 µl) was treated with trifluoroacetic acid (94.1 mg, 63.2 µl, 825 µmol) under ice bath cooling.

The mixture was stirred at room temperature for 4 hours. For the workup, the solvent was removed at reduced pressure. The residue was dissolved in water, the aqueous layer was basified with a solution of sodium carbonate (2M) and extracted 3 times with ethyl acetate. The combined extracts were dried over sodium sulphate, filtered and concentrated at reduced pressure. The crude product was purified by chromatography on silica gel using a gradient of heptan/ethyl acetate=100:0 to 30:70 as the eluent. The 4-[3-((R)-2-amino-5,5-difluoro-4-methyl-5,6-dihydro-4H-[1,3]oxazin-4-yl)-phenoxymethyl]-benzonitrile (23 mg, 78% yield) was obtained as a white gum. MS (ISP): m/z=358.1 [M+H]$^+$.

Example 35

(R)-4-[3-(4-Chloro-benzyloxy)-phenyl]-5,5-difluoro-4-methyl-5,6-dihydro-4H-[1,3]oxazin-2-ylamine a) {(R)-4-[3-(4-Chloro-benzyloxy)-phenyl]-5,5-difluoro-4-methyl-5,6-dihydro-4H-[1,3]oxazin-2-yl}-di(carbamic acid tert-butyl ester)

In a manner analogous to that described in Example 34 a) the alkylation of [(R)-5,5-difluoro-4-β-hydroxy-phenyl)-4-methyl-5,6-dihydro-4H-[1,3]oxazin-2-yl]-di(carbamic acid tert-butyl ester) (intermediate G3.1) with 4-chlorobenzyl bromide yielded the title compound (58% yield) as a colorless oil.

b) (R)-4-[3-(4-Chloro-benzyloxy)-phenyl]-5,5-difluoro-4-methyl-5,6-dihydro-4H-[1,3]oxazin-2-ylamine In a manner analogous to that described in Example 34 b) the cleavage of the protecting groups in the {(R)-4-[3-(4-chloro-benzyloxy)-phenyl]-5,5-difluoro-4-methyl-5,6-dihydro-4H-[1,3]oxazin-2-yl}-di(carbamic acid tert-butyl ester) yielded the title compound (91% yield) as an off-white solid. MS (ISP): m/z=367.0 [M+H]$^+$.

Example 36

(R)-5,5-Difluoro-4-methyl-4-[3-(4-trifluoromethyl-benzyloxy)-phenyl]-5,6-dihydro-4H-[1,3]oxazin-2-ylamine a) {(R)-5,5-Difluoro-4-methyl-4-[3-(4-trifluoromethyl-benzyloxy)-phenyl]-5,6-dihydro-4H-[1,3]oxazin-2-yl}-di(carbamic acid tert-butyl ester)

In a manner analogous to that described in Example 34 a) the alkylation of [(R)-5,5-difluoro-4-(3-hydroxy-phenyl)-4-methyl-5,6-dihydro-4H-[1,3]oxazin-2-yl]-di(carbamic acid tert-butyl ester) (intermediate G3.1) with 1-bromomethyl-4-trifluoromethyl-benzene yielded the title compound (99% yield) as a yellow oil. MS (ISP): m/z=601.3 [M+H]$^+$.

b) (R)-5,5-Difluoro-4-methyl-4-[3-(4-trifluoromethyl-benzyloxy)-phenyl]-5,6-dihydro-4H-[1,3]oxazin-2-ylamine In a manner analogous to that described in Example 34 b) the cleavage of the protecting groups in the {(R)-5,5-Difluoro-4-methyl-4-[3-(4-trifluoromethyl-benzyloxy)-phenyl]-5,6-dihydro-4H-[1,3]oxazin-2-yl}-di(carbamic acid tert-butyl ester) yielded the title compound (59% yield) as a light yellow oil. MS (ISP): m/z=401.1 [M+H]$^+$.

Example 37

(R)-5,5-Difluoro-4-methyl-4-[2-(4-methyl-benzyl)-3H-benzoimidazol-5-yl]-5,6-dihydro-4H-[1,3]oxazin-2-ylamine a) {(R)-5,5-Difluoro-4-methyl-4-[2-(4-methyl-benzyl)-3H-benzoimidazol-5-yl]-5,6-dihydro-4H-[1,3]oxazin-2-yl}-di(carbamic acid tert-butyl ester)

A solution of [(R)-4-(3,4-diamino-phenyl)-5,5-difluoro-4-methyl-5,6-dihydro-4H-[1,3]oxazin-2-yl]-di(carbamic acid tert-butyl ester) (intermediate E3.1) (20 mg, 43.8 μmol) in ethanol (333 μl) was treated under an atmosphere of nitrogen at room temperature with ethyl 2-p-tolylacetimidate hydrochloride (37.5 mg, 175 μmol) (G. Grella et al., Eur. J. Pharm. Sci. 2003, 20(3), 267-72). The reaction mixture was stirred at 80° C. for 15 hours. For the workup, the mixture was cooled to room temperature and the solvent was evaporated at reduced pressure. The residue was dissolved in ethyl acetate and the resulting solution washed with a solution of ammonium chloride. The organic layer was dried over sodium sulphate and evaporated at reduced pressure. The crude product was purified by flash column chromatography on silica eluting with a gradient n-heptane/ethyl acetate=100:0 to 40:60. The {(R)-5,5-difluoro-4-methyl-4-[2-(4-methyl-benzyl)-3H-benzoimidazol-5-yl]-5,6-dihydro-4H-[1,3]oxazin-2-yl}-di(carbamic acid tert-butyl ester) (16 mg, 64% yield) was obtained as a light yellow foam. MS (m/e): 571.3 (MH+)

b) (R)-5,5-Difluoro-4-methyl-4-[2-(4-methyl-benzyl)-3H-benzoimidazol-5-yl]-5,6-dihydro-4H-[1,3]oxazin-2-ylamine In a manner analogous to that described in Example 34 b) the cleavage of the protecting groups in the {(R)-5,5-difluoro-4-methyl-4-[2-(4-methyl-benzyl)-3H-benzoimidazol-5-yl]-5,6-dihydro-4H-[1,3]oxazin-2-yl}-di(carbamic acid tert-butyl ester) yielded the title compound (69% yield) as a white foam. MS (ISP): m/z=371.2 [M+H]$^+$.

Example 38

(R)-4-[(RS)-3-(5-Chloro-pyridin-2-yl)-7-fluoro-3,4-dihydro-2H-benzo[1,4]oxazin-6-yl]-5,5-difluoro-4-methyl-5,6-dihydro-4H-[1,3]oxazin-2-ylamine a) 2-[4-((R)-2-Amino-5,5-difluoro-4-methyl-5,6-dihydro-4H-[1,3]oxazin-4-yl)-5-fluoro-2-nitro-phenoxy]-1-(5-chloro-pyridin-2-yl)-ethanone A dispersion of 4-((R)-2-amino-5,5-difluoro-4-methyl-5,6-dihydro-4H-[1,3]oxazin-4-yl)-5-fluoro-2-nitro-phenol (intermediate F2.1) (120 mg, 393 μmol), 2-bromo-1-(5-chloro-pyridin-2-yl)ethanone (101 mg, 432 μmol), cesium carbonate (512 mg, 1.57 mmol), and potassium iodide (2 mg, 14.5 μmol) in acetone (5.51 ml) was stirred at room temperature for 20 hours. For the workup, the reaction mixture was poured into a saturated solution of sodium hydrogencarbonate (5 ml) and extracted with dichloromethane (2×5 ml). The combined organic layers were dried over sodium sulphate and evaporated at reduced pressure. The crude 2-[4-((R)-2-amino-5,5-difluoro-4-methyl-5,6-dihydro-4H-[1,3]oxazin-4-yl)-5-fluoro-2-nitro-phenoxy]-1-(5-chloro-pyridin-2-yl)-ethanone (165 mg, 92% yield) was obtained as a red gum. MS (ISP): m/z=459.1 [M+H]$^+$.

b) (R)-4-[(RS)-3-(5-Chloro-pyridin-2-yl)-7-fluoro-3,4-dihydro-2H-benzo[1,4]oxazin-6-yl]-5,5-difluoro-4-methyl-5,6-dihydro-4H-[1,3]oxazin-2-ylamine A dispersion of 2-[4-((R)-2-amino-5,5-difluoro-4-methyl-5,6-dihydro-4H-[1,3]oxazin-4-yl)-5-fluoro-2-nitro-phenoxy]-1-(5-chloro-pyridin-2-yl)-ethanone (160 mg, 349 μmol) and Raney Nickel (30 mg) in methanol (22 ml) was hydrogenated. For the workup, the reaction mixture was filtered through glass fiber paper and the solution was evaporated at reduced pressure. The crude product was purified by flash chromatography on a silica-NH$_2$ phase using a gradient of heptane/ethyl acetate=100:0 to 0 to 100 as the eluent. The (R)-4-[(RS)-3-(5-chloro-pyridin-2-yl)-7-fluoro-3,4-dihydro-2H-benzo[1,4]oxazin-6-yl]-5,5-difluoro-4-methyl-5,6-dihydro-4H-[1,3]oxazin-2-ylamine was obtained as a red solid. MS (ISP): m/z=413.2 [M+H]$^+$.

Example 39

(R)-5,5-Difluoro-4-[5-fluoro-2-(4-methoxy-benzyl)-1H-indol-6-yl]-4-methyl-5,6-dihydro-4H-[1,3]oxazin-2-ylamine A solution of (R)-4-(5-amino-2-fluoro-4-iodo-phenyl)-5,5-difluoro-4-methyl-5,6-dihydro-4H-[1,3]oxazin-2-ylamine (intermediate B6.1) (100 mg, 260 μmol) N,N-dimethylformamide (0.5 ml) was purged with argon for 10 minutes. Thereafter, 1,1,3,3-tetramethylguanidine (74.8 mg, 81.3 μl, 649 μmol), bis-(triphenylphosphin)-palladium(II)dichlorid (9.11 mg, 13.0 μmol) and copper (I) iodide (7.42 mg, 38.9 μmol) were added. After 5 minutes at room temperature, a solution of 1-methoxy-4-prop-2-ynyl-benzene (CAS [13540-76-6]) (45.5 mg, 312 μmol) in N,N-dimethylformamide (0.2 ml) was added and the reaction mixture was stirred at 80° C. for 15 hours. For the workup, the reaction mixture was allowed to cool to room temperature, then it was diluted with a saturated solution of sodium hydrogencarbonate and extracted with ethyl acetate. The combined organic layers were dried over sodium sulphate and evaporated at reduced pressure. The crude product was purified by flash chromatography on a silica-NH$_2$ phase using a gradient of heptane/ethyl acetate=100:0 to 0:100 as the eluent. The (R)-5,5-difluoro-4-[5-fluoro-2-(4-methoxy-benzyl)-1H-indol-6-yl]-4-methyl-5,6-dihydro-4H-[1,3]oxazin-2-ylamine (35 mg, 33% yield) was obtained as a light green foam. MS (ISP): m/z=404.4 [M+H]$^+$.

Example 40

(R)-5,5-Difluoro-4-[5-fluoro-2-(4-methyl-benzyl)-3H-indol-6-yl]-4-methyl-5,6-dihydro-4H-[1,3]oxazin-2-ylamine In a manner analogous to that described in Example 39, the coupling and cyclisation reaction of (R)-4-(5-amino-2-fluoro-4-iodo-phenyl)-5,5-difluoro-4-methyl-5,6-dihydro-4H-[1,3]oxazin-2-ylamine (intermediate B6.1) with 1-methyl-4-prop-2-ynyl-benzene yielded the title compound (73% yield) as a light green foam. MS (ISP): m/z=388.3 [M+H]$^+$.

Example 41

3-((R)-2-Amino-5,5-difluoro-4-methyl-5,6-dihydro-4H-[1,3]oxazin-4-yl)-4-fluoro-N-prop-2-ynyl-benzamide a) [(R)-5,5-Difluoro-4-(2-fluoro-5-prop-2-ynylcarbamoyl-phenyl)-4-methyl-5,6-dihydro-4H-[1,3]oxazin-2-yl]-carbamic acid tert-butyl ester A solution of 3-((R)-2-tert-butoxycarbonylamino-5,5-difluoro-4-methyl-5,6-dihydro-4H-[1,3]oxazin-4-yl)-4-fluoro-benzoic (intermediate H2.1) (50 mg, 129 μmol) in N,N-dimethylformamide (500 μl) was treated under an atmosphere of nitrogen at room temperature with (2-(7-aza-1H-benzotriazole-1-yl)-1,1,3,3-tetramethyluronium hexafluorophosphate) (HATU) (73.4 mg, 193 μmol), and N-ethyldiisopropylamine (66.6 mg, 88.0 μl, 515 μmol). The mixture was stirred at room temperature for 5 minutes, then propargylamine (7.88 mg, 9.16 μl, 142 μmol) was added and stirring continued for 15 hours. For the workup, the solvent was removed at reduced pressure, the residue was taken in ethyl acetate and washed once with water and once with a saturated solution of sodium hydrogencarbonate. The organic layer was dried over sodium sulphate and evaporated at reduced pressure. The crude product was purified by flash column chromatography on silica gel eluting with a gradient of n-heptane/ethyl acetate=100:0 to 50:50. The [(R)-5,5-difluoro-4-(2-fluoro-5-prop-2-ynylcarbamoyl-phenyl)-4-methyl-5,6-dihydro-4H-[1,3]oxazin-2-yl]-carbamic acid tert-butyl ester (18 mg, 33% yield) was obtained as an off white solid. MS (ISP): m/z=426.1 [M+H]$^+$.

b) 3-((R)-2-Amino-5,5-difluoro-4-methyl-5,6-dihydro-4H-[1,3]oxazin-4-yl)-4-fluoro-N-prop-2-ynyl-benzamide In a manner analogous to that described in Example 22 b), the cleavage of the protecting group by trifluoroacetic acid yielded the title compound (80% yield) as a slightly coloured oil. MS (ISP): m/z=326.3 [M+H]$^+$.

Example 42

(R)-4-[5-(2-Chloro-phenylamino)-2-fluoro-phenyl]-5,5-difluoro-4,6,6-trimethyl-5,6-dihydro-4H-[1,3]oxazin-2-ylamine a) [Bis-(4-methoxy-phenyl)-phenyl-methyl]-{(R)-4-[5-(2-chloro-phenylamino)-2-fluoro phenyl]-5,5-difluoro-4,6,6-trimethyl-5,6-dihydro-4H-[1,3]oxazin-2-yl}-amine In a manner analogous to that described in Example 3 a), the amination of [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (intermediate C4.1) with 2-chloroaniline yielded the title compound (61% yield) as an off-white foam. MS (ISP): m/z=700.4 [M+H]$^+$.

b) (R)-4-[5-(2-Chloro-phenylamino)-2-fluoro-phenyl]-5,5-difluoro-4,6,6-trimethyl-5,6-dihydro-4H-[1,3]oxazin-2-ylamine In a manner analogous to that described in Example 3 b), the cleavage of the protecting group in the [bis-(4-methoxy-phenyl)-phenyl-methyl]-{(R)-4-[5-(2-chloro-phenylamino)-2-fluoro-phenyl]-5,5-difluoro-4,6,6-trimethyl-5,6-dihydro-4H-[1,3]oxazin-2-yl}-amine yielded the title compound (84% yield) as a light yellow solid. MS (ISP): m/z=398.1 [M+H]$^+$.

Example 43

2-[3-((R)-2-Amino-5,5-difluoro-4,6,6-trimethyl-5,6-dihydro-4H-[1,3]oxazin-4-yl)-4-fluoro-phenylamino]-benzonitrile a) 2-[3-((R)-2-{[Bis-(4-methoxy-phenyl)-phenyl-methyl]-amino}-5,5-difluoro-4,6,6-trimethyl-5,6-dihydro-4H-[1,3]oxazin-4-yl)-4-fluoro-phenylamino]-benzonitrile In a manner analogous to that described in Example 3 a), the amination of [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]amine (intermediate C4.1) with 2-aminobenzonitrile yielded the title compound (50% yield) as an off-white foam. MS (ISP): m/z=691.3 [M+H]$^+$.

b) 2-[3-((R)-2-Amino-5,5-difluoro-4,6,6-trimethyl-5,6-dihydro-4H-[1,3]oxazin-4-yl)-4-fluoro-phenylamino]-benzonitrile In a manner analogous to that described in Example 3 b), the cleavage of the protecting group in the 2-[3-((R)-2-{[bis-(4-methoxy-phenyl)-phenyl-methyl]-amino}-5,5-difluoro-4,6,6-trimethyl-5,6-dihydro-4H-[1,3]oxazin-4-yl)-4-fluoro-phenylamino]-benzonitrile yielded the title compound (81% yield) as a white solid. MS (ISP): m/z=389.3 [M+H]$^+$.

Example 44

(R)-5,5-Difluoro-4-[2-fluoro-5-(2-methoxy-phenylamino)-phenyl]-4,6,6-trimethyl-5,6-dihydro-4H-[1,3]oxazin-2-ylamine a) [Bis-(4-methoxy-phenyl)-phenyl-methyl]-{(R)-5,5-difluoro-4-[2-fluoro-5-(2-methoxy-phenylamino)-phenyl]-4,6,6-trimethyl-5,6-dihydro-4H-[1,3]oxazin-2-yl}-amine In a manner analogous to that described in Example 3 a), the amination of [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (intermediate C4.1) with 2-methoxyaniline yielded the title compound (68% yield) as a yellow foam. MS (ISP): m/z=696.5 [M+H]$^+$.

b) (R)-5,5-Difluoro-4-[2-fluoro-5-(2-methoxy-phenylamino)-phenyl]-4,6,6-trimethyl-5,6-dihydro-4H-[1,3]oxazin-2-ylamine In a manner analogous to that described in Example 3 b), the cleavage of the protecting group in the [bis-(4-methoxy-phenyl)-phenyl-methyl]-{(R)-5,5-difluoro-4-[2-fluoro-5-(2-methoxy-phenylamino)-phenyl]-4,6,6-trimethyl-5,6-dihydro-4H-[1,3]oxazin-2-yl}-amine yielded the title compound (83% yield) as a white foam. MS (ISP): m/z=394.1 [M+H]$^+$.

Example 45

(R)-5,5-Difluoro-4-(2-fluoro-5-o-tolylamino-phenyl)-4,6,6-trimethyl-5,6-dihydro-4H-[1,3]oxazin-2-ylamine a) [Bis-(4-methoxy-phenyl)-phenyl-methyl]-[(R)-5,5-difluoro-4-(2-fluoro-5-o-tolylamino-phenyl)-4,6,6-trimethyl-5,6-dihydro-4H-[1,3]oxazin-2-yl]-amine In a manner analogous to that described in Example 3 a), the amination of [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (intermediate C4.1) with o-tolylamine yielded the title compound (55% yield) as a pale red foam. MS (ISP): m/z=680.4 [M+H]$^+$.

b) (R)-5,5-Difluoro-4-(2-fluoro-5-o-tolylamino-phenyl)-4,6,6-trimethyl-5,6-dihydro-4H-[1,3]oxazin-2-ylamine In a manner analogous to that described in Example 3 b), the cleavage of the protecting group in the [bis-(4-methoxy-phenyl)-phenyl-methyl]-[(R)-5,5-difluoro-4-(2-fluoro-5-o-tolylamino-phenyl)-4,6,6-trimethyl-5,6-dihydro-4H-[1,3]oxazin-2-yl]-amine yielded the title compound (80% yield) as a white foam. MS (ISP): m/z=378.3 [M+H]$^+$.

Example 46

(R)-5,5-Difluoro-4-[2-fluoro-5-(2-trifluoromethyl-phenylamino)-phenyl]-4,6,6-trimethyl-5,6-dihydro-4H-[1,3]oxazin-2-ylamine a) [Bis-(4-methoxy-phenyl)-phenyl-methyl]-{(R)-5,5-difluoro-4-[2-fluoro-5-(2-trifluoromethyl-phenylamino)-phenyl]-4,6,6-trimethyl-5,6-dihydro-4H-[1,3]oxazin-2-yl}-amine In a manner analogous to that described in Example 3 a), the amination of [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (intermediate C4.1) with 2-(trifluoromethyl)aniline yielded the title compound (37% yield) as a yellow foam. MS (ISP): m/z=734.4 [M+H]$^+$.

b) (R)-5,5-Difluoro-4-[2-fluoro-5-(2-trifluoromethyl-phenylamino)-phenyl]-4,6,6-trimethyl-5,6-dihydro-4H-[1,3]oxazin-2-ylamine In a manner analogous to that described in Example 3 b), the cleavage of the protecting group in the [bis-(4-methoxy-phenyl)-phenyl-methyl]-{(R)-5,5-difluoro-4-[2-fluoro-5-(2-trifluoromethyl-phenylamino)-phenyl]-4,6,6-trimethyl-5,6-dihydro-4H-[1,3]oxazin-2-yl}-amine yielded the title compound (81% yield) as a white solid. MS (ISP): m/z=432.2 [M+H]$^+$.

Example 47

(R)-5,5-Difluoro-4-[2-fluoro-5-(6-trifluoromethyl-pyridin-2-ylamino)-phenyl]-4,6,6-trimethyl-5,6-dihydro-4H-[1,3]oxazin-2-ylamine a) [Bis-(4-methoxy-phenyl)-phenyl-methyl]-{(R)-5,5-difluoro-4-[2-fluoro-5-(6-trifluoromethyl-pyridin-2-ylamino)-phenyl]-4,6,6-trimethyl-5,6-dihydro-4H-[1,3]oxazin-2-yl}-amine In a manner analogous to that described in Example 3 a), the amination of [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (intermediate C4.1) with 6-(trifluoromethyl)pyridin-2-amine yielded the title compound (81% yield) as a pale yellow foam. MS (ISP): m/z=735.4 [M+H]$^+$.

b) (R)-5,5-Difluoro-4-[2-fluoro-5-(6-trifluoromethyl-pyridin-2-ylamino)-phenyl]-4,6,6-trimethyl-5,6-dihydro-4H-[1,3]oxazin-2-ylamine In a manner analogous to that described in Example 3 b), the cleavage of the protecting group in the [bis-(4-methoxy-phenyl)-phenyl-methyl]-{(R)-5,5-difluoro-4-[2-fluoro-5-(6-trifluoromethyl-pyridin-2-ylamino)-phenyl]-4,6,6-trimethyl-5,6-dihydro-4H-[1,3]oxazin-2-yl}-amine yielded the title compound (55% yield) as a white solid. MS (ISP): m/z=433.2 [M+H]$^+$.

Example 48

(R)-4-(5-Cyclopentylamino-2-fluoro-phenyl)-5,5-difluoro-4,6,6-trimethyl-5,6-dihydro-4H-[1,3]oxazin-2-ylamine a) [Bis-(4-methoxy-phenyl)-phenyl-methyl]-[(R)-4-(5-cyclopentylamino-2-fluoro-phenyl)-5,5-difluoro-4,6,6-trimethyl-5,6-dihydro-4H-[1,3]oxazin-2-yl]-amine In a manner analogous to that described in Example 3 a), the amination of [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (intermediate C4.1) with cyclopentylamine yielded the title compound (92% yield) as a yellow waxy solid. MS (ISP): m/z=658.4 [M+H]$^+$.

b) (R)-4-(5-Cyclopentylamino-2-fluoro-phenyl)-5,5-difluoro-4,6,6-trimethyl-5,6-dihydro-4H-[1,3]oxazin-2-ylamine In a manner analogous to that described in Example 3 b), the cleavage of the protecting group in the [bis-(4-methoxy-phenyl)-phenyl-methyl]-[(R)-4-(5-cyclopentylamino-2-fluoro-phenyl)-5,5-difluoro-4,6,6-trimethyl-5,6-dihydro-4H-[1,3]oxazin-2-yl]-amine yielded the title compound (74% yield) as a white foam. MS (ISP): m/z=356.2 [M+H]$^+$.

Example 49

(R)-5,5-Difluoro-4-[2-fluoro-5-((1RS,3RS)-3-phenyl-cyclopentylamino)-phenyl]-4,6,6-trimethyl-5,6-dihydro-4H-[1,3]oxazin-2-ylamine a) [Bis-(4-methoxy-phenyl)-phenyl-methyl]-{(R)-5,5-difluoro-4-[2-fluoro-5-((1RS,3RS)-3-phenyl-cyclopentylamino)-phenyl]-4,6,6-trimethyl-5,6-dihydro-4H-[1,3]oxazin-2-yl}-amine In a manner analogous to that described in Example 3 a), the amination of [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (intermediate C4.1) with (RS)-3-phenyl-cyclopentylamine (CAS [103858-37-3]; WO2007135026) yielded the title compound (27% yield) as a yellow solid. MS (ISP): m/z=734.5 [M+H]$^+$.

b) (R)-5,5-Difluoro-4-[2-fluoro-5-((1RS,3RS)-3-phenyl-cyclopentylamino)-phenyl]-4,6,6-trimethyl-5,6-dihydro-4H-[1,3]oxazin-2-ylamine In a manner analogous to that described in Example 3 b), the cleavage of the protecting group in the [bis-(4-methoxy-phenyl)-phenyl-methyl]-{(R)-5,5-difluoro-4-[2-fluoro-5-((RS)-3-phenyl-cyclopentylamino)-phenyl]-4,6,6-trimethyl-5,6-dihydro-4H-[1,3]oxazin-2-yl}-amine yielded the title compound (31% yield) as a light brown waxy solid. MS (ISP): m/z=432.2 [M+H]$^+$.

Example 50

(R)-4-[5-(5-Chloro-pyridin-3-yl)-2-fluoro-phenyl]-5,5-difluoro-4,6,6-trimethyl-5,6-dihydro-4H-[1,3]oxazin-2-ylamine Hydrochloride a) [Bis-(4-methoxy-phenyl)-phenyl-methyl]-{(R)-4-[5-(5-chloro-pyridin-3-yl)-2-fluoro-phenyl]-5,5-difluoro-4,6,6-trimethyl-5,6-dihydro-4H-[1,3]oxazin-2-yl}-amine In a manner analogous to that described in Example 9 a), the cross-coupling reaction of [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (intermediate C4.1) with 5-chloropyridin-3-ylboronic acid yielded the title compound (86% yield) as a white solid. MS (ISP): m/z=686.3 [M+H]$^+$.

b) (R)-4-[5-(5-Chloro-pyridin-3-yl)-2-fluoro-phenyl]-5,5-difluoro-4,6,6-trimethyl-5,6-dihydro-4H-[1,3]oxazin-2-ylamine In a manner analogous to that described in Example 9 b), the cleavage of the protecting group in the [bis-(4-methoxy-phenyl)-phenyl-methyl]-{(R)-4-[5-(5-chloro-pyridin-3-yl)-2-fluoro-phenyl]-5,5-difluoro-4,6,6-trimethyl-5,6-dihydro-4H-[1,3]oxazin-2-yl}-amine yielded the (R)-4-[5-(5-chloro-pyridin-3-yl)-2-fluoro-phenyl]-5,5-difluoro-4,6,6-trimethyl-5,6-dihydro-4H-[1,3]oxazin-2-ylamine which was treated with hydrochloric acid (4M) and evaporated at reduced pressure. The residue was triturated with diethylether, the solid filtered and dried to yield the title compound (32% yield) as a light red solid. MS (ISP): m/z=384.2 [M+H]$^+$.

Example 51

(R)-4-(3',5'-Dichloro-4-fluoro-biphenyl-3-yl)-5,5-difluoro-4,6,6-trimethyl-5,6-dihydro-4H-[1,3]oxazin-2-ylamine a) [Bis-(4-methoxy-phenyl)-phenyl-methyl]-[(R)-4-(3',5'-dichloro-4-fluoro-biphenyl-3-yl)-5,5-difluoro-4,6,6-trimethyl-5,6-dihydro-4H-[1,3]oxazin-2-yl]-amine In a manner analogous to that described in Example 9 a), the cross-coupling reaction of [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (intermediate C4.1) with 3,5-dichlorophenylboronic acid yielded the title compound (80% yield) as a white foam. MS (ISP): m/z=719.4 [M+H]$^+$ and 721.0 [M+H]$^+$.

b) (R)-4-(3',5'-Dichloro-4-fluoro-biphenyl-3-yl)-5,5-difluoro-4,6,6-trimethyl-5,6-dihydro-4H-[1,3]oxazin-2-ylamine In a manner analogous to that described in Example 9 b), the cleavage of the protecting group in the [bis-(4-methoxy-phenyl)-phenyl-methyl]-[(R)-4-(3',5'-dichloro-4-fluoro-biphenyl-3-yl)-5,5-difluoro-4,6,6-trimethyl-5,6-dihydro-4H-[1,3]oxazin-2-yl]-amine yielded the title compound (48% yield) as a white solid. MS (ISP): m/z=417.2 [M+H]$^+$ and 419.3 [M+2+H]$^+$.

Example 52

3'-((R)-2-Amino-5,5-difluoro-4,6,6-trimethyl-5,6-dihydro-4H-[1,3]oxazin-4-yl)-6-chloro-4'-fluoro-biphenyl-3-carbonitrile a) 3'-((R)-2-{[Bis-(4-methoxy-phenyl)-phenyl-methyl]-amino}-5,5-difluoro-4,6,6-trimethyl-5,6-dihydro-4H-[1,3]oxazin-4-yl)-6-chloro-4'-fluoro-biphenyl-3-carbonitrile In a manner analogous to that described in Example 9 a), the cross-coupling reaction of [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (intermediate C4.1) with 2-chloro-5-cyanophenylboronic acid yielded the title compound (22% yield) as a white foam.

b) 3'-((R)-2-Amino-5,5-difluoro-4,6,6-trimethyl-5,6-dihydro-4H-[1,3]oxazin-4-yl)-6-chloro-4'-fluoro-biphenyl-3-carbonitrile In a manner analogous to that described in Example 9 b), the cleavage of the protecting group in the 3'-((R)-2-{[bis-(4-methoxy-phenyl)-phenyl-methyl]-amino}-5,5-difluoro-4,6,6-trimethyl-5,6-dihydro-4H-[1,3]oxazin-4-yl)-6-chloro-4'-fluoro-biphenyl-3-carbonitrile yielded the title compound (50% yield) as a white solid. MS (ISP): m/z=408.2 [M+H]$^+$.

Example 53

4-[5-(5-Chloro-pyridin-3-yl)-2-fluoro-phenyl]-4-difluoromethyl-5,6-dihydro-4H-[1,3]oxazin-2-ylamine In a manner analogous to that described in Example 31, the cross-coupling reaction of 4-(5-bromo-2-fluorophenyl)-4-(difluoromethyl)-5,6-dihydro-4H-1,3-oxazin-2-amine (intermediate A6.12) and 5-chloropyridin-3-ylboronic acid yielded the title compound as a light brown solid. MS (ISP): m/z=356.0 [M+H]$^+$ and 358.0 [M+2+H]$^+$.

Example 54A and 54B (R)-4-[5-(5-Chloro-pyridin-3-yl)-2-fluoro-phenyl]-4-difluoromethyl-5,6-dihydro-4H-[1,3]oxazin-2-ylamine (A) and (S)-4-[5-(5-Chloro-pyridin-3-yl)-2-fluoro-phenyl]-4-difluoromethyl-5,6-dihydro-4H-[1,3]oxazin-2-ylamine (B)

Separation of 4-[5-(5-chloro-pyridin-3-yl)-2-fluoro-phenyl]-4-difluoromethyl-5,6-dihydro-4H-[1,3]oxazin-2-ylamine (example 53) by preparative chiral HPLC on a chiral phase (Chiralpak AD; eluent: 85:15-mixture of heptane and isopropanol) yielded the first eluting (R)-4-[5-(5-chloro-pyridin-3-yl)-2-fluoro-phenyl]-4-difluoromethyl-5,6-dihydro-4H-[1,3]oxazin-2-ylamine (B) (44% yield) and the later eluting (S)-4-[5-(5-chloro-pyridin-3-yl)-2-fluoro-phenyl]-4-difluoromethyl-5,6-dihydro-4H-[1,3]oxazin-2-ylamine (A) (25% yield) both as a white solid.

Example 55

(R)-4-[2-(4-Ethyl-benzyl)-3H-benzoimidazol-5-yl]-5,5-difluoro-4-methyl-5,6-dihydro-4H-[1,3]oxazin-2-ylamine a) {(R)-4-[2-(4-Ethyl-benzyl)-3H-benzoimidazol-5-yl]-5,5-difluoro-4-methyl-5,6-dihydro-4H-[1,3]oxazin-2-yl}-di(carbamic acid tert-butyl ester)

In a manner analogous to that described in Example 37 a) the condensation of [(R)-4-(3,4-diamino-phenyl)-5,5-difluoro-4-methyl-5,6-dihydro-4H-[1,3]oxazin-2-yl]-di(carbamic acid tert-butyl ester) (intermediate E3.1) and ethyl 2-(4-ethylphenyl)acetimidate hydrochloride yielded the title compound (51% yield) as a light yellow oil. MS (ISP): m/z=585.3 [M+H]$^+$.

The ethyl 2-(4-ethylphenyl)acetimidate hydrochloride was prepared in close analogy to the procedure described by G. Grella et al. in Eur. J. Pharm. Sci. 2003, 20(3), 267-72 for the corresponding 4-methylphenyl derivative.

b) (R)-4-[2-(4-Ethyl-benzyl)-3H-benzoimidazol-5-yl]-5,5-difluoro-4-methyl-5,6-dihydro-4H-[1,3]oxazin-2-ylamine In a manner analogous to that described in Example 34 b) the cleavage of the protecting groups in the {(R)-4-[2-(4-ethyl-benzyl)-3H-benzoimidazol-5-yl]-5,5-difluoro-4-methyl-5,6-dihydro-4H-[1,3]oxazin-2-yl}-di(carbamic acid tert-butyl ester) yielded the title compound (57% yield) as an off-white foam. MS (ISP): m/z=385.2 [M+H]$^+$.

Example 56

(4R,5R)-4-[5-(3,5-Difluoro-benzylamino)-2-fluoro-phenyl]-5-fluoro-4-methyl-5,6-dihydro-4H-[1,3]oxazin-2-ylamine In a manner analogous to that described in Example 2, the reductive amination of (4R,5R)-4-(5-amino-2-fluoro-phenyl)-5-fluoro-4-methyl-5,6-dihydro-4H-[1,3]oxazin-2-ylamine (intermediate A8.2) with 3,5-difluorobenzaldehyde yielded the title compound (46% yield) as a white foam. MS (ISP): m/z=368.2 [M+H]$^+$.

Example 57

(R)-4-[5-((RS)-2,2-Difluoro-cyclopropylmethoxy)-phenyl]-5,5-difluoro-4-methyl-5,6-dihydro-4H-[1,3]oxazin-2-ylamine a) {(R)-4-[5-((RS)-2,2-Difluoro-cyclopropylmethoxy)-phenyl]-5,5-difluoro-4-methyl-5,6-dihydro-4H-[1,3]oxazin-2-yl}-di(carbamic acid tert-butyl ester)
In a manner analogous to that described in Example 34 a) the alkylation of [(R)-5,5-difluoro-4-(3-hydroxy-phenyl)-4-methyl-5,6-dihydro-4H-[1,3]oxazin-2-yl]-di(carbamic acid tert-butyl ester) (intermediate G3.1) with 1-bromomethyl-2,2-difluorocyclopropane at 60° C. yielded the title compound (71% yield) as a colorless oil. MS (ISP): m/z=533.3 [M+H]$^+$.

b) (R)-4-[5-((RS)-2,2-Difluoro-cyclopropylmethoxy)-phenyl]-5,5-difluoro-4-methyl-5,6-dihydro-4H-[1,3]oxazin-2-ylamine In a manner analogous to that described in Example 34 b) the cleavage of the protecting groups in the {(R)-4-[5-((RS)-2,2-difluoro-cyclopropylmethoxy)-phenyl]-5,5-difluoro-4-methyl-5,6-dihydro-4H-[1,3]oxazin-2-yl}-di(carbamic acid tert-butyl ester) yielded the title compound (79% yield) as a colorless oil. MS (ISP): m/z=333.1 [M+H]$^+$.

Example 58

(R)-5,5-Difluoro-4-methyl-4-[3-(3,3,3-trifluoro-propoxy)-phenyl]-5,6-dihydro-4H-[1,3]oxazin-2-ylamine a) {(R)-5,5-Difluoro-4-methyl-4-[3-(3,3,3-trifluoro-propoxy)-phenyl]-5,6-dihydro-4H-[1,3]oxazin-2-yl}-di(carbamic acid tert-butyl ester)

A solution of [(R)-5,5-difluoro-4-(3-hydroxy-phenyl)-4-methyl-5,6-dihydro-4H-[1,3]oxazin-2-yl]-di(carbamic acid tert-butyl ester) (intermediate G3.1) (40 mg, 90.4 μmol), 3,3,3-trifluoropropan-1-ol (20.6 mg, 181 μmol), and triphenylphosphine (48.9 mg, 181 μmol) in tetrahydrofuran (1.2 ml) was treated dropwise with a solution of diethyl azodicarboxylate (40% in toluene; 86.6 mg, 91.1 μl, 199 μmol) at room temperature over a period of 2 minutes. The mixture was stirred at room temperature for 20 hours. For the workup, the solvent was removed at reduced pressure, and the thus obtained residue was purified on a preparative silica gel TLC using a 4:1-mixture of heptane and ethyl acetate as the eluent. The {(R)-5,5-difluoro-4-methyl-4-[3-(3,3,3-trifluoro-propoxy)-phenyl]-5,6-dihydro-4H-[1,3]oxazin-2-yl}-di(carbamic acid tert-butyl ester) (8.3 mg, 17% yield) was obtained as a light yellow oil. MS (ISP): m/z=539.4 [M+H]$^+$.

b) (R)-5,5-Difluoro-4-methyl-4-[3-(3,3,3-trifluoro-propoxy)-phenyl]-5,6-dihydro-4H-[1,3]oxazin-2-ylamine In a manner analogous to that described in Example 34 b) the cleavage of the protecting groups in the {(R)-5,5-difluoro-4-methyl-4-[3-(3,3,3-trifluoro-propoxy)-phenyl]-5,6-dihydro-4H-[1,3]oxazin-2-yl}-di(carbamic acid tert-butyl ester) yielded the title compound (70% yield) as a colorless oil. MS (ISP): m/z=339.2 [M+H]$^+$.

Example 59

(R)-4-(3-Cyclopropylmethoxy-phenyl)-5,5-difluoro-4-methyl-5,6-dihydro-4H-[1,3]oxazin-2-ylamine a) [(R)-4-(3-Cyclopropylmethoxy-phenyl)-5,5-difluoro-4-methyl-5,6-dihydro-4H-[1,3]oxazin-2-yl]-di(carbamic acid tert-butyl ester)

In a manner analogous to that described in Example 34 a) the alkylation of [(R)-5,5-difluoro-4-(3-hydroxy-phenyl)-4-methyl-5,6-dihydro-4H-[1,3]oxazin-2-yl]-di(carbamic acid tert-butyl ester) (intermediate G3.1) with (bromomethyl)-cyclopropane at 60° C. yielded the title compound (51% yield) as a colorless oil. MS (ISP): m/z=497.3 [M+H]$^+$.

b) (R)-4-(3-Cyclopropylmethoxy-phenyl)-5,5-difluoro-4-methyl-5,6-dihydro-4H-[1,3]oxazin-2-ylamine In a manner analogous to that described in Example 34 b) the cleavage of the protecting groups in the [(R)-4-(3-cyclopropylmethoxy-phenyl)-5,5-difluoro-4-methyl-5,6-dihydro-

Example 60

3-[4-((R)-2-Amino-5,5-difluoro-4-methyl-5,6-dihydro-4H-[1,3]oxazin-4-yl)-pyrazol-1-yl]-benzonitrile A mixture of (R)-4-(1-(3-bromophenyl)-1H-pyrazol-4-yl)-5,5-difluoro-4-methyl-5,6-dihydro-4H-1,3-oxazin-2-amine (20 mg, 53.9 µmol) (intermediate K7.1), zinc cyanide (3.8 mg, 32.3 µmol) and tetrakis(triphenylphosphine)-palladium(0) (6.23 mg, 5.39 µmol) was heated at 160° C. in N,N-dimethylformamide (0.5 ml) for 30 minutes in a microwave oven. Thereafter, the reaction mixture was evaporated at reduced pressure and purified by preparative HPLC. The 3-[4-((R)-2-amino-5,5-difluoro-4-methyl-5,6-dihydro-4H-[1,3]oxazin-4-yl)-pyrazol-1-yl]-benzonitrile (79% yield) was obtained as a light brown solid. MS (ISP): m/z=318.1 $[M+H]^+$.

Example 61

(R)-4-[1-(3-Ethynyl-phenyl)-1H-pyrazol-4-yl]-5,5-difluoro-4-methyl-5,6-dihydro-4H-[1,3]oxazin-2-ylamine a) (R)-5,5-Difluoro-4-methyl-4-[1-(3-trimethylsilanylethynyl-phenyl)-1H-pyrazol-4-yl]-5,6-dihydro-4H-[1,3]oxazin-2-ylamine A solution of (R)-4-(1-(3-bromophenyl)-1H-pyrazol-4-yl)-5,5-difluoro-4-methyl-5,6-dihydro-4H-1,3-oxazin-2-amine (227 mg, 612 µmol) (intermediate K7.1) in tetrahydrofuran (5 ml) was treated consecutively with ethynyltrimethylsilane (120 mg, 169 µl, 1.22 mmol), triphenylphosphine (4.81 mg, 18.3 µmol) and triethylamine (186 mg, 256 µl, 1.83 mmol). The mixture was degassed by bubbling argon through the solution, then copper(I) iodide (1.16 mg, 6.12 µmol) and bis(triphenylphosphine)palladium(II) chloride (21.5 mg, 30.6 µmol) were added. The reaction mixture was stirred at 70° C. in a sealed tube. In order to complete the reaction, ethynyltrimethylsilane (120 mg, 169 µl, 1.22 mmol) and bis(triphenylphosphine)palladium(II) chloride (21.5 mg, 30.6 µmol) were added again and stirring continued at 70° C. for 20 hours. Thereafter, the reaction mixture was evaporated and the residue purified by chromatography on silica gel using a gradient of heptane/ethyl acetate=100:0 to 0:100 as the eluent. The (R)-5,5-difluoro-4-methyl-4-[1-(3-trimethylsilanylethynyl-phenyl)-1H-pyrazol-4-yl]-5,6-dihydro-4H-[1,3]oxazin-2-ylamine (105 mg, 44% yield) was obtained as a brown, amorphous material. MS (ISP): m/z=389.3 $[M+H]^+$.

b) (R)-4-[1-(3-Ethynyl-phenyl)-1H-pyrazol-4-yl]-5,5-difluoro-4-methyl-5,6-dihydro-4H-[1,3]oxazin-2-ylamine A solution of (R)-5,5-difluoro-4-methyl-4-(1-(3-((trimethylsilyl)ethynyl)phenyl)-1H-pyrazol-4-yl)-5,6-dihydro-4H-1,3-oxazin-2-amine (68.6 mg, 177 µmol) in methanol (2 ml) was treated at room temperature with sodium methoxide (5.4M in methanol; 1 µl, 5.4 µmol). After 90 minutes a small quantity of dry ice was added to neutralize the reaction mixture. After evaporation at reduced pressure the residue thus obtained was dissolved in a mixture of water and dichloromethane. The aqueous layer was extracted with dichloromethane, thereafter, the combined organic layers were washed with water, dried over sodium sulphate, and evaporated. The residue was purified by chromatography on silica gel using a gradient of heptane/ethyl acetate=100:0 to 0:100 as the eluent. The (R)-4-[1-(3-ethynyl-phenyl)-1H-pyrazol-4-yl]-5,5-difluoro-4-methyl-5,6-dihydro-4H-[1,3]oxazin-2-ylamine (29 mg, 52% yield) was obtained as a light yellow solid. MS (ISP): m/z=317.1 $[M+H]^+$.

Example 62

(1S,2S)-rel-2-((R)-2-Amino-5,5-difluoro-4-methyl-5,6-dihydro-4H-[1,3]oxazin-4-yl)-cyclopropanecarboxylic acid(3-chloro-quinolin-8-yl)-amide a) {(R)-4-[(1S,2S)-rel-2-(3-Chloro-quinolin-8-ylcarbamoyl)-cyclopropyl]-5,5-difluoro-4-methyl-5,6-dihydro-4H-[1,3]oxazin-2-yl}-carbamic acid tert-butyl ester A solution of (1S,2S)-rel-2-((R)-2-tert-butoxycarbonylamino-5,5-difluoro-4-methyl-5,6-dihydro-4H-[1,3]oxazin-4-yl)-cyclopropane-carboxylic (38 mg, 114 µmol) (intermediate J8.1) in N,N-dimethylformamide (398 µl) was treated consecutively with O-(7-azabenzotriazol-1-yl)-N,N,N',N'-tetramethyluronium hexafluorophosphate (HATU) (64.8 mg, 170 µmol) and N,N-diisopropylethylamine (60.0 mg, 79.4 µl, 455 µmol). The mixture was stirred at room temperature for 5 minutes. 3-Chloro-quinolin-8-ylamine (CAS 139399-66-9) (24.4 mg, 136 µmol) was added and the mixture was stirred at room temperature for 24 hours. For the workup, the solvent was removed at reduced pressure. The residue was taken up in ethyl acetate and washed once with water and once with a saturated solution of sodium hydrogencarbonate. After the aqueous layer was back extracted once with ethyl acetate, the combined extracts were dried over sodium sulphate and concentrated at reduced pressure. The crude brown by chromatography on silica gel using a gradient of heptane/ethyl acetate=100:0 to 80:20 as the eluent. Further purification was performed by preparative thin layer chromatography using a 1:1-mixture of heptane and ethyl acetate as the eluent. The {(R)-4-[(1S,2S)-rel-2-β-chloro-quinolin-8-ylcarbamoyl)-cyclopropyl]-5,5-difluoro-4-methyl-5,6-dihydro-4H-[1,3] oxazin-2-yl}-carbamic acid tert-butyl ester (4.7 mg, 8.4% yield) was obtained as a light yellow solid. MS (ISP): m/z=495.2 $[M+H]^+$.

b) (1S,2S)-rel-2-((R)-2-Amino-5,5-difluoro-4-methyl-5,6-dihydro-4H-[1,3]oxazin-4-yl)-cyclopropanecarboxylic acid (3-chloro-quinolin-8-yl)-amide A solution of {(R)-4-[(1S,2S)-rel-2-(3-chloro-quinolin-8-ylcarbamoyl)-cyclopropyl]-5,5-difluoro-4-methyl-5,6-dihydro-4H-[1,3]oxazin-2-yl}-carbamic acid tert-butyl ester (4.7 mg, 9.5 µmol) (intermediate J8.2) in dichloromethane (47 µl) was cooled to 0° C. Trifluoroacetic acid (11.0 mg, 7.4 µl, 95.0 µmol) was added and the solution was left to warm to room temperature. After 7 hours trifluoroacetic acid (33.1 mg, 22.3 µl, 285 µmol) was added again and the mixture stirred at room temperature for another hour. Thereafter, the solvent was removed at reduced pressure. The residue was dissolved in water, then the aqueous layer was basified with a solution of sodium carbonate (2M) and extracted 3 times with dichloromethane. The combined extracts were dried over sodium sulphate and evaporated. The (1S,2S)-rel-2-((R)-2-amino-5,5-difluoro-4-methyl-5,6-dihydro-4H-[1,3]oxazin-4-yl)-cyclopropanecarboxylic acid (3-chloro-quinolin-8-yl)-amide (3.7 mg, 99%) was obtained as a light brown solid. MS (ISP): m/z=395.0 [M+H]$^+$.

Example 63

(1R,2R)-((R)-2-Amino-5,5-difluoro-4-methyl-5,6-dihydro-4H-[1,3]oxazin-4-yl)-cyclopropanecarboxylic acid(3-chloro-quinolin-8-yl)-amide a) {(R)-4-[(1R,2R)-2-(3-Chloro-quinolin-8-ylcarbamoyl)-cyclopropyl]-5,5-difluoro-4-methyl-5,6-dihydro-4H-[1,3]oxazin-2-yl}-carbamic acid tert-butyl ester In a manner analogous to that described in Example 62.1a), the condensation reaction of (1R,2R)-2-((R)-2-tert-butoxycarbonylamino-5,5-difluoro-4-methyl-5,6-dihydro-4H-[1,3]oxazin-4-yl)-cyclopropane-carboxylic (intermediate J8.2) with 3-chloro-quinolin-8-ylamine yielded the title compound (36% yield) as a yellow solid. MS (ISP): m/z=495.2 [M+H]$^+$.

b) (1R,2R)-((R)-2-Amino-5,5-difluoro-4-methyl-5,6-dihydro-4H-[1,3]oxazin-4-yl)-cyclopropanecarboxylic acid (3-chloro-quinolin-8-yl)-amide In a manner analogous to that described in Example 62.1b), the deprotection of {(R)-4-[(1R,2R)-2-(3-chloro-quinolin-8-ylcarbamoyl)-cyclopropyl]-5,5-difluoro-4-methyl-5,6-dihydro-4H-[1,3]oxazin-2-yl}-carbamic acid tert-butyl ester with trifluoroacetic acid yielded the title compound (61% yield) as a yellow solid. MS (ISP): m/z=395.0 [M+H]$^+$.

Example 64

(1S,2S)-((R)-2-Amino-5,5-difluoro-4-methyl-5,6-dihydro-4H-[1,3]oxazin-4-yl)-cyclopropanecarboxylic acid(3-chloro-quinolin-8-yl)-amide a) {(R)-4-[(1S,2S)-2-(3-Chloro-quinolin-8-ylcarbamoyl)-cyclopropyl]-5,5-difluoro-4-methyl-5,6-dihydro-4H-[1,3]oxazin-2-yl}-carbamic acid tert-butyl ester In a manner analogous to that described in Example 62.1a), the condensation reaction of (1S,2S)-2-((R)-2-tert-butoxycarbonylamino-5,5-difluoro-4-methyl-5,6-dihydro-4H-[1,3]oxazin-4-yl)-cyclopropane-carboxylic (intermediate J8.3) with 3-chloro-quinolin-8-ylamine yielded the title compound (16% yield) as a yellow solid. MS (ISP): m/z=495.2 [M+H]$^+$.

b) (1S,2S)-((R)-2-Amino-5,5-difluoro-4-methyl-5,6-dihydro-4H-[1,3]oxazin-4-yl)-cyclopropanecarboxylic acid (3-chloro-quinolin-8-yl)-amide In a manner analogous to that described in Example 62.1b), the deprotection of {(R)-4-[(1S,2S)-2-(3-chloro-quinolin-8-ylcarbamoyl)-cyclopropyl]-5,5-difluoro-4-methyl-5,6-dihydro-4H-[1,3]oxazin-2-yl}-carbamic acid tert-butyl ester with trifluoroacetic acid yielded the title compound (84% yield) as a yellow solid. MS (ISP): m/z=395.1 [M+H]$^+$.

Example 65

(1R,2R)-2-((R)-2-Amino-5,5-difluoro-4-methyl-5,6-dihydro-4H-[1,3]oxazin-4-yl)-cyclopropanecarboxylic acid(6-cyano-thieno[3,2-b]pyridin-3-yl)-amide a) {(R)-4-[(1R,2R)-2-(6-Cyano-thieno[3,2-b]pyridin-3-ylcarbamoyl)-cyclopropyl]-5,5-difluoro-4-methyl-5,6-dihydro-4H-[1,3]oxazin-2-yl}-carbamic acid tert-butyl ester In a manner analogous to that described in Example 62.1a), the condensation reaction of (1R,2R)-2-((R)-2-tert-butoxycarbonylamino-5,5-difluoro-4-methyl-5,6-dihydro-4H-[1,3]oxazin-4-yl)-cyclopropane-carboxylic (intermediate J8.2) with 3-amino-thieno[3,2-b]pyridine-6-carbonitrile [CAS 116538-96-6; R. Benoit et al. Synthesis 1987(12), 1124-26] yielded the title compound (49% yield) as a yellow solid. MS (ISP): m/z=492.3 [M+H]$^+$.

b) (1R,2R)-2-((R)-2-Amino-5,5-difluoro-4-methyl-5,6-dihydro-4H-[1,3]oxazin-4-yl)-cyclopropanecarboxylic acid(6-cyano-thieno[3,2-b]pyridin-3-yl)-amide In a manner analogous to that described in Example 62.1b), the deprotection of {(R)-4-[(1R,2R)-2-(6-Cyano-thieno[3,2-b]pyridin-3-ylcarbamoyl)-cyclopropyl]-5,5-difluoro-4-methyl-5,6-dihydro-4H-[1,3]oxazin-2-yl}-carbamic acid tert-butyl ester with trifluoroacetic acid yielded the title compound (59% yield) as a light yellow solid. MS (ISP): m/z=392.2 [M+H]$^+$.

The invention claimed is:
1. A compound of formula I,

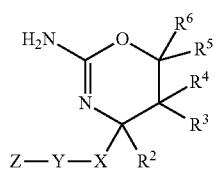

wherein
X is selected from the group consisting of
  aryl,
  aryl substituted by 1-2 substituents individually selected from $R^1$,
  heteroaryl,
  heteroaryl substituted by 1-2 substituents individually selected from $R^1$ and halogen-aryl,
  $C_{3-6}$-cycloalkyl, and
  $C_{3-6}$-cycloalkyl substituted by 1-2 substituents individually selected from $R^1$;
Y is selected from the group consisting of
  —C=O—NH—,
  —CH$_2$—,
  —NH—
  —NH—CHR$^7$—,
  —O—CH$_2$—, and
  absent;
Z is selected from the group consisting of
  aryl,
  aryl substituted by 1-2 substituents individually selected from $R^8$, heteroaryl,
heteroaryl substituted by 1-2 substituents individually selected from $R^8$,
$C_{3-6}$-cycloalkyl,
$C_{3-6}$-cycloalkyl substituted by 1-2 substituents individually selected from $R^8$,
heterocyclyl,
heterocyclyl substituted by 1-2 substituents individually selected from $R^8$,
$C_{2-6}$-alkynyl,
$C_{1-6}$-alkyl, and
$C_{1-6}$-alkyl substituted by 1-3 substituents individually selected from $R^9$;
$R^1$ is selected from the group consisting of
hydrogen,
halogen, and
$C_{1-6}$-alkyl;
$R^2$ is selected from the group consisting of
hydrogen,
$C_{1-6}$-alkyl, and
halogen-$C_{1-3}$-alkyl;
$R^3$ is selected from the group consisting of
hydrogen,
halogen, and
$C_{1-6}$-alkyl;
$R^4$ is selected from the group consisting of
hydrogen
halogen, and
$C_{1-6}$-alkyl;
$R^5$ is selected from the group consisting of
hydrogen and
$C_{1-6}$-alkyl;
$R^6$ is selected from the group consisting of
hydrogen and
$C_{1-6}$-alkyl;
$R^7$ is selected from the group consisting of
hydrogen and
$C_{1-6}$-alkyl;
$R^8$ is selected from the group consisting of
halogen,
cyano,
$C_{1-6}$-alkyl,
halogen-$C_{1-6}$-alkyl,
$C_{1-6}$-alkoxy,
halogen-$C_{1-6}$-alkoxy,
aryl,
halogen-aryl, and
$C_{3-6}$-cycloalkyl; and
$R^9$ is selected from the group consisting of
halogen,
cyano,
$C_{1-6}$-alkoxy, and
halogen-$C_{1-6}$-alkoxy;
or a pharmaceutically acceptable salt thereof.

2. The compound according to claim 1
wherein
X is selected from the group consisting of
aryl,
aryl substituted by 1-2 substituents individually selected from $R^1$,
heteroaryl, and
heteroaryl substituted by 1-2 substituents individually selected from $R^1$;
Y is selected from the group consisting of
—C=O—NH—,
—CH$_2$—,
—NH—
—NH—CHR$^7$—,
—O—CH$_2$—, and
absent;
Z is selected from the group consisting of
aryl,
aryl substituted by 1-2 substituents individually selected from $R^8$,
heteroaryl,
heteroaryl substituted by 1-2 substituents individually selected from $R^8$,
$C_{3-6}$-cycloalkyl,
$C_{3-6}$-cycloalkyl substituted by 1-2 substituents individually selected from $R^8$,
heterocyclyl,
heterocyclyl substituted by 1-2 substituents individually selected from $R^8$, and
$C_{2-6}$-alkynyl;
$R^1$ is selected from the group consisting of
hydrogen,
halogen, and
$C_{1-6}$-alkyl;
$R^2$ is selected from the group consisting of
hydrogen,
$C_{1-6}$-alkyl, and
halogen-$C_{1-3}$-alkyl;
$R^3$ is selected from the group consisting of
hydrogen,
halogen, and
$C_{1-6}$-alkyl;
$R^4$ is selected from the group consisting of
hydrogen
halogen, and
$C_{1-6}$-alkyl;
$R^5$ is selected from the group consisting of
hydrogen and
$C_{1-6}$-alkyl;
$R^6$ is selected from the group consisting of
hydrogen and
$C_{1-6}$-alkyl;
$R^7$ is selected from the group consisting of
hydrogen and
$C_{1-6}$-alkyl; and
$R^8$ is selected from the group consisting of
halogen,
cyano,
$C_{1-6}$-alkyl,
halogen-$C_{1-6}$-alkyl,
$C_{1-6}$-alkoxy,
halogen-$C_{1-6}$-alkoxy,
aryl,
halogen-aryl, and
$C_{3-6}$-cycloalkyl;
or a pharmaceutically acceptable salt thereof.

3. The compound according to claim 1, wherein $R^2$ is $C_{1-6}$-alkyl.

4. The compound according to claim 3, wherein $R^2$ is methyl.

5. The compound according to claim 1, wherein $R^3$ is halogen.

6. The compound according to claim 5, wherein $R^3$ is F.

7. The compound according to claim 1, wherein $R^4$ is H, methyl or F.

8. The compound according to claim 1, wherein $R^5$ is H.

9. The compound according to claim 1, wherein $R^6$ is H.

10. The compound according to claim 1, wherein X is aryl substituted by halogen.

11. The compound according to claim 9, wherein X is phenyl substituted by F.

12. The compound according to claim 1, wherein Y is —NHCH$_2$—, —NH— or absent.

13. The compound according to claim 1, wherein Z is heteroaryl substituted by 1-2 substituents individually selected from R$^8$ and C$_{3-6}$-cycloalkyl.

14. The compound according to claims 1, wherein R$^8$ is selected from the group consisting of
   halogen,
   cyano,
   C$_{1-6}$-alkyl, and
   halogen-C$_{1-6}$-alkyl.

15. The compound according to claim 1, selected from the group consisting of
   (S)-4-{5-[(4-Chloro-1-difluoromethyl-1H-pyrazol-3-yl-methyl)-amino]-2-fluoro-phenyl}-4-methyl-5,6-dihydro-4H-[1,3]oxazin-2-ylamine,
   (4R,5R)-5-Fluoro-4-[2-fluoro-5-(2-methoxy-phenylamino)-phenyl]-4-methyl-5,6-dihydro-4H-[1,3]oxazin-2-ylamine,
   (4R,5R)-4-[5-(2-Difluoromethoxy-phenylamino)-2-fluoro-phenyl]-5-fluoro-4-methyl-5,6-dihydro-4H-[1,3]oxazin-2-ylamine,
   (4R,5R)-5-Fluoro-4-{2-fluoro-5-[(thiophen-2-ylmethyl)-amino]-phenyl}-4-methyl-5,6-dihydro-4H-[1,3]oxazin-2-ylamine,
   (4R,5R)-5-Fluoro-4-{2-fluoro-5-[(thiophen-3-ylmethyl)-amino]-phenyl}-4-methyl-5,6-dihydro-4H-[1,3]oxazin-2-ylamine,
   (4R,5R)-5-Fluoro-4-[2-fluoro-5-(2-fluoro-benzylamino)-phenyl]-4-methyl-5,6-dihydro-4H-[1,3]oxazin-2-ylamine,
   (4R,5R)-4-[5-(Cyclopropylmethyl-amino)-2-fluoro-phenyl]-5-fluoro-4-methyl-5,6-dihydro-4H-[1,3]oxazin-2-ylamine,
   (4R,5R)-5-Fluoro-4-{2-fluoro-5-[1-(4-fluoro-phenyl)-1H-pyrazol-4-yl]-phenyl}-4-methyl-5,6-dihydro-4H-[1,3]oxazin-2-ylamine,
   (4R,5R)-5-Fluoro-4-[2-fluoro-5-(4-methyl-pyrazol-1-yl)-phenyl]-4-methyl-5,6-dihydro-4H-[1,3]oxazin-2-ylamine,
   (4R,5R)-4-{5-[(4-Chloro-1-difluoromethyl-1H-pyrazol-3-ylmethyl)-amino]-2-fluoro-phenyl}-5-fluoro-4,5-dimethyl-5,6-dihydro-4H-[1,3]oxazin-2-ylamine, and
   (4R,5R)-4-{5-[(4-Chloro-1-methyl-1H-pyrazol-3-ylmethyl)-amino]-2-fluoro-phenyl}-5-fluoro-4,5-dimethyl-5,6-dihydro-4H-[1,3]oxazin-2-ylamine,
or a pharmaceutical acceptable salt thereof.

16. The compound according to claim 1, selected from the group consisting of
   (4R,5R)-5-Fluoro-4-{2-fluoro-5-[1-(2-methyl-5-trifluoromethyl-oxazol-4-yl)-ethylamino]-phenyl}-4,5-dimethyl-5,6-dihydro-4H-[1,3]oxazin-2-ylamine,
   (R)-4-{5-[(4-Chloro-1-difluoromethyl-1H-pyrazol-3-yl-methyl)-amino]-2-fluoro-phenyl}-5,5-difluoro-4-methyl-5,6-dihydro-4H-[1,3]oxazin-2-ylamine,
   (R)-4-{5-[1-(4-Chloro-1-methyl-1H-pyrazol-3-yl)-ethylamino]-2-fluoro-phenyl}-5,5-difluoro-4-methyl-5,6-dihydro-4H-[1,3]oxazin-2-ylamine,
   (R)-4-{5-[1-(5-Cyclopropyl-isoxazol-3-yl)-ethylamino]-2-fluoro-phenyl}-5,5-difluoro-4-methyl-5,6-dihydro-4H-[1,3]oxazin-2-ylamine,
   4-[5-(5-Chloro-pyridin-3-yl)-2-fluoro-phenyl]-4-difluoromethyl-5,6-dihydro-4H-[1,3]oxazin-2-ylamine,
   (R)-4-[5-(5-Chloro-pyridin-3-yl)-2-fluoro-phenyl]-4-difluoromethyl-5,6-dihydro-4H-[1,3]oxazin-2-ylamine,
   (S)-4-[5-(5-Chloro-pyridin-3-yl)-2-fluoro-phenyl]-4-difluoromethyl-5,6-dihydro-4H-[1,3]oxazin-2-ylamine,
   (R)-5,5-Difluoro-4-methyl-4-[3-(3,3,3-trifluoro-propoxy)-phenyl]-5,6-dihydro-4H-[1,3]oxazin-2-ylamine,
   2-[3-((R)-2-Amino-5,5-difluoro-4,6,6-trimethyl-5,6-dihydro-4H-[1,3]oxazin-4-yl)-4-fluoro-phenylamino]-benzonitrile,
   (R)-5,5-Difluoro-4-(2-fluoro-5-o-tolylamino-phenyl)-4,6,6-trimethyl-5,6-dihydro-4H-[1,3]oxazin-2-ylamine, and
   (R)-4-(5-Cyclopentylamino-2-fluoro-phenyl)-5,5-difluoro-4,6,6-trimethyl-5,6-dihydro-4H-[1,3]oxazin-2-ylamine,
or a pharmaceutical acceptable salt thereof.

17. The compound according to claim 1, selected from the group consisting of
   (R)-4-(3',5'-Dichloro-4-fluoro-biphenyl-3-yl)-5,5-difluoro-4,6,6-trimethyl-5,6-dihydro-4H-[1,3]oxazin-2-ylamine,
   3'-((R)-2-Amino-5,5-difluoro-4,6,6-trimethyl-5,6-dihydro-4H-[1,3]oxazin-4-yl)-6-chloro-4'-fluoro-biphenyl-3-carbonitrile,
   (R)-4-[5-(1,1-Dioxo-2,3-dihydro-1H-1$\lambda^6$-benzo[b]thiophen-3-ylamino)-2-fluoro-phenyl]-5,5-difluoro-4-methyl-5,6-dihydro-4H-[1,3]oxazin-2-ylamine,
   5-[3-((4R,5R)-2-Amino-5-fluoro-4-methyl-5,6-dihydro-4H-[1,3]oxazin-4-yl)-4-fluoro-phenyl]-nicotinonitrile,
   7-[3-((R)-2-Amino-5,5-difluoro-4-methyl-5,6-dihydro-4H-[1,3]oxazin-4-yl)-4-fluoro-phenylamino]-6,7-dihydro-5H-[1]pyrindine-3-carbonitrile,
   [3-((R)-2-Amino-5,5-difluoro-4-methyl-5,6-dihydro-4H-[1,3]oxazin-4-yl)-4-fluoro-phenyl]-(3-chloro-6,7-dihydro-5H-[1]pyrindin-7-yl)-amine,
   8-[3-((R)-2-Amino-5,5-difluoro-4-methyl-5,6-dihydro-4H-[1,3]oxazin-4-yl)-4-fluoro-phenylamino]-5,6,7,8-tetrahydro-quinoline-3-carbonitrile,
   4-[3-((R)-2-Amino-5,5-difluoro-4-methyl-5,6-dihydro-4H-[1,3]oxazin-4-yl)-phenoxymethyl]-benzonitrile,
   3-((R)-2-Amino-5,5-difluoro-4-methyl-5,6-dihydro-4H-[1,3]oxazin-4-yl)-4-fluoro-N-prop-2-ynyl-benzamide,
   3-[4-((R)-2-Amino-5,5-difluoro-4-methyl-5,6-dihydro-4H-[1,3]oxazin-4-yl)-pyrazol-1-yl]-benzonitrile, and
   (1R,2R)-((R)-2-Amino-5,5-difluoro-4-methyl-5,6-dihydro-4H-[1,3]oxazin-4-yl)-cyclopropanecarboxylic acid (3-chloro-quinolin-8-yl)-amide,
or a pharmaceutical acceptable salt thereof.

18. The compound according to claim 1, selected from the group consisting of
   (1S,2S)-((R)-2-Amino-5,5-difluoro-4-methyl-5,6-dihydro-4H-[1,3]oxazin-4-yl)-cyclopropanecarboxylic acid (3-chloro-quinolin-8-yl)-amide,
   (1R,2R)-2-((R)-2-Amino-5,5-difluoro-4-methyl-5,6-dihydro-4H-[1,3]oxazin-4-yl)-cyclopropanecarboxylic acid (6-cyano-thieno[3,2-b]pyridin-3-yl)-amide,
   (R)-4-(5-{1-[4-Chloro-1-(2,2-difluoro-ethyl)-1H-pyrazol-3-yl]-ethylamino}-2-fluoro-phenyl)-5,5-difluoro-4-methyl-5,6-dihydro-4H-[1,3]oxazin-2-ylamine,
   (4R,5R)-4-[5-(3,5-Difluoro-benzylamino)-2-fluoro-phenyl]-5-fluoro-4-methyl-5,6-dihydro-4H-[1,3]oxazin-2-ylamine,
   (R)-4-[3-(5-Chloro-pyridin-2-yl)-7-fluoro-3,4-dihydro-2H-benzo[1,4]oxazin-6-yl]-5,5-difluoro-4-methyl-5,6-dihydro-4H-[1,3]oxazin-2-ylamine,
   (R)-4-[5-(6-Chloro-benzooxazol-2-yl)-2,4-difluoro-phenyl]-5,5-difluoro-4-methyl-5,6-dihydro-4H-[1,3]oxazin-2-ylamine, (R)-5,5-Difluoro-4-{2-fluoro-5-[1-(5-methyl-2H-pyrazol-3-yl)-ethylamino]-phenyl}-4-methyl-5,6-dihydro-4H-[1,3]oxazin-2-ylamine, (R)-5,5-Difluoro-4-{2-fluoro-5-[1-(2-methyl-5-trifluoromethyl-oxazol-4-yl)-ethylamino]-phenyl}-4-methyl-5,6-dihydro-4H-[1,3]oxazin-2-ylamine, (R)-5,5-Difluoro-4-{2-fluoro-5-[(3-methyl-oxetan-3-ylmethyl)-amino]-phenyl}-4-methyl-5,6-dihydro-4H-[1,3]oxazin-2-ylamine, (R)-4-[5-(Cyclopropylmethyl-amino)-2-fluoro-phenyl]-5,5-difluoro-4-methyl-5,6-dihydro-4H-[1,3]oxazin-2-ylamine, and (R)-5,5-Difluoro-4-[2-fluoro-5-(tetrahydro-furan-3-ylamino)-phenyl]-4-methyl-5,6-dihydro-4H-[1,3]oxazin-2-ylamine, or a pharmaceutical acceptable salt thereof.

19. The compound according to claim 1, selected from the group consisting of (R)-5,5-Difluoro-4-[2-fluoro-5-(oxetan-3-ylamino)-phenyl]-4-methyl-5,6-dihydro-4H-[1,3]oxazin-2-ylamine, (R)-5,5-Difluoro-4-{2-fluoro-5-[(tetrahydro-furan-3-ylmethyl)-amino]-phenyl}-4-methyl-5,6-dihydro-4H-[1,3]oxazin-2-ylamine, (R)-5,5-Difluoro-4-{2-fluoro-5-[1-(4-fluoro-phenyl)-1H-pyrazol-4-yl]-phenyl}-4-methyl-5,6-dihydro-4H-[1,3]oxazin-2-ylamine, (R)-4-[5-(5-Chloro-pyridin-3-yl)-2,4-difluoro-phenyl]-5,5-difluoro-4-methyl-5,6-dihydro-4H-[1,3]oxazin-2-ylamine, (R)-5,5-Difluoro-4-methyl-4-[3-(4-trifluoromethyl-benzyloxy)-phenyl]-5,6-dihydro-4H-[1,3]oxazin-2-ylamine, (R)-5,5-Difluoro-4-methyl-4-[2-(4-methyl-benzyl)-3H-benzoimidazol-5-yl]-5,6-dihydro-4H-[1,3]oxazin-2-ylamine, (R)-5,5-Difluoro-4-[5-fluoro-2-(4-methoxy-benzyl)-1H-indol-6-yl]-4-methyl-5,6-dihydro-4H-[1,3]oxazin-2-ylamine, (R)-5,5-Difluoro-4-[5-fluoro-2-(4-methyl-benzyl)-3H-indol-6-yl]-4-methyl-5,6-dihydro-4H-[1,3]oxazin-2-ylamine, (R)-5,5-Difluoro-4-[2-fluoro-5-(2-methoxy-phenylamino)-phenyl]-4,6,6-trimethyl-5,6-dihydro-4H-[1,3]oxazin-2-ylamine, (R)-5,5-Difluoro-4-[2-fluoro-5-(2-trifluoromethyl-phenylamino)-phenyl]-4,6,6-trimethyl-5,6-dihydro-4H-[1,3]oxazin-2-ylamine, (R)-5,5-Difluoro-4-[2-fluoro-5-(6-trifluoromethyl-pyridin-2-ylamino)-phenyl]-4,6,6-trimethyl-5,6-dihydro-4H-[1,3]oxazin-2-ylamine, and (R)-5,5-Difluoro-4-[2-fluoro-5-(3-phenyl-cyclopentylamino)-phenyl]-4,6,6-trimethyl-5,6-dihydro-4H-[1,3]oxazin-2-ylamine, or a pharmaceutical acceptable salt thereof.

20. The compound according to claim 1, selected from the group consisting of (R)-4-[5-(5-Chloro-pyridin-3-yl)-2-fluoro-phenyl]-5,5-difluoro-4,6,6-trimethyl-5,6-dihydro-4H-[1,3]oxazin-2-ylamine, (R)-4-[2-(4-Ethyl-benzyl)-3H-benzoimidazol-5-yl]-5,5-difluoro-4-methyl-5,6-dihydro-4H-[1,3]oxazin-2-ylamine, (R)-4-[5-((RS)-2,2-Difluoro-cyclopropylmethoxy)-phenyl]-5,5-difluoro-4-methyl-5,6-dihydro-4H-[1,3]oxazin-2-ylamine, (R)-4-[1-(3-Ethynyl-phenyl)-1H-pyrazol-4-yl]-5,5-difluoro-4-methyl-5,6-dihydro-4H-[1,3]oxazin-2-ylamine, (R)-4-(2,4-Difluoro-5-pyrimidin-5-yl-phenyl)-5,5-difluoro-4-methyl-5,6-dihydro-4H-[1,3]oxazin-2-ylamine, (R)-4-[5-(2-Chloro-phenylamino)-2-fluoro-phenyl]-5,5-difluoro-4,6,6-trimethyl-5,6-dihydro-4H-[1,3]oxazin-2-ylamine, (S)-4-(5-Cyclopentylamino-2-fluoro-phenyl)-4-methyl-5,6-dihydro-4H-[1,3]oxazin-2-ylamine, (R)-4-[3-(4-Chloro-benzyloxy)-phenyl]-5,5-difluoro-4-methyl-5,6-dihydro-4H-[1,3]oxazin-2-ylamine, (R)-4-(3-Cyclopropylmethoxy-phenyl)-5,5-difluoro-4-methyl-5,6-dihydro-4H-[1,3]oxazin-2-ylamine, and (1S,2S)-rel-2-((R)-2-Amino-5,5-difluoro-4-methyl-5,6-dihydro-4H-[1,3]oxazin-4-yl)-cyclopropanecarboxylic acid (3-chloro-quinolin-8-yl)-amide;

or a pharmaceutical acceptable salt thereof.

21. The compound according to claim 1, selected from the group consisting of (S)-4-{5-[(4-Chloro-1-difluoromethyl-1H-pyrazol-3-ylmethyl)-amino]-2-fluoro-phenyl}-4-methyl-5,6-dihydro-4H-[1,3]oxazin-2-ylamine, (4R,5R)-4-[5-(2-Difluoromethoxy-phenylamino)-2-fluoro-phenyl]-5-fluoro-4-methyl-5,6-dihydro-4H-[1,3]oxazin-2-ylamine, (4R,5R)-4-[5-(Cyclopropylmethyl-amino)-2-fluoro-phenyl]-5-fluoro-4-methyl-5,6-dihydro-4H-[1,3]oxazin-2-ylamine, (4R,5R)-4-{5-[(4-Chloro-1-difluoromethyl-1H-pyrazol-3-ylmethyl)-amino]-2-fluoro-phenyl}-5-fluoro-4,5-dimethyl-5,6-dihydro-4H-[1,3]oxazin-2-ylamine, (4R,5R)-4-{5-[(4-Chloro-1-methyl-1H-pyrazol-3-ylmethyl)-amino]-2-fluoro-phenyl}-5-fluoro-4,5-dimethyl-5,6-dihydro-4H-[1,3]oxazin-2-ylamine, (4R,5R)-5-Fluoro-4-[2-fluoro-5-(2-fluoro-benzylamino)-phenyl]-4-methyl-5,6-dihydro-4H-[1,3]oxazin-2-ylamine, (4R,5R)-5-Fluoro-4-[2-fluoro-5-(2-methoxy-phenylamino)-phenyl]-4-methyl-5,6-dihydro-4H-[1,3]oxazin-2-ylamine, (4R,5R)-5-Fluoro-4-[2-fluoro-5-(4-methyl-pyrazol-1-yl)-phenyl]-4-methyl-5,6-dihydro-4H-[1,3]oxazin-2-ylamine, (4R,5R)-5-Fluoro-4-{2-fluoro-5-[(thiophen-2-ylmethyl)-amino]-phenyl}-4-methyl-5,6-dihydro-4H-[1,3]oxazin-2-ylamine, (4R,5R)-5-Fluoro-4-{2-fluoro-5-[(thiophen-3-ylmethyl)-amino]-phenyl}-4-methyl-5,6-dihydro-4H-[1,3]oxazin-2-ylamine, and (4R,5R)-5-Fluoro-4-{2-fluoro-5-[1-(2-methyl-5-trifluoromethyl-oxazol-4-yl)-ethylamino]-phenyl}-4,5-dimethyl-5,6-dihydro-4H-[1,3]oxazin-2-ylamine, or a pharmaceutical acceptable salt thereof.

22. The compound according to claim 1, selected from the group consisting of (4R,5R)-5-Fluoro-4-{2-fluoro-5-[1-(4-fluoro-phenyl)-1H-pyrazol-4-yl]-phenyl}-4-methyl-5,6-dihydro-4H-[1,3]oxazin-2-ylamine, (R)-4-(2,4-Difluoro-5-pyrimidin-5-yl-phenyl)-5,5-difluoro-4-methyl-5,6-dihydro-4H-[1,3]oxazin-2-ylamine, (R)-4-(3',5'-Dichloro-4-fluoro-biphenyl-3-yl)-5,5-difluoro-4,6,6-trimethyl-5,6-dihydro-4H-[1,3]oxazin-2-ylamine, (R)-4-(5-{1-[4-Chloro-1-(2,2-difluoro-ethyl)-1H-pyrazol-3-yl]-ethylamino}-2-fluoro-phenyl)-5,5-difluoro-4-methyl-5,6-dihydro-4H-[1,3]oxazin-2-ylamine, (R)-4-(5-Cyclopentylamino-2-fluoro-phenyl)-5,5-difluoro-4,6,6-trimethyl-5,6-dihydro-4H-[1,3]oxazin-2-ylamine, (R)-4-[3-(4-Chloro-benzyloxy)-phenyl]-5,5-difluoro-4-methyl-5,6-dihydro-4H-[1,3]oxazin-2-ylamine, (R)-4-[3-(5-Chloro-pyridin-2-yl)-7-fluoro-3,4-dihydro-2H-benzo[1,4]oxazin-6-yl]-5,5-difluoro-4-methyl-5,6-dihydro-4H-[1,3]oxazin-2-ylamine, (R)-4-[5-(1,1-Dioxo-2,3-dihydro-1H-1λ6-benzo[b]thiophen-3-ylamino)-2-fluoro-phenyl]-5,5-difluoro-4-methyl-5,6-dihydro-4H-[1,3]oxazin-2-ylamine, (R)-4-[5-(2-Chloro-phenylamino)-2-fluoro-phenyl]-5,5-difluoro-4,6,6-trimethyl-5,6-dihydro-4H-[1,3]oxazin-2-ylamine, (R)-4-[5-(5-Chloro-pyridin-3-yl)-2,4-difluoro-phenyl]-5,5-difluoro-4-methyl-5,6-dihydro-4H-[1,3]oxazin-2-ylamine, and (R)-4-[5-(5-Chloro-pyridin-3-yl)-2-fluoro-phenyl]-5,5-difluoro-4,6,6-trimethyl-5,6-dihydro-4H-[1,3]oxazin-2-ylamine, or a pharmaceutical acceptable salt thereof.

23. The compound according to claim 1, selected from the group consisting of (R)-4-[5-(6-Chloro-benzooxazol-2-yl)-2,4-difluoro-phenyl]-5,5-difluoro-4-methyl-5,6-dihydro-4H-[1,3]oxazin-2-ylamine, (R)-4-[5-(Cyclopropylmethyl-amino)-2-fluoro-phenyl]-5,5-difluoro-4-methyl-5,6-dihydro-4H-[1,3]oxazin-2-ylamine, (R)-4-{5-[(4-Chloro-1-difluoromethyl-1H-pyrazol-3-ylmethyl)-amino]-2-fluoro-phenyl}-5,5-difluoro-4-methyl-5,6-dihydro-4H-[1,3]oxazin-2-ylamine, (R)-4-{5-[1-(4-Chloro-1-methyl-1H-pyrazol-3-yl)-ethylamino]-2-fluoro-phenyl}-5,5-difluoro-4-methyl-5,6-dihydro-4H-[1,3]oxazin-2-ylamine, (R)-4-{5-[1-(5-Cyclopropyl-isoxazol-3-yl)-ethylamino]-2-fluoro-phenyl}-5,5-difluoro-4-methyl-5,6-dihydro-4H-[1,3]oxazin-2-ylamine, (R)-5,5-Difluoro-4-(2-fluoro-5-o-tolylamino-phenyl)-4,6,6-trimethyl-5,6-dihydro-4H-[1,3]oxazin-2-ylamine, (R)-5,5-Difluoro-4-[2-fluoro-5-(2-methoxy-phenylamino)-phenyl]-4,6,6-trimethyl-5,6-dihydro-4H-[1,3]oxazin-2-ylamine, (R)-5,5-Difluoro-4-[2-fluoro-5-(2-trifluoromethyl-phenylamino)-phenyl]-4,6,6-trimethyl-5,6-dihydro-4H-[1,3]oxazin-2-ylamine, (R)-5,5-Difluoro-4-[2-fluoro-5-(3-phenyl-cyclopentylamino)-phenyl]-4,6,6-trimethyl-5,6-dihydro-4H-[1,3]oxazin-2-ylamine, (R)-5,5-Difluoro-4-[2-fluoro-5-(6-trifluoromethyl-pyridin-2-ylamino)-phenyl]-4,6,6-trimethyl-5,6-dihydro-4H-[1,3]oxazin-2-ylamine, and (R)-5,5-Difluoro-4-[2-fluoro-5-(oxetan-3-ylamino)-phenyl]-4-methyl-5,6-dihydro-4H-[1,3]oxazin-2-ylamine, or a pharmaceutical acceptable salt thereof.

24. The compound according to claim 1, selected from the group consisting of (R)-5,5-Difluoro-4-[2-fluoro-5-(tetrahydro-furan-3-ylamino)-phenyl]-4-methyl-5,6-dihydro-4H-[1,3]oxazin-2-ylamine, (R)-5,5-Difluoro-4-[5-fluoro-2-(4-methoxy-benzyl)-1H-indol-6-yl]-4-methyl-5,6-dihydro-4H-[1,3]oxazin-2-ylamine, (R)-5,5-Difluoro-4-[5-fluoro-2-(4-methyl-benzyl)-3H-indol-6-yl]-4-methyl-5,6-dihydro-4H-[1,3]oxazin-2-ylamine, (R)-5,5-Difluoro-4-{2-fluoro-5-[(3-methyl-oxetan-3-ylmethyl)-amino]-phenyl}-4-methyl-5,6-dihydro-4H-[1,3]oxazin-2-ylamine, (R)-5,5-Difluoro-4-{2-fluoro-5-[(tetrahydro-furan-3-ylmethyl)-amino]-phenyl}-4-methyl-5,6-dihydro-4H-[1,3]oxazin-2-ylamine, (R)-5,5-Difluoro-4-{2-fluoro-5-[1-(2-methyl-5-trifluoromethyl-oxazol-4-yl)-ethylamino]-phenyl}-4-methyl-5,6-dihydro-4H-[1,3]oxazin-2-ylamine, (R)-5,5-Difluoro-4-{2-fluoro-5-[1-(4-fluoro-phenyl)-1H-pyrazol-4-yl]-phenyl}-4-methyl-5,6-dihydro-4H-[1,3]oxazin-2-ylamine, (R)-5,5-Difluoro-4-{2-fluoro-5-[1-(5-methyl-2H-pyrazol-3-yl)-ethylamino]-phenyl}-4-methyl-5,6-dihydro-4H-[1,3]oxazin-2-ylamine, (R)-5,5-Difluoro-4-methyl-4-[2-(4-methyl-benzyl)-3H-benzoimidazol-5-yl]-5,6-dihydro-4H-[1,3]oxazin-2-ylamine, (R)-5,5-Difluoro-4-methyl-4-[3-(4-trifluoromethyl-benzyloxy)-phenyl]-5,6-dihydro-4H-[1,3]oxazin-2-ylamine, and (S)-4-(5-Cyclopentylamino-2-fluoro-phenyl)-4-methyl-5,6-dihydro-4H-[1,3]oxazin-2-ylamine, or a pharmaceutical acceptable salt thereof.

25. The compound according to claim 1, selected from the group consisting of

[3-((R)-2-Amino-5,5-difluoro-4-methyl-5,6-dihydro-4H-[1,3]oxazin-4-yl)-4-fluoro-phenyl]-(3-chloro-6,7-dihydro-5H-[1]pyrindin-7-yl)-amine, 2-[3-((R)-2-Amino-5,5-difluoro-4,6,6-trimethyl-5,6-dihydro-4H-[1,3]oxazin-4-yl)-4-fluoro-phenylamino]-benzonitrile, 3'-((R)-2-Amino-5,5-difluoro-4,6,6-trimethyl-5,6-dihydro-4H-[1,3]oxazin-4-yl)-6-chloro-4'-fluoro-biphenyl-3-carbonitrile, 3-((R)-2-Amino-5,5-difluoro-4-methyl-5,6-dihydro-4H-[1,3]oxazin-4-yl)-4-fluoro-N-prop-2-ynyl-benzamide, 4-[3-((R)-2-Amino-5,5-difluoro-4-methyl-5,6-dihydro-4H-[1,3]oxazin-4-yl)-phenoxymethyl]-benzonitrile, 5-[3-((4R,5R)-2-Amino-5-fluoro-4-methyl-5,6-dihydro-4H-[1,3]oxazin-4-yl)-4-fluoro-phenyl]-nicotinonitrile, 7-[3-((R)-2-Amino-5,5-difluoro-4-methyl-5,6-dihydro-4H-[1,3]oxazin-4-yl)-4-fluoro-phenylamino]-6,7-dihydro-5H-[1]pyrindine-3-carbonitrile, and 8-[3-((R)-2-Amino-5,5-difluoro-4-methyl-5,6-dihydro-4H-[1,3]oxazin-4-yl)-4-fluoro-phenylamino]-5,6,7,8-tetrahydro-quinoline-3-carbonitrile, or a pharmaceutical acceptable salt thereof.

26. The compound according to claim 1, selected from the group consisting of (4R,5R)-4-[5-(Cyclopropylmethyl-amino)-2-fluoro-phenyl]-5-fluoro-4-methyl-5,6-dihydro-4H-[1,3]oxazin-2-ylamine, (4R,5R)-4-{5-[(4-Chloro-1-difluoromethyl-1H-pyrazol-3-ylmethyl)-amino]-2-fluoro-phenyl}-5-fluoro-4,5-dimethyl-5,6-dihydro-4H-[1,3]oxazin-2-ylamine, (4R,5R)-4-{5-[(4-Chloro-1-methyl-1H-pyrazol-3-ylmethyl)-amino]-2-fluoro-phenyl}-5-fluoro-4,5-dimethyl-5,6-dihydro-4H-[1,3]oxazin-2-ylamine,

[3-((R)-2-Amino-5,5-difluoro-4-methyl-5,6-dihydro-4H-[1,3]oxazin-4-yl)-4-fluoro-phenyl]-(3-chloro-6,7-dihydro-5H-[1]pyrindin-7-yl)-amine, 5-[3-((4R,5R)-2-Amino-5-fluoro-4-methyl-5,6-dihydro-4H-[1,3]oxazin-4-yl)-4-fluoro-phenyl]-nicotinonitrile, and 7-[3-((R)-2-Amino-5,5-difluoro-4-methyl-5,6-dihydro-4H-[1,3]oxazin-4-yl)-4-fluoro-phenylamino]-6,7-dihydro-5H-[1]pyrindine-3-carbonitrile.

27. A pharmaceutical composition comprising a therapeutically effective amount of a compound of formula I

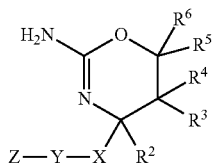

wherein

X is selected from the group consisting of
  aryl,
  aryl substituted by 1-2 substituents individually selected from $R^1$,
  heteroaryl,
  heteroaryl substituted by 1-2 substituents individually selected from $R^1$ and halogen-aryl,
  $C_{3-6}$-cycloalkyl, and
  $C_{3-6}$-cycloalkyl substituted by 1-2 substituents individually selected from $R^1$;

Y is selected from the group consisting of
  —C=O—NH—,
  —CH$_2$—,
  —NH—
  —NH—CHR$^7$—,
  —O—CH$_2$—, and
  absent;

Z is selected from the group consisting of
  aryl,
  aryl substituted by 1-2 substituents individually selected from $R^8$,
  heteroaryl,
  heteroaryl substituted by 1-2 substituents individually selected from $R^8$,
  $C_{3-6}$-cycloalkyl,
  $C_{3-6}$-cycloalkyl substituted by 1-2 substituents individually selected from $R^8$,
  heterocyclyl,
  heterocyclyl substituted by 1-2 substituents individually selected from $R^8$,
  $C_{2-6}$-alkynyl,
  $C_{1-6}$-alkyl, and
  $C_{1-6}$-alkyl substituted by 1-3 substituents individually selected from $R^9$;

$R^1$ is selected from the group consisting of
  hydrogen,
  halogen, and
  $C_{1-6}$-alkyl;

$R^2$ is selected from the group consisting of
  hydrogen,
  $C_{1-6}$-alkyl, and
  halogen-$C_{1-3}$-alkyl;

$R^3$ is selected from the group consisting of
  hydrogen,
  halogen, and
  $C_{1-6}$-alkyl;

$R^4$ is selected from the group consisting of
  hydrogen
  halogen, and
  $C_{1-6}$-alkyl;

$R^5$ is selected from the group consisting of
  hydrogen and
  $C_{1-6}$-alkyl;

$R^6$ is selected from the group consisting of
  hydrogen and
  $C_{1-6}$-alkyl;

$R^7$ is selected from the group consisting of
  hydrogen and
  $C_{1-6}$-alkyl;

$R^8$ is selected from the group consisting of
  halogen,
  cyano,
  $C_{1-6}$-alkyl,
  halogen-$C_{1-6}$-alkyl,
  $C_{1-6}$-alkoxy,
  halogen-$C_{1-6}$-alkoxy,
  aryl,
  halogen-aryl, and
  $C_{3-6}$-cycloalkyl; and $R^9$ is selected from the group consisting of
  halogen,
  cyano,
  $C_{1-6}$-alkoxy, and
  halogen-$C_{1-6}$-alkoxy;

or a pharmaceutically acceptable salt thereof and a pharmaceutically acceptable carrier.

\* \* \* \* \*